United States Patent
Yu et al.

(10) Patent No.: US 12,251,434 B2
(45) Date of Patent: Mar. 18, 2025

(54) TARGET SEQUENCE OF RNA VIRUS AND USE THEREOF

(71) Applicants: SHANGHAI PUBLIC HEALTH CLINICAL CENTER, Shanghai (CN); Shanghai Yizhe Biotechnology Co., Ltd., Shanghai (CN)

(72) Inventors: Wenqiang Yu, Shanghai (CN); Zhenyan Li, Shanghai (CN); Jianqing Xu, Shanghai (CN); Hailin Wang, Shanghai (CN); Wei Li, Shanghai (CN); Cheng Lian, Shanghai (CN); Peng Xu, Shanghai (CN)

(73) Assignees: SHANGHAI PUBLIC HEALTH CLINICAL CENTER, Shanghai (CN); Shanghai Yizhe Biotechnology Co., Ltd., Shanghai (CN)

( * ) Notice: Subject to any disclaimer, the term of this patent is extended or adjusted under 35 U.S.C. 154(b) by 334 days.

(21) Appl. No.: 17/453,574

(22) Filed: Nov. 4, 2021

(65) Prior Publication Data
US 2023/0173054 A1 Jun. 8, 2023

(51) Int. Cl.
| | |
|---|---|
| C07K 14/47 | (2006.01) |
| A61K 31/7088 | (2006.01) |
| A61K 39/12 | (2006.01) |
| A61P 31/14 | (2006.01) |
| C07K 4/00 | (2006.01) |
| C07K 14/00 | (2006.01) |
| C07K 14/005 | (2006.01) |
| C07K 14/435 | (2006.01) |
| C07K 16/18 | (2006.01) |
| C12N 7/00 | (2006.01) |
| A61K 39/00 | (2006.01) |

(52) U.S. Cl.
CPC .......... *A61K 39/12* (2013.01); *A61K 31/7088* (2013.01); *A61P 31/14* (2018.01); *C07K 14/005* (2013.01); *C12N 7/00* (2013.01); *A61K 2039/5254* (2013.01)

(58) Field of Classification Search
CPC ..... A61P 31/12; C12N 15/11; C12N 2320/11; A61K 48/00; A61K 38/00
See application file for complete search history.

(56) References Cited

FOREIGN PATENT DOCUMENTS

| CN | 112063635 A | | 12/2020 |
|---|---|---|---|
| WO | WO2005/035712 | * | 4/2005 |
| WO | WO2022/092995 | * | 5/2022 |

OTHER PUBLICATIONS

Li, W., et al., "Human Identical Sequences of SARS-CoV-2 Promote Clinical Progression of COVID-19 by Upregulating Hyaluronan via NamiRNA-Enhancer Network," bioRxiv: 1-39, Cold Spring Harbor Laboratory, United States (Nov. 2020).

* cited by examiner

*Primary Examiner* — Barry A Chestnut
(74) *Attorney, Agent, or Firm* — Sterne, Kessler, Goldstein & Fox P.L.L.C.

(57) ABSTRACT

The present invention provides a target sequence of an RNA virus. The target sequence is a nucleic acid sequence fragment in the gene sequence in the RNA virus containing 20-40 bases and having not less than 95% similarity to genome sequence of human or related species such as livestock and poultry. The above-mentioned target sequence of the RNA virus is selected from SEQ ID NO. 1-SEQ ID NO. 615. The present invention also relates to a primer composition for constructing the above-mentioned target sequence, biomaterials such as antisense RNA related to the above-mentioned target sequence, and related uses such as design of a vaccine lacking the target sequence. The virus fragment with the above-mentioned sequence constructed in the present invention has the function of interacting with human genomic DNA and is similar to viral miRNA. Moreover, the effect of overexpression of the target sequence of the RNA virus on the expression level of surrounding genes is verified, and a new concept that the above-mentioned target fragment is an important pathogenic substance of the RNA virus is proposed. The above-mentioned target sequence has important application value for the detection and diagnosis of RNA viruses, drug screening, as well as the treatment of diseases caused by RNA viruses and the design/optimization of vaccines and methods.

7 Claims, 8 Drawing Sheets
Specification includes a Sequence Listing.

SEQUENCE LISTING

<160> NUMBER OF SEQ ID NOS: 1326

<210> SEQ ID NO 1
<211> LENGTH: 26
<212> TYPE: RNA
<213> ORGANISM: Artificial Sequence
<220> FEATURE:
<223> OTHER INFORMATION: Fragment coding sequence

```
<400> SEQUENCE: 1
ugucuaugcu aauggaggua aaggcu                                          26

<210> SEQ ID NO 2
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 2
uauaacacau auaaaaauac gugu                                            24

<210> SEQ ID NO 3
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 3
uuauaugccu uauuucuuua cuuu                                            24

<210> SEQ ID NO 4
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 4
aggagaauga caaaaaaaaa aaaaaaa                                         27

<210> SEQ ID NO 5
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 5
uuguugcugc uauuuucuau uuaa                                            24

<210> SEQ ID NO 6
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 6
caugaagaaa caauuuauaa uuuacuua                                        28

<210> SEQ ID NO 7
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 7
gaguugagga agaagaagag gaagacugg                                       29

<210> SEQ ID NO 8
<211> LENGTH: 24
```

```
<212> TYPE: RNA
<213> ORGANISM: Artificial Sequence
<220> FEATURE:
<223> OTHER INFORMATION: Fragment coding sequence

<400> SEQUENCE: 8
uaacaugcuu aggauaaugg ccuc                                           24

<210> SEQ ID NO 9
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 9
aggagaauga caaaaaaaaa aaaaaaa                                        27

<210> SEQ ID NO 10
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 10
uuccauuugc acagaguauc uuuu                                           24

<210> SEQ ID NO 11
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 11
ugcuguaauu gcuguuguug cugcuguu                                       28

<210> SEQ ID NO 12
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 12
gaaaaagaga aagaaacaa ggg                                             23

<210> SEQ ID NO 13
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 13
gggaggaggg aggaagagac ucc                                            23

<210> SEQ ID NO 14
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 14
```
guucuagaga ugcaagacuu gug                                    23

<210> SEQ ID NO 15
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 15
acucauucua ccauuuuuua aauug                                  25

<210> SEQ ID NO 16
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 16
agauccugug acuucuggac uuuu                                   24

<210> SEQ ID NO 17
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 17
aaauauuauu uuuaaaauuu acuu                                   24

<210> SEQ ID NO 18
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 18
acuuuuuaaa agaaaagggg gga                                    23

<210> SEQ ID NO 19
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 19
gaaaaggaag ggaaaauuuc aaa                                    23

<210> SEQ ID NO 20
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 20
aaaugaacaa guagauaaau uag                                    23

<210> SEQ ID NO 21
<211> LENGTH: 24
<212> TYPE: RNA
<213> ORGANISM: Artificial Sequence

```
<220> FEATURE:
<223> OTHER INFORMATION: Fragment coding sequence

<400> SEQUENCE: 21
aaauuauggu accaguuaga gaaa                                              24

<210> SEQ ID NO 22
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 22
gaaagaaaaa auauaaauua aaa                                               23

<210> SEQ ID NO 23
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 23
auuuaucaag agccauuuaa aaa                                               23

<210> SEQ ID NO 24
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 24
uaaaacaggg accaaagaa ccgu                                               24

<210> SEQ ID NO 25
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 25
agaaucagau aaguagaauu aga                                               23

<210> SEQ ID NO 26
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 26
aggcagagga agaugaggcc aac                                               23

<210> SEQ ID NO 27
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 27
uaucaaaaaa uuaagaaaag guua                                              24
```

```
<210> SEQ ID NO 28
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 28
ggaucagugg agaaagugag gaggauga                                      28

<210> SEQ ID NO 29
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 29
augagagauc uuggggugg gac                                            23

<210> SEQ ID NO 30
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 30
gaaaaacuca agaugaaagg aau                                           23

<210> SEQ ID NO 31
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 31
auugauuggc uuaaggagaa aaua                                          24

<210> SEQ ID NO 32
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 32
aauuguuuac cuauuuauug guuuugug                                      28

<210> SEQ ID NO 33
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 33
cugugcugaa ccaggaccag ga                                            22

<210> SEQ ID NO 34
<211> LENGTH: 22
<212> TYPE: RNA
<213> ORGANISM: Artificial Sequence
<220> FEATURE:
<223> OTHER INFORMATION: Fragment coding sequence
```

-continued

<400> SEQUENCE: 34
agaugaagca gucaccaacc gc                                    22

<210> SEQ ID NO 35
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 35
auuagauuuc aacacaggug cuacauc                               27

<210> SEQ ID NO 36
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 36
uuggaauguu uugcuccucu uua                                   23

<210> SEQ ID NO 37
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 37
gaaauuuuau uauuuuguuc agu                                   23

<210> SEQ ID NO 38
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 38
uuagcuagau uuacagauuu gga                                   23

<210> SEQ ID NO 39
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 39
aacaagagca ggccagugug gugg                                  24

<210> SEQ ID NO 40
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 40
uugaggaaaa gggaacccug uaca                                  24

<210> SEQ ID NO 41

```
-continued

<211> LENGTH: 24
<212> TYPE: RNA
<213> ORGANISM: Artificial Sequence
<220> FEATURE:
<223> OTHER INFORMATION: Fragment coding sequence

<400> SEQUENCE: 41
ccaggcacug ggaagucagu ggca                                          24

<210> SEQ ID NO 42
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 42
aauuaggagu gauaccuuca cuaa                                          24

<210> SEQ ID NO 43
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 43
ugagaaaaag gccacugucc uuua                                          24

<210> SEQ ID NO 44
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 44
acaaauugga gaauaguga aaa                                            23

<210> SEQ ID NO 45
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 45
gaagcagaga gaaaguagag aag                                           23

<210> SEQ ID NO 46
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 46
ucaaaaggag agaacagaug cugg                                          24

<210> SEQ ID NO 47
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 47
```
caaaagaagg cauuaaaaga gga                                    23

<210> SEQ ID NO 48
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 48
gagauggacu uugauucug uga                                     23

<210> SEQ ID NO 49
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 49
ggaaauccag ggagguuuug gaa                                    23

<210> SEQ ID NO 50
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 50
aaaggaagaa auugaaaccc aga                                    23

<210> SEQ ID NO 51
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 51
guggcaggcc cauuacacca cca                                    23

<210> SEQ ID NO 52
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 52
aguuuaaauu uauauccaaa auaaauuu                               28

<210> SEQ ID NO 53
<211> LENGTH: 40
<212> TYPE: RNA
<213> ORGANISM: Artificial Sequence
<220> FEATURE:
<223> OTHER INFORMATION: Fragment coding sequence

<400> SEQUENCE: 53 aagaaaaga uaaauagaac acaaagaauu gacaaaauuu                   40

<210> SEQ ID NO 54
<211> LENGTH: 24
<212> TYPE: RNA

```
<213> ORGANISM: Artificial Sequence
<220> FEATURE:
<223> OTHER INFORMATION: Fragment coding sequence

<400> SEQUENCE: 54
ucuaagcgaa guaacaacaa gagu                                            24

<210> SEQ ID NO 55
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 55
aacagaaaga agcauuauua caucaggcuu cu                                   32

<210> SEQ ID NO 56
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 56
ugauuuauau uuacugguau aaaauagu                                        28

<210> SEQ ID NO 57
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 57
aacaaacaaa ccagagacac uaaggaaaug ca                                   32

<210> SEQ ID NO 58
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 58
auacaaucaa auugaauggc au                                              22

<210> SEQ ID NO 59
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 59
agaugacaau ugugaaauua aa                                              22

<210> SEQ ID NO 60
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 60
guuauauaug ggaaaugaug gaauuaaca                                       29
```

```
<210> SEQ ID NO 61
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 61
aaaaaacuaa gugauucaac a                                              21

<210> SEQ ID NO 62
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 62
aaauacaaaa aauauacuga auacaa                                         26

<210> SEQ ID NO 63
<211> LENGTH: 37
<212> TYPE: RNA
<213> ORGANISM: Artificial Sequence
<220> FEATURE:
<223> OTHER INFORMATION: Fragment coding sequence

<400> SEQUENCE: 63
uuuacauucc uggucaacua ugaaaugaaa cuauugc                             37

<210> SEQ ID NO 64
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 64
cuacaaaaaa augcuaaaag aa                                             22

<210> SEQ ID NO 65
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 65
augcugaaca acucaaagaa aa                                             22

<210> SEQ ID NO 66
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 66
aggaaaguga aaagauggca aa                                             22

<210> SEQ ID NO 67
<211> LENGTH: 29
<212> TYPE: RNA
<213> ORGANISM: Artificial Sequence
<220> FEATURE:
```

-continued

```
<223> OTHER INFORMATION: Fragment coding sequence

<400> SEQUENCE: 67
aaugaggaaa gugaaaagau ggcaaaaga                                            29

<210> SEQ ID NO 68
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 68
caagaaaaaa gauaguauca u                                                    21

<210> SEQ ID NO 69
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 69
ccauagaaac auuugauaac aaugaagaa                                            29

<210> SEQ ID NO 70
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 70
aaaguauaua uuauguuaca aca                                                  23

<210> SEQ ID NO 71
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 71
augauaacaa caauaaucuc uuu                                                  23

<210> SEQ ID NO 72
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 72
acuaauacac augauaacaa                                                      20

<210> SEQ ID NO 73
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 73
ugauaacaac aauaaucucu uugcua                                               26
```

-continued

```
<210> SEQ ID NO 74
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 74
gaaaaggaaa agaagauuuc uug                                               23

<210> SEQ ID NO 75
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 75
aauguacagc auccaauaaa aa                                                22

<210> SEQ ID NO 76
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 76
uaauuauuuu gaauggccac cccaug                                            26

<210> SEQ ID NO 77
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 77
aauuauuuug aauggccacc c                                                 21

<210> SEQ ID NO 78
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 78
ucuauaaaua auauaacuaa a                                                 21

<210> SEQ ID NO 79
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 79
uaaauauaga uaaaauauac auua                                              24

<210> SEQ ID NO 80
<211> LENGTH: 29
<212> TYPE: RNA
<213> ORGANISM: Artificial Sequence
<220> FEATURE:
<223> OTHER INFORMATION: Fragment coding sequence
```

-continued

<400> SEQUENCE: 80
aaauguuugu uuaauuacau ggauuagua                                    29

<210> SEQ ID NO 81
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 81
augguuaaua cauugguuua auuuaua                                      27

<210> SEQ ID NO 82
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 82
aacuauauua aaaacuuaug uau                                          23

<210> SEQ ID NO 83
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 83
uauagaacau gaaaaauuaa aauuuuc                                      27

<210> SEQ ID NO 84
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 84
uagacaauau aacuauauua aaa                                          23

<210> SEQ ID NO 85
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 85
aauguuacca uuguuaucua aua                                          23

<210> SEQ ID NO 86
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 86
agguaaauua augagagaga auggaguu                                     28

<210> SEQ ID NO 87
<211> LENGTH: 24

```
<212> TYPE: RNA
<213> ORGANISM: Artificial Sequence
<220> FEATURE:
<223> OTHER INFORMATION: Fragment coding sequence

<400> SEQUENCE: 87
uauuuuaaaa ggcagauaau uaga                                              24

<210> SEQ ID NO 88
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 88
ggaacuuggu gcauuuuuuu cua                                               23

<210> SEQ ID NO 89
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 89
auuuuucuug auugcuuuuc aa                                                22

<210> SEQ ID NO 90
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 90
uauucugaaa augguauauu uaa                                               23

<210> SEQ ID NO 91
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 91
agccuauuuu cauugaugcc uga                                               23

<210> SEQ ID NO 92
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 92
ucaacaaaua uuuacaggca aaa                                               23

<210> SEQ ID NO 93
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 93
```

-continued uuagaaaaau ggaaaaguau aga                                    23

<210> SEQ ID NO 94
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 94
aagagcucaa caaauauuua cag                                    23

<210> SEQ ID NO 95
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 95
ucuaaauauu cagaaugcac uagagaaa                               28

<210> SEQ ID NO 96
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 96 ugauggggu ugacggaguu ggggagu                                 27

<210> SEQ ID NO 97
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 97
ggggauugga aaggcucucu gug                                    23

<210> SEQ ID NO 98
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 98
aaauggagca gaaagaacac ucagg                                  25

<210> SEQ ID NO 99
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 99
uggcucgaag agcauggaga ggaa                                   24

<210> SEQ ID NO 100
<211> LENGTH: 23
<212> TYPE: RNA
<213> ORGANISM: Artificial Sequence

```
<220> FEATURE:
<223> OTHER INFORMATION: Fragment coding sequence

<400> SEQUENCE: 100 aggaaggggga uugagagacu cac                                          23

<210> SEQ ID NO 101
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 101
aaaauagacu ggagauggcc auguggagaa gc                                 32

<210> SEQ ID NO 102
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 102
cagcgcaggg gaagaguggg caggcag                                       27

<210> SEQ ID NO 103
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 103
aauaagaaaa gcaacauugu gauuuuuaau ua                                 32

<210> SEQ ID NO 104
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 104
uaaaaaaagu caaauuuaug auua                                          24

<210> SEQ ID NO 105
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 105
cuuuggcauu ucagugauuc agcaaaa                                       27

<210> SEQ ID NO 106
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 106
aaaugugcuc cccuuuccug ga                                            22
```

```
<210> SEQ ID NO 107
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 107
uuuuaaagga guggugaaga agaaaga                                      27

<210> SEQ ID NO 108
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 108
aaauaauaua aaugcauuca acu                                         23

<210> SEQ ID NO 109
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 109
ggcaggugug guugcucaag cuguaa                                      26

<210> SEQ ID NO 110
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 110
uauaacauuu uccugcuucc aa                                          22

<210> SEQ ID NO 111
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 111
ucauuggaag auggagcucu uu                                          22

<210> SEQ ID NO 112
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 112
cagcuuacuc uuccucagag uucuuu                                      26

<210> SEQ ID NO 113
<211> LENGTH: 30
<212> TYPE: RNA
<213> ORGANISM: Artificial Sequence
<220> FEATURE:
<223> OTHER INFORMATION: Fragment coding sequence
```

-continued

<400> SEQUENCE: 113
uuuaugaauu cuacagaaau aaugauaaug                              30

<210> SEQ ID NO 114
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 114
aaagauuaug gaaacuuuuc ug                                      22

<210> SEQ ID NO 115
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 115
uugcuguuuu uccaaacacu aga                                     23

<210> SEQ ID NO 116
<211> LENGTH: 34
<212> TYPE: RNA
<213> ORGANISM: Artificial Sequence
<220> FEATURE:
<223> OTHER INFORMATION: Fragment coding sequence

<400> SEQUENCE: 116
gucaauccaa auauuggaag aagcagaagu uaau                         34

<210> SEQ ID NO 117
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 117
auguggagac auuccagcac agaggaaac                               29

<210> SEQ ID NO 118
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 118
ucaggcucaa gugaucucuc auuuca                                  26

<210> SEQ ID NO 119
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 119
uuauauugaa guuuaugaag uug                                     23

<210> SEQ ID NO 120

```
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 120
agauauagga augugucuga aa                                              22

<210> SEQ ID NO 121
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 121
aaaagucaag aaaauuaaau uuaua                                           25

<210> SEQ ID NO 122
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 122
uaugccugau aauuuuucau ugg                                             23

<210> SEQ ID NO 123
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 123
auaaaggaaa agucaagaaa auu                                             23

<210> SEQ ID NO 124
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 124
agagagagag aaaagaaaau ug                                              22

<210> SEQ ID NO 125
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 125
uaugccugau aauuuuucau ug                                              22

<210> SEQ ID NO 126
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 126
```
cuguguuuuc uccuagaaug uca                                           23

<210> SEQ ID NO 127
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 127
aaagacagga uuucauuauu ugua                                          24

<210> SEQ ID NO 128
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 128
uggaugugag aaauacuugg ga                                            22

<210> SEQ ID NO 129
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 129
aaaagacagg auuucauuau uu                                            22

<210> SEQ ID NO 130
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 130
aaaagacagg auuucauuau uuguau                                        26

<210> SEQ ID NO 131
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 131
gacaggauuu cauuauuugu au                                            22

<210> SEQ ID NO 132
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 132
aguucucuuu ugacauuuug uuc                                           23

<210> SEQ ID NO 133
<211> LENGTH: 21
<212> TYPE: RNA

<213> ORGANISM: Artificial Sequence
<220> FEATURE:
<223> OTHER INFORMATION: Fragment coding sequence

<400> SEQUENCE: 133
ugacauuuug uucuuucuuu g                                    21

<210> SEQ ID NO 134
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 134
gaaaauguug uccaacaauc caaucaa                              27

<210> SEQ ID NO 135
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 135
ggaagaaaag acauuaaacu aauu                                 24

<210> SEQ ID NO 136
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 136
uaaucuucua uaagcuagu aaa                                   23

<210> SEQ ID NO 137
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 137
caggaauccu uguagugaug ggauugu                              27

<210> SEQ ID NO 138
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 138
uauauucaau ggcaaaagaa aacaaau                              27

<210> SEQ ID NO 139
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 139
aaugccuuaa ucucagauaa uuuguuaa                             28

<210> SEQ ID NO 140
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 140
uaauuuguua augaagaaua aaauuaa                                              27

<210> SEQ ID NO 141
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 141
aacaaguuuc uccuuaucau aaa                                                  23

<210> SEQ ID NO 142
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 142
cauaguaucu cuuauaaucc uuuucauuu                                            29

<210> SEQ ID NO 143
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 143
auaguaucuc uuauaauccu uuucauuu                                             28

<210> SEQ ID NO 144
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 144
uacaaacaug ggcaauucaa aauc                                                 24

<210> SEQ ID NO 145
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 145
gcucuucuuu ccuuaacaaa ugu                                                  23

<210> SEQ ID NO 146
<211> LENGTH: 23
<212> TYPE: RNA
<213> ORGANISM: Artificial Sequence
<220> FEATURE:

```
<223> OTHER INFORMATION: Fragment coding sequence

<400> SEQUENCE: 146
uguuaaacac uuucuuuccu uuu                                            23

<210> SEQ ID NO 147
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 147
auaguaucuc uuauaauccu uuu                                            23

<210> SEQ ID NO 148
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 148
acaacugaaa caaugcaagg aau                                            23

<210> SEQ ID NO 149
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 149
guucaagggc caauuauauc aca                                            23

<210> SEQ ID NO 150
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 150
uauaaaauuu ucucaggucu au                                             22

<210> SEQ ID NO 151
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 151
agaaauucag gaaaauggaa aaa                                            23

<210> SEQ ID NO 152
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 152
cacaaagcuc aagcacguau ugu                                            23
```

```
<210> SEQ ID NO 153
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 153
cuuguuuucu uucccuuucu uucug                                            25

<210> SEQ ID NO 154
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 154
uuucuuuccc uuucuuucug cuuucu                                           26

<210> SEQ ID NO 155
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 155 uuucuuucc cuuucuuucu gcuuucucu                                         29

<210> SEQ ID NO 156
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 156
uuucuuuccc uuucuuucug cuu                                              23

<210> SEQ ID NO 157
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 157
uuucuuuccc uuucuuucug cuuucu                                           26

<210> SEQ ID NO 158
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 158
auauggaugu agauuucauu ug                                               22

<210> SEQ ID NO 159
<211> LENGTH: 27
<212> TYPE: RNA
<213> ORGANISM: Artificial Sequence
<220> FEATURE:
<223> OTHER INFORMATION: Fragment coding sequence
```

```
<400> SEQUENCE: 159
uuuucuuucc cuuucuuucu gcuuucu                                          27

<210> SEQ ID NO 160
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 160
acaucuuuac aauguggaua uuucuuc                                          27

<210> SEQ ID NO 161
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 161
uucauacauu cuaaacuuaa uuccagau                                         28

<210> SEQ ID NO 162
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 162
gacuacaaga gaaggauggc aga                                              23

<210> SEQ ID NO 163
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 163
aauggcaguu augaauauau ua                                               22

<210> SEQ ID NO 164
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 164
aagguuguau uuuauuauuu aa                                               22

<210> SEQ ID NO 165
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 165
ccuuuuuccu uuucaucacu uuuuuu                                           26

<210> SEQ ID NO 166
<211> LENGTH: 22
```

<212> TYPE: RNA
<213> ORGANISM: Artificial Sequence
<220> FEATURE:
<223> OTHER INFORMATION: Fragment coding sequence

<400> SEQUENCE: 166
caggaaaaaa auggauacua aa                                                22

<210> SEQ ID NO 167
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 167
auuauuuuau aaucauuauc uaauua                                            26

<210> SEQ ID NO 168
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 168
uauauauaug caaguagcau auauaua                                           27

<210> SEQ ID NO 169
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 169
uguuagauuu cuugucauuu uuucc                                             25

<210> SEQ ID NO 170
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 170
ccacagcaac augguucag uau                                                23

<210> SEQ ID NO 171
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 171
cuuguuaagu acuugauauc ugu                                               23

<210> SEQ ID NO 172
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 172

-continued

| auucucuuau uaugaauaaa gca | 23 |

<210> SEQ ID NO 173
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 173

| agagagaaag aaagagaauu ggggagu | 27 |

<210> SEQ ID NO 174
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 174

| auauggaugu agauuucauu ug | 22 |

<210> SEQ ID NO 175
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 175

| aacaucuuau uuccuucuuu uc | 22 |

<210> SEQ ID NO 176
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 176

| uuuuuagccc uugcaaagaa cu | 22 |

<210> SEQ ID NO 177
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 177

| cuucauuaag uguuuuauc ggaaguca | 28 |

<210> SEQ ID NO 178
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 178

| ugcccugacu ucacaggcca uuu | 23 |

<210> SEQ ID NO 179
<211> LENGTH: 31
<212> TYPE: RNA
<213> ORGANISM: Artificial Sequence

```
<220> FEATURE:
<223> OTHER INFORMATION: Fragment coding sequence

<400> SEQUENCE: 179
auuaucuuaa gaaagauuaa agaagaauuu g                              31

<210> SEQ ID NO 180
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 180
ucaaagcaaa auagguucag agc                                       23

<210> SEQ ID NO 181
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 181
aacuuuuuau ugauccagug cuca                                      24

<210> SEQ ID NO 182
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 182
agauaucuuu caaaaaauuu caa                                       23

<210> SEQ ID NO 183
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 183
augcauacaa caaugggaau gucauuu                                   27

<210> SEQ ID NO 184
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 184
auuguuuaua uuuauuuuca uuu                                       23

<210> SEQ ID NO 185
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 185
caacauaaaa aaucaaccau auu                                       23
```

```
<210> SEQ ID NO 186
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 186
uccucuuuuc uuuuccuuuc uccuucuuu                                       29

<210> SEQ ID NO 187
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 187
cagaaaagca guaugagaag ga                                              22

<210> SEQ ID NO 188
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 188 uugccuggggg aaaggaggca gu                                             22

<210> SEQ ID NO 189
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 189
cagaaaagca guaugagaag ga                                              22

<210> SEQ ID NO 190
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 190
ucuuuucuuu uccuuucucc uucuuu                                          26

<210> SEQ ID NO 191
<211> LENGTH: 30
<212> TYPE: RNA
<213> ORGANISM: Artificial Sequence
<220> FEATURE:
<223> OTHER INFORMATION: Fragment coding sequence

<400> SEQUENCE: 191
guccucuuuu cuuuuccuuu cuccuucuuu                                      30

<210> SEQ ID NO 192
<211> LENGTH: 22
<212> TYPE: RNA
<213> ORGANISM: Artificial Sequence
<220> FEATURE:
<223> OTHER INFORMATION: Fragment coding sequence
```

```
<400> SEQUENCE: 192
cuuuucuuuu ccuuucuccu uc                                          22

<210> SEQ ID NO 193
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 193
cucuuuucuu uuccuuucuc cuucuu                                      26

<210> SEQ ID NO 194
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 194
uuaauaagaa uacagauuua uu                                          22

<210> SEQ ID NO 195
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 195
ucucugaguu agaaaaugag aaagu                                       25

<210> SEQ ID NO 196
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 196
cuuugcauua aaaaugugu uuga                                         24

<210> SEQ ID NO 197
<211> LENGTH: 31
<212> TYPE: RNA
<213> ORGANISM: Artificial Sequence
<220> FEATURE:
<223> OTHER INFORMATION: Fragment coding sequence

<400> SEQUENCE: 197
uuuuauaugu cuagaaaacu uagacacuau a                                31

<210> SEQ ID NO 198
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 198
cuacaggaug uagauuuuga aaaua                                       25

<210> SEQ ID NO 199
```

```
<210> SEQ ID NO 199
<211> LENGTH: 31
<212> TYPE: RNA
<213> ORGANISM: Artificial Sequence
<220> FEATURE:
<223> OTHER INFORMATION: Fragment coding sequence

<400> SEQUENCE: 199
ucuuuguauu cuggcuuucc uucuuugguu g                           31

<210> SEQ ID NO 200
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 200
agaagacaca aaaaaaugug uuaacacaaa ac                          32

<210> SEQ ID NO 201
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 201
ucaguguuuu cugacuccaa aguu                                   24

<210> SEQ ID NO 202
<211> LENGTH: 29
<212> TYPE: RNA
<213> ORGANISM: Vitex agnus-castus

<400> SEQUENCE: 202
uaccaagaaa augaagaagg cucuucuga                              29

<210> SEQ ID NO 203
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 203
uuuacuugcu uauguaaccu uauuuu                                 26

<210> SEQ ID NO 204
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 204
uuucucuauu uucucuuguu uuaaac                                 26

<210> SEQ ID NO 205
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 205
aagaugacua ucuaaaaugu cagg                                   24
```

<210> SEQ ID NO 206
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 206
auucacugcc uucuucccuc uca                                            23

<210> SEQ ID NO 207
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 207
cugucugcua accaguauga aca                                            23

<210> SEQ ID NO 208
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 208
agaaaguucu aucaaguuuu uuu                                            23

<210> SEQ ID NO 209
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 209
uuucaaauuc cuucucagaa uuc                                            23

<210> SEQ ID NO 210
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 210
auuuuguaca gaagguuuc auaa                                            24

<210> SEQ ID NO 211
<211> LENGTH: 33
<212> TYPE: RNA
<213> ORGANISM: Artificial Sequence
<220> FEATURE:
<223> OTHER INFORMATION: Fragment coding sequence

<400> SEQUENCE: 211
auugauuaga aauucaacuu ggaaaaauca aug                                 33

<210> SEQ ID NO 212
<211> LENGTH: 27
<212> TYPE: RNA
<213> ORGANISM: Artificial Sequence
<220> FEATURE:

<223> OTHER INFORMATION: Fragment coding sequence

<400> SEQUENCE: 212
ggaugucuuu gcuuucuuu uucuuug                                27

<210> SEQ ID NO 213
<211> LENGTH: 30
<212> TYPE: RNA
<213> ORGANISM: Artificial Sequence
<220> FEATURE:
<223> OTHER INFORMATION: Fragment coding sequence

<400> SEQUENCE: 213
acaccaaagg gaaacucacu gacagaaaac                            30

<210> SEQ ID NO 214
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 214
gacacagaug aagaaacuuc cuuu                                  24

<210> SEQ ID NO 215
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 215
uacaacccaa gagagcuuaa ac                                    22

<210> SEQ ID NO 216
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 216
aaagaaugaa guaaagguca gca                                   23

<210> SEQ ID NO 217
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 217
gugcuauuga ucagacuaau ua                                    22

<210> SEQ ID NO 218
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 218
gcuggacugu ggugacagcc uc                                    22

-continued

```
<210> SEQ ID NO 219
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 219
caaccucugc acaaaaugag cu                                                  22

<210> SEQ ID NO 220
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 220
acaauggagc augcaaggaa gca                                                 23

<210> SEQ ID NO 221
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 221
uagcagguag uauccaagac agagac                                              26

<210> SEQ ID NO 222
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 222
aaaaugcuga ggauaugggc aa                                                  22

<210> SEQ ID NO 223
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 223
caauaaccaa agagaaaaaa gaa                                                 23

<210> SEQ ID NO 224
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 224
aaucauggaa guuguuuucc cca                                                 23

<210> SEQ ID NO 225
<211> LENGTH: 22
<212> TYPE: RNA
<213> ORGANISM: Artificial Sequence
<220> FEATURE:
<223> OTHER INFORMATION: Fragment coding sequence
```

```
<400> SEQUENCE: 225
aagcaaccag gagauugguu ca                                              22

<210> SEQ ID NO 226
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 226
augcaacuga gaucagagca uc                                              22

<210> SEQ ID NO 227
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 227
ccagaggaca agagcucuug uu                                              22

<210> SEQ ID NO 228
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 228
gaggacgaga uggguggauc aaga                                            24

<210> SEQ ID NO 229
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 229
gaggacgaga uggguggauc aagagguc                                        28

<210> SEQ ID NO 230
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 230
uuggcucauu cucuguuuuu uuuguuuuuu uu                                   32

<210> SEQ ID NO 231
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 231
gaggacgaga uggguggauc aagagguc                                        28

<210> SEQ ID NO 232
<211> LENGTH: 28
```

```
<212> TYPE: RNA
<213> ORGANISM: Artificial Sequence
<220> FEATURE:
<223> OTHER INFORMATION: Fragment coding sequence

<400> SEQUENCE: 232
cucauucucu guuuuuuug uuuuuuuu                                          28

<210> SEQ ID NO 233
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 233
cuuuauucua aaauauuuuu aaau                                             24

<210> SEQ ID NO 234
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 234
augagcccaa gacuucuuuu gau                                              23

<210> SEQ ID NO 235
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 235
aagaaacugu gauuuuaau acuua                                             25

<210> SEQ ID NO 236
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 236
aagaaugaua aagcaaagaa aa                                               22

<210> SEQ ID NO 237
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 237
uacuuuuaaa gaugcaugcu uucauu                                           26

<210> SEQ ID NO 238
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 238
```
uuuaaaaaau gauaagaaua aa                                         22

<210> SEQ ID NO 239
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 239
agaaugauaa agcaaagaaa auguag                                     26

<210> SEQ ID NO 240
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 240
uacugaucuc caacucagaa ga                                         22

<210> SEQ ID NO 241
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 241
aaaauuugaa agaaugauaa agcaaa                                     26

<210> SEQ ID NO 242
<211> LENGTH: 33
<212> TYPE: RNA
<213> ORGANISM: Artificial Sequence
<220> FEATURE:
<223> OTHER INFORMATION: Fragment coding sequence

<400> SEQUENCE: 242
aaaaaugaau gaaauaugc auucucuuca aaa                              33

<210> SEQ ID NO 243
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 243
aaagcaagaa aaaugaauga aaa                                        23

<210> SEQ ID NO 244
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 244
caagaaaaau gaaugaaaau au                                         22

<210> SEQ ID NO 245
<211> LENGTH: 24
<212> TYPE: RNA
<213> ORGANISM: Artificial Sequence

```
<220> FEATURE:
<223> OTHER INFORMATION: Fragment coding sequence

<400> SEQUENCE: 245
aggagaaauc aaaacaaaac caua                                          24

<210> SEQ ID NO 246
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 246
gcauucaaua aauacaugcu g                                             21

<210> SEQ ID NO 247
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 247
auguaagaac uguaaauaua a                                             21

<210> SEQ ID NO 248
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 248
aaaacaaaac cauaaaagua g                                             21

<210> SEQ ID NO 249
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 249
aaaggagaaa ucaaaacaaa accauaaaa                                     29

<210> SEQ ID NO 250
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 250
uagggagcuc cccacucccg uuuugugac                                     29

<210> SEQ ID NO 251
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 251
uauaucaaaa gaaaaugaaa ucaa                                          24
```

```
<210> SEQ ID NO 252
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 252
gauuaaauuu auaucaaaag aaaaugaa                                    28

<210> SEQ ID NO 253
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 253
uauaucaaaa gaaaaugaaa ucaaua                                      26

<210> SEQ ID NO 254
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 254
aaagaaaaug aaaucaauag uugagga                                     27

<210> SEQ ID NO 255
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 255
uauaucaaaa gaaaaugaaa ucaauag                                     27

<210> SEQ ID NO 256
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 256
augaccaaau guauagauug aga                                         23

<210> SEQ ID NO 257
<211> LENGTH: 34
<212> TYPE: RNA
<213> ORGANISM: Artificial Sequence
<220> FEATURE:
<223> OTHER INFORMATION: Fragment coding sequence

<400> SEQUENCE: 257
uauaucaaaa gaaaaugaaa ucaauaguug agga                             34

<210> SEQ ID NO 258
<211> LENGTH: 26
<212> TYPE: RNA
<213> ORGANISM: Artificial Sequence
<220> FEATURE:
<223> OTHER INFORMATION: Fragment coding sequence
```

```
<400> SEQUENCE: 258
uauaucaaaa gaaaaugaaa ucaaua                                          26

<210> SEQ ID NO 259
<211> LENGTH: 30
<212> TYPE: RNA
<213> ORGANISM: Artificial Sequence
<220> FEATURE:
<223> OTHER INFORMATION: Fragment coding sequence

<400> SEQUENCE: 259
uugaaauaag aagauuagau auuuuaauu                                       30

<210> SEQ ID NO 260
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 260
ugauaucauu uucaauuaca ua                                              22

<210> SEQ ID NO 261
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 261
aagaaaaaga agauagcaag aa                                              22

<210> SEQ ID NO 262
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 262
agcuaaaguu ugguaggaaa acaa                                            24

<210> SEQ ID NO 263
<211> LENGTH: 31
<212> TYPE: RNA
<213> ORGANISM: Artificial Sequence
<220> FEATURE:
<223> OTHER INFORMATION: Fragment coding sequence

<400> SEQUENCE: 263
aaaucaagua aaauaacaau aaaugacaua c                                    31

<210> SEQ ID NO 264
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 264
cauuaaauuu auacaaacaa acacaaa                                         27

<210> SEQ ID NO 265
```

<210> SEQ ID NO 265
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 265
agcuaaaguu ugguaggaaa acaa                                    24

<210> SEQ ID NO 266
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 266
gaaauauacc auauaaauau gaugu                                   25

<210> SEQ ID NO 267
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 267
aaauaagauc agaauuuuau uua                                     23

<210> SEQ ID NO 268
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 268
agaauuauau uaauacagua ua                                      22

<210> SEQ ID NO 269
<211> LENGTH: 30
<212> TYPE: RNA
<213> ORGANISM: Artificial Sequence
<220> FEATURE:
<223> OTHER INFORMATION: Fragment coding sequence

<400> SEQUENCE: 269
agcauuaaaa cauuagaaau auuaaauaag                              30

<210> SEQ ID NO 270
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 270
agaauuauau uaauacagua uauagu                                  26

<210> SEQ ID NO 271
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 271
gaagaauuau ucacauuaau aa                                        22

<210> SEQ ID NO 272
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 272
gaagaacaaa cuauuaauaa uu                                        22

<210> SEQ ID NO 273
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 273
uaagaucaga auuuuauuua uuacua                                    26

<210> SEQ ID NO 274
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 274
uaaaccaaac auuuuccuu au                                         22

<210> SEQ ID NO 275
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 275
auuuuaaaac acuuaaaaau uu                                        22

<210> SEQ ID NO 276
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 276
caauauuucu gcuguucaau ucaaugg                                   27

<210> SEQ ID NO 277
<211> LENGTH: 33
<212> TYPE: RNA
<213> ORGANISM: Artificial Sequence
<220> FEATURE:
<223> OTHER INFORMATION: Fragment coding sequence

<400> SEQUENCE: 277 uuuuugggu uuuguugug uugauacuuu gag                              33

<210> SEQ ID NO 278
<211> LENGTH: 28
<212> TYPE: RNA

```
<213> ORGANISM: Artificial Sequence
<220> FEATURE:
<223> OTHER INFORMATION: Fragment coding sequence

<400> SEQUENCE: 278
gcaaauuuau cuuaaauuca aguacaua                                        28

<210> SEQ ID NO 279
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 279
uaacagacuu ggaaaaauac aauu                                            24

<210> SEQ ID NO 280
<211> LENGTH: 37
<212> TYPE: RNA
<213> ORGANISM: Artificial Sequence
<220> FEATURE:
<223> OTHER INFORMATION: Fragment coding sequence

<400> SEQUENCE: 280
auuaccuuca aaaucuaga acuuauuaa uucucag                                37

<210> SEQ ID NO 281
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 281
aaaauuaaaa acaaaaauga aagg                                            24

<210> SEQ ID NO 282
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 282
cuuauuuuau gucuucuuug uuguuuuu                                        28

<210> SEQ ID NO 283
<211> LENGTH: 33
<212> TYPE: RNA
<213> ORGANISM: Artificial Sequence
<220> FEATURE:
<223> OTHER INFORMATION: Fragment coding sequence

<400> SEQUENCE: 283
auuauuaaca acuuauuuuu auuuaaucuu uua                                  33

<210> SEQ ID NO 284
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 284
auaaagaaga auauuaacau ugacauua                                        28
```

```
<210> SEQ ID NO 285
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 285
uuaugaaugu uuuaucauga uuaaagau                                28

<210> SEQ ID NO 286
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 286
cccagcacag agaugucauu ga                                      22

<210> SEQ ID NO 287
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 287
agugagaaau gaugauguug aucaga                                  26

<210> SEQ ID NO 288
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 288
uucuaaggaa agcaaccaga ag                                      22

<210> SEQ ID NO 289
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 289
ugagcaagaa gaaauccuac au                                      22

<210> SEQ ID NO 290
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 290
ggaaugagaa gaaagcuaaa uu                                      22

<210> SEQ ID NO 291
<211> LENGTH: 22
<212> TYPE: RNA
<213> ORGANISM: Artificial Sequence
<220> FEATURE:
```

<223> OTHER INFORMATION: Fragment coding sequence

<400> SEQUENCE: 291
uuagaaaugu cuuaagcauu gc                                          22

<210> SEQ ID NO 292
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 292
caggacauug aaaugaaga gaag                                         24

<210> SEQ ID NO 293
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 293
aagagaaaga ccugaccaaa ga                                          22

<210> SEQ ID NO 294
<211> LENGTH: 28
<212> TYPE: RNA
<213> ORGANISM: Artificial Sequence
<220> FEATURE:
<223> OTHER INFORMATION: Fragment coding sequence

<400> SEQUENCE: 294
acuaagucau auaaaaauac aagaaaaa                                    28

<210> SEQ ID NO 295
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 295
aacaauuuga guugauagac aaugaau                                     27

<210> SEQ ID NO 296
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 296
aucauguuuc auacuucuag ccauug                                      26

<210> SEQ ID NO 297
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 297
gaaacauacu aagaacacag gaa                                         23

-continued

```
<210> SEQ ID NO 298
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 298
uuucaccauu accuucucuu cc                                              22

<210> SEQ ID NO 299
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 299
aggaagcaaa auuaaacaga gaagaaa                                         27

<210> SEQ ID NO 300
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 300
uggaaaauga aagaacuuug ga                                              22

<210> SEQ ID NO 301
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 301
aaaacaacac uuggguaaau cagaca                                          26

<210> SEQ ID NO 302
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 302
gcugcuggac agucaguggu uu                                              22

<210> SEQ ID NO 303
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 303
ggaucaagaa agaagaguuc ucugaga                                         27

<210> SEQ ID NO 304
<211> LENGTH: 22
<212> TYPE: RNA
<213> ORGANISM: Artificial Sequence
<220> FEATURE:
<223> OTHER INFORMATION: Fragment coding sequence
```

```
<400> SEQUENCE: 304 gggagacac acaaauucag ac                                              22

<210> SEQ ID NO 305
<211> LENGTH: 30
<212> TYPE: RNA
<213> ORGANISM: Artificial Sequence
<220> FEATURE:
<223> OTHER INFORMATION: Fragment coding sequence

<400> SEQUENCE: 305
accaaaugaa aacccagcuc acaagaguca                                     30

<210> SEQ ID NO 306
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 306
aaaugagaau guggaaacca ug                                             22

<210> SEQ ID NO 307
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 307
agaaauaagg agaguuggc gc                                              22

<210> SEQ ID NO 308
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 308
agaagaguag acggaaagug ga                                             22

<210> SEQ ID NO 309
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 309
agaagaguag acggaaagug ga                                             22

<210> SEQ ID NO 310
<211> LENGTH: 32
<212> TYPE: RNA
<213> ORGANISM: Artificial Sequence
<220> FEATURE:
<223> OTHER INFORMATION: Fragment coding sequence

<400> SEQUENCE: 310
gaagagagca gggcaagaau caaaacuagg cu                                  32

<210> SEQ ID NO 311
<211> LENGTH: 22
```

```
<212> TYPE: RNA
<213> ORGANISM: Artificial Sequence
<220> FEATURE:
<223> OTHER INFORMATION: Fragment coding sequence

<400> SEQUENCE: 311
agggcaagcu uucccaaaug uc                                              22

<210> SEQ ID NO 312
<211> LENGTH: 34
<212> TYPE: RNA
<213> ORGANISM: Artificial Sequence
<220> FEATURE:
<223> OTHER INFORMATION: Fragment coding sequence

<400> SEQUENCE: 312
ggacaugauu ccagagagga augaacaagg acaa                                 34

<210> SEQ ID NO 313
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 313
ggaaauugug aaaauucaau gg                                              22

<210> SEQ ID NO 314
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 314 gagcuacau ucucaguuuu guc                                              23

<210> SEQ ID NO 315
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 315
gagacagaca guaaaggaaa au                                              22

<210> SEQ ID NO 316
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 316
ugaagaaaaa cuaaagaaaa aa                                              22

<210> SEQ ID NO 317
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 317
```

```
ccagacagca gacuggaagg ca                                              22

<210> SEQ ID NO 318
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 318
aacaggaaau cauauugaau uugu                                            24

<210> SEQ ID NO 319
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 319
aguaugcaug gaaagauuuu cuuaaug                                         27

<210> SEQ ID NO 320
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 320
cagaguuuga auuuaugau cag                                              23

<210> SEQ ID NO 321
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 321 ugagguaac auuuaauuuu ggg                                              23

<210> SEQ ID NO 322
<211> LENGTH: 27
<212> TYPE: RNA
<213> ORGANISM: Artificial Sequence
<220> FEATURE:
<223> OTHER INFORMATION: Fragment coding sequence

<400> SEQUENCE: 322
uuuuuucuuu uugagaaagg gcuucau                                         27

<210> SEQ ID NO 323
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 323
agaaaacaac agguguugau gag                                             23

<210> SEQ ID NO 324
<211> LENGTH: 23
<212> TYPE: RNA
<213> ORGANISM: Artificial Sequence
```

-continued

```
<220> FEATURE:
<223> OTHER INFORMATION: Fragment coding sequence

<400> SEQUENCE: 324
uuuuuucuuu uugagaaagg gcu                                               23

<210> SEQ ID NO 325
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 325
aaaugaaaga uuuccagaaa uug                                               23

<210> SEQ ID NO 326
<211> LENGTH: 30
<212> TYPE: RNA
<213> ORGANISM: Artificial Sequence
<220> FEATURE:
<223> OTHER INFORMATION: Fragment coding sequence

<400> SEQUENCE: 326
acaacagaua caacaaaugc uggugagaau                                        30

<210> SEQ ID NO 327
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 327
agugauucau gcugaaauac agu                                               23

<210> SEQ ID NO 328
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 328
augagagauc uuggggugg gac                                                23

<210> SEQ ID NO 329
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 329
ccaauguauu uauacauuua caagua                                            26

<210> SEQ ID NO 330
<211> LENGTH: 29
<212> TYPE: RNA
<213> ORGANISM: Artificial Sequence
<220> FEATURE:
<223> OTHER INFORMATION: Fragment coding sequence

<400> SEQUENCE: 330
aaguucaaug agaaagagaa uagauaugg                                         29
```

```
<210> SEQ ID NO 331
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 331
uacuuacaug ccaaaucuca a                                              21

<210> SEQ ID NO 332
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 332
aguucaauga gaaagagaau a                                              21

<210> SEQ ID NO 333
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 333
uacauacuau uaaugugauu ua                                             22

<210> SEQ ID NO 334
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 334
uuuuguccuu ccauugugu ug                                              22

<210> SEQ ID NO 335
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 335
gaagcagaga gaaaguagag aag                                            23

<210> SEQ ID NO 336
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 336
ucaaaaggag agaacagaug cugg                                           24

<210> SEQ ID NO 337
<211> LENGTH: 23
<212> TYPE: RNA
<213> ORGANISM: Artificial Sequence
<220> FEATURE:
<223> OTHER INFORMATION: Fragment coding sequence
```

```
<400> SEQUENCE: 337
ucccuggaug gcaagcagaa gca                                              23

<210> SEQ ID NO 338
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 338
ccucuaaguu uccuaagguu cu                                               22

<210> SEQ ID NO 339
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 339
aacaagagca ggccagugug gugg                                             24

<210> SEQ ID NO 340
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 340
uugaggaaaa gggaacccug uaca                                             24

<210> SEQ ID NO 341
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 341
ccaggcacug ggaagucagu ggca                                             24

<210> SEQ ID NO 342
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 342
aauuaggagu gauaccuuca cuaa                                             24

<210> SEQ ID NO 343
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 343
ugagaaaaag gccacugucc uuua                                             24

<210> SEQ ID NO 344
```

```
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 344
acaaauugga gaaauaguga aaa                                              23

<210> SEQ ID NO 345
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 345
auuuuaaaac acuuaaaaau uu                                               22

<210> SEQ ID NO 346
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 346
aaaggaagaa auugaaaccc aga                                              23

<210> SEQ ID NO 347
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 347
gaugucauca agaaugcaga ugc                                              23

<210> SEQ ID NO 348
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 348
acaaaagaug cagaaagagg caag                                             24

<210> SEQ ID NO 349
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 349
aauguuauug aguauauaga gaga                                             24

<210> SEQ ID NO 350
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 350
```

```
cauuugauga ucuggcauuc caacu                                         25

<210> SEQ ID NO 351
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 351
gaagggaggc ugauccagaa cagu                                          24

<210> SEQ ID NO 352
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 352
ggcacaacug gaguggaguc ugcu                                          24

<210> SEQ ID NO 353
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 353
caaaagaaaa gaaagaagag cuc                                           23

<210> SEQ ID NO 354
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 354
uccaaauugc uucaaaugaa aa                                            22

<210> SEQ ID NO 355
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 355
aauuguacaa aaacccugau ac                                            22

<210> SEQ ID NO 356
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 356
augaggaaug gagggaauag cu                                            22

<210> SEQ ID NO 357
<211> LENGTH: 22
<212> TYPE: RNA
```

```
<213> ORGANISM: Artificial Sequence
<220> FEATURE:
<223> OTHER INFORMATION: Fragment coding sequence

<400> SEQUENCE: 357
auugcuccuu ugcuggaugg au                                              22

<210> SEQ ID NO 358
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 358
uuccaaucug aaugaugcaa ca                                              22

<210> SEQ ID NO 359
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 359
uaaaagcugc aucaauaggu gu                                              22

<210> SEQ ID NO 360
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 360
gggagauuga uccaaaacag ca                                              22

<210> SEQ ID NO 361
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 361 aggggggaagc ccagauccug ga                                             22

<210> SEQ ID NO 362
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 362
ugccacagag gagacacaca aa                                              22

<210> SEQ ID NO 363
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 363
gagaaaggaa aguggacaac a                                               21
```

<210> SEQ ID NO 364
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 364
cauaacaaca acaauaauaa cugaa                                         25

<210> SEQ ID NO 365
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 365
aggaagggaa aaucaaaaa au                                             22

<210> SEQ ID NO 366
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 366
gaggaaauga gaagaaggcu a                                             21

<210> SEQ ID NO 367
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 367
cuggagcugc uggagcagca g                                             21

<210> SEQ ID NO 368
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 368
ucucaaacuu gcaguugguc                                               20

<210> SEQ ID NO 369
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 369
uugacuaugg gagugauguu u                                             21

<210> SEQ ID NO 370
<211> LENGTH: 21
<212> TYPE: RNA
<213> ORGANISM: Artificial Sequence
<220> FEATURE:

<223> OTHER INFORMATION: Fragment coding sequence

<400> SEQUENCE: 370
aguuugaauu cauugcugaa g                                          21

<210> SEQ ID NO 371
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 371
gaaaaacaag auuucuccca gug                                        23

<210> SEQ ID NO 372
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 372
acagggugau ggugucccccc                                           20

<210> SEQ ID NO 373
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 373
aaauggacca caaacacaga aac                                        23

<210> SEQ ID NO 374
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 374
augucuucuu caaucacuuc aac                                        23

<210> SEQ ID NO 375
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 375
uacugcuaag gaagcacaag aug                                        23

<210> SEQ ID NO 376
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 376
aaaaauugaa acgaacaaau uc                                         22

-continued

```
<210> SEQ ID NO 377
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 377
aauaaauaca acauuacccu uu                                              22

<210> SEQ ID NO 378
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 378
aagcaagauu aaaaagagag ga                                              22

<210> SEQ ID NO 379
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 379
uuagagcauc uguuggaaga au                                              22

<210> SEQ ID NO 380
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 380
aacagaggcu gaacaagagg a                                               21

<210> SEQ ID NO 381
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 381
ugcagaagga acaggaacgg c                                               21

<210> SEQ ID NO 382
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 382
auuguaugga cacaauuaga aac                                             23

<210> SEQ ID NO 383
<211> LENGTH: 23
<212> TYPE: RNA
<213> ORGANISM: Artificial Sequence
<220> FEATURE:
<223> OTHER INFORMATION: Fragment coding sequence
```

-continued

<400> SEQUENCE: 383
augagaaacg ugccugagaa aca                                         23

<210> SEQ ID NO 384
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 384
uguuuucuuc ugucugaaga                                             20

<210> SEQ ID NO 385
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 385
cauauaauua gcaucacaau                                             20

<210> SEQ ID NO 386
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 386
acaaaucagc aguugaacu gaua                                         24

<210> SEQ ID NO 387
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 387
gaaagaggua aauuaaaaag                                             20

<210> SEQ ID NO 388
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 388
aaguagcagg cucacucugc                                             20

<210> SEQ ID NO 389
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 389
agaaggagag aaggaaaaug g                                           21

<210> SEQ ID NO 390
<211> LENGTH: 20

```
<212> TYPE: RNA
<213> ORGANISM: Artificial Sequence
<220> FEATURE:
<223> OTHER INFORMATION: Fragment coding sequence

<400> SEQUENCE: 390
acaaauaccu gcagaaaugc                                              20

<210> SEQ ID NO 391
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 391
aaugaaucaa caagaaagaa aa                                           22

<210> SEQ ID NO 392
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 392
aaugaaucaa caagaaagaa                                              20

<210> SEQ ID NO 393
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 393
gagaaugaag agaaaacucc                                              20

<210> SEQ ID NO 394
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 394
auucagugaa auuggaaaau                                              20

<210> SEQ ID NO 395
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 395
agaaauacac caagaccaca ua                                           22

<210> SEQ ID NO 396
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 396
```
cuugaacuua gaagcagaua u                                              21

<210> SEQ ID NO 397
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 397
acaaugcuau caauuguaau c                                              21

<210> SEQ ID NO 398
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 398
acaaugcuau caauuguaau                                                20

<210> SEQ ID NO 399
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 399
gaacuucagg acauagaaaa u                                              21

<210> SEQ ID NO 400
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 400
gccuuccuuu ccagaaugug                                                20

<210> SEQ ID NO 401
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 401
gauaugacuu ugaaagggag                                                20

<210> SEQ ID NO 402
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 402
agggguugga auggcugcag                                                20

<210> SEQ ID NO 403
<211> LENGTH: 24
<212> TYPE: RNA
<213> ORGANISM: Artificial Sequence -continued

```
<220> FEATURE:
<223> OTHER INFORMATION: Fragment coding sequence

<400> SEQUENCE: 403
cagaguagaa ugcaauucuc cuca                                          24

<210> SEQ ID NO 404
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 404
uuccugcuuu accauaauga cuga                                          24

<210> SEQ ID NO 405
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 405
uuucauaaug ucagcaaaua ugca                                          24

<210> SEQ ID NO 406
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 406
ggucuacaaa acauacuuug agaa                                          24

<210> SEQ ID NO 407
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 407
caaaauuaga gagacagaaa auaga                                         25

<210> SEQ ID NO 408
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 408
gaagcaaaac uguuugugcu                                               20

<210> SEQ ID NO 409
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 409
uuguuuuuau guggagcuaa uca                                           23
```

```
<210> SEQ ID NO 410
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 410
cacaaaggac aauaggaaag aaa                                          23

<210> SEQ ID NO 411
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 411
uaaagaaauu gaaucaguaa auaa                                         24

<210> SEQ ID NO 412
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 412
agugagacac agggaacaga gaaa                                         24

<210> SEQ ID NO 413
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 413
cauaugaaag aaugugcaac auc                                          23

<210> SEQ ID NO 414
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 414
uucaaugaau caacaaaaaa gaaa                                         24

<210> SEQ ID NO 415
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 415
cagcagauaa aagaauaaug gaaaug                                       26

<210> SEQ ID NO 416
<211> LENGTH: 25
<212> TYPE: RNA
<213> ORGANISM: Artificial Sequence
<220> FEATURE:
<223> OTHER INFORMATION: Fragment coding sequence
```

<400> SEQUENCE: 416
aguugauaau aacaacuggu cuggu                                              25

<210> SEQ ID NO 417
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 417
agaagaagaa aaagaggacu auuu                                               24

<210> SEQ ID NO 418
<211> LENGTH: 26
<212> TYPE: RNA
<213> ORGANISM: Artificial Sequence
<220> FEATURE:
<223> OTHER INFORMATION: Fragment coding sequence

<400> SEQUENCE: 418
cuucccaguu uuggaguguc ugggau                                             26

<210> SEQ ID NO 419
<211> LENGTH: 25
<212> TYPE: RNA
<213> ORGANISM: Artificial Sequence
<220> FEATURE:
<223> OTHER INFORMATION: Fragment coding sequence

<400> SEQUENCE: 419
aaauuuaaau aagaaaaugg aagau                                              25

<210> SEQ ID NO 420
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 420
aaucuaaugg gaauuuaaua gcuc                                               24

<210> SEQ ID NO 421
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 421
augcagaacu uucuuuuga cuc                                                 23

<210> SEQ ID NO 422
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 422
acauucuuuu caugggggc auaa                                                24

<210> SEQ ID NO 423

```
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 423
cuagucaggc uaggcagaug gu                                               22

<210> SEQ ID NO 424
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 424
caaagcagaa ugcaguucuc uu                                               22

<210> SEQ ID NO 425
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 425
ugcaccaauu aaaauacaga uau                                              23

<210> SEQ ID NO 426
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 426
agaguaagag acaacaugac ca                                               22

<210> SEQ ID NO 427
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 427
gggaauuggg acaugguga ug                                                22

<210> SEQ ID NO 428
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 428
aaugccuugu uucuacuaau ac                                               22

<210> SEQ ID NO 429
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 429
```
uaagaggauc aggaaugaga au                                              22

<210> SEQ ID NO 430
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 430
aucucauuua aggaaugaca ca                                              22

<210> SEQ ID NO 431
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 431
agacaaugcu aaggaaauag gg                                              22

<210> SEQ ID NO 432
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 432
aaagcaauga aagaguaugg ggag                                            24

<210> SEQ ID NO 433
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 433
uuggucugag gaaugugccu gcu                                             23

<210> SEQ ID NO 434
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 434
aucaaugaac aaagaggaaa ua                                              22

<210> SEQ ID NO 435
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 435
cagagagagg caaauuaaaa ag                                              22

<210> SEQ ID NO 436
<211> LENGTH: 22
<212> TYPE: RNA

```
<213> ORGANISM: Artificial Sequence
<220> FEATURE:
<223> OTHER INFORMATION: Fragment coding sequence

<400> SEQUENCE: 436
cacaaauuga agaugacaga ga                                          22

<210> SEQ ID NO 437
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 437
aaacaagaag ugcuuaugag ag                                          22

<210> SEQ ID NO 438
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 438
uuuuuuucaa augcaucuau caa                                         23

<210> SEQ ID NO 439
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 439
cagaaauucg aagaaauaaa aug                                         23

<210> SEQ ID NO 440
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 440
cagccuaauc agaccaaaug aa                                          22

<210> SEQ ID NO 441
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 441
ggacggauua agaaagaaga gu                                          22

<210> SEQ ID NO 442
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 442
uggaguugau aagggggaagg ga                                         22
```

<210> SEQ ID NO 443
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 443
acagauuuga auaauugaa gg                                               22

<210> SEQ ID NO 444
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 444
ugcaugugua aauggcucuu g                                               21

<210> SEQ ID NO 445
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 445
cuuuuccuga aagugccagc a                                               21

<210> SEQ ID NO 446
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 446
aagacaagaa auggccagua gg                                              22

<210> SEQ ID NO 447
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 447
cugcauuuga agauuuaaga uug                                             23

<210> SEQ ID NO 448
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 448
ccauuaucca aaggucuaca aa                                              22

<210> SEQ ID NO 449
<211> LENGTH: 22
<212> TYPE: RNA
<213> ORGANISM: Artificial Sequence
<220> FEATURE:

```
<223> OTHER INFORMATION: Fragment coding sequence

<400> SEQUENCE: 449
ugagacuucc aagaucaaga ug                                              22

<210> SEQ ID NO 450
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 450
gcaggagugg auagauucua ca                                              22

<210> SEQ ID NO 451
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 451
aaagcaaauu guagaaaaga uu                                              22

<210> SEQ ID NO 452
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 452
ugcagggaag aacacagauc uc                                              22

<210> SEQ ID NO 453
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 453
ucaaaugcau gaagacauuc uu                                              22

<210> SEQ ID NO 454
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 454
agaaguuaua aggaugaugg a                                               21

<210> SEQ ID NO 455
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 455
cugccccauc ggugaagcuc c                                               21
```

```
<210> SEQ ID NO 456
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 456
aauaccagcc uuccauuuca gaau                                              24

<210> SEQ ID NO 457
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 457
aaugaaucca aaucaaagga                                                   20

<210> SEQ ID NO 458
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 458
augccuuguu ucuacuaaua c                                                 21

<210> SEQ ID NO 459
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 459
ugaguugcca uuccaccauug a                                                21

<210> SEQ ID NO 460
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 460
auacauugaa guuuuacauu u                                                 21

<210> SEQ ID NO 461
<211> LENGTH: 24
<212> TYPE: RNA
<213> ORGANISM: Artificial Sequence
<220> FEATURE:
<223> OTHER INFORMATION: Fragment coding sequence

<400> SEQUENCE: 461
gugugauggg aaugguugga guau                                              24

<210> SEQ ID NO 462
<211> LENGTH: 21
<212> TYPE: RNA
<213> ORGANISM: Artificial Sequence
<220> FEATURE:
<223> OTHER INFORMATION: Fragment coding sequence
```

```
<400> SEQUENCE: 462
auaugcacaa acagaaugug u                                              21

<210> SEQ ID NO 463
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 463
uggauuuguu gccaauuuca                                                20

<210> SEQ ID NO 464
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 464
auuauaaaag gaaggucuca                                                20

<210> SEQ ID NO 465
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 465
ccaaagaggg aagacgaaag                                                20

<210> SEQ ID NO 466
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 466
uauauaaaua gaacaggaac au                                             22

<210> SEQ ID NO 467
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 467
acaauaaaaa guuggagaaa ca                                             22

<210> SEQ ID NO 468
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 468
aaagccaugg aacaaauggc ug                                             22

<210> SEQ ID NO 469
<211> LENGTH: 25
```

-continued

```
<212> TYPE: RNA
<213> ORGANISM: Artificial Sequence
<220> FEATURE:
<223> OTHER INFORMATION: Fragment coding sequence

<400> SEQUENCE: 469
ggucuacaaa acauacuuug agaaa                                              25

<210> SEQ ID NO 470
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 470
aauaguuuac uugaauaaua ca                                                 22

<210> SEQ ID NO 471
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 471
uucaagaugg agaaagggaa ga                                                 22

<210> SEQ ID NO 472
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 472
aaaagaaaua caccaaaaca gu                                                 22

<210> SEQ ID NO 473
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 473
aaccuaaauu ucucccagau uu                                                 22

<210> SEQ ID NO 474
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 474
acaaccuacu uucucaguac aga                                                23

<210> SEQ ID NO 475
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 475
```
aaauucaaac aaggagauca uu 22

<210> SEQ ID NO 476
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 476
uggucagguu auucuggcau uu 22

<210> SEQ ID NO 477
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 477
caaccuggaa ccuggaaccu 20

<210> SEQ ID NO 478
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 478
ccagcacuga gagggugacu gu 22

<210> SEQ ID NO 479
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 479
gaaaucaacc ugaauggUUU 20

<210> SEQ ID NO 480
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 480
uuaucaaaua cuugcuauau ac 22

<210> SEQ ID NO 481
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 481
cuuuucuuaa aaauuccagc gc 22

<210> SEQ ID NO 482
<211> LENGTH: 21
<212> TYPE: RNA
<213> ORGANISM: Artificial Sequence

```
<220> FEATURE:
<223> OTHER INFORMATION: Fragment coding sequence

<400> SEQUENCE: 482
agagaaggau auucucuggu c                                              21

<210> SEQ ID NO 483
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 483
ggggagacac acaaauucag ac                                             22

<210> SEQ ID NO 484
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 484
ugauuauugc ugcuagaaac aua                                            23

<210> SEQ ID NO 485
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 485
ugauuauugc ugcuagaaac au                                             22

<210> SEQ ID NO 486
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 486
uggagaaagc caacaagaua aaa                                            23

<210> SEQ ID NO 487
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 487
acaaagaaca ugaaaaaaac aag                                            23

<210> SEQ ID NO 488
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 488
agggcaagcu uucccaaaug ucu                                            23
```

```
<210> SEQ ID NO 489
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 489
agggcaagcu ucccaaaug uc                                                    22

<210> SEQ ID NO 490
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 490
ccaaaacuac auacuggugg ga                                                   22

<210> SEQ ID NO 491
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 491
aggcaaagug gugugugugu gc                                                   22

<210> SEQ ID NO 492
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 492
ucaaagagaa agacaugacc a                                                    21

<210> SEQ ID NO 493
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 493
acuuuguaau cccaugaauc c                                                    21

<210> SEQ ID NO 494
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 494
uuucaggcag aaugaaugca g                                                    21

<210> SEQ ID NO 495
<211> LENGTH: 21
<212> TYPE: RNA
<213> ORGANISM: Artificial Sequence
<220> FEATURE:
<223> OTHER INFORMATION: Fragment coding sequence
```

-continued

```
<400> SEQUENCE: 495
gaaacacagg gaacagagaa a                                              21

<210> SEQ ID NO 496
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 496
aaggaagauc ucauuugagg a                                              21

<210> SEQ ID NO 497
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 497
gauaguaagu ggaagagaug aa                                             22

<210> SEQ ID NO 498
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 498
cauaugaaag aaugugcaac au                                             22

<210> SEQ ID NO 499
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 499
auaauacuag uaguaacagu aa                                             22

<210> SEQ ID NO 500
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 500
uugacugaag auccagauga a                                              21

<210> SEQ ID NO 501
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 501
aaaaaugaug accaauucuc a                                              21

<210> SEQ ID NO 502
```

```
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 502
uauggaauuc ucucuuacug a                                              21

<210> SEQ ID NO 503
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 503
aaaaaacaaa gauugaguaa ga                                             22

<210> SEQ ID NO 504
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 504
aagcaaccag gagauugguu ca                                             22

<210> SEQ ID NO 505
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 505
ccagaggaca agagcucuug uu                                             22

<210> SEQ ID NO 506
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 506
gaaagaacau ucuuuucaug ug                                             22

<210> SEQ ID NO 507
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 507
cuguaaugag aaugggagac cu                                             22

<210> SEQ ID NO 508
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 508
```
ggaaauugug aaaauucaau gg                                              22

<210> SEQ ID NO 509
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 509
uuuugcuuug uguuguuuug cug                                             23

<210> SEQ ID NO 510
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 510
aggacuucga gaaauauguu ga                                              22

<210> SEQ ID NO 511
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 511
aaacaacaua acaacaacaa uaa                                             23

<210> SEQ ID NO 512
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 512
aaaaugcuga ggauaugggc aa                                              22

<210> SEQ ID NO 513
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 513
uuucaccauu accuucucuu cc                                              22

<210> SEQ ID NO 514
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 514
ucuuauuucu ucagagacaa ug                                              22

<210> SEQ ID NO 515
<211> LENGTH: 23
<212> TYPE: RNA

```
<213> ORGANISM: Artificial Sequence
<220> FEATURE:
<223> OTHER INFORMATION: Fragment coding sequence

<400> SEQUENCE: 515
agagaaaaua cuugaaaauu gug                                    23

<210> SEQ ID NO 516
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 516
acagaaaugu cacugagagg ag                                     22

<210> SEQ ID NO 517
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 517 aaaggggua gggacaaugg ug                                      22

<210> SEQ ID NO 518
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 518
gacuacagau auacauauag au                                     22

<210> SEQ ID NO 519
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 519
gaaaaaggag agugagagac aa                                     22

<210> SEQ ID NO 520
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 520
uagauauaaa ugugaaagau ua                                     22

<210> SEQ ID NO 521
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 521
ucagacagcu gcccagaggg ca                                     22
```

```
<210> SEQ ID NO 522
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 522
acuuaccagu cucaucuucu a                                           21

<210> SEQ ID NO 523
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 523
uuuucuaucc cucagaaaau cc                                          22

<210> SEQ ID NO 524
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 524
cuuugaucuc gggcuugaga                                             20

<210> SEQ ID NO 525
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 525
ucucucugcc uuguaguugg                                             20

<210> SEQ ID NO 526
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 526
uauaacuuau uacuucagaa                                             20

<210> SEQ ID NO 527
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 527
agaaaucaua ucaaauccuu                                             20

<210> SEQ ID NO 528
<211> LENGTH: 20
<212> TYPE: RNA
<213> ORGANISM: Artificial Sequence
<220> FEATURE:
```

```
<223> OTHER INFORMATION: Fragment coding sequence

<400> SEQUENCE: 528
uucagacaga ucagaccuca                                              20

<210> SEQ ID NO 529
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 529
aauauccaga augguuucug                                              20

<210> SEQ ID NO 530
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 530
aagucaacau gaaaaaaaca g                                            21

<210> SEQ ID NO 531
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 531
ugaaaaaaac aagaucuuaa                                              20

<210> SEQ ID NO 532
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 532
gggggguucu uuugaaaaa                                               20

<210> SEQ ID NO 533
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 533
gagauggcca agguggaga                                               20

<210> SEQ ID NO 534
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 534
uuuuuaccaa uaguagaggg                                              20
```

```
<210> SEQ ID NO 535
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 535
gugcuccuca ugaaaugucu gu                                              22

<210> SEQ ID NO 536
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 536
uaccaccuua aauaucagag                                                 20

<210> SEQ ID NO 537
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 537
cucagccaua aaaaugaacg                                                 20

<210> SEQ ID NO 538
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 538
auugcagaaa guuucuccaa aa                                              22

<210> SEQ ID NO 539
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 539
agacuggacc agcuauggaa uc                                              22

<210> SEQ ID NO 540
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 540
auguaaucac cuuauacaug aac                                             23

<210> SEQ ID NO 541
<211> LENGTH: 20
<212> TYPE: RNA
<213> ORGANISM: Artificial Sequence
<220> FEATURE:
<223> OTHER INFORMATION: Fragment coding sequence
```

```
<400> SEQUENCE: 541
ggaaggacuu gguaaaguuc                                              20

<210> SEQ ID NO 542
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 542 aaauccgag gcacuucaac au                                            22

<210> SEQ ID NO 543
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 543
gucugucauc ucacuggauc                                              20

<210> SEQ ID NO 544
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 544
ugggcacagu ugucacugcu                                              20

<210> SEQ ID NO 545
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 545
aaacauugca gacaggauag                                              20

<210> SEQ ID NO 546
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 546
uguaauucua gccugagucu                                              20

<210> SEQ ID NO 547
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 547
ccaggaaagu cuucagagga u                                            21

<210> SEQ ID NO 548
<211> LENGTH: 20
```

```
<212> TYPE: RNA
<213> ORGANISM: Artificial Sequence
<220> FEATURE:
<223> OTHER INFORMATION: Fragment coding sequence

<400> SEQUENCE: 548
uaaaagaucu uuucuugucu                                              20

<210> SEQ ID NO 549
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 549
agacaaauaa ggucaggaga                                              20

<210> SEQ ID NO 550
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 550
agacaacacc cacuccuucu                                              20

<210> SEQ ID NO 551
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 551
uagguucaag ucugccagau aca                                          23

<210> SEQ ID NO 552
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 552
cuuaccaguc ucaucuucua c                                            21

<210> SEQ ID NO 553
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 553
ggccuugcuc uucagagagg                                              20

<210> SEQ ID NO 554
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 554
```
caugcagcua gaaccaugac                                            20

<210> SEQ ID NO 555
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 555
ggggaagaaa agugguaggc a                                          21

<210> SEQ ID NO 556
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 556
acaggauaga gcagauuuuu                                            20

<210> SEQ ID NO 557
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 557
uugaaaauga accuugauga                                            20

<210> SEQ ID NO 558
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 558
caugagcaag aucuuuguca a                                          21

<210> SEQ ID NO 559
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 559
ucuugugaca uuuuuaccaa u                                          21

<210> SEQ ID NO 560
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 560
caggaacaca agaaccaaag                                            20

<210> SEQ ID NO 561
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 561
uucacauuaa aaaagugaua                                          20

<210> SEQ ID NO 562
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 562
cuguuggaau ggccaggaug                                          20

<210> SEQ ID NO 563
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 563
aagguggaga acucagaguu u                                        21

<210> SEQ ID NO 564
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 564
gcauuuggaa gguaucuugc                                          20

<210> SEQ ID NO 565
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 565
cucuauuucu ugcacuugug                                          20

<210> SEQ ID NO 566
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 566
aagaagagac cauguguagu uau                                      23

<210> SEQ ID NO 567
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 567
auaaugcauu uggaaggguau                                         20

```
<210> SEQ ID NO 568
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 568
cuaugaaguc aucaaaauau                                                    20

<210> SEQ ID NO 569
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 569
uucucauuuu uguuguuuau uu                                                 22

<210> SEQ ID NO 570
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 570
auaacagacc uauaacuuau                                                    20

<210> SEQ ID NO 571
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 571
agagagacac aaggcuaaga                                                    20

<210> SEQ ID NO 572
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 572
uuaguccaga gagcagaaaa                                                    20

<210> SEQ ID NO 573
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 573
cacugccucc uucagcaauc a                                                  21

<210> SEQ ID NO 574
<211> LENGTH: 20
<212> TYPE: RNA
<213> ORGANISM: Artificial Sequence
<220> FEATURE:
<223> OTHER INFORMATION: Fragment coding sequence
```

-continued

```
<400> SEQUENCE: 574
uaugaaguca ucaaaauauu                                              20

<210> SEQ ID NO 575
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 575
cauuaaaaaa gugauagaua                                              20

<210> SEQ ID NO 576
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 576
agagagcauc caaagggagu g                                            21

<210> SEQ ID NO 577
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 577
aaaaaaugua ccagguguga                                              20

<210> SEQ ID NO 578
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 578
aacaugagca agaucuuugu                                              20

<210> SEQ ID NO 579
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 579
aaucacauuc uuucaccaga a                                            21

<210> SEQ ID NO 580
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 580
ccucacucuu auuucaucca                                              20

<210> SEQ ID NO 581
```

```
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 581
cauucacuuu guaggaugcu                                                    20

<210> SEQ ID NO 582
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 582
aucagaaagg cuuuauauga c                                                  21

<210> SEQ ID NO 583
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 583
uguauuuaua aaagacaagg u                                                  21

<210> SEQ ID NO 584
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 584
cucauuuuug uuguuuauuu                                                    20

<210> SEQ ID NO 585
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 585
ugccaagcuu guguucaaca                                                    20

<210> SEQ ID NO 586
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 586
ugggcucuga caggaggcau g                                                  21

<210> SEQ ID NO 587
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 587
```
aaguuaauua ccuuuacauu                                          20

<210> SEQ ID NO 588
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 588
uacuaugaug uaucuaucua                                          20

<210> SEQ ID NO 589
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 589
aggaggguau ucuucuguau                                          20

<210> SEQ ID NO 590
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 590
gaacccagag gaaccccac                                           20

<210> SEQ ID NO 591
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 591
cacugccucc uucagcaauc a                                        21

<210> SEQ ID NO 592
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 592
agagcucaag aaggagacaa                                          20

<210> SEQ ID NO 593
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 593
aagaggggcu ccucuaugaa                                          20

<210> SEQ ID NO 594
<211> LENGTH: 20
<212> TYPE: RNA

```
<213> ORGANISM: Artificial Sequence
<220> FEATURE:
<223> OTHER INFORMATION: Fragment coding sequence

<400> SEQUENCE: 594
ucuacugcuu uaggugacgu                                               20

<210> SEQ ID NO 595
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 595 agauggugg aucaagaggu                                                20

<210> SEQ ID NO 596
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 596
aacggugacg aggcugagga                                               20

<210> SEQ ID NO 597
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 597
cagaggaugu auuuucuguc                                               20

<210> SEQ ID NO 598
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 598
cacauccacu gccuccuuca                                               20

<210> SEQ ID NO 599
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 599
agggaugucu ugugacauuu uu                                            22

<210> SEQ ID NO 600
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 600
cuucagaaag caagucauuc ua                                            22
```

<210> SEQ ID NO 601
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 601
uacaucucag ccauaaaaau g                                               21

<210> SEQ ID NO 602
<211> LENGTH: 22
<212> TYPE: RNA
<213> ORGANISM: Artificial Sequence
<220> FEATURE:
<223> OTHER INFORMATION: Fragment coding sequence

<400> SEQUENCE: 602
uuacugagug caggggcccu ga                                              22

<210> SEQ ID NO 603
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 603
ucaacuuucc caacccucca                                                 20

<210> SEQ ID NO 604
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 604
cagagggaca gggagggagg u                                               21

<210> SEQ ID NO 605
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 605
agucagaacu uggaaugaga u                                               21

<210> SEQ ID NO 606
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 606
ucaaagauua gagucaacag a                                               21

<210> SEQ ID NO 607
<211> LENGTH: 21
<212> TYPE: RNA
<213> ORGANISM: Artificial Sequence
<220> FEATURE:

<223> OTHER INFORMATION: Fragment coding sequence

<400> SEQUENCE: 607
caugaacugg guauacaagu u                                          21

<210> SEQ ID NO 608
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 608
cugaugacau gcuggagaag a                                          21

<210> SEQ ID NO 609
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 609
uggucacgug uucaaucuca u                                          21

<210> SEQ ID NO 610
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 610
uuaugaagac uguucaggac u                                          21

<210> SEQ ID NO 611
<211> LENGTH: 23
<212> TYPE: RNA
<213> ORGANISM: Artificial Sequence
<220> FEATURE:
<223> OTHER INFORMATION: Fragment coding sequence

<400> SEQUENCE: 611
cugguggaga uaaaacguac uga                                        23

<210> SEQ ID NO 612
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 612
uugauuguuu uucucauuuu                                            20

<210> SEQ ID NO 613
<211> LENGTH: 21
<212> TYPE: RNA
<213> ORGANISM: Artificial Sequence
<220> FEATURE:
<223> OTHER INFORMATION: Fragment coding sequence

<400> SEQUENCE: 613
ugguuucugg ggcugugccu c                                          21

```
<210> SEQ ID NO 614
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 614
gagccagggc aggagacagc                                              20

<210> SEQ ID NO 615
<211> LENGTH: 20
<212> TYPE: RNA
<213> ORGANISM: Artificial Sequence
<220> FEATURE:
<223> OTHER INFORMATION: Fragment coding sequence

<400> SEQUENCE: 615
ggguucuuuu ugaaaaaaaa                                              20

<210> SEQ ID NO 616
<211> LENGTH: 59
<212> TYPE: DNA
<213> ORGANISM: Artificial Sequence
<220> FEATURE:
<223> OTHER INFORMATION: Primer

<400> SEQUENCE: 616
attctagagc tagcgaattc tcatcaactt gtatgatgtg ttacaaacgt aatagagca   59

<210> SEQ ID NO 617
<211> LENGTH: 59
<212> TYPE: DNA
<213> ORGANISM: Artificial Sequence
<220> FEATURE:
<223> OTHER INFORMATION: Primer

<400> SEQUENCE: 617
gaccttctaa caccattaac aatagttgta cattcgactc ttgttgctct attacgttt   59

<210> SEQ ID NO 618
<211> LENGTH: 59
<212> TYPE: DNA
<213> ORGANISM: Artificial Sequence
<220> FEATURE:
<223> OTHER INFORMATION: Primer

<400> SEQUENCE: 618
gtagtttgca aaagcccttta cctccattag catagacata aaaggaccttt ctaacacca  59

<210> SEQ ID NO 619
<211> LENGTH: 57
<212> TYPE: DNA
<213> ORGANISM: Artificial Sequence
<220> FEATURE:
<223> OTHER INFORMATION: Primer

<400> SEQUENCE: 619
tccttcgcgg ccgcggatca caattaacac aattccaatt gtgtagtttg caaaagc     57

<210> SEQ ID NO 620
<211> LENGTH: 57
<212> TYPE: DNA
<213> ORGANISM: Artificial Sequence
<220> FEATURE:
<223> OTHER INFORMATION: Primer
```

```
<400> SEQUENCE: 620
attctagagc tagcgaattc aacaacatta tcaacaatgc aagagatggt tgtgttc          57

<210> SEQ ID NO 621
<211> LENGTH: 59
<212> TYPE: DNA
<213> ORGANISM: Artificial Sequence
<220> FEATURE:
<223> OTHER INFORMATION: Primer

<400> SEQUENCE: 621
aaccattagt ttggctgctg ttgtaagagg tattatgttc aagggaacac aaccatctc       59

<210> SEQ ID NO 622
<211> LENGTH: 59
<212> TYPE: DNA
<213> ORGANISM: Artificial Sequence
<220> FEATURE:
<223> OTHER INFORMATION: Primer

<400> SEQUENCE: 622
gtaccatcac acgtattttt atatgtgtta tagtctggta tgacaaccat tagtttggc       59

<210> SEQ ID NO 623
<211> LENGTH: 59
<212> TYPE: DNA
<213> ORGANISM: Artificial Sequence
<220> FEATURE:
<223> OTHER INFORMATION: Primer

<400> SEQUENCE: 623
tccttcgcgg ccgcggatcc aatgctgatg cataagtaaa tgttgtacca tcacacgta       59

<210> SEQ ID NO 624
<211> LENGTH: 59
<212> TYPE: DNA
<213> ORGANISM: Artificial Sequence
<220> FEATURE:
<223> OTHER INFORMATION: Primer

<400> SEQUENCE: 624
attctagagc tagcgaattc cttaacaaag ttgttagtac aactactaac atagttaca       59

<210> SEQ ID NO 625
<211> LENGTH: 59
<212> TYPE: DNA
<213> ORGANISM: Artificial Sequence
<220> FEATURE:
<223> OTHER INFORMATION: Primer

<400> SEQUENCE: 625
aagaaataag gcatataatt agtacaaaca cggtttaaac accgtgtaac tatgttagt       59

<210> SEQ ID NO 626
<211> LENGTH: 59
<212> TYPE: DNA
<213> ORGANISM: Artificial Sequence
<220> FEATURE:
<223> OTHER INFORMATION: Primer

<400> SEQUENCE: 626
aatttgtact tctagtaaaa gtacacaatt gtagcaataa agtaaagaaa taaggcata       59

<210> SEQ ID NO 627
<211> LENGTH: 59
```

```
<212> TYPE: DNA
<213> ORGANISM: Artificial Sequence
<220> FEATURE:
<223> OTHER INFORMATION: Primer

<400> SEQUENCE: 627
tccttcgcgg ccgcggatcc tcggcataga tgctttaatt ctagaatttg tacttctag      59

<210> SEQ ID NO 628
<211> LENGTH: 59
<212> TYPE: DNA
<213> ORGANISM: Artificial Sequence
<220> FEATURE:
<223> OTHER INFORMATION: Primer

<400> SEQUENCE: 628
attctagagc tagcgaattc ggagtacgat cgagtgtaca gtgaacaatg ctagggaga      59

<210> SEQ ID NO 629
<211> LENGTH: 59
<212> TYPE: DNA
<213> ORGANISM: Artificial Sequence
<220> FEATURE:
<223> OTHER INFORMATION: Primer

<400> SEQUENCE: 629
actaaaatta attttacaca ttagggctct tccatatagg cagctctccc tagcattgt      59

<210> SEQ ID NO 630
<211> LENGTH: 59
<212> TYPE: DNA
<213> ORGANISM: Artificial Sequence
<220> FEATURE:
<223> OTHER INFORMATION: Primer

<400> SEQUENCE: 630
actaaaatta attttacaca ttagggctct tccatatagg cagctctccc tagcattgt      59

<210> SEQ ID NO 631
<211> LENGTH: 59
<212> TYPE: DNA
<213> ORGANISM: Artificial Sequence
<220> FEATURE:
<223> OTHER INFORMATION: Primer

<400> SEQUENCE: 631
tccttcgcgg ccgcggatcc tttttttttt tttttttttt ttttgtcatt ctcctaaga      59

<210> SEQ ID NO 632
<211> LENGTH: 59
<212> TYPE: DNA
<213> ORGANISM: Artificial Sequence
<220> FEATURE:
<223> OTHER INFORMATION: Primer

<400> SEQUENCE: 632
attctagagc tagcgaattc gttaataatt ggttgaagca gttaattaaa gttacactt      59

<210> SEQ ID NO 633
<211> LENGTH: 59
<212> TYPE: DNA
<213> ORGANISM: Artificial Sequence
<220> FEATURE:
<223> OTHER INFORMATION: Primer

<400> SEQUENCE: 633
```
acaggtgtta ttaaatagaa aatagcagca acaaaaagga acacaagtgt aactttaat    59

<210> SEQ ID NO 634
<211> LENGTH: 59
<212> TYPE: DNA
<213> ORGANISM: Artificial Sequence
<220> FEATURE:
<223> OTHER INFORMATION: Primer

<400> SEQUENCE: 634
ctatgatttc acttgaaaag tcagtatgtt tagacatgac atgaacaggt gttattaaa    59

<210> SEQ ID NO 635
<211> LENGTH: 59
<212> TYPE: DNA
<213> ORGANISM: Artificial Sequence
<220> FEATURE:
<223> OTHER INFORMATION: Primer

<400> SEQUENCE: 635
tccttcgcgg ccgcggatcc caccaccatc aatagccttg tatcctatga tttcacttg    59

<210> SEQ ID NO 636
<211> LENGTH: 59
<212> TYPE: DNA
<213> ORGANISM: Artificial Sequence
<220> FEATURE:
<223> OTHER INFORMATION: Primer

<400> SEQUENCE: 636
ctccctctgg aatttggtgc ctcagctgaa acagttcgag ttgaggaaga agaagagga    59

<210> SEQ ID NO 637
<211> LENGTH: 59
<212> TYPE: DNA
<213> ORGANISM: Artificial Sequence
<220> FEATURE:
<223> OTHER INFORMATION: Primer

<400> SEQUENCE: 637
tggctcaatc tctgattgct cagtagtatc atccagccag tcttcctctt cttcttcct    59

<210> SEQ ID NO 638
<211> LENGTH: 40
<212> TYPE: DNA
<213> ORGANISM: Artificial Sequence
<220> FEATURE:
<223> OTHER INFORMATION: Primer

<400> SEQUENCE: 638
attctagagc tagcgaattc ctccctctgg aatttggtgc    40

<210> SEQ ID NO 639
<211> LENGTH: 40
<212> TYPE: DNA
<213> ORGANISM: Artificial Sequence
<220> FEATURE:
<223> OTHER INFORMATION: Primer

<400> SEQUENCE: 639
tccttcgcgg ccgcggatca tggctcaatc tctgattgct    40

<210> SEQ ID NO 640
<211> LENGTH: 59
<212> TYPE: DNA
<213> ORGANISM: Artificial Sequence

```
<220> FEATURE:
<223> OTHER INFORMATION: Primer

<400> SEQUENCE: 640
tatgggttgg gattatccaa aatgtgacag agccatgcct aacatgctta ggataatgg      59

<210> SEQ ID NO 641
<211> LENGTH: 58
<212> TYPE: DNA
<213> ORGANISM: Artificial Sequence
<220> FEATURE:
<223> OTHER INFORMATION: Primer

<400> SEQUENCE: 641
aagttacagc aagtgttatg tttgcgagca agaacaagag aggccattat cctaagca       58

<210> SEQ ID NO 642
<211> LENGTH: 40
<212> TYPE: DNA
<213> ORGANISM: Artificial Sequence
<220> FEATURE:
<223> OTHER INFORMATION: Primer

<400> SEQUENCE: 642
attctagagc tagcgaattc tatgggttgg gattatccaa                            40

<210> SEQ ID NO 643
<211> LENGTH: 40
<212> TYPE: DNA
<213> ORGANISM: Artificial Sequence
<220> FEATURE:
<223> OTHER INFORMATION: Primer

<400> SEQUENCE: 643
tccttcgcgg ccgcggatca aagttacagc aagtgttatg                            40

<210> SEQ ID NO 644
<211> LENGTH: 59
<212> TYPE: DNA
<213> ORGANISM: Artificial Sequence
<220> FEATURE:
<223> OTHER INFORMATION: Primer

<400> SEQUENCE: 644
gtgttggctg gactgctggc ttatcctcct tgctgctat tccatttgca cagagtatc       59

<210> SEQ ID NO 645
<211> LENGTH: 59
<212> TYPE: DNA
<213> ORGANISM: Artificial Sequence
<220> FEATURE:
<223> OTHER INFORMATION: Primer

<400> SEQUENCE: 645
gaaagaacct gttgagtaat gccaacaccg tttaacctat aaaagatact ctgtgcaaa       59

<210> SEQ ID NO 646
<211> LENGTH: 40
<212> TYPE: DNA
<213> ORGANISM: Artificial Sequence
<220> FEATURE:
<223> OTHER INFORMATION: Primer

<400> SEQUENCE: 646
attctagagc tagcgaattc gtgttggctg gactgctggc                            40
```

```
<210> SEQ ID NO 647
<211> LENGTH: 40
<212> TYPE: DNA
<213> ORGANISM: Artificial Sequence
<220> FEATURE:
<223> OTHER INFORMATION: Primer

<400> SEQUENCE: 647
tccttcgcgg ccgcggatca gaaagaacct gttgagtaat                   40

<210> SEQ ID NO 648
<211> LENGTH: 59
<212> TYPE: DNA
<213> ORGANISM: Artificial Sequence
<220> FEATURE:
<223> OTHER INFORMATION: Primer

<400> SEQUENCE: 648
aataaagtaa aacgtgcttt tgcagattac acccagtgtg ctgtaattgc tgttgttgc     59

<210> SEQ ID NO 649
<211> LENGTH: 59
<212> TYPE: DNA
<213> ORGANISM: Artificial Sequence
<220> FEATURE:
<223> OTHER INFORMATION: Primer

<400> SEQUENCE: 649
gtatagaggt aacaaagcag atgcacaagc tattaagaac agcagcaaca acagcaatt     59

<210> SEQ ID NO 650
<211> LENGTH: 40
<212> TYPE: DNA
<213> ORGANISM: Artificial Sequence
<220> FEATURE:
<223> OTHER INFORMATION: Primer

<400> SEQUENCE: 650
attctagagc tagcgaattc aataaagtaa aacgtgcttt                   40

<210> SEQ ID NO 651
<211> LENGTH: 40
<212> TYPE: DNA
<213> ORGANISM: Artificial Sequence
<220> FEATURE:
<223> OTHER INFORMATION: Primer

<400> SEQUENCE: 651
tccttcgcgg ccgcggatca gtatagaggt aacaaagcag                   40

<210> SEQ ID NO 652
<211> LENGTH: 59
<212> TYPE: DNA
<213> ORGANISM: Artificial Sequence
<220> FEATURE:
<223> OTHER INFORMATION: Primer

<400> SEQUENCE: 652
tgagaggaga gtgccagagt tgtgtgtaca acatgatggg aaaaagagaa aagaaacaa     59

<210> SEQ ID NO 653
<211> LENGTH: 59
<212> TYPE: DNA
<213> ORGANISM: Artificial Sequence
<220> FEATURE:
<223> OTHER INFORMATION: Primer
```

```
<400> SEQUENCE: 653
tataccagat ggcgcggctg cccttggcct ttccaaattc cccttgtttc ttttctctt         59

<210> SEQ ID NO 654
<211> LENGTH: 45
<212> TYPE: DNA
<213> ORGANISM: Artificial Sequence
<220> FEATURE:
<223> OTHER INFORMATION: Primer

<400> SEQUENCE: 654
gaagattcta gagctagcga attctgagag gagagtgcca gagtt                       45

<210> SEQ ID NO 655
<211> LENGTH: 45
<212> TYPE: DNA
<213> ORGANISM: Artificial Sequence
<220> FEATURE:
<223> OTHER INFORMATION: Primer

<400> SEQUENCE: 655
cagatccttc gcggccgcgg atcctatacc agatggcgcg gctgc                       45

<210> SEQ ID NO 656
<211> LENGTH: 59
<212> TYPE: DNA
<213> ORGANISM: Artificial Sequence
<220> FEATURE:
<223> OTHER INFORMATION: Primer

<400> SEQUENCE: 656
gtgatcaaaa atgggagtta tgttagtgcc atcacccaag ggaggaggga ggaagagac         59

<210> SEQ ID NO 657
<211> LENGTH: 59
<212> TYPE: DNA
<213> ORGANISM: Artificial Sequence
<220> FEATURE:
<223> OTHER INFORMATION: Primer

<400> SEQUENCE: 657
ctgcttcttc ttcagcatcg aaggctcgaa gcactcaaca ggagtctctt cctccctcc         59

<210> SEQ ID NO 658
<211> LENGTH: 45
<212> TYPE: DNA
<213> ORGANISM: Artificial Sequence
<220> FEATURE:
<223> OTHER INFORMATION: Primer

<400> SEQUENCE: 658
gaagattcta gagctagcga attcgtgatc aaaaatggga gttat                       45

<210> SEQ ID NO 659
<211> LENGTH: 45
<212> TYPE: DNA
<213> ORGANISM: Artificial Sequence
<220> FEATURE:
<223> OTHER INFORMATION: Primer

<400> SEQUENCE: 659
cagatccttc gcggccgcgg atccctgctt cttcttcagc atcga                       45

<210> SEQ ID NO 660
```

<211> LENGTH: 59
<212> TYPE: DNA
<213> ORGANISM: Artificial Sequence
<220> FEATURE:
<223> OTHER INFORMATION: Primer

<400> SEQUENCE: 660
ctagtggtgc aactcattcg gaatatggag gctgaggaag ttctagagat gcaagactt      59

<210> SEQ ID NO 661
<211> LENGTH: 59
<212> TYPE: DNA
<213> ORGANISM: Artificial Sequence
<220> FEATURE:
<223> OTHER INFORMATION: Primer

<400> SEQUENCE: 661
ctgcaaccag ttggtcactt tctctgacct ccgcagcagc cacaagtctt gcatctcta      59

<210> SEQ ID NO 662
<211> LENGTH: 45
<212> TYPE: DNA
<213> ORGANISM: Artificial Sequence
<220> FEATURE:
<223> OTHER INFORMATION: Primer

<400> SEQUENCE: 662
gaagattcta gagctagcga attcctagtg gtgcaactca ttcgg                    45

<210> SEQ ID NO 663
<211> LENGTH: 45
<212> TYPE: DNA
<213> ORGANISM: Artificial Sequence
<220> FEATURE:
<223> OTHER INFORMATION: Primer

<400> SEQUENCE: 663
cagatccttc gcggccgcgg atccctgcaa ccagttggtc acttt                    45

<210> SEQ ID NO 664
<211> LENGTH: 59
<212> TYPE: DNA
<213> ORGANISM: Artificial Sequence
<220> FEATURE:
<223> OTHER INFORMATION: Primer

<400> SEQUENCE: 664
aatactccac caacagatga tgtatcaagt cctcaccgac tcattctacc attttttaa      59

<210> SEQ ID NO 665
<211> LENGTH: 59
<212> TYPE: DNA
<213> ORGANISM: Artificial Sequence
<220> FEATURE:
<223> OTHER INFORMATION: Primer

<400> SEQUENCE: 665
ttcttgggca tcttgatcat gtgcatggtt gtgatttccc aatttaaaaa atggtagaa      59

<210> SEQ ID NO 666
<211> LENGTH: 45
<212> TYPE: DNA
<213> ORGANISM: Artificial Sequence
<220> FEATURE:
<223> OTHER INFORMATION: Primer

<400> SEQUENCE: 666

```
gaagattcta gagctagcga attcaatact ccaccaacag atgat          45
```

<210> SEQ ID NO 667
<211> LENGTH: 45
<212> TYPE: DNA
<213> ORGANISM: Artificial Sequence
<220> FEATURE:
<223> OTHER INFORMATION: Primer

<400> SEQUENCE: 667

```
cagatccttc gcggccgcgg atccttcttg ggcatcttga tcatg          45
```

<210> SEQ ID NO 668
<211> LENGTH: 59
<212> TYPE: DNA
<213> ORGANISM: Artificial Sequence
<220> FEATURE:
<223> OTHER INFORMATION: Primer

<400> SEQUENCE: 668

```
ttttctaaat ccagaaaagt gttttatcg aaacttcgga gatcctgtga cttctggac    59
```

<210> SEQ ID NO 669
<211> LENGTH: 59
<212> TYPE: DNA
<213> ORGANISM: Artificial Sequence
<220> FEATURE:
<223> OTHER INFORMATION: Primer

<400> SEQUENCE: 669

```
tctttcatgt taaccatttc taggtacacc cgtagctgga aaagtccaga agtcacagg    59
```

<210> SEQ ID NO 670
<211> LENGTH: 45
<212> TYPE: DNA
<213> ORGANISM: Artificial Sequence
<220> FEATURE:
<223> OTHER INFORMATION: Primer

<400> SEQUENCE: 670

```
gaagattcta gagctagcga attcttttct aaatccagaa aagtg           45
```

<210> SEQ ID NO 671
<211> LENGTH: 45
<212> TYPE: DNA
<213> ORGANISM: Artificial Sequence
<220> FEATURE:
<223> OTHER INFORMATION: Primer

<400> SEQUENCE: 671

```
cagatccttc gcggccgcgg atcctctttc atgttaacca tttct           45
```

<210> SEQ ID NO 672
<211> LENGTH: 46
<212> TYPE: DNA
<213> ORGANISM: Artificial Sequence
<220> FEATURE:
<223> OTHER INFORMATION: Primer

<400> SEQUENCE: 672

```
gaagattcta gagctagcga attcagatct gagagagaaa aatctc          46
```

<210> SEQ ID NO 673
<211> LENGTH: 45
<212> TYPE: DNA

```
<213> ORGANISM: Artificial Sequence
<220> FEATURE:
<223> OTHER INFORMATION: Primer

<400> SEQUENCE: 673
cagatccttc gcggccgcgg atcctattat taattgctca tttaa                45

<210> SEQ ID NO 674
<211> LENGTH: 59
<212> TYPE: DNA
<213> ORGANISM: Artificial Sequence
<220> FEATURE:
<223> OTHER INFORMATION: Primer

<400> SEQUENCE: 674
agatctgaga gagaaaaatc tcagggttac tctaaggaga aatattattt ttaaaattt    59

<210> SEQ ID NO 675
<211> LENGTH: 59
<212> TYPE: DNA
<213> ORGANISM: Artificial Sequence
<220> FEATURE:
<223> OTHER INFORMATION: Primer

<400> SEQUENCE: 675
tattattaat tgctcattta agataagtgg tcagcattca agtaaatttt aaaaataat    59

<210> SEQ ID NO 676
<211> LENGTH: 59
<212> TYPE: DNA
<213> ORGANISM: Artificial Sequence
<220> FEATURE:
<223> OTHER INFORMATION: Primer

<400> SEQUENCE: 676
tttaagacca atgacttaca aggcagctgt agatcttagc cacttttaa aagaaaagg     59

<210> SEQ ID NO 677
<211> LENGTH: 59
<212> TYPE: DNA
<213> ORGANISM: Artificial Sequence
<220> FEATURE:
<223> OTHER INFORMATION: Primer

<400> SEQUENCE: 677
atatcttgtc ttctttggga gtgaattagc ccttccagtc cccccttttc ttttaaaaa    59

<210> SEQ ID NO 678
<211> LENGTH: 44
<212> TYPE: DNA
<213> ORGANISM: Artificial Sequence
<220> FEATURE:
<223> OTHER INFORMATION: Primer

<400> SEQUENCE: 678
gaagattcta gagctagcga attctttaag accaatgact taca                   44

<210> SEQ ID NO 679
<211> LENGTH: 44
<212> TYPE: DNA
<213> ORGANISM: Artificial Sequence
<220> FEATURE:
<223> OTHER INFORMATION: Primer

<400> SEQUENCE: 679
cagatccttc gcggccgcgg atccatatct tgtcttcttt ggga                   44
```

<210> SEQ ID NO 680
<211> LENGTH: 59
<212> TYPE: DNA
<213> ORGANISM: Artificial Sequence
<220> FEATURE:
<223> OTHER INFORMATION: Primer

<400> SEQUENCE: 680
aagaaaaaat aaaagcatta gtagaaattt gtacagagat ggaaaaggaa gggaaaatt    59

<210> SEQ ID NO 681
<211> LENGTH: 59
<212> TYPE: DNA
<213> ORGANISM: Artificial Sequence
<220> FEATURE:
<223> OTHER INFORMATION: Primer

<400> SEQUENCE: 681
caaatactgg agtattgtat ggattttcag gcccaatttt tgaaattttc ccttcctttt    59

<210> SEQ ID NO 682
<211> LENGTH: 44
<212> TYPE: DNA
<213> ORGANISM: Artificial Sequence
<220> FEATURE:
<223> OTHER INFORMATION: Primer

<400> SEQUENCE: 682
gaagattcta gagctagcga attcaagaaa aaataaaagc atta                    44

<210> SEQ ID NO 683
<211> LENGTH: 44
<212> TYPE: DNA
<213> ORGANISM: Artificial Sequence
<220> FEATURE:
<223> OTHER INFORMATION: Primer

<400> SEQUENCE: 683
cagatccttc gcggccgcgg atcccaaata ctggagtatt gtat                    44

<210> SEQ ID NO 684
<211> LENGTH: 59
<212> TYPE: DNA
<213> ORGANISM: Artificial Sequence
<220> FEATURE:
<223> OTHER INFORMATION: Primer

<400> SEQUENCE: 684
ggtctatctg gcatgggtac cagcacacaa aggaattgga ggaaatgaac aagtagata    59

<210> SEQ ID NO 685
<211> LENGTH: 59
<212> TYPE: DNA
<213> ORGANISM: Artificial Sequence
<220> FEATURE:
<223> OTHER INFORMATION: Primer

<400> SEQUENCE: 685
ccatctaaaa atagtacttt cctgattcca gcactgacta atttatctac ttgttcatt    59

<210> SEQ ID NO 686
<211> LENGTH: 44
<212> TYPE: DNA
<213> ORGANISM: Artificial Sequence
<220> FEATURE:

<223> OTHER INFORMATION: Primer

<400> SEQUENCE: 686
gaagattcta gagctagcga attcggtcta tctggcatgg gtac                44

<210> SEQ ID NO 687
<211> LENGTH: 44
<212> TYPE: DNA
<213> ORGANISM: Artificial Sequence
<220> FEATURE:
<223> OTHER INFORMATION: Primer

<400> SEQUENCE: 687
cagatccttc gcggccgcgg atccccatct aaaaatagta cttt                44

<210> SEQ ID NO 688
<211> LENGTH: 59
<212> TYPE: DNA
<213> ORGANISM: Artificial Sequence
<220> FEATURE:
<223> OTHER INFORMATION: Primer

<400> SEQUENCE: 688
cctgagtggg agtttgttaa tacccctccc ttagtgaaat tatggtacca gttagagaa      59

<210> SEQ ID NO 689
<211> LENGTH: 59
<212> TYPE: DNA
<213> ORGANISM: Artificial Sequence
<220> FEATURE:
<223> OTHER INFORMATION: Primer

<400> SEQUENCE: 689
tgccccatct acatagaagg tttctgctcc tactatgggt tctttctcta actggtacc      59

<210> SEQ ID NO 690
<211> LENGTH: 45
<212> TYPE: DNA
<213> ORGANISM: Artificial Sequence
<220> FEATURE:
<223> OTHER INFORMATION: Primer

<400> SEQUENCE: 690
gaagattcta gagctagcga attccctgag tgggagtttg ttaat               45

<210> SEQ ID NO 691
<211> LENGTH: 44
<212> TYPE: DNA
<213> ORGANISM: Artificial Sequence
<220> FEATURE:
<223> OTHER INFORMATION: Primer

<400> SEQUENCE: 691
cagatccttc gcggccgcgg atcctgcccc atctacatag aagg                44

<210> SEQ ID NO 692
<211> LENGTH: 59
<212> TYPE: DNA
<213> ORGANISM: Artificial Sequence
<220> FEATURE:
<223> OTHER INFORMATION: Primer

<400> SEQUENCE: 692
ggagaattag atcgatggga aaaaattcgg ttaaggccag ggggaaagaa aaatataa       59

-continued

```
<210> SEQ ID NO 693
<211> LENGTH: 59
<212> TYPE: DNA
<213> ORGANISM: Artificial Sequence
<220> FEATURE:
<223> OTHER INFORMATION: Primer

<400> SEQUENCE: 693
gaatcgttct agctccctgc ttgcccatac tatatgtttt aatttatatt ttttctttc      59

<210> SEQ ID NO 694
<211> LENGTH: 44
<212> TYPE: DNA
<213> ORGANISM: Artificial Sequence
<220> FEATURE:
<223> OTHER INFORMATION: Primer

<400> SEQUENCE: 694
gaagattcta gagctagcga attcggagaa ttagatcgat ggga                     44

<210> SEQ ID NO 695
<211> LENGTH: 44
<212> TYPE: DNA
<213> ORGANISM: Artificial Sequence
<220> FEATURE:
<223> OTHER INFORMATION: Primer

<400> SEQUENCE: 695
cagatccttc gcggccgcgg atccgaatcg ttctagctcc ctgc                     44

<210> SEQ ID NO 696
<211> LENGTH: 59
<212> TYPE: DNA
<213> ORGANISM: Artificial Sequence
<220> FEATURE:
<223> OTHER INFORMATION: Primer

<400> SEQUENCE: 696
cagaagcagg ggcaaggcca atggacatat caaatttatc aagagccatt taaaaatct     59

<210> SEQ ID NO 697
<211> LENGTH: 59
<212> TYPE: DNA
<213> ORGANISM: Artificial Sequence
<220> FEATURE:
<223> OTHER INFORMATION: Primer

<400> SEQUENCE: 697
attagtgtgg gcacccctca ttcttgcata ttttcctgtt ttcagatttt taaatggct     59

<210> SEQ ID NO 698
<211> LENGTH: 44
<212> TYPE: DNA
<213> ORGANISM: Artificial Sequence
<220> FEATURE:
<223> OTHER INFORMATION: Primer

<400> SEQUENCE: 698
gaagattcta gagctagcga attccagaag cagggggcaag gcca                    44

<210> SEQ ID NO 699
<211> LENGTH: 44
<212> TYPE: DNA
<213> ORGANISM: Artificial Sequence
<220> FEATURE:
<223> OTHER INFORMATION: Primer
```

<400> SEQUENCE: 699
cagatccttc gcggccgcgg atccattagt gtgggcaccc ctca    44

<210> SEQ ID NO 700
<211> LENGTH: 59
<212> TYPE: DNA
<213> ORGANISM: Artificial Sequence
<220> FEATURE:
<223> OTHER INFORMATION: Primer

<400> SEQUENCE: 700
aagtgtgtca gaaagtacaa cccaactaac atcttagaca taaaacaggg accaaaaga    59

<210> SEQ ID NO 701
<211> LENGTH: 59
<212> TYPE: DNA
<213> ORGANISM: Artificial Sequence
<220> FEATURE:
<223> OTHER INFORMATION: Primer

<400> SEQUENCE: 701
cctcaagctt ttgtagaacc tgtctacata gctttggaac ggttcttttg gtccctgtt    59

<210> SEQ ID NO 702
<211> LENGTH: 44
<212> TYPE: DNA
<213> ORGANISM: Artificial Sequence
<220> FEATURE:
<223> OTHER INFORMATION: Primer

<400> SEQUENCE: 702
gaagattcta gagctagcga attcaagtgt gtcagaaagt acaa    44

<210> SEQ ID NO 703
<211> LENGTH: 44
<212> TYPE: DNA
<213> ORGANISM: Artificial Sequence
<220> FEATURE:
<223> OTHER INFORMATION: Primer

<400> SEQUENCE: 703
cagatccttc gcggccgcgg atcccctcaa gcttttgtag aacc    44

<210> SEQ ID NO 704
<211> LENGTH: 59
<212> TYPE: DNA
<213> ORGANISM: Artificial Sequence
<220> FEATURE:
<223> OTHER INFORMATION: Primer

<400> SEQUENCE: 704
caaagccagg gagtagtaga agcaatgaat caccacctaa agaatcagat aagtagaat    59

<210> SEQ ID NO 705
<211> LENGTH: 59
<212> TYPE: DNA
<213> ORGANISM: Artificial Sequence
<220> FEATURE:
<223> OTHER INFORMATION: Primer

<400> SEQUENCE: 705
tgccatcagt actattgttt ctattgtatt tgcctgttct ctaattctac ttatctgat    59

<210> SEQ ID NO 706
<211> LENGTH: 44

<212> TYPE: DNA
<213> ORGANISM: Artificial Sequence
<220> FEATURE:
<223> OTHER INFORMATION: Primer

<400> SEQUENCE: 706
gaagattcta gagctagcga attccaaagc cagggagtag taga                    44

<210> SEQ ID NO 707
<211> LENGTH: 44
<212> TYPE: DNA
<213> ORGANISM: Artificial Sequence
<220> FEATURE:
<223> OTHER INFORMATION: Primer

<400> SEQUENCE: 707
cagatccttc gcggccgcgg atcctgccat cagtactatt gttt                    44

<210> SEQ ID NO 708
<211> LENGTH: 59
<212> TYPE: DNA
<213> ORGANISM: Artificial Sequence
<220> FEATURE:
<223> OTHER INFORMATION: Primer

<400> SEQUENCE: 708
gggtggctgt ggaagctagt atcagtagaa ctctcacaag aggcagagga agatgaggc     59

<210> SEQ ID NO 709
<211> LENGTH: 59
<212> TYPE: DNA
<213> ORGANISM: Artificial Sequence
<220> FEATURE:
<223> OTHER INFORMATION: Primer

<400> SEQUENCE: 709
atcatcatgt ctgcttgttt gtgctgggtg tactaagcag ttggcctcat cttcctctg     59

<210> SEQ ID NO 710
<211> LENGTH: 44
<212> TYPE: DNA
<213> ORGANISM: Artificial Sequence
<220> FEATURE:
<223> OTHER INFORMATION: Primer

<400> SEQUENCE: 710
gaagattcta gagctagcga attcgggtgg ctgtggaagc tagt                    44

<210> SEQ ID NO 711
<211> LENGTH: 44
<212> TYPE: DNA
<213> ORGANISM: Artificial Sequence
<220> FEATURE:
<223> OTHER INFORMATION: Primer

<400> SEQUENCE: 711
cagatccttc gcggccgcgg atccatcatc atgtctgctt gttt                    44

<210> SEQ ID NO 712
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 712

```
acagauacga uuaccuccau uuccga                                          26

<210> SEQ ID NO 713
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 713
auauugugua uauuuuaug caca                                             24

<210> SEQ ID NO 714
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 714
aauauacgga auaaagaaau gaaa                                            24

<210> SEQ ID NO 715
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 715
uccucuuacu guuuuuuuu uuuuuuu                                          27

<210> SEQ ID NO 716
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 716
aacaacgacg auaaaagaua aauu                                            24

<210> SEQ ID NO 717
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 717
guacuucuuu guuaaauauu aaaugaau                                        28

<210> SEQ ID NO 718
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 718
cucaacuccu ucuucuucuc cuucugacc                                       29

<210> SEQ ID NO 719
<211> LENGTH: 24
<212> TYPE: RNA
<213> ORGANISM: Artificial Sequence
```

```
<220> FEATURE:
<223> OTHER INFORMATION: Antisense fragment coding sequence

<400> SEQUENCE: 719
auuguacgaa uccuauuacc ggag                                              24

<210> SEQ ID NO 720
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 720
uccucuuacu guuuuuuuu uuuuuuu                                            27

<210> SEQ ID NO 721
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 721
aagguaaacg ugucucauag aaaa                                              24

<210> SEQ ID NO 722
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 722
acgacauuaa cgacaacaac gacgacaa                                          28

<210> SEQ ID NO 723
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 723 cuuuucucu uuucuuuguu ccc                                                23

<210> SEQ ID NO 724
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 724
cccuccuccc uccuucucug agg                                               23

<210> SEQ ID NO 725
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 725
caagaucucu acguucugaa cac                                               23
```

```
<210> SEQ ID NO 726
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 726
ugaguaagau gguaaaaaau uuaac                                        25

<210> SEQ ID NO 727
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 727
ucuaggacac ugaagaccug aaaa                                         24

<210> SEQ ID NO 728
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 728
uuuauaauaa aaauuuuaaa ugaa                                         24

<210> SEQ ID NO 729
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 729
ugaaaaauuu ucuuuucccc ccu                                          23

<210> SEQ ID NO 730
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 730
cuuuuccuuc ccuuuuaaag uuu                                          23

<210> SEQ ID NO 731
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 731
uuuacuuguu caucuauuua auc                                          23

<210> SEQ ID NO 732
<211> LENGTH: 24
<212> TYPE: RNA
<213> ORGANISM: Artificial Sequence
<220> FEATURE:
<223> OTHER INFORMATION: Antisense fragment coding sequence
```

-continued

```
<400> SEQUENCE: 732
uuuaauacca uggucaaucu cuuu                                              24

<210> SEQ ID NO 733
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 733
cuuucuuuuu uauauuuaau uuu                                               23

<210> SEQ ID NO 734
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 734
uaaauaguuc ucgguaaauu uuu                                               23

<210> SEQ ID NO 735
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 735
auuuugaccc ugguuuucuu ggca                                              24

<210> SEQ ID NO 736
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 736
ucuuagucua uucaucuuaa ucu                                               23

<210> SEQ ID NO 737
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 737
uccgucuccu ucuacuccgg uug                                               23

<210> SEQ ID NO 738
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 738
auaguuuuuu aauucuuuuc caau                                              24

<210> SEQ ID NO 739
```

```
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 739 ccagucacc ucuuucacuc cuccuacu                                          28

<210> SEQ ID NO 740
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 740
uacucucuag aaccccacc cug                                               23

<210> SEQ ID NO 741
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 741
cuuuuugagu ucuacuuucc uua                                              23

<210> SEQ ID NO 742
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 742
uaacuaaccg aauuccucuu uuau                                             24

<210> SEQ ID NO 743
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 743
uuaacaaaug gauaaauaac caaaacac                                         28

<210> SEQ ID NO 744
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 744
gacacgacuu gguccugguc cu                                               22

<210> SEQ ID NO 745
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 745
```

```
ucuacuucgu cagugguugg cg                                              22

<210> SEQ ID NO 746
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 746
uaaucuaaag uuguguccac gauguag                                         27

<210> SEQ ID NO 747
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 747
aaccuuacaa aacgaggaga aau                                             23

<210> SEQ ID NO 748
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 748
cuuuaaaaua auaaaacaag uca                                             23

<210> SEQ ID NO 749
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 749
aaucgaucua aaugucuaaa ccu                                             23

<210> SEQ ID NO 750
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 750
uuguucucgu ccgucacac cacc                                             24

<210> SEQ ID NO 751
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 751
aacuccuuuu cccuugggac augu                                            24

<210> SEQ ID NO 752
<211> LENGTH: 24
<212> TYPE: RNA
```

```
<213> ORGANISM: Artificial Sequence
<220> FEATURE:
<223> OTHER INFORMATION: Antisense fragment coding sequence

<400> SEQUENCE: 752
gguccgugac ccuucaguca ccgu                                              24

<210> SEQ ID NO 753
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 753
uuaauccuca cuauggaagu gauu                                              24

<210> SEQ ID NO 754
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 754
acucuuuuuc cggugacagg aaau                                              24

<210> SEQ ID NO 755
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 755
uguuuaaccu cuuuaucacu uuu                                               23

<210> SEQ ID NO 756
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 756
cuucgucucu cuuucaucuc uuc                                               23

<210> SEQ ID NO 757
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 757 aguuuccuc ucuugcuac gacc                                                24

<210> SEQ ID NO 758
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 758 guuucuucc guaauuucu ccu                                                 23
```

<210> SEQ ID NO 759
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 759
cucuaccuga aacuaaagac acu                                           23

<210> SEQ ID NO 760
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 760
ccuuuagguc ccuccaaaac cuu                                           23

<210> SEQ ID NO 761
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 761
uuuccuucuu uaacuuuggg ucu                                           23

<210> SEQ ID NO 762
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 762
caccguccgg guaauguggu ggu                                           23

<210> SEQ ID NO 763
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 763
ucaaauuuaa auauagguuu uauuuaaa                                      28

<210> SEQ ID NO 764
<211> LENGTH: 40
<212> TYPE: RNA
<213> ORGANISM: Artificial Sequence
<220> FEATURE:
<223> OTHER INFORMATION: Antisense fragment coding sequence

<400> SEQUENCE: 764
uucuuuuucu auuuaucuug uguuucuuaa cuguuuuaaa                         40

<210> SEQ ID NO 765
<211> LENGTH: 24
<212> TYPE: RNA
<213> ORGANISM: Artificial Sequence
<220> FEATURE:

<223> OTHER INFORMATION: Antisense fragment coding sequence

<400> SEQUENCE: 765
agauucgcuu cauuguuguu cuca                                              24

<210> SEQ ID NO 766
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 766
uugucuuucu ucguaauaau guaguccgaa ga                                     32

<210> SEQ ID NO 767
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 767
acuaaauaua aaugaccaua uuuuauca                                          28

<210> SEQ ID NO 768
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 768
uuguuuguuu ggucucugug auuccuuuac gu                                     32

<210> SEQ ID NO 769
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 769
uauguuaguu uaacuuaccg ua                                                22

<210> SEQ ID NO 770
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 770
ucuacuguua acacuuuaau uu                                                22

<210> SEQ ID NO 771
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 771
caauauauac ccuuuacuac cuuaauugu                                         29

-continued

```
<210> SEQ ID NO 772
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 772
uuuuuugauu cacuaaguug u                                             21

<210> SEQ ID NO 773
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 773
uuuauguuuu uuauaugacu uauguu                                        26

<210> SEQ ID NO 774
<211> LENGTH: 37
<212> TYPE: RNA
<213> ORGANISM: Artificial Sequence
<220> FEATURE:
<223> OTHER INFORMATION: Antisense fragment coding sequence

<400> SEQUENCE: 774
aaauguaagg accaguugau acuuuacuuu gauaacg                            37

<210> SEQ ID NO 775
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 775
gauguuuuuu uacgauuuuc uu                                            22

<210> SEQ ID NO 776
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 776
uacgacuugu ugaguuucuu uu                                            22

<210> SEQ ID NO 777
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 777
uccuuucacu uuucuaccgu uu                                            22

<210> SEQ ID NO 778
<211> LENGTH: 29
<212> TYPE: RNA
<213> ORGANISM: Artificial Sequence
<220> FEATURE:
<223> OTHER INFORMATION: Antisense fragment coding sequence
```

-continued

<400> SEQUENCE: 778
uuacuccuuu cacuuuucua ccguuuucu                                       29

<210> SEQ ID NO 779
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 779
guucuuuuuu cuaucauagu a                                               21

<210> SEQ ID NO 780
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 780
gguaucuuug uaaacuauug uuacuucuu                                       29

<210> SEQ ID NO 781
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 781
uuucauauau aaaucaaugu ugu                                             23

<210> SEQ ID NO 782
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 782
uacuauuguu guuauuagag aaa                                             23

<210> SEQ ID NO 783
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 783
ugauuaugug uacuauuguu                                                 20

<210> SEQ ID NO 784
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 784
acuauuguug uuauuagaga aacgau                                          26

<210> SEQ ID NO 785
<211> LENGTH: 23

```
<212> TYPE: RNA
<213> ORGANISM: Artificial Sequence
<220> FEATURE:
<223> OTHER INFORMATION: Antisense fragment coding sequence

<400> SEQUENCE: 785
cuuuuccuuu ucuucuaaag aac                                        23

<210> SEQ ID NO 786
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 786
uuacaugucg uagguuauuu uu                                         22

<210> SEQ ID NO 787
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 787
auuaauaaaa cuuaccggug gggUac                                     26

<210> SEQ ID NO 788
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 788
uuaauaaaac uuaccggugg g                                          21

<210> SEQ ID NO 789
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 789
agauauuuau uauauugauu u                                          21

<210> SEQ ID NO 790
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 790
auuuauaucu auuuuauaug uaau                                       24

<210> SEQ ID NO 791
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 791
```

```
uuuacaaaca aauuaaugua ccuaaucau                                    29

<210> SEQ ID NO 792
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 792
uaccaauuau guaaccaaau uaaauau                                       27

<210> SEQ ID NO 793
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 793
uugauauaau uuugaauac aua                                            23

<210> SEQ ID NO 794
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 794
auaucuugua cuuuuuaauu uuaaaag                                       27

<210> SEQ ID NO 795
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 795
aucuguuaua uugauauaau uuu                                           23

<210> SEQ ID NO 796
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 796
uuacaauggu aacaauagau uau                                           23

<210> SEQ ID NO 797
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 797
uccauuuaau uacucucucu uaccucaa                                      28

<210> SEQ ID NO 798
<211> LENGTH: 24
<212> TYPE: RNA
<213> ORGANISM: Artificial Sequence
```

```
<220> FEATURE:
<223> OTHER INFORMATION: Antisense fragment coding sequence

<400> SEQUENCE: 798
auaaaauuuu ccgucauua aucu                                           24

<210> SEQ ID NO 799
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 799
ccuugaacca cguaaaaaaa gau                                           23

<210> SEQ ID NO 800
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 800
uaaaaagaac uaacgaaaag uu                                            22

<210> SEQ ID NO 801
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 801
auaagacuuu uaccauauaa auu                                           23

<210> SEQ ID NO 802
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 802
ucggauaaaa guaacuacgg acu                                           23

<210> SEQ ID NO 803
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 803
aguuguuuau aaauguccgu uuu                                           23

<210> SEQ ID NO 804
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 804
aaucuuuuua ccuuucaua ucu                                            23
```

```
<210> SEQ ID NO 805
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 805
uucucgaguu guuuauaaau guc                                           23

<210> SEQ ID NO 806
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 806
agauuuauaa gucuuacgug aucucuuu                                      28

<210> SEQ ID NO 807
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 807
acuaccccca acugccucaa ccccuca                                       27

<210> SEQ ID NO 808
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 808
ccccuaaccu uuccgagaga cac                                           23

<210> SEQ ID NO 809
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 809
uuuaccucgu cuuucuugug agucc                                         25

<210> SEQ ID NO 810
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 810
accgagcuuc ucguaccucu ccuu                                          24

<210> SEQ ID NO 811
<211> LENGTH: 23
<212> TYPE: RNA
<213> ORGANISM: Artificial Sequence
<220> FEATURE:
<223> OTHER INFORMATION: Antisense fragment coding sequence
```

```
<400> SEQUENCE: 811 uccuucccu aacucucuga gug                                          23

<210> SEQ ID NO 812
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 812
uuuuaucuga ccucuaccgg uacaccucuu cg                               32

<210> SEQ ID NO 813
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 813
gucgcguccc cuucucaccc guccguc                                     27

<210> SEQ ID NO 814
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 814
uuauucuuuu cguuguaaca cuaaaaauua au                               32

<210> SEQ ID NO 815
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 815
auuuuuuuca guuuaaauac uaau                                        24

<210> SEQ ID NO 816
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 816
gaaaccguaa agucacuaag ucguuuu                                     27

<210> SEQ ID NO 817
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 817
uuuacacgag gggaaaggac cu                                          22

<210> SEQ ID NO 818
```

-continued

```
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 818
aaaauuuccu caccacuucu ucuuucu                                          27

<210> SEQ ID NO 819
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 819
uuuauuauau uuacguaagu uga                                              23

<210> SEQ ID NO 820
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 820
ccguccacac caacgaguuc gacauu                                           26

<210> SEQ ID NO 821
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 821
auauuguaaa aggacgaagg uu                                               22

<210> SEQ ID NO 822
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 822
aguaaccuuc uaccucgaga aa                                               22

<210> SEQ ID NO 823
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 823
gucgaaugag aaggagucuc aagaaa                                           26

<210> SEQ ID NO 824
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 824
```
aaauacuuaa gaugucuuua uuacuauuac                                    30

<210> SEQ ID NO 825
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 825
uuucuaauac cuuugaaaag ac                                            22

<210> SEQ ID NO 826
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 826
aacgacaaaa agguuuguga ucu                                           23

<210> SEQ ID NO 827
<211> LENGTH: 34
<212> TYPE: RNA
<213> ORGANISM: Artificial Sequence
<220> FEATURE:
<223> OTHER INFORMATION: Antisense fragment coding sequence

<400> SEQUENCE: 827 caguagguu uauaaccuuc uucgucuuca auua                                34

<210> SEQ ID NO 828
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 828
uacaccucug uaaggucgug ucuccuuug                                     29

<210> SEQ ID NO 829
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 829
aguccgaguu cacuagagag uaaagu                                        26

<210> SEQ ID NO 830
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 830
aauauaacuu caaauacuuc aac                                           23

<210> SEQ ID NO 831
<211> LENGTH: 22
<212> TYPE: RNA

```
<213> ORGANISM: Artificial Sequence
<220> FEATURE:
<223> OTHER INFORMATION: Antisense fragment coding sequence

<400> SEQUENCE: 831
ucuauauccu uacacagacu uu                                              22

<210> SEQ ID NO 832
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 832
uuuucaguuc uuuuaauuua aauau                                           25

<210> SEQ ID NO 833
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 833
auacggacua uuaaaaagua acc                                             23

<210> SEQ ID NO 834
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 834
uauuuccuuu ucaguucuuu uaa                                             23

<210> SEQ ID NO 835
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 835
ucucucucuc uuuucuuuua ac                                              22

<210> SEQ ID NO 836
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 836
auacggacua uuaaaaagua ac                                              22

<210> SEQ ID NO 837
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 837
gacacaaaag aggaucuuac agu                                             23
```

<210> SEQ ID NO 838
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 838
uuucuguccu aaaguaauaa acau                                          24

<210> SEQ ID NO 839
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 839
accuacacuc uuuaugaacc cu                                            22

<210> SEQ ID NO 840
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 840
uuuucugucc uaaaguaaua aa                                            22

<210> SEQ ID NO 841
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 841
uuuucugucc uaaaguaaua aacaua                                        26

<210> SEQ ID NO 842
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 842
cuguccuaaa guaauaaaca ua                                            22

<210> SEQ ID NO 843
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 843
ucaagagaaa acuguaaaac aag                                           23

<210> SEQ ID NO 844
<211> LENGTH: 21
<212> TYPE: RNA
<213> ORGANISM: Artificial Sequence
<220> FEATURE:

```
<223> OTHER INFORMATION: Antisense fragment coding sequence

<400> SEQUENCE: 844
acuguaaaac aagaaagaaa c                                              21

<210> SEQ ID NO 845
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 845
cuuuuacaac agguuguuag guuaguu                                        27

<210> SEQ ID NO 846
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 846
ccuucuuuuc uguaauuuga uuaa                                           24

<210> SEQ ID NO 847
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 847
auuagaagau auucagauca uuu                                            23

<210> SEQ ID NO 848
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 848
guccuuagga acaucacuac ccuaaca                                        27

<210> SEQ ID NO 849
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 849
auauaaguua ccguuuucuu uuguuua                                        27

<210> SEQ ID NO 850
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 850
uuacggaauu agagucuauu aaacaauu                                       28
```

-continued

```
<210> SEQ ID NO 851
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 851
auuaaacaau uacuucuuau uuuaauu                                          27

<210> SEQ ID NO 852
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 852
uuguucaaag aggaauagua uuu                                              23

<210> SEQ ID NO 853
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 853
guaucauaga gaauauuagg aaaaguaaa                                        29

<210> SEQ ID NO 854
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 854
uaucauagag aauauuagga aaaguaaa                                         28

<210> SEQ ID NO 855
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 855 auguuguac ccguuaaguu uuag                                              24

<210> SEQ ID NO 856
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 856
cgagaagaaa ggaauuguuu aca                                              23

<210> SEQ ID NO 857
<211> LENGTH: 23
<212> TYPE: RNA
<213> ORGANISM: Artificial Sequence
<220> FEATURE:
<223> OTHER INFORMATION: Antisense fragment coding sequence
```

```
<400> SEQUENCE: 857
acaauuugug aaagaaagga aaa                                              23

<210> SEQ ID NO 858
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 858
uaucauagag aauauuagga aaa                                              23

<210> SEQ ID NO 859
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 859
uguugacuuu guuacguucc uua                                              23

<210> SEQ ID NO 860
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 860
caaguucccg guuaauauag ugu                                              23

<210> SEQ ID NO 861
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 861
auauuuuaaa agaguccaga ua                                               22

<210> SEQ ID NO 862
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 862
ucuuuaaguc cuuuuaccuu uuu                                              23

<210> SEQ ID NO 863
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 863
guguuucgag uucgugcaua aca                                              23

<210> SEQ ID NO 864
<211> LENGTH: 25
```

```
<212> TYPE: RNA
<213> ORGANISM: Artificial Sequence
<220> FEATURE:
<223> OTHER INFORMATION: Antisense fragment coding sequence

<400> SEQUENCE: 864
gaacaaaaga aagggaaaga aagac                                    25

<210> SEQ ID NO 865
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 865
aaagaaaggg aaagaaagac gaaaga                                   26

<210> SEQ ID NO 866
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 866
aaaagaaagg gaaagaaaga cgaaagaga                                29

<210> SEQ ID NO 867
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 867
aaagaaaggg aaagaaagac gaa                                      23

<210> SEQ ID NO 868
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 868
aaagaaaggg aaagaaagac gaaaga                                   26

<210> SEQ ID NO 869
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 869
uauaccuaca ucuaaaguaa ac                                       22

<210> SEQ ID NO 870
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 870
```
aaaagaaagg gaaagaaaga cgaaaga                                          27

<210> SEQ ID NO 871
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 871
uguagaaaug uuacaccuau aaagaag                                          27

<210> SEQ ID NO 872
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 872
aaguauguaa gauuugaauu aaggucua                                         28

<210> SEQ ID NO 873
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 873
cugauguucu cuuccuaccg ucu                                              23

<210> SEQ ID NO 874
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 874
uuaccgucaa uacuuauaua au                                               22

<210> SEQ ID NO 875
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 875
uuccaacaua aaauaauaaa uu                                               22

<210> SEQ ID NO 876
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 876
ggaaaaagga aaaguaguga aaaaaa                                           26

<210> SEQ ID NO 877
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 877
guccuuuuuu uaccuaugau uu                                    22

<210> SEQ ID NO 878
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 878
uaauaaaaua uuaguaauag auuaau                                26

<210> SEQ ID NO 879
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 879
auauauauac guucaucgua uauauau                               27

<210> SEQ ID NO 880
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 880
acaaucuaaa gaacaguaaa aaagg                                 25

<210> SEQ ID NO 881
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 881
ggugucguug uaccaaaguc aua                                   23

<210> SEQ ID NO 882
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 882
gaacaauuca ugaacuauag aca                                   23

<210> SEQ ID NO 883
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 883
uaagagaaua auacuuauuu cgu                                   23

```
<210> SEQ ID NO 884
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 884
ucucucuuuc uuucucuuaa ccccuca                                        27

<210> SEQ ID NO 885
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 885
uauaccuaca ucuaaaguaa ac                                             22

<210> SEQ ID NO 886
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 886
uuguagaaua aaggaagaaa ag                                             22

<210> SEQ ID NO 887
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 887
aaaaaucggg aacguuucuu ga                                             22

<210> SEQ ID NO 888
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 888
gaaguaauuc acaaaaauag ccuucagu                                       28

<210> SEQ ID NO 889
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 889
acgggacuga aguguccggu aaa                                            23

<210> SEQ ID NO 890
<211> LENGTH: 31
<212> TYPE: RNA
<213> ORGANISM: Artificial Sequence
<220> FEATURE:
<223> OTHER INFORMATION: Antisense fragment coding sequence
```

-continued

<400> SEQUENCE: 890
uaauagaauu cuuucuaauu ucuucuuaaa c                                    31

<210> SEQ ID NO 891
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 891
aguuucguuu uauccaaguc ucg                                             23

<210> SEQ ID NO 892
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 892
uugaaaaaua acuaggucac gagu                                            24

<210> SEQ ID NO 893
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 893
ucuauagaaa guuuuuaaa guu                                              23

<210> SEQ ID NO 894
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 894
uacguauguu guuacccuua caguaaa                                         27

<210> SEQ ID NO 895
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 895
uaacaaauau aaauaaaagu aaa                                             23

<210> SEQ ID NO 896
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 896
guuguauuuu uuaguuggua uaa                                             23

<210> SEQ ID NO 897

```
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 897
aggagaaaag aaaaggaaag aggaagaaa                                            29

<210> SEQ ID NO 898
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 898
gucuuuucgu cauacucuuc cu                                                   22

<210> SEQ ID NO 899
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 899
aacggacccc uuuccuccgu ca                                                   22

<210> SEQ ID NO 900
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 900
agaaaagaaa aggaaagagg aagaaa                                               26

<210> SEQ ID NO 901
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 901 agaaagaaa aggaaagagg aagaaa                                                26

<210> SEQ ID NO 902
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 902
caggagaaaa gaaaaggaaa gaggaagaaa                                           30

<210> SEQ ID NO 903
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 903
```
gaaaagaaaa ggaaagagga ag                                    22

<210> SEQ ID NO 904
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 904
gagaaaagaa aaggaaagag gaagaa                                26

<210> SEQ ID NO 905
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 905
aauuauucuu augucuaaau aa                                    22

<210> SEQ ID NO 906
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 906
agagacucaa ucuuuuacuc uuuca                                 25

<210> SEQ ID NO 907
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 907
gaaacguaau uuuuuacaca aacu                                  24

<210> SEQ ID NO 908
<211> LENGTH: 31
<212> TYPE: RNA
<213> ORGANISM: Artificial Sequence
<220> FEATURE:
<223> OTHER INFORMATION: Antisense fragment coding sequence

<400> SEQUENCE: 908
aaaauauaca gaucuuuuga aucugugaua u                          31

<210> SEQ ID NO 909
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 909
gauguccuac aucuaaaacu uuuau                                 25

<210> SEQ ID NO 910
<211> LENGTH: 31
<212> TYPE: RNA

```
<213> ORGANISM: Artificial Sequence
<220> FEATURE:
<223> OTHER INFORMATION: Antisense fragment coding sequence

<400> SEQUENCE: 910
agaaacauaa gaccgaaagg aagaaaccaa c                              31

<210> SEQ ID NO 911
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 911
ucuucugugu uuuuuacac aauuguguuu ug                              32

<210> SEQ ID NO 912
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 912
agucacaaaa gacugagguu ucaa                                      24

<210> SEQ ID NO 913
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 913
augguucuuu uacuucuucc gagaagacu                                 29

<210> SEQ ID NO 914
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 914
aaaugaacga auacauugga auaaaa                                    26

<210> SEQ ID NO 915
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 915
aaagagauaa aagagaacaa aauuug                                    26

<210> SEQ ID NO 916
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 916
uucuacugau agauuuuaca gucc                                      24
```

<210> SEQ ID NO 917
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 917
uaagugacgg aagaagggag agu                                              23

<210> SEQ ID NO 918
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 918
gacagacgau uggucauacu ugu                                              23

<210> SEQ ID NO 919
<211> LENGTH: 23
<212> TYPE: DNA
<213> ORGANISM: Artificial Sequence
<220> FEATURE:
<223> OTHER INFORMATION: Antisense fragment coding sequence

<400> SEQUENCE: 919
ucuuucaaga uaguuctttt ttt                                              23

<210> SEQ ID NO 920
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 920
aaaguuuaag gaagagucuu aag                                              23

<210> SEQ ID NO 921
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 921
uaaaacaugu cuuccaaaag uauu                                             24

<210> SEQ ID NO 922
<211> LENGTH: 33
<212> TYPE: RNA
<213> ORGANISM: Artificial Sequence
<220> FEATURE:
<223> OTHER INFORMATION: Antisense fragment coding sequence

<400> SEQUENCE: 922
uaacuaaucu uuaaguugaa ccuuuuagu uac                                    33

<210> SEQ ID NO 923
<211> LENGTH: 27
<212> TYPE: RNA
<213> ORGANISM: Artificial Sequence
<220> FEATURE:

```
<223> OTHER INFORMATION: Antisense fragment coding sequence

<400> SEQUENCE: 923
ccuacagaaa cagaaagaaa aagaaac                                           27

<210> SEQ ID NO 924
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 924
ugugguuucc cuuugaguga cugucuuuug                                        30

<210> SEQ ID NO 925
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 925
cugugucuac uucuuugaag gaaa                                              24

<210> SEQ ID NO 926
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 926
auguuggguu cucucgaauu ug                                                22

<210> SEQ ID NO 927
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 927
uuucuuacuu cauuuccagu cgu                                               23

<210> SEQ ID NO 928
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 928
cacgauaacu agucugauua au                                                22

<210> SEQ ID NO 929
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 929
cgaccugaca ccacugucgg ag                                                22
```

```
<210> SEQ ID NO 930
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 930
guuggagacg uguuuuacuc ga                                          22

<210> SEQ ID NO 931
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 931
uguuaccucg uacguuccuu cgu                                         23

<210> SEQ ID NO 932
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 932
aucguccauc auagguucug ucucug                                      26

<210> SEQ ID NO 933
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 933
uuuuacgacu ccuauacccg uu                                          22

<210> SEQ ID NO 934
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 934
guuauugguu ucucuuuuuu cuu                                         23

<210> SEQ ID NO 935
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 935
uuaguaccuu caacaaaagg ggu                                         23

<210> SEQ ID NO 936
<211> LENGTH: 22
<212> TYPE: RNA
<213> ORGANISM: Artificial Sequence
<220> FEATURE:
<223> OTHER INFORMATION: Antisense fragment coding sequence
```

```
<400> SEQUENCE: 936
uucguugguc cucuaaccaa gu                                          22

<210> SEQ ID NO 937
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 937
uacguugacu cuagucucgu ag                                          22

<210> SEQ ID NO 938
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 938
ggucuccugu ucucgagaac aa                                          22

<210> SEQ ID NO 939
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 939
cuccugcucu acccaccuag uucu                                        24

<210> SEQ ID NO 940
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 940
cuccugcucu acccaccuag uucuccag                                    28

<210> SEQ ID NO 941
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 941
aaccgaguaa gagacaaaaa aaacaaaaaa aa                               32

<210> SEQ ID NO 942
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 942
cuccugcucu acccaccuag uucuccag                                    28

<210> SEQ ID NO 943
<211> LENGTH: 28
```

```
<212> TYPE: RNA
<213> ORGANISM: Artificial Sequence
<220> FEATURE:
<223> OTHER INFORMATION: Antisense fragment coding sequence

<400> SEQUENCE: 943
gaguaagaga caaaaaaaac aaaaaaaa                                          28

<210> SEQ ID NO 944
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 944
gaaauaagau uuuauaaaaa uuua                                              24

<210> SEQ ID NO 945
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 945
uacucggguu cugaagaaaa cua                                               23

<210> SEQ ID NO 946
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 946
uucuuugaca cuaaaaauua ugaau                                             25

<210> SEQ ID NO 947
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 947
uucuuacuau uucguuucuu uu                                                22

<210> SEQ ID NO 948
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 948
augaaaauuu cuacguacga aaguaa                                            26

<210> SEQ ID NO 949
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 949
```

-continued aaauuuuuua cuauucuuau uu         22

<210> SEQ ID NO 950
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 950
ucuuacuauu ucguuucuuu uacauc         26

<210> SEQ ID NO 951
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 951
augacuagag guugagucuu cu         22

<210> SEQ ID NO 952
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 952
uuuuaaacuu ucuuacuauu ucguuu         26

<210> SEQ ID NO 953
<211> LENGTH: 33
<212> TYPE: RNA
<213> ORGANISM: Artificial Sequence
<220> FEATURE:
<223> OTHER INFORMATION: Antisense fragment coding sequence

<400> SEQUENCE: 953
uuuuuacuua cuuuuauacg uaagagaagu uuu         33

<210> SEQ ID NO 954
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 954
uuucguucuu uuuacuuacu uuu         23

<210> SEQ ID NO 955
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 955
guucuuuuua cuuacuuuua ua         22

<210> SEQ ID NO 956
<211> LENGTH: 24
<212> TYPE: RNA
<213> ORGANISM: Artificial Sequence

```
<220> FEATURE:
<223> OTHER INFORMATION: Antisense fragment coding sequence

<400> SEQUENCE: 956
uccucuuuag uuuguuuug guau                                          24

<210> SEQ ID NO 957
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 957
cguaaguuau uuauguacga c                                            21

<210> SEQ ID NO 958
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 958
uacauucuug acauuuauau u                                            21

<210> SEQ ID NO 959
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 959
uuuuguuuug guauuuucau c                                            21

<210> SEQ ID NO 960
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 960
uuuccucuuu aguuuuguuu ugguauuuu                                    29

<210> SEQ ID NO 961
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 961
aucccucgag gggugagggc aaaacacug                                    29

<210> SEQ ID NO 962
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 962
auauaguuuu cuuuuacuuu aguu                                         24
```

```
<210> SEQ ID NO 963
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 963
cuaauuuaaa uauaguuuc uuuuacuu                                              28

<210> SEQ ID NO 964
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 964
auauaguuuu cuuuuacuuu aguuau                                               26

<210> SEQ ID NO 965
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 965
uuucuuuuac uuuaguuauc aacuccu                                              27

<210> SEQ ID NO 966
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 966
auauaguuuu cuuuuacuuu aguuauc                                              27

<210> SEQ ID NO 967
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 967
uacugguuua cauaucuaac ucu                                                  23

<210> SEQ ID NO 968
<211> LENGTH: 34
<212> TYPE: RNA
<213> ORGANISM: Artificial Sequence
<220> FEATURE:
<223> OTHER INFORMATION: Antisense fragment coding sequence

<400> SEQUENCE: 968
auauaguuuu cuuuuacuuu aguuaucaac uccu                                      34

<210> SEQ ID NO 969
<211> LENGTH: 26
<212> TYPE: RNA
<213> ORGANISM: Artificial Sequence
<220> FEATURE:
<223> OTHER INFORMATION: Antisense fragment coding sequence
```

```
<400> SEQUENCE: 969
auauaguuuu cuuuuacuuu aguuau                                    26

<210> SEQ ID NO 970
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 970
aacuuuauuc uucuaaucua uaaaaauuaa                                30

<210> SEQ ID NO 971
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 971
acuauaguaa aaguuaaugu au                                        22

<210> SEQ ID NO 972
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 972
uucuuuuucu ucuaucguuc uu                                        22

<210> SEQ ID NO 973
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 973
ucgauuucaa accauccuuu uguu                                      24

<210> SEQ ID NO 974
<211> LENGTH: 31
<212> TYPE: RNA
<213> ORGANISM: Artificial Sequence
<220> FEATURE:
<223> OTHER INFORMATION: Antisense fragment coding sequence

<400> SEQUENCE: 974
uuuaguucau uuuauuguua uuuacuguau g                              31

<210> SEQ ID NO 975
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 975
guaauuuaaa uauguuuguu uguguuu                                   27

<210> SEQ ID NO 976
```

```
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 976
ucgauuucaa accauccuuu uguu                                              24

<210> SEQ ID NO 977
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 977
cuuuauaugg uauauuuaua cuaca                                             25

<210> SEQ ID NO 978
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 978
uuuauucuag ucuuaaaaua aau                                               23

<210> SEQ ID NO 979
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 979
ucuuaauaua auuaugucau au                                                22

<210> SEQ ID NO 980
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 980
ucguaauuuu guaacuuua uaauuuauuc                                         30

<210> SEQ ID NO 981
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 981
ucuuaauaua auuaugucau auauca                                            26

<210> SEQ ID NO 982
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 982
```

```
cuucuuaaua aguguaauua uu                                                    22

<210> SEQ ID NO 983
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 983
cuucuuguuu gauaauuauu aa                                                    22

<210> SEQ ID NO 984
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 984
auucuagucu uaaaauaaau aaugau                                                26

<210> SEQ ID NO 985
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 985
auuugguuug uaaaaaggaa ua                                                    22

<210> SEQ ID NO 986
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 986
uaaaauuuug ugaauuuuua aa                                                    22

<210> SEQ ID NO 987
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 987
guuauaaaga cgacaaguua aguuacc                                               27

<210> SEQ ID NO 988
<211> LENGTH: 33
<212> TYPE: RNA
<213> ORGANISM: Artificial Sequence
<220> FEATURE:
<223> OTHER INFORMATION: Antisense fragment coding sequence

<400> SEQUENCE: 988
aaaaaaccca aaacaaacac aacuaugaaa cuc                                        33

<210> SEQ ID NO 989
<211> LENGTH: 28
<212> TYPE: RNA
```

<213> ORGANISM: Artificial Sequence
<220> FEATURE:
<223> OTHER INFORMATION: Antisense fragment coding sequence

<400> SEQUENCE: 989 cguuaaaua gaauuuaagu ucauguau                28

<210> SEQ ID NO 990
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 990
auugucugaa ccuuuuaug uuaa                24

<210> SEQ ID NO 991
<211> LENGTH: 37
<212> TYPE: RNA
<213> ORGANISM: Artificial Sequence
<220> FEATURE:
<223> OTHER INFORMATION: Antisense fragment coding sequence

<400> SEQUENCE: 991
uaauggaagu uuuagaucu ugaaauaauu aagaguc                37

<210> SEQ ID NO 992
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 992
uuuuaauuuu uguuuuacu uucc                24

<210> SEQ ID NO 993
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 993
gaauaaaaua cagaagaaac aacaaaaa                28

<210> SEQ ID NO 994
<211> LENGTH: 33
<212> TYPE: RNA
<213> ORGANISM: Artificial Sequence
<220> FEATURE:
<223> OTHER INFORMATION: Antisense fragment coding sequence

<400> SEQUENCE: 994
uaauaauugu ugaauaaaaa uaaauuagaa aau                33

<210> SEQ ID NO 995
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 995
uauuucuucu uauaauugua acuguaau                28

-continued

```
<210> SEQ ID NO 996
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 996
aauacuuaca aaauaguacu aauuucua                                              28

<210> SEQ ID NO 997
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 997
gggucguguc ucuacaguaa cu                                                    22

<210> SEQ ID NO 998
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 998
ucacucuuua cuacuacaac uagucu                                                26

<210> SEQ ID NO 999
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 999
aagauuccuu ucguuggucu uc                                                    22

<210> SEQ ID NO 1000
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1000
acucguucuu cuuuaggaug ua                                                    22

<210> SEQ ID NO 1001
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1001
ccuuacucuu cuuucgauuu aa                                                    22

<210> SEQ ID NO 1002
<211> LENGTH: 22
<212> TYPE: RNA
<213> ORGANISM: Artificial Sequence
<220> FEATURE:
```

```
<223> OTHER INFORMATION: Antisense fragment coding sequence

<400> SEQUENCE: 1002
aaucuuuaca gaauucguaa cg                                              22

<210> SEQ ID NO 1003
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1003
guccuguaac uuuuacuucu cuuc                                            24

<210> SEQ ID NO 1004
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1004
uucucuuucu ggacugguuu cu                                              22

<210> SEQ ID NO 1005
<211> LENGTH: 28
<212> TYPE: RNA
<213> ORGANISM: Artificial Sequence
<220> FEATURE:
<223> OTHER INFORMATION: Antisense fragment coding sequence

<400> SEQUENCE: 1005
ugauucagua uauuuuaug uucuuuuu                                         28

<210> SEQ ID NO 1006
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 1006
uuguuaaacu caacuaucug uuacuua                                         27

<210> SEQ ID NO 1007
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 1007
uaguacaaag uaugaagauc gguaac                                          26

<210> SEQ ID NO 1008
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1008
cuuuguauga uucuuguguc cuu                                             23
```

```
<210> SEQ ID NO 1009
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1009
aaagugguaa uggaagagaa gg                                                22

<210> SEQ ID NO 1010
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 1010
uccuucguuu uaauuugucu cuucuuu                                           27

<210> SEQ ID NO 1011
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1011
accuuuuacu uucuugaaac cu                                                22

<210> SEQ ID NO 1012
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 1012
uuuuguugug aacccauuua gucugu                                            26

<210> SEQ ID NO 1013
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1013
cgacgaccug ucagucacca aa                                                22

<210> SEQ ID NO 1014
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 1014
ccuaguucuu ucuucucaag agacucu                                           27

<210> SEQ ID NO 1015
<211> LENGTH: 22
<212> TYPE: RNA
<213> ORGANISM: Artificial Sequence
<220> FEATURE:
<223> OTHER INFORMATION: Antisense fragment coding sequence
```

```
<400> SEQUENCE: 1015
ccccucugug uguuuaaguc ug                                        22

<210> SEQ ID NO 1016
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 1016
ugguuuacuu uugggucgag uguucucagu                                30

<210> SEQ ID NO 1017
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1017
uuuacucuua caccuuuggu ac                                        22

<210> SEQ ID NO 1018
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1018
ucuuuauucc ucucaaaccg cg                                        22

<210> SEQ ID NO 1019
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1019
ucuucucauc ugccuuucac cu                                        22

<210> SEQ ID NO 1020
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 1020
cuguaagaaa ccgaccuuuc ucggauu                                   27

<210> SEQ ID NO 1021
<211> LENGTH: 32
<212> TYPE: RNA
<213> ORGANISM: Artificial Sequence
<220> FEATURE:
<223> OTHER INFORMATION: Antisense fragment coding sequence

<400> SEQUENCE: 1021
cuucucucgu cccguucuua guuugaucc ga                              32

<210> SEQ ID NO 1022
<211> LENGTH: 22
```

```
<212> TYPE: RNA
<213> ORGANISM: Artificial Sequence
<220> FEATURE:
<223> OTHER INFORMATION: Antisense fragment coding sequence

<400> SEQUENCE: 1022
ucccguucga aaggguuuac ag                                             22

<210> SEQ ID NO 1023
<211> LENGTH: 34
<212> TYPE: RNA
<213> ORGANISM: Artificial Sequence
<220> FEATURE:
<223> OTHER INFORMATION: Antisense fragment coding sequence

<400> SEQUENCE: 1023
ccuguacuaa ggucucuccu uacuuguucc uguu                                34

<210> SEQ ID NO 1024
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1024
ccuuuaacac uuuuaaguua cc                                             22

<210> SEQ ID NO 1025
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1025
cucagaugua agagucaaaa cag                                            23

<210> SEQ ID NO 1026
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1026
cucugucugu cauuccuuu ua                                              22

<210> SEQ ID NO 1027
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1027
acuucuuuuu gauucuuuu uu                                              22

<210> SEQ ID NO 1028
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1028
```
ggucugucgu cugaccuucc gu                                              22

<210> SEQ ID NO 1029
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1029
uuguccuuua guauaacuua aaca                                            24

<210> SEQ ID NO 1030
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 1030 ucaucguac cuuucuaaaa gaauuac                                          27

<210> SEQ ID NO 1031
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1031
gucucaaacu uaaaauacua guc                                             23

<210> SEQ ID NO 1032
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1032
acucccauug uaaauuaaaa ccc                                             23

<210> SEQ ID NO 1033
<211> LENGTH: 27
<212> TYPE: RNA
<213> ORGANISM: Artificial Sequence
<220> FEATURE:
<223> OTHER INFORMATION: Antisense fragment coding sequence

<400> SEQUENCE: 1033
aaaaaagaaa aacucuuucc cgaagua                                         27

<210> SEQ ID NO 1034
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1034
ucuuuuguug uccacaacua cuc                                             23

<210> SEQ ID NO 1035
<211> LENGTH: 23
<212> TYPE: RNA
<213> ORGANISM: Artificial Sequence -continued

```
<220> FEATURE:
<223> OTHER INFORMATION: Antisense fragment coding sequence

<400> SEQUENCE: 1035
aaaaaagaaa aacucuuucc cga                                           23

<210> SEQ ID NO 1036
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1036
uuuacuuucu aaaggucuuu aac                                           23

<210> SEQ ID NO 1037
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 1037
uguugucuau guuguuuacg accacucuua                                    30

<210> SEQ ID NO 1038
<211> LENGTH: 30
<212> TYPE: RNA
<213> ORGANISM: Artificial Sequence
<220> FEATURE:
<223> OTHER INFORMATION: Antisense fragment coding sequence

<400> SEQUENCE: 1038
uguugucuau guuguuuacg accacucuua                                    30

<210> SEQ ID NO 1039
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1039
uacucucuag aaccccacc cug                                            23

<210> SEQ ID NO 1040
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 1040
gguuacauaa auauguaaau guucau                                        26

<210> SEQ ID NO 1041
<211> LENGTH: 29
<212> TYPE: RNA
<213> ORGANISM: Artificial Sequence
<220> FEATURE:
<223> OTHER INFORMATION: Antisense fragment coding sequence

<400> SEQUENCE: 1041
uucaaguuac ucuuucucuu aucuauacc                                     29
```

```
<210> SEQ ID NO 1042
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1042
augaauguac gguuuagagu u                                              21

<210> SEQ ID NO 1043
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1043
ucaaguuacu cuuucucuua u                                              21

<210> SEQ ID NO 1044
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1044
auguaugaua auuacacuaa au                                             22

<210> SEQ ID NO 1045
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1045
aaaacaggaa gguuaacaca ac                                             22

<210> SEQ ID NO 1046
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1046
cuucgucucu cuuucaucuc uuc                                            23

<210> SEQ ID NO 1047
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1047 aguuuccuc ucuugucuac gacc                                            24

<210> SEQ ID NO 1048
<211> LENGTH: 23
<212> TYPE: RNA
<213> ORGANISM: Artificial Sequence
<220> FEATURE:
<223> OTHER INFORMATION: Antisense fragment coding sequence
```

<400> SEQUENCE: 1048
agggaccuac cguucgucuu cgu                                           23

<210> SEQ ID NO 1049
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1049
guccuguaac uuuuacuucu cuuc                                          24

<210> SEQ ID NO 1050
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1050
uuguucucgu ccggucacac cacc                                          24

<210> SEQ ID NO 1051
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1051
aacuccuuuu cccuugggac augu                                          24

<210> SEQ ID NO 1052
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1052
gguccgugac ccuucaguca ccgu                                          24

<210> SEQ ID NO 1053
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1053
uuaauccuca cuauggaagu gauu                                          24

<210> SEQ ID NO 1054
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1054
acucuuuuuc cggugacagg aaau                                          24

<210> SEQ ID NO 1055

-continued

```
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1055
uguuuaaccu cuuuaucacu uuu                                              23

<210> SEQ ID NO 1056
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1056
auaaucuuua uugggauac u                                                 21

<210> SEQ ID NO 1057
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1057 uuccuucuu uaacuuuggg ucu                                               23

<210> SEQ ID NO 1058
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1058
cuacaguagu ucuuacgucu acg                                              23

<210> SEQ ID NO 1059
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1059
uguuuucuac gucuuucucc guuc                                             24

<210> SEQ ID NO 1060
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1060
uuacaauaac ucauauaucu cucu                                             24

<210> SEQ ID NO 1061
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 1061
```

```
guaaacuacu agaccguaag guuga                                          25

<210> SEQ ID NO 1062
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1062
cuucccuccg acuaggucuu guca                                           24

<210> SEQ ID NO 1063
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1063
ccguguugac cucaccucag acga                                           24

<210> SEQ ID NO 1064
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1064 guuucuuuu cuucuucuc gag                                              23

<210> SEQ ID NO 1065
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1065
agguuuaacg aaguuuacuu uu                                             22

<210> SEQ ID NO 1066
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1066
uuaacauguu uuugggacua ug                                             22

<210> SEQ ID NO 1067
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1067
uacuccuuac cucccuuauc ga                                             22

<210> SEQ ID NO 1068
<211> LENGTH: 22
<212> TYPE: RNA
```

```
<213> ORGANISM: Artificial Sequence
<220> FEATURE:
<223> OTHER INFORMATION: Antisense fragment coding sequence

<400> SEQUENCE: 1068
uaacgaggaa acgaccuacc ua                                    22

<210> SEQ ID NO 1069
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1069
aagguuagac uuacuacguu gu                                    22

<210> SEQ ID NO 1070
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1070
auuuucgacg uaguuaucca ca                                    22

<210> SEQ ID NO 1071
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1071
cccucuaacu agguuuuguc gu                                    22

<210> SEQ ID NO 1072
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1072 uccccuucg ggucuaggac cu                                     22

<210> SEQ ID NO 1073
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1073
acggucucuc cucugugugu uu                                    22

<210> SEQ ID NO 1074
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1074
cucuuuccuu ucaccuguug u                                     21
```

<210> SEQ ID NO 1075
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 1075 guauguugu uguuauuauu gacuu                                       25

<210> SEQ ID NO 1076
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1076
uccuucccuu uuauguuuuu ua                                         22

<210> SEQ ID NO 1077
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1077
cuccuuuacu cuucuuccga u                                          21

<210> SEQ ID NO 1078
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1078
gaccucgacg accucgucgu c                                          21

<210> SEQ ID NO 1079
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1079
agaguuugaa cgucaaccag                                            20

<210> SEQ ID NO 1080
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1080
aacugauacc cucacuacaa a                                          21

<210> SEQ ID NO 1081
<211> LENGTH: 21
<212> TYPE: RNA
<213> ORGANISM: Artificial Sequence
<220> FEATURE:

<223> OTHER INFORMATION: Antisense fragment coding sequence

<400> SEQUENCE: 1081
ucaaacuuaa guaacgacuu c                                              21

<210> SEQ ID NO 1082
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1082
cuuuuuguuc uaaagagggu cac                                            23

<210> SEQ ID NO 1083
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1083
ugucccacua ccacaggggg                                                20

<210> SEQ ID NO 1084
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1084
uuuaccuggu guugugucu uug                                             23

<210> SEQ ID NO 1085
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1085
uacagaagaa guuagugaag uug                                            23

<210> SEQ ID NO 1086
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1086
augacgauuc cuucguguuc uac                                            23

<210> SEQ ID NO 1087
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1087
uuuuuaacuu ugcuuguuua ag                                             22

-continued

```
<210> SEQ ID NO 1088
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1088
uuauuuaugu uguaauggga aa                                                  22

<210> SEQ ID NO 1089
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1089
uucguucuaa uuuuucucuc cu                                                  22

<210> SEQ ID NO 1090
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1090
aaucucguag acaaccuucu ua                                                  22

<210> SEQ ID NO 1091
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1091
uugucuccga cuuguucucc u                                                   21

<210> SEQ ID NO 1092
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1092
acgucuuccu uguccuugcc g                                                   21

<210> SEQ ID NO 1093
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1093
uaacauaccu guguuaaucu uug                                                 23

<210> SEQ ID NO 1094
<211> LENGTH: 23
<212> TYPE: RNA
<213> ORGANISM: Artificial Sequence
<220> FEATURE:
<223> OTHER INFORMATION: Antisense fragment coding sequence
```

```
<400> SEQUENCE: 1094
uacucuuugc acggacucuu ugu                                          23

<210> SEQ ID NO 1095
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1095 acaaagaag acagacuucu                                               20

<210> SEQ ID NO 1096
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1096
guauauuaau cguaguguua                                              20

<210> SEQ ID NO 1097
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1097
uguuuagucg ucaaacuuga cuau                                         24

<210> SEQ ID NO 1098
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1098
cuuucuccau uuaauuuuuc                                              20

<210> SEQ ID NO 1099
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1099
uucaucgucc gagugagacg                                              20

<210> SEQ ID NO 1100
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1100
ucuuccucuc uuccuuuuac c                                            21

<210> SEQ ID NO 1101
<211> LENGTH: 20
```

```
<212> TYPE: RNA
<213> ORGANISM: Artificial Sequence
<220> FEATURE:
<223> OTHER INFORMATION: Antisense fragment coding sequence

<400> SEQUENCE: 1101
uguuuaugga cgucuuuacg                                                    20

<210> SEQ ID NO 1102
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1102
uuacuuaguu guucuuucuu uu                                                 22

<210> SEQ ID NO 1103
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1103
uuacuuaguu guucuuucuu                                                    20

<210> SEQ ID NO 1104
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1104
cucuuacuuc ucuuuugagg                                                    20

<210> SEQ ID NO 1105
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1105
uaagucacuu uaaccuuuua                                                    20

<210> SEQ ID NO 1106
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1106
ucuuuaugug guucggugu au                                                  22

<210> SEQ ID NO 1107
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1107
```

```
gaacuugaau cuucgucuau a                                              21

<210> SEQ ID NO 1108
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1108
uguuacgaua guuaacauua g                                              21

<210> SEQ ID NO 1109
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1109
uguuacgaua guuaacauua                                                20

<210> SEQ ID NO 1110
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1110
cuugaagucc uguaucuuuu a                                              21

<210> SEQ ID NO 1111
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1111
cggaaggaaa ggucuuacac                                                20

<210> SEQ ID NO 1112
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1112
cuauacugaa acuuucccuc                                                20

<210> SEQ ID NO 1113
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1113
uccccaaccu uaccgacguc                                                20

<210> SEQ ID NO 1114
<211> LENGTH: 24
<212> TYPE: RNA
<213> ORGANISM: Artificial Sequence
```

```
<220> FEATURE:
<223> OTHER INFORMATION: Antisense fragment coding sequence

<400> SEQUENCE: 1114
gucucaucuu acguuagag gagu                                          24

<210> SEQ ID NO 1115
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1115
aaggacgaaa ugguauuacu gacu                                         24

<210> SEQ ID NO 1116
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1116
aaaguauuac agucguuuau acgu                                         24

<210> SEQ ID NO 1117
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1117
ccagauguuu uguaugaaac ucuu                                         24

<210> SEQ ID NO 1118
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 1118
guuuuaaucu cucugucuuu uaucu                                        25

<210> SEQ ID NO 1119
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1119
cuucguuuug acaaacacga                                              20

<210> SEQ ID NO 1120
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1120
aacaaaaaua caccucgauu agu                                          23
```

```
<210> SEQ ID NO 1121
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1121
guguuuccug uuauccuuuc uuu                                              23

<210> SEQ ID NO 1122
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1122
auuucuuuaa cuuagucauu uauu                                             24

<210> SEQ ID NO 1123
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1123
ucacucugug ucccuugucu cuuu                                             24

<210> SEQ ID NO 1124
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1124
guauacuuuc uuacacguug uag                                              23

<210> SEQ ID NO 1125
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1125 aaguacuua guuguuuuuu cuuu                                              24

<210> SEQ ID NO 1126
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 1126
gucgucuauu uucuuauuac cuuuac                                           26

<210> SEQ ID NO 1127
<211> LENGTH: 25
<212> TYPE: RNA
<213> ORGANISM: Artificial Sequence
<220> FEATURE:
<223> OTHER INFORMATION: Antisense fragment coding sequence
```

```
<400> SEQUENCE: 1127
ucaacuauua uuguugacca gacca                                      25

<210> SEQ ID NO 1128
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1128
ucuucuucuu uuucuccuga uaaa                                       24

<210> SEQ ID NO 1129
<211> LENGTH: 26
<212> TYPE: RNA
<213> ORGANISM: Artificial Sequence
<220> FEATURE:
<223> OTHER INFORMATION: Antisense fragment coding sequence

<400> SEQUENCE: 1129
gaagggucaa aaccucacag acccua                                     26

<210> SEQ ID NO 1130
<211> LENGTH: 25
<212> TYPE: RNA
<213> ORGANISM: Artificial Sequence
<220> FEATURE:
<223> OTHER INFORMATION: Antisense fragment coding sequence

<400> SEQUENCE: 1130
uuuaaauuua uucuuuuacc uucua                                      25

<210> SEQ ID NO 1131
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1131
uuagauuacc cuuaaauuau cgag                                       24

<210> SEQ ID NO 1132
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1132
uacgucuuga aagaaaaacu gag                                        23

<210> SEQ ID NO 1133
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1133
uguaagaaaa guacaccccg uauu                                       24

<210> SEQ ID NO 1134
```

```
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1134
gaucaguccg auccgucuac ca                                              22

<210> SEQ ID NO 1135
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1135
guuucgucuu acgucaagag aa                                              22

<210> SEQ ID NO 1136
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1136
acgugguuaa uuuuaugucu aua                                             23

<210> SEQ ID NO 1137
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1137
ucucauucuc uguguacug gu                                               22

<210> SEQ ID NO 1138
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1138
cccuuaaccc uguuaccacu ac                                              22

<210> SEQ ID NO 1139
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1139
uuacggaaca aagaugauua ug                                              22

<210> SEQ ID NO 1140
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1140
```
auucuccuag uccuuacucu ua                                                   22

<210> SEQ ID NO 1141
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1141
uagaguaaau uccuuacugu gu                                                   22

<210> SEQ ID NO 1142
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1142
ucuguuacga uuccuuuauc cc                                                   22

<210> SEQ ID NO 1143
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1143
ucuguuacga uuccuuuauc cc                                                   22

<210> SEQ ID NO 1144
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1144
aaccagacuc cuuacacgga cga                                                  23

<210> SEQ ID NO 1145
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1145
uaguuacuug uuucuccuuu au                                                   22

<210> SEQ ID NO 1146
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1146
gucucucucc guuuaauuuu uc                                                   22

<210> SEQ ID NO 1147
<211> LENGTH: 22
<212> TYPE: RNA

```
<213> ORGANISM: Artificial Sequence
<220> FEATURE:
<223> OTHER INFORMATION: Antisense fragment coding sequence

<400> SEQUENCE: 1147
guguuuaacu ucuacugucu cu                                    22

<210> SEQ ID NO 1148
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1148
uuuguucuuc acgaauacuc uc                                    22

<210> SEQ ID NO 1149
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1149
aaaaaaaguu uacguagaua guu                                   23

<210> SEQ ID NO 1150
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1150
gucuuuaagc uucuuuauuu uac                                   23

<210> SEQ ID NO 1151
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1151
gucggauuag ucugguuuac uu                                    22

<210> SEQ ID NO 1152
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1152
ccugccuaau ucuuucuucu ca                                    22

<210> SEQ ID NO 1153
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1153
uuucguuacu uucucauacc ccuc                                  24
```

<210> SEQ ID NO 1154
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1154
ugucuaaacu uuauuaacuu cc                                              22

<210> SEQ ID NO 1155
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1155
acguacacau uuaccgagaa c                                               21

<210> SEQ ID NO 1156
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1156
gaaaaggacu uucacggucg u                                               21

<210> SEQ ID NO 1157
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1157
uucuguucuu uaccggucau cc                                              22

<210> SEQ ID NO 1158
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1158
gacguaaacu ucuaaauucu aac                                             23

<210> SEQ ID NO 1159
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1159
gguaauaggu uuccagaugu uu                                              22

<210> SEQ ID NO 1160
<211> LENGTH: 22
<212> TYPE: RNA
<213> ORGANISM: Artificial Sequence
<220> FEATURE:

<223> OTHER INFORMATION: Antisense fragment coding sequence

<400> SEQUENCE: 1160
acucugaagg uucuaguucu ac                                          22

<210> SEQ ID NO 1161
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1161
cguccucacc uaucuaagau gu                                          22

<210> SEQ ID NO 1162
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1162
uuucguuuaa caucuuuucu aa                                          22

<210> SEQ ID NO 1163
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1163
acgucccuuc uugugucuag ag                                          22

<210> SEQ ID NO 1164
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1164
aguuuacgua cuucuguaag aa                                          22

<210> SEQ ID NO 1165
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1165
ucuucaauau uccuacuacc u                                           21

<210> SEQ ID NO 1166
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1166
gacgggguag ccacuucgag g                                           21

```
<210> SEQ ID NO 1167
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1167
uuauggucgg aagguaaagu cuua                                          24

<210> SEQ ID NO 1168
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1168
uuacuuaggu uuaguuuccu                                               20

<210> SEQ ID NO 1169
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1169
uacggaacaa agaugauuau g                                             21

<210> SEQ ID NO 1170
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1170
acucaacggu aagugguaac u                                             21

<210> SEQ ID NO 1171
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1171
uauguaacuu caaaauguaa a                                             21

<210> SEQ ID NO 1172
<211> LENGTH: 24
<212> TYPE: RNA
<213> ORGANISM: Artificial Sequence
<220> FEATURE:
<223> OTHER INFORMATION: Antisense fragment coding sequence

<400> SEQUENCE: 1172
cacacuaccc uuaccaaccu caua                                          24

<210> SEQ ID NO 1173
<211> LENGTH: 21
<212> TYPE: RNA
<213> ORGANISM: Artificial Sequence
<220> FEATURE:
<223> OTHER INFORMATION: Antisense fragment coding sequence
```

```
<400> SEQUENCE: 1173
uauacguguu ugucuuacac a                                              21

<210> SEQ ID NO 1174
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1174
accuaaacaa cgguuaaagu                                                20

<210> SEQ ID NO 1175
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1175
uaauauuuuc cuuccagagu                                                20

<210> SEQ ID NO 1176
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1176
uaauauuuuc cuuccagagu                                                20

<210> SEQ ID NO 1177
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1177
auauauuuau cuuguccuug ua                                             22

<210> SEQ ID NO 1178
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1178
uguuauuuuu caaccucuuu gu                                             22

<210> SEQ ID NO 1179
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1179
uuucgguacc uuguuuaccg ac                                             22

<210> SEQ ID NO 1180
<211> LENGTH: 25
```

-continued

```
<212> TYPE: RNA
<213> ORGANISM: Artificial Sequence
<220> FEATURE:
<223> OTHER INFORMATION: Antisense fragment coding sequence

<400> SEQUENCE: 1180
ccagauguuu uguaugaaac ucuuu                                          25

<210> SEQ ID NO 1181
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1181
uuaucaaaug aacuuauuau gu                                             22

<210> SEQ ID NO 1182
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1182
aaguucuacc ucuuucccuu cu                                             22

<210> SEQ ID NO 1183
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1183
uuuucuuuau gugguuuugu ca                                             22

<210> SEQ ID NO 1184
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1184
uuggauuuaa agagggucua aa                                             22

<210> SEQ ID NO 1185
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1185
uguuggauga aagagucaug ucu                                            23

<210> SEQ ID NO 1186
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1186
```
uuuaaguuug uuccucuagu aa 22

<210> SEQ ID NO 1187
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1187
accaguccaa uaagaccgua aa 22

<210> SEQ ID NO 1188
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1188
guuggaccuu ggaccuugga 20

<210> SEQ ID NO 1189
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1189
ggucgugacu cucccacuga ca 22

<210> SEQ ID NO 1190
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1190
cuuuaguugg acuuaccaaa 20

<210> SEQ ID NO 1191
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1191
aauaguuuau gaacgauaua ug 22

<210> SEQ ID NO 1192
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1192
gaaaagaauu uuuaaggucg cg 22

<210> SEQ ID NO 1193
<211> LENGTH: 21
<212> TYPE: RNA
<213> ORGANISM: Artificial Sequence -continued

```
<220> FEATURE:
<223> OTHER INFORMATION: Antisense fragment coding sequence

<400> SEQUENCE: 1193
ucucuuccua uaagagacca g                                             21

<210> SEQ ID NO 1194
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1194
ccccucugug uguuuaaguc ug                                            22

<210> SEQ ID NO 1195
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1195
acuaauaacg acgaucuuug uau                                           23

<210> SEQ ID NO 1196
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1196
acuaauaacg acgaucuuug ua                                            22

<210> SEQ ID NO 1197
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1197
accucuuucg guuguucuau uuu                                           23

<210> SEQ ID NO 1198
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1198
uguuucuugu acuuuuuug uuc                                            23

<210> SEQ ID NO 1199
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1199
ucccguucga aaggguuuac aga                                           23
```

-continued

<210> SEQ ID NO 1200
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1200
ucccguucga aaggguuuac ag                                              22

<210> SEQ ID NO 1201
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1201
gguuuugaug uaugaccacc cu                                              22

<210> SEQ ID NO 1202
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1202
uccguuucac cacacacaca cg                                              22

<210> SEQ ID NO 1203
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1203
aguuucucuu ucuguacugg u                                               21

<210> SEQ ID NO 1204
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1204
ugaaacauua ggguacuuag g                                               21

<210> SEQ ID NO 1205
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1205
aaaguccguc uuacuuacgu c                                               21

<210> SEQ ID NO 1206
<211> LENGTH: 21
<212> TYPE: RNA
<213> ORGANISM: Artificial Sequence
<220> FEATURE:
<223> OTHER INFORMATION: Antisense fragment coding sequence

```
<400> SEQUENCE: 1206
cuuugugucc cuugucucuu u                                              21

<210> SEQ ID NO 1207
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1207
uuccuucuag aguaaacucc u                                              21

<210> SEQ ID NO 1208
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1208
cuaucauuca ccuucucuac uu                                             22

<210> SEQ ID NO 1209
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1209
guauacuuuc uuacacguug ua                                             22

<210> SEQ ID NO 1210
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1210
uauuaugauc aucauuguca uu                                             22

<210> SEQ ID NO 1211
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1211
aacugacuuc uaggucuacu u                                              21

<210> SEQ ID NO 1212
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1212
uuuuuacuac ugguuaagag u                                              21

<210> SEQ ID NO 1213
```

```
-continued

<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1213
auaccuuaag agagaaugac u                                              21

<210> SEQ ID NO 1214
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1214
uuuuuuguuu cuaacucauu cu                                             22

<210> SEQ ID NO 1215
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1215
uucguugguc cucuaaccaa gu                                             22

<210> SEQ ID NO 1216
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1216
ggucuccugu ucucgagaac aa                                             22

<210> SEQ ID NO 1217
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1217
cuuucuugua agaaaaguac ac                                             22

<210> SEQ ID NO 1218
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1218
gacauuacuc uuacccucug ga                                             22

<210> SEQ ID NO 1219
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1219
```
ccuuuaacac uuuuaaguua cc                                          22

<210> SEQ ID NO 1220
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1220
aaaacgaaac acaacaaaac gac                                         23

<210> SEQ ID NO 1221
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1221
uccugaagcu cuuuauacaa cu                                          22

<210> SEQ ID NO 1222
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1222
uuuguuguau uguuguuguu auu                                         23

<210> SEQ ID NO 1223
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1223
uuuuacgacu ccuauacccg uu                                          22

<210> SEQ ID NO 1224
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1224
aaagugguaa uggaagagaa gg                                          22

<210> SEQ ID NO 1225
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1225
agaauaaaga agucucuguu ac                                          22

<210> SEQ ID NO 1226
<211> LENGTH: 23
<212> TYPE: RNA

```
<213> ORGANISM: Artificial Sequence
<220> FEATURE:
<223> OTHER INFORMATION: Antisense fragment coding sequence

<400> SEQUENCE: 1226
ucucuuuuau gaacuuuuaa cac                                           23

<210> SEQ ID NO 1227
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1227
ugucuuuaca gugacucucc uc                                            22

<210> SEQ ID NO 1228
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1228 uuuccccau cccuguuacc ac                                             22

<210> SEQ ID NO 1229
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1229
cugaugucua uauguauauc ua                                            22

<210> SEQ ID NO 1230
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1230
cuuuuuccuc ucacucucug uu                                            22

<210> SEQ ID NO 1231
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1231
aucuauauuu acacuuucua au                                            22

<210> SEQ ID NO 1232
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1232
agucugucga cgggucuccc gu                                            22
```

-continued

```
<210> SEQ ID NO 1233
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1233
ugaaugguca gaguagaaga u                                              21

<210> SEQ ID NO 1234
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1234
aaaagauagg gagucuuuua gg                                             22

<210> SEQ ID NO 1235
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1235
gaaacuagag cccgaacucu                                                20

<210> SEQ ID NO 1236
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1236
agagagacgg aacaucaacc                                                20

<210> SEQ ID NO 1237
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1237
auauugaaua augaagucuu                                                20

<210> SEQ ID NO 1238
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1238
ucuuuaguau aguuuaggaa                                                20

<210> SEQ ID NO 1239
<211> LENGTH: 20
<212> TYPE: RNA
<213> ORGANISM: Artificial Sequence
<220> FEATURE:
```

<223> OTHER INFORMATION: Antisense fragment coding sequence

<400> SEQUENCE: 1239
aagucugucu agucuggagu                                              20

<210> SEQ ID NO 1240
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1240
uuauaggucu uaccaaagac                                              20

<210> SEQ ID NO 1241
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1241
uucaguugua cuuuuuugu c                                             21

<210> SEQ ID NO 1242
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1242 acuuuuuug uucuagaauu                                               20

<210> SEQ ID NO 1243
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1243 cccccaaga aaacuuuuu                                                20

<210> SEQ ID NO 1244
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1244
cucuaccggu uccacccucu                                              20

<210> SEQ ID NO 1245
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1245
aaaaaugguu aucaucuccc                                              20

```
<210> SEQ ID NO 1246
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1246
cacgaggagu acuuuacaga ca                                              22

<210> SEQ ID NO 1247
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1247
augguggaau uuauagucuc                                                 20

<210> SEQ ID NO 1248
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1248
gagucgguau uuuuacuugc                                                 20

<210> SEQ ID NO 1249
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1249
uaacgucuuu caaagagguu uu                                              22

<210> SEQ ID NO 1250
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1250
ucugaccugg ucgauaccuu ag                                              22

<210> SEQ ID NO 1251
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1251
uacauuagug gaauauguac uug                                             23

<210> SEQ ID NO 1252
<211> LENGTH: 20
<212> TYPE: RNA
<213> ORGANISM: Artificial Sequence
<220> FEATURE:
<223> OTHER INFORMATION: Antisense fragment coding sequence
```

```
<400> SEQUENCE: 1252
ccuuccugaa ccauuucaag                                               20

<210> SEQ ID NO 1253
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1253
uuuaggacuc cgugaaguug ua                                            22

<210> SEQ ID NO 1254
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1254
cagacaguag agugaccuag                                               20

<210> SEQ ID NO 1255
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1255
acccguguca acagugacga                                               20

<210> SEQ ID NO 1256
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1256
uuuguaacgu cguccuauc                                                20

<210> SEQ ID NO 1257
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1257
acauuaagau cggacucaga                                               20

<210> SEQ ID NO 1258
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1258
gguccuuuca gaagucuccu a                                             21

<210> SEQ ID NO 1259
<211> LENGTH: 20
```

```
<212> TYPE: RNA
<213> ORGANISM: Artificial Sequence
<220> FEATURE:
<223> OTHER INFORMATION: Antisense fragment coding sequence

<400> SEQUENCE: 1259 auuucuaga aaagaacaga                                          20

<210> SEQ ID NO 1260
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1260
ucuguuuauu ccaguccucu                                         20

<210> SEQ ID NO 1261
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1261
ucuguugugg gugaggaaga                                         20

<210> SEQ ID NO 1262
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1262
auccaaguuc agacggucua ugu                                     23

<210> SEQ ID NO 1263
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1263
gaauggucag aguagaagau g                                       21

<210> SEQ ID NO 1264
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1264
ccggaacgag aagucucucc                                         20

<210> SEQ ID NO 1265
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1265
```
guacgucgau cuugguacug                                                        20

<210> SEQ ID NO 1266
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1266
ccccuucuuu ucaccauccg u                                                      21

<210> SEQ ID NO 1267
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1267
uguccuaucu cgucuaaaaa                                                        20

<210> SEQ ID NO 1268
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1268
aacuuuuacu uggaacuacu                                                        20

<210> SEQ ID NO 1269
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1269
guacucguuc uagaaacagu u                                                      21

<210> SEQ ID NO 1270
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1270
agaacacugu aaaaaugguu a                                                      21

<210> SEQ ID NO 1271
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1271
guccuugugu ucuugguuuc                                                        20

<210> SEQ ID NO 1272
<211> LENGTH: 20
<212> TYPE: RNA
<213> ORGANISM: Artificial Sequence

```
<220> FEATURE:
<223> OTHER INFORMATION: Antisense fragment coding sequence

<400> SEQUENCE: 1272
aaguguaauu uuucacuau                                                    20

<210> SEQ ID NO 1273
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1273
gacaaccuua ccgguccuac                                                   20

<210> SEQ ID NO 1274
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1274
uuccaccucu ugagucucaa a                                                 21

<210> SEQ ID NO 1275
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1275
cguaaaccuu ccauagaacg                                                   20

<210> SEQ ID NO 1276
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1276
gagauaaaga acgugaacac                                                   20

<210> SEQ ID NO 1277
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1277
uucuucucug guacacauca aua                                               23

<210> SEQ ID NO 1278
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1278
uauuacguaa accuuccaua                                                   20
```

```
<210> SEQ ID NO 1279
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1279
gauacuucag uaguuuaua                                                      20

<210> SEQ ID NO 1280
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1280
aagaguaaaa acaacaaaua aa                                                  22

<210> SEQ ID NO 1281
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1281
uauugucugg auauugaaua                                                     20

<210> SEQ ID NO 1282
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1282
ucucucugug uuccgauucu                                                     20

<210> SEQ ID NO 1283
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1283
aaucaggucu cucgucuuuu                                                     20

<210> SEQ ID NO 1284
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1284
gugacggagg aagucguuag u                                                   21

<210> SEQ ID NO 1285
<211> LENGTH: 20
<212> TYPE: RNA
<213> ORGANISM: Artificial Sequence
<220> FEATURE:
<223> OTHER INFORMATION: Antisense fragment coding sequence
```

```
<400> SEQUENCE: 1285
auacuucagu aguuuuauaa                                            20

<210> SEQ ID NO 1286
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1286
guaauuuuuu cacuaucuau                                            20

<210> SEQ ID NO 1287
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1287
ucucucguag guuucccuca c                                          21

<210> SEQ ID NO 1288
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1288
uuuuuuacau gguccacacu                                            20

<210> SEQ ID NO 1289
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1289
uuguacucgu ucuagaaaca                                            20

<210> SEQ ID NO 1290
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1290
uuaguguaag aaaguggucu u                                          21

<210> SEQ ID NO 1291
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1291
ggagugagaa uaaaguaggu                                            20

<210> SEQ ID NO 1292
```

```
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1292
guaagugaaa cauccuacga                                                   20

<210> SEQ ID NO 1293
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1293
uagucuuucc gaaauauacu g                                                 21

<210> SEQ ID NO 1294
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1294
acauaaauau uuucuguucc a                                                 21

<210> SEQ ID NO 1295
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1295
gaguaaaaac aacaaauaaa                                                   20

<210> SEQ ID NO 1296
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1296
acgguucgaa cacaaguugu                                                   20

<210> SEQ ID NO 1297
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1297
acccgagacu guccuccgua c                                                 21

<210> SEQ ID NO 1298
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1298
```

-continued uucaauuaau ggaaauguaa         20

<210> SEQ ID NO 1299
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1299
augauacuac auagauagau         20

<210> SEQ ID NO 1300
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1300
uccucccaua agaagacaua         20

<210> SEQ ID NO 1301
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1301
cuugggucuc cuuggggug         20

<210> SEQ ID NO 1302
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1302
gugacggagg aagucguuag u        21

<210> SEQ ID NO 1303
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1303
ucucgaguuc uuccucuguu         20

<210> SEQ ID NO 1304
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1304
uucuccccga ggagauacuu         20

<210> SEQ ID NO 1305
<211> LENGTH: 20
<212> TYPE: RNA

```
<213> ORGANISM: Artificial Sequence
<220> FEATURE:
<223> OTHER INFORMATION: Antisense fragment coding sequence

<400> SEQUENCE: 1305
agaugacgaa auccacugca                                                    20

<210> SEQ ID NO 1306
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1306
ucuacccacc uaguucucca                                                    20

<210> SEQ ID NO 1307
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1307
uugccacugc uccgacuccu                                                    20

<210> SEQ ID NO 1308
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1308
gucuccuaca uaaaagacag                                                    20

<210> SEQ ID NO 1309
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1309
guguagguga cggaggaagu                                                    20

<210> SEQ ID NO 1310
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1310
ucccuacaga acacuguaaa aa                                                 22

<210> SEQ ID NO 1311
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1311
gaagucuuuc guucaguaag au                                                 22
```

```
<210> SEQ ID NO 1312
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1312
auguagaguc gguauuuuua c                                              21

<210> SEQ ID NO 1313
<211> LENGTH: 22
<212> TYPE: RNA
<213> ORGANISM: Artificial Sequence
<220> FEATURE:
<223> OTHER INFORMATION: Antisense fragment coding sequence

<400> SEQUENCE: 1313
aaugacucac gucccgggga cu                                             22

<210> SEQ ID NO 1314
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1314
aguugaaagg guugggaggu                                                20

<210> SEQ ID NO 1315
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1315
gucucccugu cccucccucc a                                              21

<210> SEQ ID NO 1316
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1316
ucagucuuga accuuacucu a                                              21

<210> SEQ ID NO 1317
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1317
aguuucuaau cucaguuguc u                                              21

<210> SEQ ID NO 1318
<211> LENGTH: 21
<212> TYPE: RNA
<213> ORGANISM: Artificial Sequence
<220> FEATURE:
```

```
<223> OTHER INFORMATION: Antisense fragment coding sequence

<400> SEQUENCE: 1318
guacuugacc cauauguuca a                                              21

<210> SEQ ID NO 1319
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1319
gacuacugua cgaccucuuc u                                              21

<210> SEQ ID NO 1320
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1320
accagugcac aaguuagagu a                                              21

<210> SEQ ID NO 1321
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1321
aauacuucug acaaguccug a                                              21

<210> SEQ ID NO 1322
<211> LENGTH: 23
<212> TYPE: RNA
<213> ORGANISM: Artificial Sequence
<220> FEATURE:
<223> OTHER INFORMATION: Antisense fragment coding sequence

<400> SEQUENCE: 1322
gaccaccucu auuuugcaug acu                                            23

<210> SEQ ID NO 1323
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1323
aacuaacaaa aagaguaaaa                                                20

<210> SEQ ID NO 1324
<211> LENGTH: 21
<212> TYPE: RNA
<213> ORGANISM: Artificial Sequence
<220> FEATURE:
<223> OTHER INFORMATION: Antisense fragment coding sequence

<400> SEQUENCE: 1324
accaaagacc ccgacacgga g                                              21
```

```
<210> SEQ ID NO 1325
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1325 cucgucccg uccucugucg                                           20

<210> SEQ ID NO 1326
<211> LENGTH: 20
<212> TYPE: RNA
<213> ORGANISM: Artificial Sequence
<220> FEATURE:
<223> OTHER INFORMATION: Antisense fragment coding sequence

<400> SEQUENCE: 1326
cccaagaaaa acuuuuuuu                                           20
```

TARGET SEQUENCE OF RNA VIRUS AND USE THEREOF

REFERENCE TO A SEQUENCE LISTING SUBMITTED ELECTRONICALLY VIA EFS-WEB

The content of the electronically submitted sequence listing in ASCII text file (Name: 4969_0020000_Seglisting_ST25; Size: 269,003 bytes; and Date of Creation: Jan. 31, 2022) is herein incorporated by reference in its entirety.

TECHNICAL FIELD

The present invention relates to the field of biotechnology, in particular to a target sequence of an RNA virus and the use thereof.

BACKGROUND OF THE INVENTION

RNA viruses are also called RNA-type viruses, which refer to viruses whose genetic material is RNA. In the process of virus RNA replication, the activity of enzymes responsible for the error repair mechanism is very low to almost none, thereby leading to very fast mutation. Furthermore, vaccines are developed based on the stable nucleotides sequence or proteins of viruses, and therefore vaccines against RNA viruses are difficult to develop. The RNA viruses cannot be reproduced by themselves, and can be reproduced only in living cells. Common RNA viruses are: HIV, poliovirus, tobacco mosaic virus, SARS virus, MERS virus, ebola virus, severe acute respiratory syndrome-related coronavirus 2 (2019-nCoV), etc. Coronavirus is a type of unsegmented positive-sense RNA virus with an envelope, can infect a variety of hosts such as mammals and birds, and can cause mild to moderate respiratory diseases especially in humans. In the past two decades, the emergence of two highly pathogenic coronaviruses has appeared in the process of zoonotic infection: severe acute respiratory syndrome-related coronavirus (SARS-CoV) and Middle East respiratory syndrome coronavirus (MERS-CoV). Corona Virus Disease 2019, referred to as "COVID-19" briefly, refers to pneumonia caused by the infection of 2019 severe acute respiratory syndrome-related coronavirus 2. COVID-19 is an acute infectious pneumonia. Researchers have discovered that its pathogen is a new type of β-coronavirus that has not previously been found in humans. The virus was subsequently named severe acute respiratory syndrome-related coronavirus 2 (SARS-CoV-2) by the World Health Organization (WHO). The initial symptoms of a patient with COVID-19 are mostly fever, fatigue and dry cough, and they gradually develop severe symptoms such as dyspnea. In some severe cases, acute respiratory distress syndrome, septic shock and even death may occur. As of Jul. 7, 2020, SARS-CoV-2 has continued to spread in 188 countries and regions around the world, causing more than 11.62 million confirmed cases and 538,000 deaths. There is currently no effective target specifically for coronavirus.

Nucleic acid is an important carrier for the storage and transmission of genetic information in organisms, and also plays an extremely important role in the regulation of biological functions. With people's deepening understanding of the structure and function of the nucleic acid, the value of nucleic acid as a target for drug design has been paid more and more attention by everyone. MicroRNA (miRNA) is a type of small single-stranded short-sequence RNA with a length of about 22-25 nucleotides, it does not code a protein, but the nucleotides at positions 2-8 from its 5' end can bind to the 3' UTR (3' untranslated region) of homologous mRNA by means of incomplete base pairing. At first, it is believed that only the sequence in one of the strands of the miRNA hairpin structure has a regulatory effect to exert function by negatively regulating gene expression by inducing messenger RNA (mRNA) degradation and post-transcriptional gene silencing, and the other strand would be degraded. However, more and more evidences later show that the upper and lower strands of miRNA can function as an independent miRNA. In addition to negative regulation by miRNA, some cases reported that miRNA can promote gene expression or translation under special circumstances (Vasudevan et al., 2007, Vasudevan and Steitz, 2007, Place et al., 2008). XIAOM et al. found in 2015 that, for example, has-miR-26a-1, has-miR-3179, has-24-1, etc. can bind to an enhancer (the result was published in the journal RNABiology) and activate gene expression at the genome-wide level (XIAO M, LI J, LI W, et al. 2017. MicroRNAs activate gene transcription epigenetically as an enhancer trigger. RNA Biol [J], 14: 1326-1334.). Our previous work has shown that this feature of miRNA is not a single case, but is suitable for many tissues and cells. When studying the epigenetic regulation mechanism of miRNA itself, 1594 miRNA precursors were systematically analyzed in 7 different tissues and cells. It was unexpectedly found that the positions of more than 300 miRNA precursors in the genome highly overlapped with that of the histone modification marker H3K4mel or H3K27ac of the enhancer. This allowed the inventors to link the two important molecular biological events, i.e., miRNA and enhancer that are both histocyte-specific (Xiao et al., 2017). Based on this, the inventors believe that miRNA is an important bifunctional molecule. When miRNA is located in the cytoplasm, it can act on the 3' UTR region of mRNA, thereby blocking the translation of mRNA and exerting a negative regulatory effect on genes, like a fire extinguisher; in contrast, when miRNA is located in the nucleus, it changes the chromatin state of the enhancer by binding to the enhancer, thereby activating the transcriptional expression of genes, like an igniter. The inventors call the RNA that is located in the nucleus and has an activating effect as NamiRNA (nuclear activating miRNA). Based on this, the inventors propose a NamiRNA-enhancer-target gene network activation model to reveal the function of miRNA in the nucleus. Surprisingly, there is a direct positive regulatory relationship between NamiRNA and target genes, and NamiRNA is also involved in the biological behaviors such as the proliferation, migration and invasion of tumor cells.

Hyaluronic acid (HA) is one of the main components of glycosaminoglycan (GAG) in proteoglycans, is also one of the components of extracellular matrix (ECM) that has been studied extensively, and plays an important role in the function and development of normal tissues, comprising providing support and anchoring for cells, promoting signaling between cells, and promoting cell movement and migration. HA is synthesized by a type of integral membrane protein called HA synthase (hyaluronic acid synthase, HAS), of which there are three types in vertebrates: HAS1, HAS2 and HAS3. HA is extended by these enzymes which are capable of repeatedly adding glucuronic acid and N-acetylglucosamine to the nascent polysaccharide, and extruded through the cell membrane to enter the extracellular space. HA is a macromolecular viscous glycosaminoglycan that can be secreted by type II lung epithelial cells, endothelial cells and lung fibroblasts, wherein fibroblasts can be stimulated by pathogenic factors, such as oxygen free radicals, to synthesize large amounts of HA. The basic structure of HA is β-D gluconic acid and 2-acetyl-2-deoxy-D-glucose, which are linear chain molecular polymers of repeating disaccharides connected by β1.3 and β2.4 glucosidic hond, respectively, and are the most important glycosaminoglycan. HA is mainly distributed in the interstitium around capillaries and bronchioles in lung tissue, and is widely expressed in the extracellular matrix, and can also be expressed on the cell surface. The greatest function of hyaluronic acid is to absorb and store water. One molecule of hyaluronic acid can absorb 9 molecules of water. The increase of hyaluronic acid will undoubtedly aggravate the increase of local water. Studies have shown that HA can increase local edema and promote the inflammatory cascade, leading to leukocyte migration, proliferation and differentiation.

Hyaluronic acid synthase inhibitor (4-Methylumbelliferone, 4-MU) is a selective inhibitor of HA synthesis. 4-MU is a derivative of the coumarin family. Other coumarin derivatives, such as Marcumar® and Coumadin®, are mostly used as preventive drugs to reduce the occurrence of cardiovascular disease due to the anticoagulant mechanisms thereof.

ACE2 is a receptor of severe acute respiratory syndrome-related coronavirus 2, and the expression level thereof is closely related to the course of the diseases caused by severe acute respiratory syndrome-related coronavirus 2.

HAS1, HAS2, and HAS3 belong to the family of hyaluronic acid synthases, and the increase of their expression level and deposition in the extracellular matrix is closely related to the diseases caused by severe acute respiratory syndrome-related coronavirus 2 and the complications thereof.

FBXO15 is a member of the F-box protein family, and the expression level thereof is closely related to the inflammatory response.

MYL9 is myosin light chain 9, and the expression level thereof is closely related to inflammatory response.

KALRN is a RhoGEF kinase, and the expression level thereof is related to the progression of sarcoidosis and inflammation of multiple organs such as kidney and lung.

ATP8B1 is a member of the type P cation transport ATPase family, and the expression level thereof is closely related to the inflammatory response.

IGF2R is a receptor for insulin-like growth factor 2 and mannose 6-phosphate, and the expression level thereof is closely related to the inflammatory response.

C5AR1 is complement component 5a receptor 1, and the expression level thereof is closely related to the regulation of the inflammatory response.

EPAS1 is endothelial PAS domain protein 1, and the expression level thereof is closely related to the regulation of the inflammatory response.

TIMM21 is internal mitochondrial membrane translocase 21, and the expression level thereof is closely related to the regulation of the inflammatory response.

So far, the mechanism of severe acute respiratory syndrome caused by RNA viruses, especially severe acute respiratory syndrome-related coronavirus 2, is not clear. There are also many problems in understanding the pathogenic mechanism and designing or producing vaccines of other related RNA viruses. In addition, the diseases caused by RNA viruses lack effective treatment drugs and treatment regimens, and the virus virulence and susceptible populations are difficult to determine. There is an urgent need to study the pathogenic mechanism of RNA viruses, and develop the detection for the pathogenicity and population susceptibility of RNA viruses, seek for specific drugs and treatment regimens for RNA viruses, prepare RNA virus vaccines with high efficiency and low toxicity, and propose practical Chinese solutions for humans to overcome RNA virus infections.

SUMMARY OF THE INVENTION

The RNA sequence of severe acute respiratory syndrome-related coronavirus 2 has about 30,000 bases. The inventors found that, when comparing severe acute respiratory syndrome-related coronavirus 2 with the human genome in the early stage, the nucleic acid sequence of severe acute respiratory syndrome-related coronavirus 2 contains 5 human genome sequences, ranging in length from 24-28 bp. These 5 sequences are extremely conserved and identical in humans and primates. The conservation of the 5 sequences suggests that they are of great significance. In order to facilitate the research on the function and use of the above-mentioned conservative sequences, the inventors named the above-mentioned conservative sequences as HISs (Human Insert Sequences).

Furthermore, the inventors found that there are 3 and 2 human genome sequences (HIS) in the genomes of SARS and MERS viruses, respectively. The location distribution of HIS in the genomes of severe acute respiratory syndrome-related coronavirus 2, SARS, and MERS viruses is mainly in the enhancer region in human, suggesting that HISs are related to gene activation; there are a large number of inflammatory factor genes in the upstream and downstream 200K range of the enhancer where the HIS in SARS-CoV-2 is located; the RNA region where HIS is located can form a virus derived hairpin structure. It is found from further analysis that HIS can form a hairpin structure with miRNA precursor characteristics; based on HIS, most of target genes in relation to HIS are also related to inflammatory factors by means of bioinformatics analysis and prediction; the HIS target area of SARS virus and severe acute respiratory syndrome-related coronavirus 2 has hyaluronic acid synthase (HAS) genes; According to the NamiRNA-enhancer-gene activation theory (Xiao et al., 2017) discovered and proposed by the inventors in the previous research work, the inventors believe that the HIS sequences of severe acute respiratory syndrome-related coronavirus 2 and SARS virus will activate inflammatory factors after the human body being infected with the viruses, which causes a storm of inflammatory factors and may produce excessive hyaluronic acid by activating hyaluronic acid synthase to cause ground-glass changes in lung and then lead to ARDS. In view of the fact that the HIS sequences in severe acute respiratory syndrome-related coronavirus 2 are an important material basis and an important pathogenesis for the pathogenicity of the coronavirus, the inventors further confirm by experiments that the HIS sequences in SARS-COV-2, SARS-COV and MERS virus, when overexpressed in cells, can activate the expression of HAS and inflammatory factors, and increase the production of the extracellular hyaluronic acid. More importantly, it is found that the content of hyaluronic acid in the serum of a patient with COVID-19 is closely related to the severity of the patient's condition. The inventors believe that the target sequences of the virus can also cause changes in hematological indicators and can be used for clinical detection of patient's condition combined with clinical data. Therefore, the targets in coronaviruses can be used in clinical diagnosis, drug therapy design against this target and possible design/optimization of vaccines. The development of such targets can be extended to other RNA viruses, and similar results are obtained by verifying with the typical coronaviruses, HIV, zika virus and ebola virus. In particular, the regions where the HIS sequences of other RNA viruses pair with the human genome are mostly related to the pathogenicity and characteristics of such RNA viruses.

Comparing with the prior art, the above technical solutions are used in the present invention, and the following technical effects are achieved:

In the present invention, the gene sequence of the RNA virus is aligned with the human genome to screen out multiple target sequences with not less than 95% similarity to the human genome (i.e., more than 95% of complementary pairing) and stable structure, and the successfully constructed virus fragment has the function of interacting with human genomic DNA and is similar to viral miRNA. In addition, the effect of overexpression of the target sequences of the RNA virus on the expression level of surrounding genes has been verified. The above-mentioned screening and verification have good application value in the diagnosis and detection of RNA viruses, screening of drugs for the treatment of conditions caused by RNA viruses, and design/optimization of vaccines.

The RNA viruses involved in the present invention comprise RNA viruses that infect humans, RNA viruses that infect poultry, livestock, and zoonotic animals. Specifically, the target sequence consistent with the human genome is named HIS (Human Insert Sequence), the target sequence consistent with the chicken genome is named CIS (Chicken Insert Sequence), and the target sequence consistent with the pig genome is named PIS (Pig Insert Sequence), the target sequence consistent with the dog genome is named DIS (Dog Insert Sequence), and the target sequence consistent with mallard genome is named MIS (Mallard Insert Sequence). The specific target sequences of these viruses, as same as that of SARS-COV-2, can activate gene expression through an enhancer, and are closely related to diseases caused by viruses in humans and other species, and then can be used as targets for the determination of virus virulence. The antisense RNA sequences of the specific target sequences can be used for drug development, and deletion of the target sequences is an important strategy for the design of an attenuated vaccine.

The present invention overcomes the defects in the prior art, provides a target sequence of an RNA virus which has the function of interacting with the human genome, and verifies the effect of overexpression of the target sequence of the RNA virus on the expression level of surrounding genes.

The target sequence and the antisense RNA sequence thereof are developed and used for the diagnosis and treatment of RNA viruses and the design/optimization of vaccines.

In order to achieve the above objective, the following technical solutions are used in the present invention:

In the first aspect, the present invention provides a target sequence of an RNA virus. The target sequence is a nucleic acid sequence fragment in the nucleotide sequence of the RNA virus containing not less than 20-40 bases and having not less than 95% similarity to human genome sequence (i.e., more than 95% identity or complementary pairing).

In order to further optimize the above-mentioned target sequence of the RNA virus, the technical measures used in the present invention also comprise: further, the RNA virus comprises but is not limited to: severe acute respiratory syndrome-related coronavirus 2 (SARS-CoV-2), severe acute respiratory syndrome-related coronavirus (SARS-CoV), middle east respiratory syndrome coronavirus (MERS-CoV), zika virus, ebola virus, HIV, norwalk virus, alkhurma virus, enterovirus, kemerovo virus, coxsackievirus, hepatitis A virus, dengue virus 2, rubella virus, marburg marburgvirus, poliovirus, respiratory syncytial virus, mumps virus, australian bat lyssavirus, andes virus, powassan virus, langat virus, eyach virus, colorado tick fever virus, lassa virus, omsk hemorrhagic fever virus, machupo virus, junin virus, guanarito virus, sin nombre virus, hantaan virus, puumala virus, dobrava virus, seoul virus, crimean-congo hemorrhagic fever virus, sabia virus, thogoto virus, european bat lyssavirus 1, european bat lyssavirus 2, chapare virus, rotavirus, tai forest ebolavirus, bundibugyo ebolavirus, rift valley fever virus, irkut virus, influenza A virus, bayou virus, kyasanur forest disease virus, black creek canal virus, japanese encephalitis virus, duvenhage lyssavirus, Lujo mammarenavirus, measles morbillivirus, tick-borne encephalitis virus, avian influenza virus, swine influenza virus, Rabies virus, etc.

Further, the target sequence of the RNA virus is selected from any one or more of SEQ ID NO. 1-SEQ ID NO. 615. Further, the target sequence of the severe acute respiratory syndrome-related coronavirus 2 comprises SEQ ID NO. 1-SEQ ID NO. 6; and/or, the target sequence of severe acute respiratory syndrome-related coronavirus comprises SEQ ID NO. 7-SEQ ID NO. 9; and/or, the target sequence of middle east respiratory syndrome coronavirus comprises SEQ ID NO. 10, SEQ ID NO. 11; and/or, the target sequence of zika virus comprises SEQ ID NO. 12-SEQ ID NO. 14; and/or, the target sequence of ebola virus comprises SEQ ID NO. 15-SEQ ID NO. 17; and/or, the target sequence of HIV comprises SEQ ID NO. 18-SEQ ID NO. 26; and/or, the target sequence of norwalk virus comprises SEQ ID NO. 27; and/or, the target sequence of alkhurma virus comprises SEQ ID NO. 28-SEQ ID NO. 30; and/or, the target sequence of enterovirus comprises SEQ ID NO. 31, SEQ ID NO. 32; and/or, the target sequence of kemerovo virus comprises SEQ ID NO. 33, SEQ ID NO. 34; and/or, the target sequence of coxsackievirus comprises SEQ ID NO. 35; and/or, the target sequence of hepatitis A virus comprises SEQ ID NO. 36-SEQ ID NO. 46; and/or, the target sequence of dengue virus 2 comprises SEQ ID NO. 47-SEQ ID NO. 50; and/or, the target sequence of rubella virus comprises SEQ ID NO. 51; and/or, the target sequence of marburg marburgvirus comprises SEQ ID NO. 52-SEQ ID NO. 56; and/or, the target sequence of poliovirus comprises SEQ ID NO. 57; and/or, the target sequence of respiratory syncytial virus comprises SEQ ID NO. 58 SEQ ID NO. 85; and/or, the target sequence of mumps virus comprises SEQ ID NO. 86; and/or, the target sequence of australian bat lyssavirus comprises SEQ ID NO. 87; and/or, the target sequence of andes virus comprises SEQ ID NO. 88-SEQ ID NO. 95; and/or, the target sequence of powassan virus comprises SEQ ID NO. 96, SEQ ID NO. 97; and/or, the target sequence of langat virus comprises SEQ ID NO. 98-SEQ ID NO. 102; and/or, the target sequence of eyach virus comprises SEQ ID NO. 103-SEQ ID NO. 113; and/or, the target sequence of colorado tick fever virus comprises SEQ ID NO. 114-SEQ ID NO. 134; and/or, the target sequence of lassa virus comprises SEQ ID NO. 135, SEQ ID NO. 136; and/or, the target sequence of omsk hemorrhagic fever virus comprises SEQ ID NO. 137, SEQ ID NO. 138; and/or, the target sequence of machupo virus comprises SEQ ID NO. 139-SEQ ID NO. 140; and/or, the target sequence of junin virus comprises SEQ ID NO. 141; and/or, the target sequence of guanarito virus comprises SEQ ID NO. 142-SEQ ID NO. 147; and/or, the target sequence of sin nombre virus comprises SEQ ID NO. 148-SEQ ID NO. 152; and/or, the target sequence of hantaan virus comprises SEQ ID NO. 153-SEQ ID NO. 161; and/or, the target sequence of puumala virus comprises SEQ ID NO. 162-SEQ ID NO. 173; and/or, the target sequence of dobrava virus comprises SEQ ID NO. 174-SEQ ID NO. 185; and/or, the target sequence of seoul virus comprises SEQ ID NO. 186-SEQ ID NO. 199; and/or, the target sequence of crimean-congo hemorrhagic fever virus comprises SEQ ID NO. 200-SEQ ID NO. 204; and/or, the target sequence of sabia virus comprises SEQ ID NO. 205-SEQ ID NO. 212; and/or, the target sequence of thogoto virus comprises SEQ ID NO. 213-SEQ ID NO. 227; and/or, the target sequence of european bat lyssavirus 1 comprises SEQ ID NO. 228-SEQ ID NO. 232; and/or, the target sequence of european bat lyssavirus 2 comprises SEQ ID NO. 233; and/or, the target sequence of chapare virus comprises SEQ ID NO. 234; and/or, the target sequence of rotavirus comprises SEQ ID NO. 235-SEQ ID NO. 277; and/or, the target sequence of tai forest ebolavirus comprises SEQ ID NO. 278, SEQ ID NO. 279; and/or, the target sequence of bundibugyo ebolavirus comprises SEQ ID NO. 280; and/or, the target sequence of rift valley fever virus comprises SEQ ID NO. 281; and/or, the target sequence of irkut virus comprises SEQ ID NO. 282-SEQ ID NO. 285; and/or, the target sequence of influenza A virus comprises SEQ ID NO. 286-SEQ ID NO. 313; and/or, the target sequence of bayou virus comprises SEQ ID NO. 314-SEQ ID NO. 327; and/or, the target sequence of kyasanur forest disease virus comprises SEQ ID NO. 328; and/or, the target sequence of black creek canal virus comprises SEQ ID NO. 329-SEQ ID NO. 334; and/or, the target sequence of japanese encephalitis virus comprises SEQ ID NO. 335-SEQ ID NO. 337; and/or, the target sequence of duvenhage lyssavirus comprises SEQ ID NO. 338-SEQ ID NO. 344; and/or, the target sequence of Lujo alkhurma virus comprises SEQ ID NO. 345; and/or, the target sequence of measles morbillivirus comprises SEQ ID NO. 346; and/or, the target sequence of tick-borne encephalitis virus comprises SEQ ID NO. 347; and/or, the target sequence of avian influenza virus comprises SEQ ID NO. 348-SEQ ID NO. 420; and/or, the target sequence of swine influenza virus comprises SEQ ID NO. 421-SEQ ID NO. 521; and/or, the target sequence of rabies virus comprises SEQ ID NO. 522 SEQ ID NO. 615.

The naming method of each fragment of the above target sequences is the virus name plus HIS or other assigned name plus the fragment number. The specific target sequences are shown in the following table:

TABLE 1

Target sequence listing of RNA virus

| Virus type | Fragment number | Fragment coding sequence | ID number |
|---|---|---|---|
| Severe acute respiratory syndrome-related coronavirus 2 (SARS-CoV-2) | SARS-CoV-2-HIS-1 | 5'-UGUCUAUGCUAAUGGAGG UAAAGGCU-3' | SEQ ID NO. 1 |
| | SARS-CoV-2-HIS-2 | 5'-UAUAACACAUAUAAAAAU ACGUGU-3' | SEQ ID NO. 2 |
| | SARS-CoV-2-HIS-3 | 5'-UUAUAUGCCUUAUUUCUU UACUUU-3' | SEQ ID NO. 3 |
| | SARS-CoV-2-HIS-4 | 5'-AGGAGAAUGACAAAAAAA AAAAAAAA-3' | SEQ ID NO. 4 |
| | SARS-CoV-2-HIS-5 | 5'-UUGUUGCUGCUAUUUUCU AUUUAA-3' | SEQ ID NO. 5 |
| | SARS-CoV-2-HIS-6 | 5'-CAUGAAGAAACAAUUUAU AAUUUACUUA-3' | SEQ ID NO. 6 |
| severe acute respiratory syndrome-related coronavirus (SARS-CoV) | SARS-CoV-HIS-1 | 5'-GAGUUGAGGAAGAAGAAG AGGAAGACUGG-3' | SEQ ID NO. 7 |
| | SARS-CoV-HIS-2 | 5'-UAACAUGCUUAGGAUAAU GGCCUC-3' | SEQ ID NO. 8 |
| | SARS-CoV-HIS-3 | 5'-AGGAGAAUGACAAAAAAA AAAAAAAA-3' | SEQ ID NO. 9 |
| Middle East respiratory syndrome coronavirus (MERS-CoV) | MERS-CoV-HIS-1 | 5'-UUCCAUUUGCACAGAGUA UCUUUU-3' | SEQ ID NO. 10 |
| | MERS-CoV-HIS-2 | 5'-UGCUGUAAUUGCUGUUGU UGCUGCUGUU-3' | SEQ ID NO. 11 |
| Zika virus | Zika-HIS-1 | 5'-GAAAAGAGAAAAGAAAC AAGGG-3' | SEQ ID NO. 12 |
| | Zika-HIS-2 | 5'-GGGAGGAGGGAGGAAGAG ACUCC-3' | SEQ ID NO. 13 |
| | Zika-HIS-3 | 5'-GUUCUAGAGAUGCAAGAC UUGUG-3' | SEQ ID NO. 14 |
| Ebola virus | Ebola-HIS-1 | 5'-ACUCAUUCUACCAUUUUU UAAAUUG-3' | SEQ ID NO. 15 |
| | Ebola-HIS-2 | 5'-AGAUCCUGUGACUUCUGG ACUUUU-3' | SEQ ID NO. 16 |
| | Ebola-HIS-3 | 5'-AAAUAUUAUUUUUAAAAU UUACUU-3' | SEQ ID NO. 17 |
| HIV | HIV-1-HIS-1 | 5'-ACUUUUUAAAAGAAAAGG GGGGA-3' | SEQ ID NO. 18 |

TABLE 1-continued

Target sequence listing of RNA virus

| Virus type | Fragment number | Fragment coding sequence | ID number |
|---|---|---|---|
| | HIV-1-HIS-2 | 5'-GAAAAGGAAGGGAAAAUUUCAAA-3' | SEQ ID NO. 19 |
| | HIV-1-HIS-3 | 5'-AAAUGAACAAGUAGAUAAAUUAG-3' | SEQ ID NO. 20 |
| | HIV-1-HIS-4 | 5'-AAAUUAUGGUACCAGUUAGAGAAA-3' | SEQ ID NO. 21 |
| | HIV-1-HIS-5 | 5'-GAAAGAAAAAAUAUAAAUUAAAA-3' | SEQ ID NO. 22 |
| | HIV-1-HIS-6 | 5'-AUUUAUCAAGAGCCAUUUAAAAA-3' | SEQ ID NO. 23 |
| | HIV-2-HIS-1 | 5'-UAAAACAGGGACCAAAGAACCGU-3' | SEQ ID NO. 24 |
| | HIV-2-HIS-2 | 5'-AGAAUCAGAUAAGUAGAAUUAGA-3' | SEQ ID NO. 25 |
| | HIV-2-HIS-3 | 5'-AGGCAGAGGAAGAUGAGGCCAAC-3' | SEQ ID NO. 26 |
| Norwalk virus | Norwalk virus-HIS | 5'-UAUCAAAAAAUUAAGAAAAGGUUA-3' | SEQ ID NO. 27 |
| Alkhurma virus | Alkhurma virus-HIS-1 | 5'-GGAUCAGUGGAGAAAGUGAGGAGGAUGA-3' | SEQ ID NO. 28 |
| | Alkhurma virus-HIS-2 | 5'-AUGAGAGAUCUUGGGGGUGGGAC-3' | SEQ ID NO. 129 |
| | Alkhurma virus-HIS-3 | 5'-GAAAAACUCAAGAUGAAAGGAAU-3' | SEQ ID NO. 30 |
| Enterovirus | enterovirus-HIS-1 | 5'-AUUGAUUGGCUUAAGGAGAAAAUA-3' | SEQ ID NO. 31 |
| | enterovirus-HIS-2 | 5'-AAUUGUUUACCUAUUUAUUGGUUUUGUG-3' | SEQ ID NO. 32 |
| Kemerovo virus | Kemerovo virus-HIS-1 | 5'-CUGUGCUGAACCAGGACCAGGA-3' | SEQ ID NO. 33 |
| | Kemerovo virus-HIS-2 | 5'-AGAUGAAGCAGUCACCAACCGC-3' | SEQ ID NO. 34 |
| Coxsackievirus | Coxsackievirus-HIS | 5'-AUUAGAUUUCAACACAGGUGCUACAUC-3' | SEQ ID NO. 35 |
| Hepatitis A virus | Hepatitis A virus-HIS-1 | 5'-UUGGAAUGUUUUGCUCCUCUUUA-3' | SEQ ID NO. 36 |
| | Hepatitis A virus-HIS-2 | 5'-GAAAUUUUAUUAUUUUGUUCAGU-3' | SEQ ID NO. 37 |
| | Hepatitis A virus-HIS-3 | 5'-UUAGCUAGAUUUACAGAUUUGGA-3' | SEQ ID NO. 38 |
| | Hepatitis A virus-HIS-4 | 5'-AACAAGAGCAGGCCAGUGUGGUGG-3' | SEQ ID NO. 39 |
| | Hepatitis A virus-HIS-5 | 5'-UUGAGGAAAAGGGAACCCUGUACA-3' | SEQ ID NO. 40 |
| | Hepatitis A virus-HIS-6 | 5'-CCAGGCACUGGGAAGUCAGUGGCA-3' | SEQ ID NO. 41 |
| | Hepatitis A virus-HIS-7 | 5'-AAUUAGGAGUGAUACCUUCACUAA-3' | SEQ ID NO. 42 |
| | Hepatitis A virus-HIS-8 | 5'-UGAGAAAAAGGCCACUGUCCUUUA-3' | SEQ ID NO. 43 |
| | Hepatitis A virus-HIS-9 | 5'-ACAAAUUGGAGAAAUAGUGAAAA-3' | SEQ ID NO. 44 |
| | Hepatitis A virus-HIS-10 | 5'-GAAGCAGAGAGAAAGUAGAGAAG-3' | SEQ ID NO. 45 |
| | Hepatitis A virus-HIS-11 | 5'-UCAAAAGGAGAGAACAGAUGCUGG-3' | SEQ ID NO. 46 |
| Dengue virus 2 | Dengue virus 2-HIS-1 | 5'-CAAAAGAAGGCAUUAAAAGAGGA-3' | SEQ ID NO. 47 |
| | Dengue virus 2-HIS-2 | 5'-GAGAUGGACUUUGAUUUCUGUGA-3' | SEQ ID NO. 48 |
| | Dengue virus 2-HIS-3 | 5'-GGAAAUCCAGGGAGGUUUUGGAA-3' | SEQ ID NO. 49 |
| | Dengue virus 2-HIS-4 | 5'-AAAGGAAGAAAUUGAAACCCAGA-3' | SEQ ID NO. 150 |
| Rubella virus | Rubella virus-HIS | 5'-GUGGCAGGCCCAUUACACCACCA-3' | SEQ ID NO. 51 |
| Marburg Marburgvirus | Marburg Marburgvirus-HIS-1 | 5'-AGUUUAAAUUUAUAUCCAAAAUAAAAUUU-3' | SEQ ID NO. 52 |

TABLE 1-continued

Target sequence listing of RNA virus

| Virus type | Fragment number | Fragment coding sequence | ID number |
|---|---|---|---|
| | Marburg Marburgvirus-HIS-2 | 5'-AAGAAAAAGAUAAAUAGA ACACAAAGAAUUGACAAAAUU U-3' | SEQ ID NO. 53 |
| | Marburg Marburgvirus-HIS-3 | 5'-UCUAAGCGAAGUAACAAC AAGAGU-3' | SEQ ID NO. 54 |
| | Marburg Marburgvirus-HIS-4 | 5'-AACAGAAAGAAGCAUUAU UACAUCAGGCUUCU-3' | SEQ ID NO. 55 |
| | Marburg Marburgvirus-HIS-5 | 5'-UGAUUUAUAUUUACUGGU AUAAAAUAGU-3' | SEQ ID NO. 56 |
| Poliovirus | Poliovirus-HIS | 5'-AACAAACAAACCAGAGAC ACUAAGGAAAUGCA-3' | SEQ ID NO. 57 |
| Respiratory syncytial virus | Respiratory syncytial virus-HIS-1 | 5'-AUACAAUCAAAUUGAAUG GCAU-3' | SEQ ID NO. 58 |
| | Respiratory syncytial virus-HIS-2 | 5'-AGAUGACAAUUGUGAAAU UAAA-3' | SEQ ID NO. 59 |
| | Respiratory syncytial virus-HIS-3 | 5'-GUUAUAUAUGGGAAAUGA UGGAAUUAACA-3' | SEQ ID NO. 60 |
| | Respiratory syncytial virus-HIS-4 | 5'-AAAAAACUAAGUGAUUCA ACA-3' | SEQ ID NO. 61 |
| | Respiratory syncytial virus-HIS-5 | 5'-AAAUCAAAAAAUAUACU GAAUACAA-3' | SEQ ID NO. 62 |
| | Respiratory syncytial virus-HIS-6 | 5'-UUUACAUUCCUGGUCAAC UAUGAAAUGAAACUAUUGC-3' | SEQ ID NO. 63 |
| | Respiratory syncytial virus-HIS-7 | 5'-CUACAAAAAAAUGCUAAA AGAA-3' | SEQ ID NO. 64 |
| | Respiratory syncytial virus-HIS-8 | 5'-AUGCUGAACAACUCAAAG AAAA-3' | SEQ ID NO. 65 |
| | Respiratory syncytial virus-HIS-9 | 5'-AGGAAAGUGAAAAGAUGG CAAA-3' | SEQ ID NO. 66 |
| | Respiratory syncytial virus-HIS-10 | 5'-AAUGAGGAAAGUGAAAAG AUGGCAAAGA-3' | SEQ ID NO. 67 |
| | Respiratory syncytial virus-HIS-11 | 5'-CAAGAAAAAAGAUAGUAU CAU-3' | SEQ ID NO. 68 |
| | Respiratory syncytial virus-HIS-12 | 5'-CCAUAGAAACAUUUGAUA ACAAUGAAGAA-3' | SEQ ID NO. 69 |
| | Respiratory syncytial virus-HIS-13 | 5'-AAAGUAUAUAUUAUGUUA CAACA-3' | SEQ ID NO. 70 |
| | Respiratory syncytial virus-HIS-14 | 5'-AUGAUAACAACAAUAAUC UCUUU-3' | SEQ ID NO. 71 |
| | Respiratory syncytial virus-HIS-15 | 5'-ACUAAUACACAUGAUAACAA-3' | SEQ ID NO. 72 |
| | Respiratory syncytial virus-HIS-16 | 5'-UGAUAACAACAAUAAUCU CUUUGCUA-3' | SEQ ID NO. 73 |
| | Respiratory syncytial virus-HIS-17 | 5'-GAAAAGGAAAAGAAGAUU UCUUG-3' | SEQ ID NO. 74 |
| | Respiratory syncytial virus-HIS-18 | 5'-AAUGUACAGCAUCCAAUA AAAA-3' | SEQ ID NO. 75 |
| | Respiratory syncytial virus-HIS-19 | 5'-UAAUUAUUUUGAAUGGCC ACCCCAUG-3' | SEQ ID NO. 76 |
| | Respiratory syncytial virus-HIS-20 | 5'-AAUUAUUUUGAAUGGCCA CCC-3' | SEQ ID NO. 77 |
| | Respiratory syncytial virus-HIS-21 | 5'-UCUAUAAAUAAUAUAACU AAA-3' | SEQ ID NO. 78 |
| | Respiratory syncytial virus-HIS-22 | 5'-UAAAUAUAGAUAAAAUAU ACAUUA-3' | SEQ ID NO. 79 |
| | Respiratory syncytial virus-HIS-23 | 5'-AAAUGUUUGUUUAAUUAC AUGGAUUAGUA-3' | SEQ ID NO. 80 |
| | Respiratory syncytial virus-HIS-24 | 5'-AUGGUUAAUACAUUGGUU UAAUUUAUA-3' | SEQ ID NO. 81 |
| | Respiratory syncytial virus-HIS-25 | 5'-AACUAUAUUAAAAACUUA UGUAU-3' | SEQ ID NO. 82 |
| | Respiratory syncytial virus-HIS-26 | 5'-UAUAGAACAUGAAAAAUU AAAAUUUC-3' | SEQ ID NO. 83 |
| | Respiratory syncytial virus-HIS-27 | 5'-UAGACAAUAUAACUAUAU UAAAA-3' | SEQ ID NO. 84 |
| | Respiratory syncytial virus-HIS-28 | 5'-AAUGUUACCAUUGUUAUC UAAUA-3' | SEQ ID NO. 85 |
| Mumps virus | Mumps virus-HIS | 5'-AGGUAAAUUAAUGAGAGA GAAUGGAGUU-3' | SEQ ID NO. 86 |

TABLE 1-continued

Target sequence listing of RNA virus

| Virus type | Fragment number | Fragment coding sequence | ID number |
|---|---|---|---|
| Australian batlyssavirus | Australian bat lyssavirus-HIS | 5'-UAUUUUAAAAGGCAGAUA AUUAGA-3' | SEQ ID NO. 87 |
| Andes virus | Andes virus-HIS-1 | 5'-GGAACUUGGUGCAUUUUU UUCUA-3' | SEQ ID NO. 88 |
| | Andes virus-HIS-2 | 5'-AUUUUUCUUGAUUGCUUU UCAA-3' | SEQ ID NO. 89 |
| | Andes virus-HIS-3 | 5'-UAUUCUGAAAAUGGUAUA UUUAA-3' | SEQ ID NO. 90 |
| | Andes virus-HIS-4 | 5'-AGCCUAUUUUCAUUGAUG CCUGA-3' | SEQ ID NO. 91 |
| | Andes virus-HIS-5 | 5'-UCAACAAAUAUUUACAGG CAAAA-3' | SEQ ID NO. 92 |
| | Andes virus-HIS-6 | 5'-UUAGAAAAAUGGAAAAGU AUAGA-3' | SEQ ID NO. 93 |
| | Andes virus-HIS-7 | 5'-AAGAGCUCAACAAAUAUU UACAG-3' | SEQ ID NO. 94 |
| | Andes virus-HIS-8 | 5'-UCUAAAUAUUCAGAAUGC ACUAGAGAAA-3' | SEQ ID NO. 95 |
| Powassan virus | Powassan virus-HIS-1 | 5'-UGAUGGGGGUUGACGGAG UUGGGGAGU-3' | SEQ ID NO. 96 |
| | Powassan virus-HIS-2 | 5'-GGGGAUUGGAAAGGCUCU CUGUG-3' | SEQ ID NO. 97 |
| Langat virus | Langat virus-HIS-1 | 5'-AAAUGGAGCAGAAAGAAC ACUCAGG-3' | SEQ ID NO. 98 |
| | Langat virus-HIS-2 | 5'-UGGCUCGAAGAGCAUGGA GAGGAA-3' | SEQ ID NO. 99 |
| | Langat virus-HIS-3 | 5'-AGGAAGGGGAUUGAGAGA CUCAC-3' | SEQ ID NO. 100 |
| | Langat virus-HIS-4 | 5'-AAAAUAGACUGGAGAUGG CCAUGUGGAGAAGC-3' | SEQ ID NO. 101 |
| | Langat virus-HIS-5 | 5'-CAGCGCAGGGGAAGAGUG GGCAGGCAG-3' | SEQ ID NO. 102 |
| Eyach virus | Eyach virus-HIS-1 | 5'-AAUAAGAAAAGCAACAUU GUGAUUUUUAAUUA-3' | SEQ ID NO. 103 |
| | Eyach virus-HIS-2 | 5'-UAAAAAAAGUCAAAUUUA UGAUUA-3' | SEQ ID NO. 104 |
| | Eyach virus-HIS-3 | 5'-CUUUGGCAUUUCAGUGAU UCAGCAAAA-3' | SEQ ID NO. 105 |
| | Eyach virus-HIS-4 | 5'-AAAUGUGCUCCCCUUUCC UGGA-3' | SEQ ID NO. 106 |
| | Eyach virus-HIS-5 | 5'-UUUUAAAGGAGUGGUGAA GAAGAAAGA-3' | SEQ ID NO. 107 |
| | Eyach virus-HIS-6 | 5'-AAAUAAUAUAAAUGCAUU CAACU-3' | SEQ ID NO. 108 |
| | Eyach virus-HIS-7 | 5'-GGCAGGUGUGGUUGCUCA AGCUGUAA-3' | SEQ ID NO. 109 |
| | Eyach virus-HIS-8 | 5'-UAUAACAUUUUCCUGCUU CCAA-3' | SEQ ID NO. 110 |
| | Eyach virus-HIS-9 | 5'-UCAUUGGAAGAUGGAGCU CUUU-3' | SEQ ID NO. 111 |
| | Eyach virus-HIS-10 | 5'-CAGCUUACUCUUCCUCAG AGUUCUUU-3' | SEQ ID NO. 112 |
| | Eyach virus-HIS-11 | 5'-UUUAUGAAUUCUACAGAA AUAAUGAUAAUG-3' | SEQ ID NO. 113 |
| Colorado tick fever virus | Colorado tick fever virus-HIS-1 | 5'-AAAGAUUAUGGAAACUUUUCUG-3' | SEQ ID NO. 114 |
| | Colorado tick fever virus-HIS-2 | 5'-UUGCUGUUUUUCCAAACA CUAGA-3' | SEQ ID NO. 115 |
| | Colorado tick fever virus-HIS-3 | 5'-GUCAAUCCAAAUAUUGGA AGAAGCAGAAGUUAAU-3' | SEQ ID NO. 116 |
| | Colorado tick fever virus-HIS-4 | 5'-AUGUGGAGACAUUCCAGC ACAGAGGAAAC-3' | SEQ ID NO. 117 |
| | Colorado tick fever virus-HIS-5 | 5'-UCAGGCUCAAGUGAUCUC UCAUUCA-3' | SEQ ID NO. 118 |
| | Colorado tick fever virus-HIS-6 | 5'-UUUAUAUUGAAGUUUAUGA AGUUG-3' | SEQ ID NO. 119 |
| | Colorado tick fever virus-HIS-7 | 5'-AGAUAUAGGAAUGUGUCU GAAA-3' | SEQ ID NO. 120 |

TABLE 1-continued

Target sequence listing of RNA virus

| Virus type | Fragment number | Fragment coding sequence | ID number |
|---|---|---|---|
| | Colorado tick fever virus-HIS-8 | 5'-AAAAGUCAAGAAAAUUAA AUUUAUA-3' | SEQ ID NO. 121 |
| | Colorado tick fever virus-HIS-9 | 5'-UAUGCCUGAUAAUUUUUC AUUGG-3' | SEQ ID NO. 122 |
| | Colorado tick fever virus-HIS-10 | 5'-AUAAAGGAAAAGUCAAGA AAAUU-3' | SEQ ID NO. 123 |
| | Colorado tick fever virus-HIS-11 | 5'-AGAGAGAGAGAAAAGAAA AUUG-3' | SEQ ID NO. 124 |
| | Colorado tick fever virus-HIS-12 | 5'-UAUGCCUGAUAAUUUUUC AUUG-3' | SEQ ID NO. 125 |
| | Colorado tick fever virus-HIS-13 | 5'-CUGUGUUUUCUCCUAGAA UGUCA-3' | SEQ ID NO. 126 |
| | Colorado tick fever virus-HIS-14 | 5'-AAAGACAGGAUUUCAUUA UUUGUA-3' | SEQ ID NO. 127 |
| | Colorado tick fever virus-HIS-15 | 5'-UGGAUGUGAGAAAUACUU GGGA-3' | SEQ ID NO. 128 |
| | Colorado tick fever virus-HIS-16 | 5'-AAAAGACAGGAUUUCAUU AUUU-3' | SEQ ID NO. 129 |
| | Colorado tick fever virus-HIS-17 | 5'-AAAAGACAGGAUUUCAUU AUUUGUAU-3' | SEQ ID NO. 130 |
| | Colorado tick fever virus-HIS-18 | 5'-GACAGGAUUUCAUUAUUU GUAU-3' | SEQ ID NO. 131 |
| | Colorado tick fever virus-HIS-19 | 5'-AGUUCUCUUUUGACAUUU UGUUC-3' | SEQ ID NO. 132 |
| | Colorado tick fever virus-HIS-20 | 5'-UGACAUUUUGUUCUUUCU UUG-3 | SEQ ID NO. 133 |
| | Colorado tick fever virus-HIS-21 | 5'-GAAAAUGUUGUCCAACAA UCCAAUCAA-3' | SEQ ID NO. 134 |
| Lassa virus | Lassa virus-HIS-1 | 5'-GGAAGAAAAGACAUUAAA CUAAUU-3' | SEQ ID NO. 135 |
| | Lassa virus-HIS-2 | 5'-UAAUCUUCUAUAAGUCUA GUAAA-3' | SEQ ID NO. 136 |
| Omsk hemorrhagic fever virus | Omsk hemorrhagic fever virus-HIS-1 | 5'-CAGGAAUCCUUGUAGUGA UGGGAUUGU-3' | SEQ ID NO. 137 |
| | Omsk hemorrhagic fever virus-HIS-2 | 5'-UAUAUUCAAUGGCAAAAG AAAACAAAU-3' | SEQ ID NO. 138 |
| Machupo virus | Machupo virus-HIS-1 | 5'-AAUGCCUUAAUCUCAGAU AAUUUGUUAA-3' | SEQ ID NO. 139 |
| | Machupo virus-HIS-2 | 5'-UAAUUUGUUAAUGAAGAA UAAAAUUAA-3' | SEQ ID NO. 140 |
| Junin virus | Junin virus-HIS | 5'-AACAAGUUUCUCCUUAUC AUAAA-3' | SEQ ID NO. 141 |
| Guanarito virus | Guanarito virus-HIS-1 | 5'-CAUAGUAUCUCUUAUAAU CCUUUUCAUUU-3' | SEQ ID NO. 142 |
| | Guanarito virus-HIS-2 | 5'-AUAGUAUCUCUUAUAAUC CUUUUCAUUU-3' | SEQ ID NO. 143 |
| | Guanarito virus-HIS-3 | 5'-UACAAACAUGGGCAAUUC AAAAUC-3' | SEQ ID NO. 144 |
| | Guanarito virus-HIS-4 | 5'-GCUCUUCUUUUCCUUAACA AAUGU-3' | SEQ ID NO. 145 |
| | Guanarito virus-HIS-5 | 5'-UGUUAAACACUUUCUUUC CUUUU-3' | SEQ ID NO. 146 |
| | Guanarito virus-HIS-6 | 5'-AUAGUAUCUCUUAUAAUC CUUUU-3' | SEQ ID NO. 147 |
| Sin Nombre virus | Sin Nombre virus-HIS-1 | 5'-ACAACUGAAACAAUGCAA GGAAU-3' | SEQ ID NO. 148 |
| | Sin Nombre virus-HIS-2 | 5'-GUUCAAGGGCCAAUUAUA UCACA-3' | SEQ ID NO. 149 |
| | Sin Nombre virus-HIS-3 | 5'-UAUAAAAUUUUCUCAGGU CUAU-3' | SEQ ID NO. 150 |
| | Sin Nombre virus-HIS-4 | 5'-AGAAAUUCAGGAAAAUGG AAAAA-3' | SEQ ID NO. 151 |
| | Sin Nombre virus-HIS-5 | 5'-CACAAAGCUCAAGCACGU AUUGU-3' | SEQ ID NO. 152 |

TABLE 1-continued

Target sequence listing of RNA virus

| Virus type | Fragment number | Fragment coding sequence | ID number |
|---|---|---|---|
| Hantaan virus | Hantaan virus-HIS-1 | 5'-CUUGUUUUCUUUCCCUUU CUUUCUG-3' | SEQ ID NO. 153 |
| | Hantaan virus-HIS-2 | 5'-UUUCUUUCCCUUUCUUUC UGCUUUCU-3' | SEQ ID NO. 154 |
| | Hantaan virus-HIS-3 | 5'-UUUUCUUUCCCUUUCUUU CUGCUUUCUCU-3' | SEQ ID NO. 155 |
| | Hantaan virus-HIS-4 | 5'-UUUCUUUCCCUUUCUUUC UGCUU-3' | SEQ ID NO. 156 |
| | Hantaan virus-HIS-5 | 5'-UUUCUUUCCCUUUCUUUC UGCUUUCU-3' | SEQ ID NO. 157 |
| | Hantaan virus-HIS-6 | 5'-AUAUGGAUGUAGAUUUCA UUUG-3' | SEQ ID NO. 158 |
| | Hantaan virus-HIS-7 | 5'-UUUUCUUUCCCUUUCUUU CUGCUUUCU-3' | SEQ ID NO. 159 |
| | Hantaan virus-HIS-8 | 5'-ACAUCUUUACAAUGUGGA UAUUUCUUC-3' | SEQ ID NO. 160 |
| | Hantaan virus-HIS-9 | 5'-UUCAUACAUUCUAAACUU AAUUCCAGAU-3' | SEQ ID NO. 161 |
| Puumala virus | Puumala virus-HIS-1 | 5'-GACUACAAGAGAAGGAUG GCAGA-3' | SEQ ID NO. 162 |
| | Puumala virus-HIS-2 | 5'-AAUGGCAGUUAUGAAUAU AUUA-3' | SEQ ID NO. 163 |
| | Puumala virus-HIS-3 | 5'-AAGGUUGUAUUUUAUUAU UUAA-3' | SEQ ID NO. 164 |
| | Puumala virus-HIS-4 | 5'-CCUUUUUCCUUUUCAUCA CUUUUUUU-3' | SEQ ID NO. 165 |
| | Puumala virus-HIS-5 | 5'-CAGGAAAAAAAUGGAUAC UAAA-3' | SEQ ID NO. 166 |
| | Puumala virus-HIS-6 | 5'-AUUAUUUUAUAAUCAUUA UCUAAUUA-3' | SEQ ID NO. 167 |
| | Puumala virus-HIS-7 | 5'-UAUAUAUAUGCAAGUAGC AUAUAUAUA-3' | SEQ ID NO. 168 |
| | Puumala virus-HIS-8 | 5'-UGUUAGAUUUCUUGUCAU UUUUUCC-3' | SEQ ID NO. 169 |
| | Puumala virus-HIS-9 | 5'-CCACAGCAACAUGGUUUC AGUAU-3' | SEQ ID NO. 170 |
| | Puumala virus-HIS-10 | 5'-CUUGUUAAGUACUUGAUA UCUGU-3' | SEQ ID NO. 171 |
| | Puumala virus-HIS-11 | 5'-AUUCUCUUUAUUAUGAAUA AAGCA-3' | SEQ ID NO. 172 |
| | Puumala virus-HIS-12 | 5'-AGAGAGAAAGAAAGAGAA UUGGGGAGU-3' | SEQ ID NO. 173 |
| Dobrava virus | Dobrava virus-HIS-1 | 5'-AUAUGGAUGUAGAUUUCA UUUG-3' | SEQ ID NO. 174 |
| | Dobrava virus-HIS-2 | 5'-AACAUCUUAUUUCCUUCU UUUC-3' | SEQ ID NO. 175 |
| | Dobrava virus-HIS-3 | 5'-UUUUUAGCCCUUGCAAAG AACU-3' | SEQ ID NO. 176 |
| | Dobrava virus-HIS-4 | 5'-CUUCAUUAAGUGUUUUUA UCGGAAGUCA-3' | SEQ ID NO. 177 |
| | Dobrava virus-HIS-5 | 5'-UGCCCUGACUUCACAGGC CAUUU-3 | SEQ ID NO. 178 |
| | Dobrava virus-HIS-6 | 5'-AUUAUCUUAAGAAAGAUU AAAGAAGAAUUUG-3' | SEQ ID NO. 179 |
| | Dobrava virus-HIS-7 | 5'-UCAAAGCAAAAUAGGUUC AGAGC-3' | SEQ ID NO. 180 |
| | Dobrava virus-HIS-8 | 5'-AACUUUUUAUUGAUCCAG UGCUCA-3' | SEQ ID NO. 181 |
| | Dobrava virus-HIS-9 | 5'-AGAUAUCUUUCAAAAAAU UUCAA-3' | SEQ ID NO. 182 |
| | Dobrava virus-HIS-10 | 5'-AUGCAUACAACAAUGGGA AUGUCAUUU-3' | SEQ ID NO. 183 |
| | Dobrava virus-HIS-11 | 5'-AUUGUUUAUAUUUAUUUU CAUUU-3' | SEQ ID NO. 184 |
| | Dobrava virus-HIS-12 | 5'-CAACAUAAAAAAUCAACC AUAUU-3' | SEQ ID NO. 185 |
| Seoul virus | Seoul virus-HIS-1 | 5'-UCCUCUUUUCUUUUCCUU UCUCCUUCUUU-3' | SEQ ID NO. 186 |
| | Seoul virus-HIS-2 | 5'-CAGAAAAGCAGUAUGAGA AGGA-3' | SEQ ID NO. 187 |
| | Seoul virus-HIS-3 | 5'-UUGCCUGGGGAAAGGAGG CAGU-3' | SEQ ID NO. 188 |

TABLE 1-continued

Target sequence listing of RNA virus

| Virus type | Fragment number | Fragment coding sequence | ID number |
|---|---|---|---|
| | Seoul virus-HIS-4 | 5'-CAGAAAAGCAGUAUGAGA AGGA-3' | SEQ ID NO. 189 |
| | Seoul virus-HIS-5 | 5'-UCUUUUCUUUUCCUUUCU CCUUCUUU-3' | SEQ ID NO. 190 |
| | Seoul virus-HIS-6 | 5'-GUCCUCUUUUCUUUUCCU UUCUCCUUCUUU-3' | SEQ ID NO. 191 |
| | Seoul virus-HIS-7 | 5'-CUUUUCUUUUCCUUUCUC CUUC-3' | SEQ ID NO. 192 |
| | Seoul virus-HIS-8 | 5'-CUCUUUUCUUUUCCUUUC UCCUUCUU-3' | SEQ ID NO. 193 |
| | Seoul virus-HIS-9 | 5'-UUAAUAAGAAUACAGAUU UAUU-3' | SEQ ID NO. 194 |
| | Seoul virus-HIS-10 | 5'-UCUCUGAGUUAGAAAAUG AGAAAGU-3' | SEQ ID NO. 195 |
| | Seoul virus-HIS-11 | 5'-CUUUGCAUUAAAAAAUGU GUUUGA-3' | SEQ ID NO. 196 |
| | Seoul virus-HIS-12 | 5'-UUUUAUAUGUCUAGAAAA CUUAGACACUAUA-3' | SEQ ID NO. 197 |
| | Seoul virus-HIS-13 | 5'-CUACAGGAUGUAGAUUUU GAAAAUA-3' | SEQ ID NO. 198 |
| | Seoul virus-HIS-14 | 5'-UCUUUGUAUUCUGGCUUU CCUUCUUUGGUUG-3' | SEQ ID NO. 199 |
| Crimean-Congo hemorrhagic fever virus | Crimean-Congo hemorrhagic fever virus-HIS-1 | 5'-AGAAGACACAAAAAAAUG UGUUAACACAAAAC-3' | SEQ ID NO. 200 |
| | Crimean-Congo hemorrhagic fever virus-HIS-2 | 5'-UCAGUGUUUUCUGACUCC AAAGUU-3' | SEQ ID NO. 201 |
| | Crimean-Congo hemorrhagic fever virus-HIS-3 | 5'-UACCAAGAAAAUGAAGAA GGCUCUUCUGA-3' | SEQ ID NO. 202 |
| | Crimean-Congo hemorrhagic fever virus-HIS-4 | 5'-UUUACUUGCUUAUGUAAC CUUAUUUU-3' | SEQ ID NO. 203 |
| | Crimean-Congo hemorrhagic fever virus-HIS-5 | 5'-UUUCUCUAUUUUCUCUUG UUUUAAAC-3' | SEQ ID NO. 204 |
| Sabia virus | Sabia virus-HIS-1 | 5'-AAGAUGACUAUCUAAAAU GUCAGG-3' | SEQ ID NO. 205 |
| | Sabia virus-HIS-2 | 5'-AUUCACUGCCUUCUUCCC UCUCA-3' | SEQ ID NO. 206 |
| | Sabia virus-HIS-3 | 5'-CUGUCUGCUAACCAGUAU GAACA-3' | SEQ ID NO. 207 |
| | Sabia virus-HIS-4 | 5'-AGAAAGUUCUAUCAAGUU UUUUU-3' | SEQ ID NO. 208 |
| | Sabia virus-HIS-5 | 5'-UUUCAAAUUCCUUCUCAG AAUUC-3' | SEQ ID NO. 209 |
| | Sabia virus-HIS-6 | 5'-AUUUUGUACAGAAGGUUU UCAUAA-3' | SEQ ID NO. 210 |
| | Sabia virus-HIS-7 | 5'-AUUGAUUAGAAAUUCAAC UUGGAAAAAUCAAUG-3' | SEQ ID NO. 211 |
| | Sabia virus-HIS-8 | 5'-GGAUGUCUUUGUCUUUCU UUUUCUUUG-3' | SEQ ID NO. 212 |
| Thogoto virus | Thogoto virus-HIS-1 | 5'-ACACCAAAGGGAAACUCA CUGACAGAAAAC-3' | SEQ ID NO. 213 |
| | Thogoto virus-HIS-2 | 5'-GACACAGAUGAAGAAACU UCCUUU-3' | SEQ ID NO. 214 |
| | Thogoto virus-HIS-3 | 5'-UACAACCCAAGAGAGCUU AAAC-3' | SEQ ID NO. 215 |
| | Thogoto virus-HIS-4 | 5'-AAAGAAUGAAGUAAAGGU CAGCA-3' | SEQ ID NO. 216 |
| | Thogoto virus-HIS-5 | 5'-GUGCUAUUGAUCAGACUA AUUA-3' | SEQ ID NO. 217 |
| | Thogoto virus-HIS-6 | 5'-GCUGGACUGUGGUGACAG CCUC-3' | SEQ ID NO. 218 |
| | Thogoto virus-HIS-7 | 5'-CAACCUCUGCACAAAAUG AGCU-3' | SEQ ID NO. 219 |
| | Thogoto virus-HIS-8 | 5'-ACAAUGGAGCAUGCAAGG AAGCA-3' | SEQ ID NO. 220 |
| | Thogoto virus-HIS-9 | 5'-UAGCAGGUAGUAUCCAAG ACAGAGAC-3' | SEQ ID NO. 221 |
| | Thogoto virus-HIS-10 | 5'-AAAAUGCUGAGGAUAUGG GCAA-3' | SEQ ID NO. 222 |
| | Thogoto virus-HIS-11 | 5'-CAAUAACCAAAGAGAAAA AAGAA-3' | SEQ ID NO. 223 |
| | Thogoto virus-HIS-12 | 5'-AAUCAUGGAAGUUGUUUU CCCCA-3' | SEQ ID NO. 224 |
| | Thogoto virus-HIS-13 | 5'-AAGCAACCAGGAGAUUGG UUCA-3' | SEQ ID NO. 225 |

TABLE 1-continued

Target sequence listing of RNA virus

| Virus type | Fragment number | Fragment coding sequence | ID number |
|---|---|---|---|
| | Thogoto virus-HIS-14 | 5'-AUGCAACUGAGAUCAGAGCAUC-3' | SEQ ID NO. 226 |
| | Thogoto virus-HIS-15 | 5'-CCAGAGGACAAGAGCUCUUGUU-3' | SEQ ID NO. 227 |
| European trinidad rabies virus 1 | European trinidad rabies virus 1-HIS-1 | 5'-GAGGACGAGAUGGGUGGAUCAAGA-3' | SEQ ID NO. 228 |
| | European trinidad rabies virus 1-HIS-2 | 5'-GAGGACGAGAUGGGUGGAUCAAGAGGUC-3' | SEQ ID NO. 229 |
| | European bat lyssavirus 1-HIS-3 | 5'-UUGGCUCAUUCUCUGUUUUUUUUGUUUUUUU-3' | SEQ ID NO. 230 |
| | European trinidad rabies virus 1-HIS-4 | 5'-GAGGACGAGAUGGGUGGAUCAAGAGGUC-3' | SEQ ID NO. 231 |
| | European trinidad rabies virus 1-HIS-5 | 5'-CUCAUUCUCUGUUUUUUUUGUUUUUUUU-3' | SEQ ID NO. 232 |
| European trinidad rabies virus 2 | European trinidad rabies virus 2-HIS | 5'-CUUUAUUCUAAAAUAUUUUUAAAU-3' | SEQ ID NO. 233 |
| Chapare virus | Chapare virus-HIS | 5'-AUGAGCCCAAGACUUCUUUUGAU-3' | SEQ ID NO. 234 |
| Rotavirus | Rotavirus A-HIS-1 | 5'-AAGAAACUGUGAUUUUUAAUACUUA-3' | SEQ ID NO. 235 |
| | Rotavirus A-HIS-2 | 5'-AAGAAUGAUAAAGCAAAGAAAA-3' | SEQ ID NO. 236 |
| | Rotavirus A-HIS-3 | 5'-UACUUUUAAAGAUGCAUGCUUUCAUU-3' | SEQ ID NO. 237 |
| | Rotavirus A-HIS-4 | 5'-UUUAAAAAAUGAUAAGAAUAAA-3' | SEQ ID NO. 238 |
| | Rotavirus A-HIS-5 | 5'-AGAAUGAUAAAGCAAAGAAAUGUAG-3' | SEQ ID NO. 239 |
| | Rotavirus A-HIS-6 | 5'-UACUGAUCUCCAACUCAGAAGA-3' | SEQ ID NO. 240 |
| | Rotavirus A-HIS-7 | 5'-AAAAUUUGAAAGAAUGAUAAAGCAAA-3' | SEQ ID NO. 241 |
| | Rotavirus A-HIS-8 | 5'-AAAAAUGAAUGAAAAUAUGCAUUCUCUUCAAAA-3' | SEQ ID NO. 242 |
| | Rotavirus A-HIS-9 | 5'-AAAGCAAGAAAAAUGAAUGAAAA-3' | SEQ ID NO. 243 |
| | Rotavirus A-HIS-10 | 5'-CAAGAAAAAUGAAUGAAAUAU-3' | SEQ ID NO. 244 |
| | Rotavirus A-HIS-11 | 5'-AGGAGAAAUCAAAACAAAACCAUA-3' | SEQ ID NO. 245 |
| | Rotavirus A-HIS-12 | 5'-GCAUUCAAUAAAUACAUGCUG-3' | SEQ ID NO. 246 |
| | Rotavirus A-HIS-13 | 5'-AUGUAAGAACUGUAAAUAUAA-3' | SEQ ID NO. 247 |
| | Rotavirus A-HIS-14 | 5'-AAAACAAAACCAUAAAAGUAG-3' | SEQ ID NO. 248 |
| | Rotavirus A-HIS-15 | 5'-AAAGGAGAAAUCAAAACAAAACCAUAAAA-3' | SEQ ID NO. 249 |
| | Rotavirus A-HIS-16 | 5'-UAGGGAGCUCCCCACUCCCGUUUUGUGAC-3' | SEQ ID NO. 250 |
| | Rotavirus A-HIS-17 | 5'-UAUAUCAAAAGAAAAUGAAAUCAA-3' | SEQ ID NO. 251 |
| | Rotavirus A-HIS-18 | 5'-GAUUAAAUUUAUAUCAAAAGAAAAUGAA-3' | SEQ ID NO. 252 |
| | Rotavirus A-HIS-19 | 5'-UAUAUCAAAAGAAAAUGAAAUCAAUA-3' | SEQ ID NO. 253 |
| | Rotavirus A-HIS-20 | 5'-AAAGAAAAUGAAAAUCAAUAGUUGAGGA-3' | SEQ ID NO. 254 |
| | Rotavirus A-HIS-21 | 5'-UAUAUCAAAAGAAAAUGAAAUCAAUAG-3' | SEQ ID NO. 255 |
| | Rotavirus A-HIS-22 | 5'-AUGACCAAAUGUAUAGAUUGAGA-3' | SEQ ID NO. 256 |
| | Rotavirus A-HIS-23 | 5'-UAUAUCAAAAGAAAAUGAAAUCAAUAGUUGAGGA-3' | SEQ ID NO. 257 |
| | Rotavirus A-HIS-24 | 5'-UAUAUCAAAAGAAAAUGAAAUCAAUA-3' | SEQ ID NO. 258 |
| | Rotavirus A-HIS-25 | 5'-UUGAAAUAAGAAGAUUAGAUAUUUUUAAUU-3' | SEQ ID NO. 259 |
| | Rotavirus A-HIS-26 | 5'-UGAUAUCAUUUUCAAUUACAUA-3' | SEQ ID NO. 260 |

TABLE 1-continued

Target sequence listing of RNA virus

| Virus type | Fragment number | Fragment coding sequence | ID number |
|---|---|---|---|
| | Rotavirus A-HIS-27 | 5'-AAGAAAAAGAAGAUAGCAAGAA-3' | SEQ ID NO. 261 |
| | Rotavirus A-HIS-28 | 5'-AGCUAAAGUUUGGUAGGAAAACAA-3' | SEQ ID NO. 262 |
| | Rotavirus A-HIS-29 | 5'-AAAUCAAGUAAAAUAACAAUAAAUGACAUAC-3' | SEQ ID NO. 263 |
| | Rotavirus A-HIS-30 | 5'-CAUUAAAUUUAUACAAACAAACACAAA-3' | SEQ ID NO. 264 |
| | Rotavirus A-HIS-31 | 5'-AGCUAAAGUUUGGUAGGAAAACAA-3' | SEQ ID NO. 265 |
| | Rotavirus A-HIS-32 | 5'-GAAAUAUACCAUAUAAAUAUGAUGU-3' | SEQ ID NO. 266 |
| | Rotavirus A-HIS-33 | 5'-AAAUAAGAUCAGAAUUUUAUUUA-3' | SEQ ID NO. 267 |
| | Rotavirus A-HIS-34 | 5'-AGAAUUAUAUUAAUACAGUAUA-3' | SEQ ID NO. 268 |
| | Rotavirus A-HIS-35 | 5'-AGCAUUAAAACAUUAGAAAUAUUAAAUAAG-3' | SEQ ID NO. 269 |
| | Rotavirus A-HIS-36 | 5'-AGAAUUAUAUUAAUACAGUAUAUAGU-3' | SEQ ID NO. 270 |
| | Rotavirus A-HIS-37 | 5'-GAAGAAUUAUUCACAUUAAUAA-3' | SEQ ID NO. 271 |
| | Rotavirus A-HIS-38 | 5'-GAAGAACAAACUAUUAAUAAUU-3' | SEQ ID NO. 272 |
| | Rotavirus A-HIS-39 | 5'-UAAGAUCAGAAUUUUAUUUAUUACUA-3' | SEQ ID NO. 273 |
| | Rotavirus A-HIS-40 | 5'-UAAACCAAACAUUUUUCCUUAU-3' | SEQ ID NO. 274 |
| | Rotavirus A-HIS-41 | 5'-AUUUUAAAACACUUAAAAAUUU-3' | SEQ ID NO. 275 |
| | Rotavirus A-HIS-42 | 5'-CAAUAUUUCUGCUGUUCAAUUCAAUGG-3' | SEQ ID NO. 276 |
| | Rotavirus A-HIS-43 | 5'-UUUUUUGGGUUUUGUUUGUGUUGAUACUUUGAG-3' | SEQ ID NO. 277 |
| Tai Forest ebolavirus | Tai Forest ebolavirus-HIS-1 | 5'-GCAAAUUUAUCUUAAAUUCAAGUACAUA-3' | SEQ ID NO. 278 |
| | Tai Forest ebolavirus-HIS-2 | 5'-UAACAGACUUGGAAAAAUACAAUU-3' | SEQ ID NO. 279 |
| Bundibugyo ebolavirus | Bundibugyo ebolavirus-HIS | 5'-AUUACCUUCAAAAAUCUAGAACUUUAUUAAUUCUCAG-3' | SEQ ID NO. 280 |
| Rift Valley fever virus | Rift Valley fever virus-HIS | 5'-AAAAUUAAAAACAAAAAUGAAAGG-3' | SEQ ID NO. 281 |
| Irkut virus | Irkut virus-HIS-1 | 5'-CUUAUUUUAUGUCUUCUUUGUUGUUUUU-3' | SEQ ID NO. 282 |
| | Irkut virus-HIS-2 | 5'-AUUAUUAACAACUUAUUUUUAUUUAAUCUUUUA-3' | SEQ ID NO. 283 |
| | Irkut virus-HIS-3 | 5'-AUAAAGAAGAAUAUUAACAUUGACAUUA-3' | SEQ ID NO. 284 |
| | Irkut virus-HIS-4 | 5'-UUAUGAAUGUUUUAUCAUGAUUAAAGAU-3' | SEQ ID NO. 285 |
| Influenza A virus | Influenza A virus-HIS-1 | 5'-CCCAGCACAGAGAUGUCAUUGA-3' | SEQ ID NO. 286 |
| | Influenza A virus-HIS-2 | 5'-AGUGAGAAAUGAUGAUGUUGAUCAGA-3' | SEQ ID NO. 287 |
| | Influenza A virus-HIS-3 | 5'-UUCUAAGGAAAGCAACCAGAAG-3' | SEQ ID NO. 288 |
| | Influenza A virus-HIS-4 | 5'-UGAGCAAGAAGAAAUCCUACAU-3' | SEQ ID NO. 289 |
| | Influenza A virus-HIS-5 | 5'-GGAAUGAGAAGAAAGCUAAAUU-3' | SEQ ID NO. 290 |
| | Influenza A virus-HIS-6 | 5'-UUAGAAAUGUCUUAAGCAUUGC-3' | SEQ ID NO. 291 |
| | Influenza A virus-HIS-7 | 5'-CAGGACAUUGAAAAUGAAGAGAAG-3' | SEQ ID NO. 292 |
| | Influenza A virus-HIS-8 | 5'-AAGAGAAAGACCUGACCAAAGA-3' | SEQ ID NO. 293 |
| | Influenza A virus-HIS-9 | 5'-ACUAAGUCAUAUAAAAAUACAAGAAAAA-3' | SEQ ID NO. 294 |
| | Influenza A virus-HIS-10 | 5'-AACAAUUUGAGUUGAUAGACAAUGAAU-3' | SEQ ID NO. 295 |

TABLE 1-continued

Target sequence listing of RNA virus

| Virus type | Fragment number | Fragment coding sequence | ID number |
| --- | --- | --- | --- |
| | Influenza A virus-HIS-11 | 5'-AUCAUGUUUCAUACUUCU AGCCAUUG-3' | SEQ ID NO. 296 |
| | Influenza A virus-HIS-12 | 5'-GAAACAUACUAAGAACAC AGGAA-3' | SEQ ID NO. 297 |
| | Influenza A virus-HIS-13 | 5'-UUUCACCAUUACCUUCUC UUCC-3' | SEQ ID NO. 298 |
| | Influenza A virus-HIS-14 | 5'-AGGAAGCAAAAUUAAACA GAGAAGAAA-3' | SEQ ID NO. 299 |
| | Influenza A virus-HIS-15 | 5'-UGGAAAAUGAAAGAACUU UGGA-3' | SEQ ID NO. 300 |
| | Influenza A virus-HIS-16 | 5'-AAAACAACACUUGGGUAA AUCAGACA-3' | SEQ ID NO. 301 |
| | Influenza A virus-HIS-17 | 5'-GCUGCUGGACAGUCAGUG GUUU-3' | SEQ ID NO. 302 |
| | Influenza A virus-HIS-18 | 5'-GGAUCAAGAAAGAAGAGU UCUCUGAGA-3' | SEQ ID NO. 303 |
| | Influenza A virus-HIS-19 | 5'-GGGGAGACACACAAAUUC AGAC-3' | SEQ ID NO. 304 |
| | Influenza A virus-HIS-20 | 5'-ACCAAAUGAAAACCCAGC UCACAAGAGUCA-3' | SEQ ID NO. 305 |
| | Influenza A virus-HIS-21 | 5'-AAAUGAGAAUGUGGAAAC CAUG-3' | SEQ ID NO. 306 |
| | Influenza A virus-HIS-22 | 5'-AGAAAUAAGGAGAGUUUG GCGC-3' | SEQ ID NO. 307 |
| | Influenza A virus-HIS-23 | 5'-AGAAGAGUAGACGGAAAG UGGA-3' | SEQ ID NO. 308 |
| | Influenza A virus-HIS-24 | 5'-GACAUUCUUUGGCUGGAA AGAGCCUAA-3' | SEQ ID NO. 309 |
| | Influenza A virus-HIS-25 | 5'-GAAGAGAGCAGGGCAAGA AUCAAAACUAGGCU-3' | SEQ ID NO. 310 |
| | Influenza A virus-HIS-26 | 5'-AGGGCAAGCUUUCCCAAA UGUC-3' | SEQ ID NO. 311 |
| | Influenza A virus-HIS-27 | 5'-GGACAUGAUUCCAGAGAG GAAUGAACAAGGACAA-3' | SEQ ID NO. 312 |
| | Influenza A virus-HIS-28 | 5'-GGAAAUUGUGAAAAUUCA AUGG-3' | SEQ ID NO. 313 |
| Bayou virus | Bayou virus-HIS-1 | 5'-GAGUCUACAUUCUCAGUU UUGUC-3' | SEQ ID NO. 314 |
| | Bayou virus-HIS-2 | 5'-GAGACAGACAGUAAAGGA AAAU-3' | SEQ ID NO. 315 |
| | Bayou virus-HIS-3 | 5'-UGAAGAAAAACUAAAGAA AAAA-3' | SEQ ID NO. 316 |
| | Bayou virus-HIS-4 | 5'-CCAGACAGCAGACUGGAA GGCA-3' | SEQ ID NO. 317 |
| | Bayou virus-HIS-5 | 5'-AACAGGAAAUCAUAUUGA AUUUGU-3' | SEQ ID NO. 318 |
| | Bayou virus-HIS-6 | 5'-AGUAUGCAUGGAAAGAUU UUCUUAAUG-3' | SEQ ID NO. 319 |
| | Bayou virus-HIS-7 | 5'-CAGAGUUUGAAUUUUAUG AUCAG-3' | SEQ ID NO. 320 |
| | Bayou virus-HIS-8 | 5'-UGAGGGUAACAUUUAAUU UUGGG-3' | SEQ ID NO. 321 |
| | Bayou virus-HIS-9 | 5'-UUUUUUCUUUUUGAGAAA GGGCUUCAU-3' | SEQ ID NO. 322 |
| | Bayou virus-HIS-10 | 5'-AGAAAACAACAGGUGUUG AUGAG-3' | SEQ ID NO. 323 |
| | Bayou virus-HIS-11 | 5'-UUUUUUCUUUUUGAGAAA GGGCU-3' | SEQ ID NO. 324 |
| | Bayou virus-HIS-12 | 5'-AAAUGAAAGAUUUCCAGA AAUUG-3' | SEQ ID NO. 325 |
| | Bayou virus-HIS-13 | 5'-ACAACAGAUACAACAAAU GCUGGUGAGAAU-3' | SEQ ID NO. 326 |
| | Bayou virus-HIS-14 | 5'-AGUGAUUCAUGCUGAAAU ACAGU-3' | SEQ ID NO. 327 |
| Kyasanur forest disease virus | Kyasanur forest disease virus-HIS | 5'-AUGAGAGAUCUUGGGGGU GGGAC-3' | SEQ ID NO. 328 |
| Black Creek Canal virus | Black Creek Canal virus-HIS-1 | 5'-CCAAUGUAUUUAUACAUU UACAAGUA-3' | SEQ ID NO. 329 |
| | Black Creek Canal virus-HIS-2 | 5'-AAGUUCAUGAGAAAGAG AAUAGAUGG-3' | SEQ ID NO. 330 |
| | Black Creek Canal virus-HIS-3 | 5'-UACUUACAUGCCAAAUCU CAA-3' | SEQ ID NO. 331 |

TABLE 1-continued

Target sequence listing of RNA virus

| Virus type | Fragment number | Fragment coding sequence | ID number |
|---|---|---|---|
| | Black Creek Canal virus-HIS-4 | 5'-AGUUCAAUGAGAAAGAGA AUA-3' | SEQ ID NO. 332 |
| | Black Creek Canal virus-HIS-5 | 5'-UACAUACUAUUAAUGUGA UUUA-3' | SEQ ID NO. 333 |
| | Black Creek Canal virus-HIS-6 | 5'-UUUUGUCCUUCCAAUUGU GUUG-3' | SEQ ID NO. 334 |
| Japanese encephalitis virus | Japanese encephalitis virus-HIS-1 | 5'-GAAGCAGAGAGAAAGUAG AGAAG-3' | SEQ ID NO. 335 |
| | Japanese encephalitis virus-HIS-2 | 5'-UCAAAAGGAGAGAACAGA UGCUGG-3' | SEQ ID NO. 336 |
| | Japanese encephalitis virus-HIS-3 | 5'-UCCCUGGAUGGCAAGCAG AAGCA-3' | SEQ ID NO. 337 |
| Duvenhage lyssavirus | Duvenhage lyssavirus-HIS | 5'-CCUCUAAGUUUCCUAAGG UUCU-3' | SEQ ID NO. 338 |
| | Human enterovirus D-HIS | 5'-AACAAGAGCAGGCCAGUG UGGUGG-3' | SEQ ID NO. 339 |
| | Human enterovirus D-HIS | 5'-UUGAGGAAAAGGGAACCC UGUACA-3' | SEQ ID NO. 340 |
| | Human enterovirus D-HIS | 5'-CCAGGCACUGGGAAGUCA GUGGCA-3' | SEQ ID NO. 341 |
| | Human enterovirus D-HIS | 5'-AAUUAGGAGUGAUACCUU CACUAA-3' | SEQ ID NO. 342 |
| | Human enterovirus D-HIS | 5'-UGAGAAAAAGGCCACUGU CCUUUA-3' | SEQ ID NO. 343 |
| | Human enterovirus D-HIS | 5'-ACAAAUUGGAGAAAUAGU GAAAA-3' | SEQ ID NO. 344 |
| Lujo mammarenavirus | Lujo mammarenavirus-HIS | 5'-AUUUUAAAACACUUAAAA AUUU-3' | SEQ ID NO. 345 |
| Measles morbillivirus | Measles morbillivirus-HIS | 5'-AAAGGAAGAAAUUGAAAC\|CCAGA-3' | SEQ ID NO. 346 |
| Tick-borne encephalitis virus | Tick-borne encephalitis virus-HIS | 5'-GAUGUCAUCAAGAAUGCA GAUGC-3' | SEQ ID NO. 347 |
| Avian influenza virus | Avian influenza virus-CIS-1 | 5'-ACAAAAGAUGCAGAAAGA GGCAAG-3' | SEQ ID NO. 348 |
| | Avian influenza virus-CIS-2 | 5'-AAUGUUAUUGAGUAUAUA GAGAGA-3' | SEQ ID NO. 349 |
| | Avian influenza virus-CIS-3 | 5'-CAUUUGAUGAUCUGGCAU UCCAACU-3' | SEQ ID NO. 350 |
| | Avian influenza virus-CIS-4 | 5'-GAAGGGAGGCUGAUCCAG AACAGU-3' | SEQ ID NO. 351 |
| | Avian influenza virus-CIS-5 | 5'-GGCACAACUGGAGUGGAG UCUGCU-3' | SEQ ID NO. 352 |
| | Avian influenza virus-CIS-6 | 5'-CAAAAGAAAAGAAAGAAG AGCUC-3' | SEQ ID NO. 353 |
| | Avian influenza virus-CIS-7 | 5'-UCCAAAUUGCUUCAAAUG AAAA-3' | SEQ ID NO. 354 |
| | Avian influenza virus-CIS-8 | 5'-AAUUGUACAAAAACCCUG AUAC-3' | SEQ ID NO. 355 |
| | Avian influenza virus-CIS-9 | 5'-AUGAGGAAUGGAGGGAAU AGCU-3' | SEQ ID NO. 356 |
| | Avian influenza virus-CIS-10 | 5'-AUUGCUCCUUUGCUGGAU GGAU-3' | SEQ ID NO. 357 |
| | Avian influenza virus-CIS-11 | 5'-UUCCAAUCUGAAUGAUGC AACA-3' | SEQ ID NO. 358 |
| | Avian influenza virus-CIS-12 | 5'-UAAAAGCUGCAUCAAUAG GUGU-3' | SEQ ID NO. 359 |
| | Avian influenza virus-CIS-13 | 5'-GGGAGAUUGAUCCAAAAC AGCA-3' | SEQ ID NO. 360 |
| | Avian influenza virus-CIS-14 | 5'-AGGGGGAAGCCCAGAUCC UGGA-3' | SEQ ID NO. 361 |
| | Avian influenza virus-CIS-15 | 5'-UGCCACAGAGGAGACACA CAAA-3' | SEQ ID NO. 362 |
| | Avian influenza virus-CIS-16 | 5'-GAGAAAGGAAAGUGGACA ACA-3' | SEQ ID NO. 363 |
| | Avian influenza virus-CIS-17 | 5'-CAUAACAACAACAAUAAU AACUGAA-3' | SEQ ID NO. 364 |
| | Avian influenza virus-CIS-18 | 5'-AGGAAGGGAAAAUACAAA AAAU-3' | SEQ ID NO. 365 |

TABLE 1-continued

Target sequence listing of RNA virus

| Virus type | Fragment number | Fragment coding sequence | ID number |
|---|---|---|---|
| | Avian influenza virus-CIS-19 | 5'-GAGGAAAUGAGAAGAAGG CUA-3' | SEQ ID NO. 366 |
| | Avian influenza virus-CIS-20 | 5'-CUGGAGCUGCUGGAGCAG CAG-3' | SEQ ID NO. 367 |
| | Avian influenza virus-CIS-21 | 5'-UCUCAAACUUGCAGUUGG UC-3' | SEQ ID NO. 368 |
| | Avian influenza virus-CIS-22 | 5'-UUGACUAUGGGAGUGAUG UUU-3' | SEQ ID NO. 369 |
| | Avian influenza virus-CIS-23 | 5'-AGUUUGAAUUCAUUGCUG AAG-3' | SEQ ID NO. 370 |
| | Avian influenza virus-CIS-24 | 5'-GAAAAACAAGAUUUCUCC CAGUG-3' | SEQ ID NO. 371 |
| | Avian influenza virus-CIS-25 | 5'-ACAGGGUGAUGGUGUCCC CC-3' | SEQ ID NO. 372 |
| | Avian influenza virus-MIS-1 | 5'-AAAUGGACCACAAACACA GAAAC-3' | SEQ ID NO. 373 |
| | Avian influenza virus-MIS-2 | 5'-AUGUCUUCUUCAAUCACU UCAAC-3' | SEQ ID NO. 374 |
| | Avian influenza virus-MIS-3 | 5'-UACUGCUAAGGAAGCACA AGAUG-3' | SEQ ID NO. 375 |
| | Avian influenza virus-MIS-4 | 5'-AAAAAUUGAAACGAACAA AUUC-3' | SEQ ID NO. 376 |
| | Avian influenza virus-MIS-5 | 5'-AAUAAAUACAACAUUACC CUUU-3' | SEQ ID NO. 377 |
| | Avian influenza virus-MIS-6 | 5'-AAGCAAGAUUAAAAAGAG AGGA-3' | SEQ ID NO. 378 |
| | Avian influenza virus-MIS-7 | 5'-UUAGAGCAUCUGUUGGAA GAAU-3' | SEQ ID NO. 379 |
| | Avian influenza virus-MIS-8 | 5'-AACAGAGGCUGAACAAGA GGA-3' | SEQ ID NO. 380 |
| | Avian influenza virus-MIS-9 | 5'-UGCAGAAGGAACAGGAAC GGC-3' | SEQ ID NO. 381 |
| | Avian influenza virus-MIS-10 | 5'-AUUGUAUGGACACAAUUA GAAAC-3' | SEQ ID NO. 382 |
| | Avian influenza virus-MIS-11 | 5'-AUGAGAAACGUGCCUGAG AAACA-3' | SEQ ID NO. 383 |
| | Avian influenza virus-MIS-12 | 5'-UGUUUUCUUCUGUCUGAA GA-3' | SEQ ID NO. 384 |
| | Avian influenza virus-MIS-13 | 5'-CAUAUAAUUAGCAUCACAAU-3' | SEQ ID NO. 385 |
| | Avian influenza virus-MIS-14 | 5'-ACAAAUCAGCAGUUUGAA CUGAUA-3' | SEQ ID NO. 386 |
| | Avian influenza virus-MIS-15 | 5'-GAAAGAGGUAAAUUAAAA AG-3' | SEQ ID NO. 387 |
| | Avian influenza virus-MIS-16 | 5'-AAGUAGCAGGCUCACACUCU GC-3' | SEQ ID NO. 388 |
| | Avian influenza virus-MIS-17 | 5'-AGAAGGAGAGAAGGAAAA UGG-3' | SEQ ID NO. 389 |
| | Avian influenza virus-MIS-18 | 5'-ACAAAUACCUGCAGAAAU GC-3' | SEQ ID NO. 390 |
| | Avian influenza virus-MIS-19 | 5'-AAUGAAUCAACAAGAAAG AAAA-3' | SEQ ID NO. 391 |
| | Avian influenza virus-MIS-20 | 5'-AAUGAAUCAACAAGAAAG AA-3' | SEQ ID NO. 392 |
| | Avian influenza virus-MIS-21 | 5'-GAGAAUGAAGAGAAAACU CC-3' | SEQ ID NO. 393 |
| | Avian influenza virus-MIS-22 | 5'-AUUCAGUGAAAUUGGAAAAU-3' | SEQ ID NO. 394 |
| | Avian influenza virus-MIS-23 | 5'-AGAAAUACACCAAGACCA CAUA-3' | SEQ ID NO. 395 |
| | Avian influenza virus-MIS-24 | 5'-CUUGAACUUAGAAGCAGA UAU-3' | SEQ ID NO. 396 |
| | Avian influenza virus-MIS-25 | 5'-ACAAUGCUAUCAAUUGUA AUC-3' | SEQ ID NO. 397 |
| | Avian influenza virus-MIS-26 | 5'-ACAAUGCUAUCAAUUGUAAU-3' | SEQ ID NO. 398 |
| | Avian influenza virus-MIS-27 | 5'-GAACUUCAGGACAUAGAA AAU-3' | SEQ ID NO. 399 |
| | Avian influenza virus-MIS-28 | 5'-GCCUUCCUUUCCAGAAUG UG-3' | SEQ ID NO. 400 |
| | Avian influenza virus-MIS-29 | 5'-GAUAUGACUUUGAAAGGG AG-3' | SEQ ID NO. 401 |
| | Avian influenza virus-MIS-30 | 5'-AGGGGUUGGAAUGGCUGC AG-3' | SEQ ID NO. 402 |
| | Avian influenza virus-HIS-1 | 5'-CAGAGUAGAAUGCAAUUC UCCUCA-3' | SEQ ID NO. 403 |

TABLE 1-continued

Target sequence listing of RNA virus

| Virus type | Fragment number | Fragment coding sequence | ID number |
|---|---|---|---|
| | Avian influenza virus-HIS-2 | 5'-UUCCUGCUUUACCAUAAU GACUGA-3' | SEQ ID NO. 404 |
| | Avian influenza virus-HIS-3 | 5'-UUUCAUAAUGUCAGCAAA UAUGCA-3' | SEQ ID NO. 405 |
| | Avian influenza virus-HIS-4 | 5'-GGUCUACAAAACAUACUU UGAGAA-3' | SEQ ID NO. 406 |
| | Avian influenza virus-HIS-5 | 5'-CAAAAUUAGAGAGACAGA AAAUAGA-3' | SEQ ID NO. 1407 |
| | Avian influenza virus-HIS-6 | 5'-GAAGCAAAACUGUUUGUG CU-3' | SEQ ID NO. 408 |
| | Avian influenza virus-HIS-7 | 5'-UUGUUUUUAUGUGGAGCU AAUCA-3' | SEQ ID NO. 409 |
| | Avian influenza virus-HIS-8 | 5'-CACAAAGGACAAUAGGAA AGAAA-3' | SEQ ID NO. 410 |
| | Avian influenza virus-HIS-9 | 5'-UAAAGAAAUUGAAUCAGU AAAUAA-3' | SEQ ID NO. 411 |
| | Avian influenza virus-HIS-10 | 5'-AGUGAGACACAGGGAACA GAGAAA-3' | SEQ ID NO. 412 |
| | Avian influenza virus-HIS-11 | 5'-CAUAUGAAAGAAUGUGCA ACAUC-3' | SEQ ID NO. 413 |
| | Avian influenza virus-HIS-12 | 5'-UUCAAUGAAUCAACAAAA AAGAAA-3' | SEQ ID NO. 414 |
| | Avian influenza virus-HIS-13 | 5'-CAGCAGAUAAAAGAAUAA UGGAAAUG-3' | SEQ ID NO. 415 |
| | Avian influenza virus-HIS-14 | 5'-AGUUGAUAAUAACAACUG GUCUGGU-3' | SEQ ID NO. 416 |
| | Avian influenza virus-HIS-15 | 5'-AGAAGAAGAAAAAGAGGA CUAUUU-3' | SEQ ID NO. 417 |
| | Avian influenza virus-HIS-16 | 5'-CUUCCCAGUUUUGGAGUG UCUGGGAU-3' | SEQ ID NO. 418 |
| | Avian influenza virus-HIS-17 | 5'-AAAUUUAAAUAAGAAAAU GGAAGAU-3' | SEQ ID NO. 419 |
| | Avian influenza virus-HIS-18 | 5'-AAUCUAAUGGGAAUUUAA UAGCUC-3' | SEQ ID NO. 420 |
| Swine influenza virus | Swine influenza virus-PIS-1 | 5'-AUGCAGAACUUUCUUUUU GACUC-3' | SEQ ID NO. 421 |
| | Swine influenza virus-PIS-2 | 5'-ACAUUCUUUUCAUGUGGG GCAUAA-3' | SEQ ID NO. 422 |
| | Swine influenza virus-PIS-3 | 5'-CUAGUCAGGCUAGGCAGA UGGU-3' | SEQ ID NO. 423 |
| | Swine influenza virus-PIS-4 | 5'-CAAAGCAGAAUGCAGUUC UCUU-3' | SEQ ID NO. 424 |
| | Swine influenza virus-PIS-5 | 5'-UGCACCAAUUAAAAUACA GAUAU-3' | SEQ ID NO. 425 |
| | Swine influenza virus-PIS-6 | 5'-AGAGUAAGAGACAACAUG ACCA-3' | SEQ ID NO. 426 |
| | Swine influenza virus-PIS-7 | 5'-GGGAAUUGGGACAAUGGU GAUG-3' | SEQ ID NO. 427 |
| | Swine influenza virus-PIS-8 | 5'-AAUGCCUUGUUUCUACUA AUAC-3' | SEQ ID NO. 428 |
| | Swine influenza virus-PIS-9 | 5'-UAAGAGGAUCAGGAAUGA GAAU-3' | SEQ ID NO. 429 |
| | Swine influenza virus-PIS-10 | 5'-AUCUCAUUUAAGGAAUGA CACA-3' | SEQ ID NO. 430 |
| | Swine influenza virus-PIS-11 | 5'-AGACAAUGCUAAGGAAAU AGGG-3' | SEQ ID NO. 431 |
| | Swine influenza virus-PIS-12 | 5'-AAAGCAAUGAAAGAGUAU GGGGAG-3' | SEQ ID NO. 432 |
| | Swine influenza virus-PIS-13 | 5'-UUGGUCUGAGGAAUGUGC CUGCU-3' | SEQ ID NO. 433 |
| | Swine influenza virus-PIS-14 | 5'-AUCAAUGAACAAAGGAGGA AAUA-3' | SEQ ID NO. 434 |
| | Swine influenza virus-PIS-15 | 5'-CAGAGAGAGGCAAAUUAA AAAG-3' | SEQ ID NO. 435 |
| | Swine influenza virus-PIS-16 | 5'-CACAAAUUGAAGAUGACA GAGA-3' | SEQ ID NO. 436 |
| | Swine influenza virus-PIS-17 | 5'-AAACAAGAAGUGCUUAUG AGAG-3' | SEQ ID NO. 437 |
| | Swine influenza virus-PIS-18 | 5'-UUUUUUUCAAAUGCAUCU AUCAA-3' | SEQ ID NO. 438 |
| | Swine influenza virus-PIS-19 | 5'-CAGAAAUUCGAAGAAAUA AAAUG-3' | SEQ ID NO. 439 |
| | Swine influenza virus-PIS-20 | 5'-CAGCCUAAUCAGACCAAA UGAA-3' | SEQ ID NO. 440 |

TABLE 1-continued

Target sequence listing of RNA virus

| Virus type | Fragment number | Fragment coding sequence | ID number |
|---|---|---|---|
| | Swine influenza virus-PIS-21 | 5'-GGACGGAUUAAGAAAGAA GAGU-3' | SEQ ID NO. 441 |
| | Swine influenza virus-PIS-22 | 5'-UGGAGUUGAUAAGGGGAA GGGA-3' | SEQ ID NO. 442 |
| | Swine influenza virus-PIS-23 | 5'-ACAGAUUUGAAAUAAUUG AAGG-3' | SEQ ID NO. 443 |
| | Swine influenza virus-PIS-24 | 5'-UGCAUGUGUAAAUGGCUC UUG-3' | SEQ ID NO. 444 |
| | Swine influenza virus-PIS-25 | 5'-CUUUUCCUGAAAGUGCCA GCA-3' | SEQ ID NO. 445 |
| | Swine influenza virus-PIS-26 | 5'-AAGACAAGAAAUGGCCAG UAGG-3' | SEQ ID NO. 446 |
| | Swine influenza virus-PIS-27 | 5'-CUGCAUUUGAAGAUUUAA GAUUG-3' | SEQ ID NO. 447 |
| | Swine influenza virus-PIS-28 | 5'-CCAUUAUCCAAAGGUCUA CAAA-3' | SEQ ID NO. 448 |
| | Swine influenza virus-PIS-29 | 5'-UGAGACUUCCAAGAUCAA GAUG-3' | SEQ ID NO. 449 |
| | Swine influenza virus-PIS-30 | 5'-GCAGGAGUGGAUAGAUUC UACA-3' | SEQ ID NO. 450 |
| | Swine influenza virus-PIS-31 | 5'-AAAGCAAAUUGUAGAAAA GAUU-3' | SEQ ID NO. 451 |
| | Swine influenza virus-PIS-32 | 5'-UGCAGGGAAGAACACAGA UCUC-3' | SEQ ID NO. 452 |
| | Swine influenza virus-PIS-33 | 5'-UCAAAUGCAUGAAGACAU UCUU-3' | SEQ ID NO. 1453 |
| | Swine influenza virus-PIS-34 | 5'-AGAAGUUAUAAGGAUGAU GGA-3' | SEQ ID NO. 454 |
| | Swine influenza virus-PIS-35 | 5'-CUGCCCCAUCGGUGAAGC UCC-3 | SEQ ID NO. 455 |
| | Swine influenza virus-PIS-36 | 5'-AAUACCAGCCUUCCAUUU CAGAAU-3' | SEQ ID NO. 456 |
| | Swine influenza virus-PIS-37 | 5'-AAUGAAUCCAAAUCAAAG GA-3' | SEQ ID NO. 457 |
| | Swine influenza virus-PIS-38 | 5'-AUGCCUUGUUUCUACUAA UAC-3' | SEQ ID NO. 458 |
| | Swine influenza virus-PIS-39 | 5'-UGAGUUGCCAUUCACCAU UGA-3' | SEQ ID NO. 459 |
| | Swine influenza virus-PIS-40 | 5'-AUACAUUGAAGUUUUACA UUU-3' | SEQ ID NO. 460 |
| | Swine influenza virus-PIS-41 | 5'-GUGUGAUGGGAAUGGUUG GAGUAU-3' | SEQ ID NO. 461 |
| | Swine influenza virus-PIS-42 | 5'-AUAUGCACAAACAGAAUG UGU-3' | SEQ ID NO. 462 |
| | Swine influenza virus-PIS-43 | 5'-UGGAUUUGUUGCCAUUUU CA-3' | SEQ ID NO. 463 |
| | Swine influenza virus-PIS-44 | 5'-AUUAUAAAAGGAAGGUCU CA-3' | SEQ ID NO. 464 |
| | Swine influenza virus-PIS-45 | 5'-CCAAAGAGGGAAGACGAAAG-3' | SEQ ID NO. 465 |
| | Swine influenza virus-HIS-1 | 5'-UAUAUAAAUAGAACAGGA ACAU-3' | SEQ ID NO. 466 |
| | Swine influenza virus-HIS-2 | 5'-ACAAUAAAAAGUUGGAGA AACA-3' | SEQ ID NO. 467 |
| | Swine influenza virus-HIS-3 | 5'-AAAGCCAUGGAACAAAUG GCUG-3' | SEQ ID NO. 468 |
| | Swine influenza virus-HIS-4 | 5'-GGUCUACAAAACAUACUU UGAGAAA-3' | SEQ ID NO. 469 |
| | Swine influenza virus-HIS-5 | 5'-AAUAGUUUACUUGAAUAA UACA-3' | SEQ ID NO. 470 |
| | Swine influenza virus-HIS-6 | 5'-UUCAAGAUGGAGAAAGGG AAGA-3' | SEQ ID NO. 471 |
| | Swine influenza virus-HIS-7 | 5'-AAAAGAAAUACACCAAAA CAGU-3' | SEQ ID NO. 472 |
| | Swine influenza virus-HIS-8 | 5'-AACCUAAAUUUCUCCCAG AUUU-3' | SEQ ID NO. 473 |
| | Swine influenza virus-HIS-9 | 5'-ACAACCUACUUUCUCAGU ACAGA-3' | SEQ ID NO. 474 |
| | Swine influenza virus-HIS-10 | 5'-AAAUUCAAACAAGGAGAU CAUU-3' | SEQ ID NO. 475 |
| | Swine influenza virus-HIS-11 | 5'-UGGUCAGGUUAUUCUGGC AUUU-3' | SEQ ID NO. 476 |
| | Swine influenza virus-HIS-12 | 5'-CAACCUGGAACCUGGAAC CU-3' | SEQ ID NO. 477 |
| | Swine influenza virus-HIS-13 | 5'-CCAGCACUGAGAGGGUGA CUGU-3' | SEQ ID NO. 478 |

TABLE 1-continued

Target sequence listing of RNA virus

| Virus type | Fragment number | Fragment coding sequence | ID number |
|---|---|---|---|
| | Swine influenza virus-HIS-14 | 5'-GAAAUCAACCUGAAUGGU UU-3' | SEQ ID NO. 479 |
| | Swine influenza virus-HIS-15 | 5'-UUAUCAAAUACUUGCUAU AUAC-3' | SEQ ID NO. 480 |
| | Swine influenza virus-HIS-16 | 5'-CUUUUCUUAAAAAUUCCA GCGC-3' | SEQ ID NO. 481 |
| | Swine influenza virus-HIS-17 | 5'-AGAGAAGGAUAUUCUCUG GUC-3' | SEQ ID NO. 482 |
| | Swine influenza virus-HIS-18 | 5'-GGGGAGACACACAAAUUC AGAC-3' | SEQ ID NO. 483 |
| | Swine influenza virus-HIS-19 | 5'-UGAUUAUUGCUGCUAGAA ACAUA-3' | SEQ ID NO. 484 |
| | Swine influenza virus-HIS-20 | 5'-UGAUUAUUGCUGCUAGAA ACAU-3' | SEQ ID NO. 485 |
| | Swine influenza virus-HIS-21 | 5'-UGGAGAAAGCCAACAAGA UAAAA-3' | SEQ ID NO. 486 |
| | Swine influenza virus-HIS-22 | 5'-ACAAAGAACAUGAAAAAA ACAAG-3' | SEQ ID NO. 487 |
| | Swine influenza virus-HIS-23 | 5'-AGGGCAAGCUUUCCCAAA UGUCU-3' | SEQ ID NO. 488 |
| | Swine influenza virus-HIS-24 | 5'-AGGGCAAGCUUUCCCAAA UGUC-3' | SEQ ID NO. 489 |
| | Swine influenza virus-HIS-25 | 5'-CCAAAACUACAUACUGGU GGGA-3' | SEQ ID NO. 490 |
| | Swine influenza virus-HIS-26 | 5'-AGGCAAAGUGGUGUGUGU GUGC-3' | SEQ ID NO. 491 |
| | Swine influenza virus-HIS-27 | 5'-UCAAAGAGAAAGACAUGA CCA-3' | SEQ ID NO. 492 |
| | Swine influenza virus-HIS-28 | 5'-ACUUUGUAAUCCCAUGAA UCC-3' | SEQ ID NO. 493 |
| | Swine influenza virus-HIS-29 | 5'-UUUCAGGCAGAAUGAAUG CAG-3' | SEQ ID NO. 494 |
| | Swine influenza virus-HIS-30 | 5'-GAAACACAGGGAACAGAG AAA-3' | SEQ ID NO. 495 |
| | Swine influenza virus-HIS-31 | 5'-AAGGAAGAUCUCAUUUGA GGA-3' | SEQ ID NO. 496 |
| | Swine influenza virus-HIS-32 | 5'-GAUAGUAAGUGGAAGAGA UGAA-3' | SEQ ID NO. 497 |
| | Swine influenza virus-HIS-33 | 5'-CAUAUGAAAGAAUGUGCA ACAU-3' | SEQ ID NO. 498 |
| | Swine influenza virus-HIS-34 | 5'-AUAAUACUAGUAGUAACA GUAA-3' | SEQ ID NO. 499 |
| | Swine influenza virus-HIS-35 | 5'-UUGACUGAAGAUCCAGAU GAA-3' | SEQ ID NO. 500 |
| | Swine influenza virus-HIS-36 | 5'-AAAAAUGAUGACCAAUUC UCA-3' | SEQ ID NO. 501 |
| | Swine influenza virus-HIS-37 | 5'-UAUGGAAUUCUCUCUUAC UGA-3' | SEQ ID NO. 502 |
| | Swine influenza virus-HIS-38 | 5'-AAAAAACAAAGAUUGAGU AAGA-3' | SEQ ID NO. 503 |
| | Swine influenza virus-HIS-39 | 5'-AAGCAACCAGGAGAUUGG UUCA-3' | SEQ ID NO. 504 |
| | Swine influenza virus-HIS-40 | 5'-CCAGAGGACAAGAGCUCU UGUU-3' | SEQ ID NO. 505 |
| | Swine influenza virus-HIS-41 | 5'-GAAAGAACAUUCUUUUCA UGUG-3' | SEQ ID NO. 506 |
| | Swine influenza virus-HIS-42 | 5'-CUGUAAUGAGAAUGGGAG ACCU-3' | SEQ ID NO. 507 |
| | Swine influenza virus-HIS-43 | 5'-GGAAAUUGUGAAAAUUCA AUGG-3' | SEQ ID NO. 508 |
| | Swine influenza virus-HIS-44 | 5'-UUUUGCUUUGUGUUGUUU UGCUG-3' | SEQ ID NO. 509 |
| | Swine influenza virus-HIS-45 | 5'-AGGACUUCGAGAAAUAUG UUGA-3' | SEQ ID NO. 510 |
| | Swine influenza virus-HIS-46 | 5'-AAACAACAUAACAACAAC AAUAA-3' | SEQ ID NO. 511 |
| | Swine influenza virus-HIS-47 | 5'-AAAAUGCUGAGGAUAUGG GCAA-3' | SEQ ID NO. 512 |
| | Swine influenza virus-HIS-48 | 5'-UUUCACCAUUACCUUCUC UUCC-3' | SEQ ID NO. 513 |
| | Swine influenza virus-HIS-49 | 5'-UCUUAUUUCUUCAGAGAC AAUG-3' | SEQ ID NO. 514 |
| | Swine influenza virus-HIS-50 | 5'-AGAGAAAUACUUGAAAA UUGUG-3' | SEQ ID NO. 515 |
| | Swine influenza virus-HIS-51 | 5'-ACAGAAAUGUCACUGAGA GGAG-3' | SEQ ID NO. 516 |

TABLE 1-continued

Target sequence listing of RNA virus

| Virus type | Fragment number | Fragment coding sequence | ID number |
|---|---|---|---|
| | Swine influenza virus-HIS-52 | 5'-AAAGGGGUAGGGACAAU GGUG-3' | SEQ ID NO. 517 |
| | Swine influenza virus-HIS-53 | 5'-GACUACAGAUAUACAUAU AGAU-3' | SEQ ID NO. 518 |
| | Swine influenza virus-HIS-54 | 5'-GAAAAAGGAGAGUGAGAG ACAA-3' | SEQ ID NO. 519 |
| | Swine influenza virus-HIS-55 | 5'-UAGAUAUAAAUGUGAAAG AUUA-3' | SEQ ID NO. 520 |
| | Swine influenza virus-HIS-56 | 5'-UCAGACAGCUGCCCAGAG GGCA-3' | SEQ ID NO. 521 |
| Rabies virus | Rabies virus-DIS-1 | 5'-ACUUACCAGUCUCAUCUU CUA-3' | SEQ ID NO. 522 |
| | Rabies virus-DIS-2 | 5'-UUUUCUAUCCCUCAGAAA AUCC-3' | SEQ ID NO. 523 |
| | Rabies virus-DIS-3 | 5'-CUUUGAUCUCGGGCUUGA GA-3' | SEQ ID NO. 524 |
| | Rabies virus-DIS-4 | 5'-UCUCUCUGCCUUGUAGUU GG-3' | SEQ ID NO. 525 |
| | Rabies virus-DIS-5 | 5'-UAUAACUUAUUACUUCAGAA-3' | SEQ ID NO. 526 |
| | Rabies virus-DIS-6 | 5'-AGAAAUCAUAUCAAAUCC UU-3 | SEQ ID NO. 527 |
| | Rabies virus-DIS-7 | 5'-UUCAGACAGAUCAGACCU CA-3' | SEQ ID NO. 528 |
| | Rabies virus-DIS-8 | 5'-AAUAUCCAGAAUGGUUUC UG-3' | SEQ ID NO. 529 |
| | Rabies virus-DIS-9 | 5'-AAGUCAACAUGAAAAAAA CAG-3' | SEQ ID NO. 530 |
| | Rabies virus-DIS-10 | 5'-UGAAAAAACAAGAUCUU AA-3' | SEQ ID NO. 531 |
| | Rabies virus-DIS-11 | 5'-GGGGGGUUCUUUUUGAAAAA-3' | SEQ ID NO. 532 |
| | Rabies virus-DIS-12 | 5'-GAGAUGGCCAAGGUGGGA GA-3' | SEQ ID NO. 533 |
| | Rabies virus-DIS-13 | 5'-UUUUUACCAAUAGUAGAG GG-3' | SEQ ID NO. 534 |
| | Rabies virus-DIS-14 | 5'-GUGCUCCUCAUGAAAUGU CUGU-3' | SEQ ID NO. 535 |
| | Rabies virus-DIS-15 | 5'-UACCACCUUAAAUAUCAGAG-3' | SEQ ID NO. 536 |
| | Rabies virus-DIS-16 | 5'-CUCAGCCAUAAAAAUGAA CG-3' | SEQ ID NO. 537 |
| | Rabies virus-DIS-17 | 5'-AUUGCAGAAAGUUUCUCC AAAA-3' | SEQ ID NO. 538 |
| | Rabies virus-DIS-18 | 5'-AGACUGGACCAGCUAUGG AAUC-3' | SEQ ID NO. 539 |
| | Rabies virus-DIS-19 | 5'-AUGUAAUCACCUUAUACA UGAAC-3' | SEQ ID NO. 540 |
| | Rabies virus-DIS-20 | 5'-GGAAGGACUUGGUAAAGU UC-3' | SEQ ID NO. 541 |
| | Rabies virus-DIS-21 | 5'-AAAUCCUGAGGCACUUCA ACAU-3' | SEQ ID NO. 542 |
| | Rabies virus-DIS-22 | 5'-GUCUGUCAUCUCACUGGA UC-3 | SEQ ID NO. 543 |
| | Rabies virus-DIS-23 | 5'-UGGGCACAGUUGUCACUG CU-3 | SEQ ID NO. 544 |
| | Rabies virus-DIS-24 | 5'-AAACAUUGCAGACAGGAU AG-3' | SEQ ID NO. 545 |
| | Rabies virus-DIS-25 | 5'-UGUAAUUCUAGCCUGAGU CU-3' | SEQ ID NO. 546 |
| | Rabies virus-DIS-26 | 5'-CCAGGAAAGUCUUCAGAG GAU-3' | SEQ ID NO. 547 |
| | Rabies virus-DIS-27 | 5'-UAAAAGAUCUUUUCUUGU CU-3' | SEQ ID NO. 548 |
| | Rabies virus-DIS-28 | 5'-AGACAAAUAAGGUCAGGA GA-3' | SEQ ID NO. 549 |
| | Rabies virus-DIS-29 | 5'-AGACAACACCCACUCCUU CU-3' | SEQ ID NO. 550 |
| | Rabies virus-DIS-30 | 5'-UAGGUUCAAGUCUGCCAG AUACA-3' | SEQ ID NO. 551 |
| | Rabies virus-DIS-31 | 5'-CUUACCAGUCUCAUCUUC UAC-3' | SEQ ID NO. 552 |
| | Rabies virus-DIS-32 | 5'-GGCCUUGCUCUUCAGAGA GG-3' | SEQ ID NO. 553 |
| | Rabies virus-DIS-33 | 5'-CAUGCAGCUAGAACCAUG AC-3' | SEQ ID NO. 554 |

TABLE 1-continued

Target sequence listing of RNA virus

| Virus type | Fragment number | Fragment coding sequence | ID number |
|---|---|---|---|
| | Rabies virus-DIS-34 | 5'-GGGGAAGAAAAGUGGUAG GCA-3' | SEQ ID NO. 555 |
| | Rabies virus-DIS-35 | 5'-ACAGGAUAGAGCAGAUUU UU-3' | SEQ ID NO. 556 |
| | Rabies virus-DIS-36 | 5'-UUGAAAAUGAACCUUGAU GA-3' | SEQ ID NO. 557 |
| | Rabies virus-DIS-37 | 5'-CAUGAGCAAGAUCUUUGU CAA-3' | SEQ ID NO. 558 |
| | Rabies virus-DIS-38 | 5'-UCUUGUGACAUUUUUACC AAU-3' | SEQ ID NO. 559 |
| | Rabies virus-DIS-39 | 5'-CAGGAACACAAGAACCAAAG-3' | SEQ ID NO. 560 |
| | Rabies virus-DIS-40 | 5'-UUCACAUUAAAAAAGUGA UA-3' | SEQ ID NO. 561 |
| | Rabies virus-DIS-41 | 5'-CUGUUGGAAUGGCCAGGA UG-3 | SEQ ID NO. 562 |
| | Rabies virus-DIS-42 | 5'-AAGGUGGAGAACUCAGAG UUU-3' | SEQ ID NO. 563 |
| | Rabies virus-DIS-43 | 5'-GCAUUUGGAAGGUAUCUU GC-3' | SEQ ID NO. 564 |
| | Rabies virus-DIS-44 | 5'-CUCUAUUUCUUGCACUUG UG-3' | SEQ ID NO. 565 |
| | Rabies virus-DIS-45 | 5'-AAGAAGAGACCAUGUGUA GUUAU-3' | SEQ ID NO. 566 |
| | Rabies virus-DIS-46 | 5'-AUAAUGCAUUUGGAAGGU AU-3' | SEQ ID NO. 567 |
| | Rabies virus-DIS-47 | 5'-CUAUGAAGUCAUCAAAAU AU-3' | SEQ ID NO. 568 |
| | Rabies virus-DIS-48 | 5'-UUCUCAUUUUUGUUGUUU AUUU-3' | SEQ ID NO. 569 |
| | Rabies virus-DIS-49 | 5'-AUAACAGACCUAUAACUU AU-3' | SEQ ID NO. 570 |
| | Rabies virus-DIS-50 | 5'-AGAGAGACACAAGGCUAA GA-3' | SEQ ID NO. 571 |
| | Rabies virus-DIS-51 | 5'-UUAGUCCAGAGAGCAGAAAA-3' | SEQ ID NO. 572 |
| | Rabies virus-DIS-52 | 5'-CACUGCCUCCUUCAGCAA UCA-3' | SEQ ID NO. 573 |
| | Rabies virus-DIS-53 | 5'-UAUGAAGUCAUCAAAAUA UU-3' | SEQ ID NO. 574 |
| | Rabies virus-DIS-54 | 5'-CAUUAAAAAAGUGAUAGA UA-3' | SEQ ID NO. 575 |
| | Rabies virus-DIS-55 | 5'-AGAGAGCAUCCAAAGGGA GUG-3' | SEQ ID NO. 576 |
| | Rabies virus-DIS-56 | 5'-AAAAAAUGUACCAGGUGU GA-3' | SEQ ID NO. 577 |
| | Rabies virus-DIS-57 | 5'-AACAUGAGCAAGAUCUUU GU-3' | SEQ ID NO. 578 |
| | Rabies virus-DIS-58 | 5'-AAUCACAUUCUUUCACCA GAA-3' | SEQ ID NO. 579 |
| | Rabies virus-DIS-59 | 5'-CCUCACUCUUAUUUCAUC CA-3' | SEQ ID NO. 580 |
| | Rabies virus-DIS-60 | 5'-CAUUCACUUUGUAGGAUG CU-3' | SEQ ID NO. 581 |
| | Rabies virus-HIS-1 | 5'-AUCAGAAAGGCUUUAUAU GAC-3' | SEQ ID NO. 582 |
| | Rabies virus-HIS-2 | 5'-UGUAUUUAUAAAAGACAA GGU-3' | SEQ ID NO. 583 |
| | Rabies virus-HIS-3 | 5'-CUCAUUUUUGUUGUUUAU UU-3' | SEQ ID NO. 584 |
| | Rabies virus-HIS-4 | 5'-UGCCAAGCUUGUGUUCAA CA-3' | SEQ ID NO. 585 |
| | Rabies virus-HIS-5 | 5'-UGGGCUCUGACAGGAGGC AUG-3' | SEQ ID NO. 586 |
| | Rabies virus-HIS-6 | 5'-AAGUUAAUUACCUUUACA UU-3' | SEQ ID NO. 587 |
| | Rabies virus-HIS-7 | 5'-UACUAUGAUGUAUCUAUC UA-3' | SEQ ID NO. 588 |
| | Rabies virus-HIS-8 | 5'-AGGAGGGUAUUCUUCUGU AU-3' | SEQ ID NO. 589 |
| | Rabies virus-HIS-9 | 5'-GAACCCAGAGGAACCCCC AC-3' | SEQ ID NO. 590 |
| | Rabies virus-HIS-10 | 5'-CACUGCCUCCUUCAGCAA UCA-3' | SEQ ID NO. 591 |
| | Rabies virus-HIS-11 | 5'-AGAGCUCAAGAAGGAGAC AA-3' | SEQ ID NO. 592 |

TABLE 1-continued

Target sequence listing of RNA virus

| Virus type | Fragment number | Fragment coding sequence | ID number |
|---|---|---|---|
| | Rabies virus-HIS-12 | 5'-AAGAGGGGCUCCUCUAUG AA-3' | SEQ ID NO. 593 |
| | Rabies virus-HIS-13 | 5'-UCUACUGCUUUAGGUGAC GU-3' | SEQ ID NO. 594 |
| | Rabies virus-HIS-14 | 5'-AGAUGGGUGGAUCAAGAG GU-3' | SEQ ID NO. 595 |
| | Rabies virus-HIS-15 | 5'-AACGGUGACGAGGCUGAG GA-3' | SEQ ID NO. 596 |
| | Rabies virus-HIS-16 | 5'-CAGAGGAUGUAUUUCUG UC-3' | SEQ ID NO. 597 |
| | Rabies virus-HIS-17 | 5'-CACAUCCACUGCCUCCUU CA-3' | SEQ ID NO. 598 |
| | Rabies virus-HIS-18 | 5'-AGGGAUGUCUUGUGACAU UUUU-3' | SEQ ID NO. 599 |
| | Rabies virus-HIS-19 | 5'-CUUCAGAAAGCAAGUCAU UCUA-3' | SEQ ID NO. 600 |
| | Rabies virus-HIS-20 | 5'-UACAUCUCAGCCAUAAAA AUG-3' | SEQ ID NO. 601 |
| | Rabies virus-HIS-21 | 5'-UUACUGAGUGCAGGGGCC CUGA-3' | SEQ ID NO. 602 |
| | Rabies virus-HIS-22 | 5'-UCAACUUUCCCAACCCUC CA-3' | SEQ ID NO. 603 |
| | Rabies virus-HIS-23 | 5'-CAGAGGGACAGGGAGGGA GGU-3' | SEQ ID NO. 604 |
| | Rabies virus-HIS-24 | 5'-AGUCAGAACUUGGAAUGA GAU-3' | SEQ ID NO. 605 |
| | Rabies virus-HIS-25 | 5'-UCAAAGAUUAGAGUCAAC AGA-3' | SEQ ID NO. 606 |
| | Rabies virus-HIS-26 | 5'-CAUGAACUGGGUAUACAA GUU-3' | SEQ ID NO. 607 |
| | Rabies virus-HIS-27 | 5'-CUGAUGACAUGCUGGAGA AGA-3' | SEQ ID NO. 608 |
| | Rabies virus-HIS-28 | 5'-UGGUCACGUGUUCAAUCU CAU-3' | SEQ ID NO. 609 |
| | Rabies virus-HIS-29 | 5'-UUAUGAAGACUGUUCAGG ACU-3' | SEQ ID NO. 610 |
| | Rabies virus-HIS-30 | 5'-CUGGUGGAGAUAAAACGU ACUGA-3' | SEQ ID NO. 611 |
| | Rabies virus-HIS-31 | 5'-UUGAUUGUUUUUCUCAUU UU-3' | SEQ ID NO. 612 |
| | Rabies virus-HIS-32 | 5'-UGGUUUCUGGGGCUGUGC CUC-3' | SEQ ID NO. 613 |
| | Rabies virus-HIS-33 | 5'-GAGCCAGGGCAGGAGACA GC-3' | SEQ ID NO. 614 |
| | Rabies virus-HIS-34 | 5'-GGGUUCUUUUUGAAAAAAA-3' | SEQ ID NO. 615 |

TABLE 2

Antisense sequence listing of the target of the RNA virus

| Antisense fragment coding sequence | ID number |
|---|---|
| 3'-ACAGAUACGAUUACCUCCAUUUCCGA-5' | SEQ ID NO. 712 |
| 3'-AUAUUGUGUAUAUUUUUAUGCACA-5' | SEQ ID NO. 713 |
| 3'-AAUAUACGGAAUAAAGAAAUGAAA-5' | SEQ ID NO. 714 |
| 3'-UCCUCUUACUGUUUUUUUUUUUUUU-5' | SEQ ID NO. 715 |
| 3'-AACAACGACGAUAAAAGAUAAAUU-5' | SEQ ID NO. 716 |
| 3'-GUACUUCUUUGUUAAAUAUUAAAUGAAU-5' | SEQ ID NO. 717 |
| 3'-CUCAACUCCUUCUUCUUCUCCUUCUGACC-5' | SEQ ID NO. 718 |
| 3'-AUUGUACGAAUCCUAUUACCGGAG-5' | SEQ ID NO. 719 |
| 3'-UCCUCUUACUGUUUUUUUUUUUUUU-5' | SEQ ID NO. 720 |
| 3'-AAGGUAAACGUGUCUCAUAGAAAA-5' | SEQ ID NO. 721 |

TABLE 2-continued

Antisense sequence listing of the target of the RNA virus

| Antisense fragment coding sequence | ID number |
|---|---|
| 3'-ACGACAUUAACGACAACAACGACGACAA-5' | SEQ ID NO.722 |
| 3'-CUUUUUCUCUUUUCUUUGUUCCC-5' | SEQ ID NO.723 |
| 3'-CCCUCCUCCCUCCUUCUCUGAGG-5' | SEQ ID NO.724 |
| 3'-CAAGAUCUCUACGUUCUGAACAC-5' | SEQ ID NO.725 |
| 3'-UGAGUAAGAUGGUAAAAAAUUUAAC-5' | SEQ ID NO.726 |
| 3'-UCUAGGACACUGAAGACCUGAAAA-5' | SEQ ID NO.727 |
| 3'-UUUAUAAUAAAAAUUUUAAAUGAA-5' | SEQ ID NO.728 |
| 3'-UGAAAAAUUUUCUUUUCCCCCCU-5' | SEQ ID NO.729 |
| 3'-CUUUUCCUUCCCUUUUAAAGUUU-5' | SEQ ID NO.730 |
| 3'-UUUACUUGUUCAUCUAUUUAAUC-5' | SEQ ID NO.731 |
| 3'-UUUAAUACCAUGGUCAAUCUCUUU-5' | SEQ ID NO.732 |
| 3'-CUUUCUUUUUUAUAUUUAAUUUU-5' | SEQ ID NO.733 |
| 3'-UAAAUAGUUCUCGGUAAAUUUUU-5' | SEQ ID NO.734 |
| 3'-AUUUUGUCCCUGGUUUUCUUGGCA-5' | SEQ ID NO.735 |
| 3'-UCUUAGUCUAUUCAUCUUAAUCU-5' | SEQ ID NO.736 |
| 3'-UCCGUCUCCUUCUACUCCGGUUG-5' | SEQ ID NO.737 |
| 3'-AUAGUUUUUUAAUUCUUUUCCAAU-5' | SEQ ID NO.738 |
| 3'-CCUAGUCACCUCUUUCACUCCUCCUACU-5' | SEQ ID NO.739 |
| 3'-UACUCUCUAGAACCCCCACCCUG-5' | SEQ ID NO.740 |
| 3'-CUUUUUGAGUUCUACUUUCCUUA -5' | SEQ ID NO.741 |
| 3'-UAACUAACCGAAUUCCUCUUUUAU-5' | SEQ ID NO.742 |
| 3'-UUAACAAAUGGAUAAAUAACCAAAACAC-5' | SEQ ID NO.743 |
| 3'-GACACGACUUGGUCCUGGUCCU-5' | SEQ ID NO.744 |
| 3'-UCUACUUCGUCAGUGGUUGGCG-5' | SEQ ID NO.745 |
| 3'-UAAUCUAAAGUUGUGUCCACGAUGUAG-5' | SEQ ID NO.746 |
| 3'-AACCUUACAAAACGAGGAGAAAU-5' | SEQ ID NO.747 |
| 3'-CUUUAAAAUAAUAAAACAAGUCA-5' | SEQ ID NO.748 |
| 3'-AAUCGAUCUAAAUGUCUAAACCU-5' | SEQ ID NO.749 |
| 3'-UUGUUCUCGUCCGGUCACACCACC-5' | SEQ ID NO.750 |
| 3'-AACUCCUUUUCCCUUGGGACAUGU-5' | SEQ ID NO.751 |
| 3'-GGUCCGUGACCCUUCAGUCACCGU-5' | SEQ ID NO.752 |
| 3'-UUAAUCCUCACUAUGGAAGUGAUU-5' | SEQ ID NO.753 |
| 3'-ACUCUUUUUCCGGUGACAGGAAAU-5' | SEQ ID NO.754 |
| 3'-UGUUUAACCUCUUUAUCACUUUU-5' | SEQ ID NO.755 |
| 3'-CUUCGUCUCUCUUUCAUCUCUUC-5' | SEQ ID NO.756 |
| 3'-AGUUUUCCUCUCUUGUCUACGACC-5' | SEQ ID NO.757 |
| 3'-GUUUUCUUCCGUAAUUUUCUCCU-5' | SEQ ID NO.758 |
| 3'-CUCUACCUGAAACUAAAGACACU-5' | SEQ ID NO.759 |

TABLE 2-continued

Antisense sequence listing of the target of the RNA virus

| Antisense fragment coding sequence | ID number |
|---|---|
| 3'-CCUUUAGGUCCCUCCAAAACCUU-5' | SEQ ID NO.760 |
| 3'-UUUCCUUCUUUAACUUUGGGUCU-5' | SEQ ID NO.761 |
| 3'-CACCGUCCGGGUAAUGUGGUGGU-5' | SEQ ID NO.762 |
| 3'-UCAAAUUUAAAUAUAGGUUUUAUUUAAA-5' | SEQ ID NO.763 |
| 3'-UUCUUUUCUAUUUAUCUUGUGUUUCUUAACUGUUU UAAA-5' | SEQ ID NO.764 |
| 3'-AGAUUCGCUUCAUUGUUGUUCUCA-5' | SEQ ID NO.765 |
| 3'-UUGUCUUUCUUCGUAAUAAUGUAGUCCGAAGA-5' | SEQ ID NO.766 |
| 3'-ACUAAAUAUAAAUGACCAUAUUUUAUCA-5' | SEQ ID NO.767 |
| 3'-UUGUUUGUUUGGUCUCUGUGAUUCCUUUACGU-5' | SEQ ID NO.768 |
| 3'-UAUGUUAGUUUAACUUACCGUA-5' | SEQ ID NO.769 |
| 3'-UCUACUGUUAACACUUUAAUUU-5' | SEQ ID NO.770 |
| 3'-CAAUAUAUACCCUUUACUACCUUAAUUGU-5' | SEQ ID NO.771 |
| 3'-UUUUUUGAUUCACUAAGUUGU-5' | SEQ ID NO.772 |
| 3'-UUUAUGUUUUUUAUAUGACUUAUGUU-5' | SEQ ID NO.773 |
| 3'-AAAUGUAAGGACCAGUUGAUACUUUACUUUGAUAAC G-5' | SEQ ID NO.774 |
| 3'-GAUGUUUUUUUACGAUUUUCUU-5' | SEQ ID NO.775 |
| 3'-UACGACUUGUUGAGUUUCUUUU-5' | SEQ ID NO.776 |
| 3'-UCCUUUCACUUUUCUACCGUUU-5' | SEQ ID NO.777 |
| 3'-UUACUCCUUUCACUUUUCUACCGUUUUCU-5' | SEQ ID NO.778 |
| 3'-GUUCUUUUUUCUAUCAUAGUA-5' | SEQ ID NO.779 |
| 3'-GGUAUCUUUGUAAACUAUUGUUACUUCUU-5' | SEQ ID NO.780 |
| 3'-UUUCAUAUAUAAUACAAUGUUGU-5' | SEQ ID NO.781 |
| 3'-UACUAUUGUUGUUAUUAGAGAAA-5' | SEQ ID NO.782 |
| 3'-UGAUUAUGUGUACUAUUGUU-5' | SEQ ID NO.783 |
| 3'-ACUAUUGUUGUUAUUAGAGAAACGAU-5' | SEQ ID NO.784 |
| 3'-CUUUUCCUUUUCUUCUAAAGAAC-5' | SEQ ID NO.785 |
| 3'-UUACAUGUCGUAGGUUAUUUUU-5' | SEQ ID NO.786 |
| 3'-AUUAAUAAAACUUACCGGUGGGGUAC-5' | SEQ ID NO.787 |
| 3'-UUAAUAAAACUUACCGGUGGG-5' | SEQ ID NO.788 |
| 3'-AGAUAUUUAUUAUAUUGAUUU-5' | SEQ ID NO.789 |
| 3'-AUUUAUAUCUAUUUUAUAUGUAAU-5' | SEQ ID NO.790 |
| 3'-UUUACAAACAAAUUAAUGUACCUAAUCAU-5' | SEQ ID NO.791 |
| 3'-UACCAAUUAUGUAACCAAAUUAAAUAU-5' | SEQ ID NO.792 |
| 3'-UUGAUAUAAUUUUUGAAUACAUA-5' | SEQ ID NO.793 |
| 3'-AUAUCUUGUACUUUUUAAUUUUAAAAG-5' | SEQ ID NO.794 |
| 3'-AUCUGUUAUAUUGAUAUAAUUUU-5' | SEQ ID NO.795 |
| 3'-UUACAAUGGUAACAAUAGAUUAU-5' | SEQ ID NO.796 |

TABLE 2-continued

Antisense sequence listing of the target of the RNA virus

| Antisense fragment coding sequence | ID number |
|---|---|
| 3'-UCCAUUUAAUUACUCUCUCUUACCUCAA-5' | SEQ ID NO.797 |
| 3'-AUAAAAUUUUCCGUCUAUUAAUCU-5' | SEQ ID NO.798 |
| 3'-CCUUGAACCACGUAAAAAAAGAU-5' | SEQ ID NO.799 |
| 3'-UAAAAAGAACUAACGAAAAGUU-5' | SEQ ID NO.800 |
| 3'-AUAAGACUUUUACCAUAUAAAUU-5' | SEQ ID NO.801 |
| 3'-UCGGAUAAAAGUAACUACGGACU-5' | SEQ ID NO.802 |
| 3'-AGUUGUUUAUAAAUGUCCGUUUU-5' | SEQ ID NO.803 |
| 3'-AAUCUUUUUACCUUUUCAUAUCU-5' | SEQ ID NO.804 |
| 3'-UUCUCGAGUUGUUUAUAAAUGUC-5' | SEQ ID NO.805 |
| 3'-AGAUUUAUAAGUCUUACGUGAUCUCUUU-5' | SEQ ID NO.806 |
| 3'-ACUACCCCCAACUGCCUCAACCCCUCA-5' | SEQ ID NO.807 |
| 3'-CCCCUAACCUUUCCGAGAGACAC-5' | SEQ ID NO.808 |
| 3'-UUUACCUCGUCUUUCUUGUGAGUCC-5' | SEQ ID NO.809 |
| 3'-ACCGAGCUUCUCGUACCUCUCCUU-5' | SEQ ID NO.810 |
| 3'-UCCUUCCCCUAACUCUCUGAGUG-5' | SEQ ID NO.811 |
| 3'-UUUUAUCUGACCUCUACCGGUACACCUCUUCG-5' | SEQ ID NO.812 |
| 3'-GUCGCGUCCCCUUCUCACCCGUCCGUC-5' | SEQ ID NO.813 |
| 3'-UUAUUCUUUUCGUUGUAACACUAAAAAUUAAU-5' | SEQ ID NO.814 |
| 3'-AUUUUUUUCAGUUUAAAUACUAAU-5' | SEQ ID NO.815 |
| 3'-GAAACCGUAAAGUCACUAAGUCGUUUU-5' | SEQ ID NO.816 |
| 3'-UUUACACGAGGGGAAAGGACCU-5' | SEQ ID NO.817 |
| 3'-AAAAUUUCCUCACCACUUCUUCUUUCU-5' | SEQ ID NO.818 |
| 3'-UUUAUUAUAUUUACGUAAGUUGA-5' | SEQ ID NO.819 |
| 3'-CCGUCCACACCAACGAGUUCGACAUU-5' | SEQ ID NO.820 |
| 3'-AUAUUGUAAAAGGACGAAGGUU-5' | SEQ ID NO.821 |
| 3'-AGUAACCUUCUACCUCGAGAAA-5' | SEQ ID NO.822 |
| 3'-GUCGAAUGAGAAGGAGUCUCAAGAAA-5' | SEQ ID NO.823 |
| 3'-AAAUACUUAAGAUGUCUUUAUUACUAUUAC-5' | SEQ ID NO.824 |
| 3'-UUUCUAAUACCUUUGAAAAGAC-5' | SEQ ID NO.825 |
| 3'-AACGACAAAAAGGUUUGUGAUCU-5' | SEQ ID NO.826 |
| 3'-CAGUUAGGUUUAUAACCUUCUUCGUCUUCAAUUA-5' | SEQ ID NO.827 |
| 3'-UACACCUCUGUAAGGUCGUGUCUCCUUUG-5' | SEQ ID NO.828 |
| 3'-AGUCCGAGUUCACUAGAGAGUAAAGU-5' | SEQ ID NO.829 |
| 3'-AAUAUAACUUCAAAUACUUCAAC-5' | SEQ ID NO.830 |
| 3'-UCUAUAUCCUUACACAGACUUU-5' | SEQ ID NO.831 |
| 3'-UUUUCAGUUCUUUUAAUUUAAAUAU-5' | SEQ ID NO.832 |
| 3'-AUACGGACUAUUAAAAAGUAACC-5' | SEQ ID NO.833 |
| 3'-UAUUUCCUUUUCAGUUCUUUUAA-5' | SEQ ID NO.834 |

TABLE 2-continued

Antisense sequence listing of the target of the RNA virus

| Antisense fragment coding sequence | ID number |
|---|---|
| 3'-UCUCUCUCUCUUUUCUUUUAAC-5' | SEQ ID NO.835 |
| 3'-AUACGGACUAUUAAAAAGUAAC-5' | SEQ ID NO.836 |
| 3'-GACACAAAAGAGGAUCUUACAGU-5' | SEQ ID NO.837 |
| 3'-UUUCUGUCCUAAAGUAAUAAACAU-5' | SEQ ID NO.838 |
| 3'-ACCUACACUCUUUAUGAACCCU-5' | SEQ ID NO.839 |
| 3'-UUUUCUGUCCUAAAGUAAUAAA-5' | SEQ ID NO.840 |
| 3'-UUUUCUGUCCUAAAGUAAUAAACAUA-5' | SEQ ID NO.841 |
| 3'-CUGUCCUAAAGUAAUAAACAUA-5' | SEQ ID NO.842 |
| 3'-UCAAGAGAAAACUGUAAAACAAG-5' | SEQ ID NO.843 |
| 3'-ACUGUAAAACAAGAAAGAAAC-5' | SEQ ID NO.844 |
| 3'-CUUUUACAACAGGUUGUUAGGUUAGUU-5' | SEQ ID NO.845 |
| 3'-CCUUCUUUUCUGUAAUUUGAUUAA-5' | SEQ ID NO.846 |
| 3'-AUUAGAAGAUAUUCAGAUCAUUU-5' | SEQ ID NO.847 |
| 3'-GUCCUUAGGAACAUCACUACCCUAACA-5' | SEQ ID NO.848 |
| 3'-AUAUAAGUUACCGUUUUCUUUUGUUUA-5' | SEQ ID NO.849 |
| 3'-UUACGGAAUUAGAGUCUAUUAAACAAUU-5' | SEQ ID NO.850 |
| 3'-AUUAAACAAUUACUUCUUAUUUUAAUU-5' | SEQ ID NO.851 |
| 3'-UUGUUCAAAGAGGAAUAGUAUUU-5' | SEQ ID NO.852 |
| 3'-GUAUCAUAGAGAAUAUUAGGAAAAGUAAA-5' | SEQ ID NO.853 |
| 3'-UAUCAUAGAGAAUAUUAGGAAAAGUAAA-5' | SEQ ID NO.854 |
| 3'-AUGUUUGUACCCGUUAAGUUUUAG-5' | SEQ ID NO.855 |
| 3'-CGAGAAGAAAGGAAUUGUUUACA-5' | SEQ ID NO.856 |
| 3'-ACAAUUUGUGAAAGAAAGGAAAA-5' | SEQ ID NO.857 |
| 3'-UAUCAUAGAGAAUAUUAGGAAAA-5' | SEQ ID NO.858 |
| 3'-UGUUGACUUUGUUACGUUCCUUA-5' | SEQ ID NO.859 |
| 3'-CAAGUUCCCGGUUAAUAUAGUGU-5' | SEQ ID NO.860 |
| 3'-AUAUUUUAAAAGAGUCCAGAUA-5' | SEQ ID NO.861 |
| 3'-UCUUUAAGUCCUUUUACCUUUUU-5' | SEQ ID NO.862 |
| 3'-GUGUUUCGAGUUCGUGCAUAACA-5' | SEQ ID NO.863 |
| 3'-GAACAAAAGAAAGGGAAAGAAAGAC-5' | SEQ ID NO.864 |
| 3'-AAAGAAAGGGAAAGAAAGACGAAAGA-5' | SEQ ID NO.865 |
| 3'-AAAAGAAAGGGAAAGAAAGACGAAAGAGA-5' | SEQ ID NO.866 |
| 3'-AAAGAAAGGGAAAGAAAGACGAA-5' | SEQ ID NO.867 |
| 3'-AAAGAAAGGGAAAGAAAGACGAAAGA-5' | SEQ ID NO.868 |
| 3'-UAUACCUACAUCUAAAGUAAAC-5' | SEQ ID NO.869 |
| 3'-AAAAGAAAGGGAAAGAAAGACGAAAGA-5' | SEQ ID NO.870 |
| 3'-UGUAGAAAUGUUACACCUAUAAAGAAG-5' | SEQ ID NO.871 |
| 3'-AAGUAUGUAAGAUUUGAAUUAAGGUCUA-5' | SEQ ID NO.872 |

TABLE 2-continued

Antisense sequence listing of the target of the RNA virus

| Antisense fragment coding sequence | ID number |
|---|---|
| 3'-CUGAUGUUCUCUUCCUACCGUCU-5' | SEQ ID NO.873 |
| 3'-UUACCGUCAAUACUUAUAUAAU-5' | SEQ ID NO.874 |
| 3'-UUCCAACAUAAAAUAAUAAAUU-5' | SEQ ID NO.875 |
| 3'-GGAAAAAGGAAAAGUAGUGAAAAAAA-5' | SEQ ID NO.876 |
| 3'-GUCCUUUUUUUACCUAUGAUUU-5' | SEQ ID NO.877 |
| 3'-UAAUAAAAUAUUAGUAAUAGAUUAAU-5' | SEQ ID NO.878 |
| 3'-AUAUAUAUACGUUCAUCGUAUAUAUAU-5' | SEQ ID NO.879 |
| 3'-ACAAUCUAAAGAACAGUAAAAAAGG-5' | SEQ ID NO.880 |
| 3'-GGUGUCGUUGUACCAAAGUCAUA-5' | SEQ ID NO.881 |
| 3'-GAACAAUUCAUGAACUAUAGACA-5' | SEQ ID NO.882 |
| 3'-UAAGAGAAUAAUACUUAUUUCGU-5' | SEQ ID NO.883 |
| 3'-UCUCUCUUUCUUUCUCUUAACCCCUCA-5' | SEQ ID NO.884 |
| 3'-UAUACCUACAUCUAAAGUAAAC-5' | SEQ ID NO.885 |
| 3'-UUGUAGAAUAAAGGAAGAAAAG-5' | SEQ ID NO.886 |
| 3'-AAAAAUCGGGAACGUUUCUUGA-5' | SEQ ID NO.887 |
| 3'-GAAGUAAUUCACAAAAAUAGCCUUCAGU-5' | SEQ ID NO.888 |
| 3'-ACGGGACUGAAGUGUCCGGUAAA-5' | SEQ ID NO.889 |
| 3'-UAAUAGAAUUCUUUCUAAUUUCUUCUUAAAC-5' | SEQ ID NO.890 |
| 3'-AGUUUCGUUUUAUCCAAGUCUCG-5' | SEQ ID NO.891 |
| 3'-UUGAAAAAUAACUAGGUCACGAGU-5' | SEQ ID NO.892 |
| 3'-UCUAUAGAAAGUUUUUUAAAGUU-5' | SEQ ID NO.893 |
| 3'-UACGUAUGUUGUUACCCUUACAGUAAA-5' | SEQ ID NO.894 |
| 3'-UAACAAAUAUAAAUAAAAGUAAA-5' | SEQ ID NO.895 |
| 3'-GUUGUAUUUUUUAGUUGGUAUAA-5' | SEQ ID NO.896 |
| 3'-AGGAGAAAAGAAAAGGAAAGAGGAAGAAA-5' | SEQ ID NO.897 |
| 3'-GUCUUUUCGUCAUACUCUUCCU-5' | SEQ ID NO.898 |
| 3'-AACGGACCCCUUUCCUCCGUCA-5' | SEQ ID NO.899 |
| 3'-GUCUUUUCGUCAUACUCUUCCU-5' | SEQ ID NO.900 |
| 3'-AGAAAAGAAAAGGAAAGAGGAAGAAA-5' | SEQ ID NO.901 |
| 3'-CAGGAGAAAAGAAAAGGAAAGAGGAAGAAA-5' | SEQ ID NO.902 |
| 3'-GAAAAGAAAAGGAAAGAGGAAG-5' | SEQ ID NO.903 |
| 3'-GAGAAAAGAAAAGGAAAGAGGAAGAA-5' | SEQ ID NO.904 |
| 3'-AAUUAUUCUUAUGUCUAAAUAA-5' | SEQ ID NO.905 |
| 3'-AGAGACUCAAUCUUUUACUCUUUCA-5' | SEQ ID NO.906 |
| 3'-GAAACGUAAUUUUUUACACAAACU-5' | SEQ ID NO.907 |
| 3'-AAAAUAUACAGAUCUUUUGAAUCUGUGAUAU-5' | SEQ ID NO.908 |
| 3'-GAUGUCCUACAUCUAAAACUUUUAU-5' | SEQ ID NO.909 |
| 3'-AGAAACAUAAGACCGAAAGGAAGAAACCAAC-5' | SEQ ID NO.910 |

TABLE 2-continued

Antisense sequence listing of the target of the RNA virus

| Antisense fragment coding sequence | ID number |
|---|---|
| 3'-UCUUCUGUGUUUUUUUACACAAUUGUGUUUUG-5' | SEQ ID NO.911 |
| 3'-AGUCACAAAAGACUGAGGUUUCAA-5' | SEQ ID NO.912 |
| 3'-AUGGUUCUUUUACUUCUUCCGAGAAGACU-5' | SEQ ID NO.913 |
| 3'-AAAUGAACGAAUACAUUGGAAUAAAA-5' | SEQ ID NO.914 |
| 3'-AAAGAGAUAAAAGAGAACAAAAUUUG-5' | SEQ ID NO.915 |
| 3'-UUCUACUGAUAGAUUUUACAGUCC-5' | SEQ ID NO.916 |
| 3'-UAAGUGACGGAAGAAGGGAGAGU-5' | SEQ ID NO.917 |
| 3'-GACAGACGAUUGGUCAUACUUGU-5' | SEQ ID NO.918 |
| 3'-UCUUUCAAGAUAGUUCttttttt-5' | SEQ ID NO.919 |
| 3'-AAAGUUUAAGGAAGAGUCUUAAG-5' | SEQ ID NO.920 |
| 3'-UAAAACAUGUCUUCCAAAAGUAUU-5' | SEQ ID NO.921 |
| 3'-UAACUAAUCUUUAAGUUGAACCUUUUUAGUUAC-5' | SEQ ID NO.922 |
| 3'-CCUACAGAAACAGAAAGAAAAAGAAAC-5' | SEQ ID NO.923 |
| 3'-UGUGGUUUCCCUUUGAGUGACUGUCUUUUG-5' | SEQ ID NO.924 |
| 3'-CUGUGUCUACUUCUUUGAAGGAAA-5' | SEQ ID NO.925 |
| 3'-AUGUUGGGUUCUCUCGAAUUUG-5' | SEQ ID NO.926 |
| 3'-UUUCUUACUUCAUUUCCAGUCGU-5' | SEQ ID NO.927 |
| 3'-CACGAUAACUAGUCUGAUUAAU-5' | SEQ ID NO.928 |
| 3'-CGACCUGACACCACUGUCGGAG-5' | SEQ ID NO.929 |
| 3'-GUUGGAGACGUGUUUUACUCGA-5' | SEQ ID NO.930 |
| 3'-UGUUACCUCGUACGUUCCUUCGU-5' | SEQ ID NO.931 |
| 3'-AUCGUCCAUCAUAGGUUCUGUCUCUG-5' | SEQ ID NO.932 |
| 3'-UUUUACGACUCCUAUACCCGUU-5' | SEQ ID NO.933 |
| 3'-GUUAUUGGUUUCUCUUUUUUCUU-5' | SEQ ID NO.934 |
| 3'-UUAGUACCUUCAACAAAAGGGGU-5' | SEQ ID NO.935 |
| 3'-UUCGUUGGUCCUCUAACCAAGU-5' | SEQ ID NO.936 |
| 3'-UACGUUGACUCUAGUCUCGUAG-5' | SEQ ID NO.937 |
| 3'-GGUCUCCUGUUCUCGAGAACAA-5' | SEQ ID NO.938 |
| 3'-CUCCUGCUCUACCCACCUAGUUCU-5' | SEQ ID NO.939 |
| 3'-CUCCUGCUCUACCCACCUAGUUCUCCAG-5' | SEQ ID NO.940 |
| 3'-AACCGAGUAAGAGACAAAAAAAACAAAAAAAA-5' | SEQ ID NO.941 |
| 3'-CUCCUGCUCUACCCACCUAGUUCUCCAG-5' | SEQ ID NO.942 |
| 3'-GAGUAAGAGACAAAAAAAACAAAAAAAA-5' | SEQ ID NO.943 |
| 3'-GAAAUAAGAUUUUAUAAAAAUUUA-5' | SEQ ID NO.944 |
| 3'-UACUCGGGUUCUGAAGAAAACUA-5' | SEQ ID NO.945 |
| 3'-UUCUUUGACACUAAAAAUUAUGAAU-5' | SEQ ID NO.946 |
| 3'-UUCUUACUAUUUCGUUUCUUUU-5' | SEQ ID NO.947 |
| 3'-AUGAAAAUUUCUACGUACGAAAGUAA-5' | SEQ ID NO.948 |

TABLE 2-continued

Antisense sequence listing of the target of the RNA virus

| Antisense fragment coding sequence | ID number |
|---|---|
| 3'-AAAUUUUUUACUAUUCUUAUUU-5' | SEQ ID NO.949 |
| 3'-UCUUACUAUUUCGUUUCUUUUACAUC-5' | SEQ ID NO.950 |
| 3'-AUGACUAGAGGUUGAGUCUUCU-5' | SEQ ID NO.951 |
| 3'-UUUUAAACUUUCUUACUAUUUCGUUU-5' | SEQ ID NO.952 |
| 3'-UUUUUACUUACUUUUAUACGUAAGAGAAGUUUU-5' | SEQ ID NO.953 |
| 3'-UUUCGUUCUUUUUACUUACUUUU-5' | SEQ ID NO.954 |
| 3'-GUUCUUUUUACUUACUUUUAUA-5' | SEQ ID NO.955 |
| 3'-UCCUCUUUAGUUUUGUUUUGGUAU-5' | SEQ ID NO.956 |
| 3'-CGUAAGUUAUUUAUGUACGAC-5' | SEQ ID NO.957 |
| 3'-UACAUUCUUGACAUUUAUAUU-5' | SEQ ID NO.958 |
| 3'-UUUUGUUUUGGUAUUUUCAUC-5' | SEQ ID NO.959 |
| 3'-UUUCCUCUUUAGUUUUGUUUUGGUAUUUU-5' | SEQ ID NO.960 |
| 3'-AUCCCUCGAGGGGUGAGGGCAAAACACUG-5' | SEQ ID NO.961 |
| 3'-AUAUAGUUUUCUUUUACUUUAGUU-5' | SEQ ID NO.962 |
| 3'-CUAAUUUAAAUAUAGUUUUCUUUUACUU-5' | SEQ ID NO.963 |
| 3'-AUAUAGUUUUCUUUUACUUUAGUUAU-5' | SEQ ID NO.964 |
| 3'-UUUCUUUUACUUUAGUUAUCAACUCCU-5' | SEQ ID NO.965 |
| 3'-AUAUAGUUUUCUUUUACUUUAGUUAUC-5' | SEQ ID NO.966 |
| 3'-UACUGGUUUACAUAUCUAACUCU-5' | SEQ ID NO.967 |
| 3'-AUAUAGUUUUCUUUUACUUUAGUUAUCAACUCCU-5' | SEQ ID NO.968 |
| 3'-AUAUAGUUUUCUUUUACUUUAGUUAU-5' | SEQ ID NO.969 |
| 3'-AACUUUAUUCUUCUAAUCUAUAAAAAUUAA-5' | SEQ ID NO.970 |
| 3'-ACUAUAGUAAAAGUUAAUGUAU-5' | SEQ ID NO.971 |
| 3'-UUCUUUUUCUUCUAUCGUUCUU-5' | SEQ ID NO.972 |
| 3'-UCGAUUUCAAACCAUCCUUUUGUU-5' | SEQ ID NO.973 |
| 3'-UUUAGUUCAUUUUAUUGUUAUUUACUGUAUG-5' | SEQ ID NO.974 |
| 3'-GUAAUUUAAAUAUGUUUGUUUGUGUUU-5' | SEQ ID NO.975 |
| 3'-UCGAUUUCAAACCAUCCUUUUGUU-5' | SEQ ID NO.976 |
| 3'-CUUUAUAUGGUAUAUUUAUACUACA-5' | SEQ ID NO.977 |
| 3'-UUUAUUCUAGUCUUAAAAUAAAU-5' | SEQ ID NO.978 |
| 3'-UCUUAAUAUAAUUAUGUCAUAU-5' | SEQ ID NO.979 |
| 3'-UCGUAAUUUUGUAAUCUUUAUAAUUUAUUC-5' | SEQ ID NO.980 |
| 3'-UCUUAAUAUAAUUAUGUCAUAUAUCA-5' | SEQ ID NO.981 |
| 3'-CUUCUUAAUAAGUGUAAUUAUU-5' | SEQ ID NO.982 |
| 3'-CUUCUUGUUUGAUAAUUAUUAA-5' | SEQ ID NO.983 |
| 3'-AUUCUAGUCUUAAAAUAAAUAAUGAU-5' | SEQ ID NO.984 |
| 3'-AUUUGGUUUGUAAAAAGGAAUA-5' | SEQ ID NO.985 |
| 3'-UAAAAUUUUGUGAAUUUUUAAA-5' | SEQ ID NO.986 |

TABLE 2-continued

Antisense sequence listing of the target of the RNA virus

| Antisense fragment coding sequence | ID number |
|---|---|
| 3'-GUUAUAAAGACGACAAGUUAAGUUACC-5' | SEQ ID NO.987 |
| 3'-AAAAAACCCAAAACAAACACAACUAUGAAACUC-5' | SEQ ID NO.988 |
| 3'-CGUUUAAAUAGAAUUUAAGUUCAUGUAU-5' | SEQ ID NO.989 |
| 3'-AUUGUCUGAACCUUUUUAUGUUAA-5' | SEQ ID NO.990 |
| 3'-UAAUGGAAGUUUUUAGAUCUUGAAAUAAUUAAGAG UC-5' | SEQ ID NO.991 |
| 3'-UUUUAAUUUUGUUUUUACUUUCC-5' | SEQ ID NO.992 |
| 3'-GAAUAAAAUACAGAAGAAACAACAAAAA-5' | SEQ ID NO.993 |
| 3'-UAAUAAUUGUUGAAUAAAAAUAAAUUAGAAAAU-5' | SEQ ID NO.994 |
| 3'-UAUUUCUUCUUAUAAUUGUAACUGUAAU-5' | SEQ ID NO.995 |
| 3'-AAUACUUACAAAAUAGUACUAAUUUCUA-5' | SEQ ID NO.996 |
| 3'-GGGUCGUGUCUCUACAGUAACU-5' | SEQ ID NO.997 |
| 3'-UCACUCUUUACUACUACAACUAGUCU-5' | SEQ ID NO.998 |
| 3'-AAGAUUCCUUUCGUUGGUCUUC-5' | SEQ ID NO.999 |
| 3'-ACUCGUUCUUCUUUAGGAUGUA-5' | SEQ ID NO.1000 |
| 3'-CCUUACUCUUCUUUCGAUUUAA-5' | SEQ ID NO.1001 |
| 3'-AAUCUUUACAGAAUUCGUAACG-5' | SEQ ID NO.1002 |
| 3'-GUCCUGUAACUUUUACUUCUCUUC-5' | SEQ ID NO.1003 |
| 3'-UUCUCUUUCUGGACUGGUUUCU-5' | SEQ ID NO.1004 |
| 3'-UGAUUCAGUAUAUUUUUAUGUUCUUUUU-5' | SEQ ID NO.1005 |
| 3'-UUGUUAAACUCAACUAUCUGUUACUUA-5' | SEQ ID NO.1006 |
| 3'-UAGUACAAAGUAUGAAGAUCGGUAAC-5' | SEQ ID NO.1007 |
| 3'-CUUUGUAUGAUUCUUGUGUCCUU-5' | SEQ ID NO.1008 |
| 3'-AAAGUGGUAAUGGAAGAGAAGG-5' | SEQ ID NO.1009 |
| 3'-UCCUUCGUUUUAAUUUGUCUCUUCUUU-5' | SEQ ID NO.1010 |
| 3'-ACCUUUUACUUUCUUGAAACCU-5' | SEQ ID NO.1011 |
| 3'-UUUUGUUGUGAACCCAUUUAGUCUGU-5' | SEQ ID NO.1012 |
| 3'-CGACGACCUGUCAGUCACCAAA-5' | SEQ ID NO.1013 |
| 3'-CCUAGUUCUUUCUUCUCAAGAGACUCU-5' | SEQ ID NO.1014 |
| 3'-CCCCUCUGUGUGUUUAAGUCUG-5' | SEQ ID NO.1015 |
| 3'-UGGUUUACUUUUGGGUCGAGUGUUCUCAGU-5' | SEQ ID NO.1016 |
| 3'-UUUACUCUUACACCUUUGGUAC-5' | SEQ ID NO.1017 |
| 3'-UCUUUAUUCCUCUCAAACCGCG-5' | SEQ ID NO.1018 |
| 3'-UCUUCUCAUCUGCCUUUCACCU-5' | SEQ ID NO.1019 |
| 3'-CUGUAAGAAACCGACCUUUCUCGGAUU-5' | SEQ ID NO.1020 |
| 3'-CUUCUCUCGUCCCGUUCUUAGUUUUGAUCCGA-5' | SEQ ID NO.1021 |
| 3'-UCCCGUUCGAAAGGGUUUACAG-5' | SEQ ID NO.1022 |
| 3'-CCUGUACUAAGGUCUCUCCUUACUUGUUCCUGUU-5' | SEQ ID NO.1023 |
| 3'-CCUUUAACACUUUUAAGUUACC-5' | SEQ ID NO.1024 |

TABLE 2-continued

Antisense sequence listing of the target of the RNA virus

| Antisense fragment coding sequence | ID number |
|---|---|
| 3'-CUCAGAUGUAAGAGUCAAAACAG-5' | SEQ ID NO.1025 |
| 3'-CUCUGUCUGUCAUUUCCUUUUA-5' | SEQ ID NO.1026 |
| 3'-ACUUCUUUUUGAUUUCUUUUUU-5' | SEQ ID NO.1027 |
| 3'-GGUCUGUCGUCUGACCUUCCGU-5' | SEQ ID NO.1028 |
| 3'-UUGUCCUUUAGUAUAACUUAAACA-5' | SEQ ID NO.1029 |
| 3'-UCAUACGUACCUUUCUAAAAGAAUUAC-5' | SEQ ID NO.1030 |
| 3'-GUCUCAAACUUAAAAUACUAGUC-5' | SEQ ID NO.1031 |
| 3'-ACUCCCAUUGUAAAUUAAAACCC-5' | SEQ ID NO.1032 |
| 3'-AAAAAAGAAAAACUCUUUCCCGAAGUA-5' | SEQ ID NO.1033 |
| 3'-UCUUUUGUUGUCCACAACUACUC-5' | SEQ ID NO.1034 |
| 3'-AAAAAAGAAAAACUCUUUCCCGA-5' | SEQ ID NO.1035 |
| 3'-UUUACUUUCUAAAGGUCUUUAAC-5' | SEQ ID NO.1036 |
| 3'-UGUUGUCUAUGUUGUUUACGACCACUCUUA-5' | SEQ ID NO.1037 |
| 3'-UCACUAAGUACGACUUUAUGUCA-5' | SEQ ID NO.1038 |
| 3'-UACUCUCUAGAACCCCCACCCUG-5' | SEQ ID NO.1039 |
| 3'-GGUUACAUAAAUAUGUAAAUGUUCAU-5' | SEQ ID NO.1040 |
| 3'-UUCAAGUUACUCUUUCUCUUAUCUAUACC-5' | SEQ ID NO.1041 |
| 3'-AUGAAUGUACGGUUUAGAGUU-5' | SEQ ID NO.1042 |
| 3'-UCAAGUUACUCUUUCUCUUAU-5' | SEQ ID NO.1043 |
| 3'-AUGUAUGAUAAUUACACUAAAU-5' | SEQ ID NO.1044 |
| 3'-AAAACAGGAAGGUUAACACAAC-5' | SEQ ID NO.1045 |
| 3'-CUUCGUCUCUCUUUCAUCUCUUC-5' | SEQ ID NO.1046 |
| 3'-AGUUUUCCUCUCUUGUCUACGACC-5' | SEQ ID NO.1047 |
| 3'-AGGGACCUACCGUUCGUCUUCGU-5' | SEQ ID NO.1048 |
| 3'-GUCCUGUAACUUUUACUUCUCUUC-5' | SEQ ID NO.1049 |
| 3'-UUGUUCUCGUCCGGUCACACCACC-5' | SEQ ID NO.1050 |
| 3'-AACUCCUUUUCCCUUGGGACAUGU-5' | SEQ ID NO.1051 |
| 3'-GGUCCGUGACCCUUCAGUCACCGU-5' | SEQ ID NO.1052 |
| 3'-UUAAUCCUCACUAUGGAAGUGAUU-5' | SEQ ID NO.1053 |
| 3'-ACUCUUUUUCCGGUGACAGGAAAU-5' | SEQ ID NO.1054 |
| 3'-UGUUUAACCUCUUUAUCACUUUU-5' | SEQ ID NO.1055 |
| 3'-AUAAUCUUUAUUGUGGAUACU-5' | SEQ ID NO.1056 |
| 3'-UUUCCUUCUUUAACUUUGGGUCU-5' | SEQ ID NO.1057 |
| 3'-CUACAGUAGUUCUUACGUCUACG-5' | SEQ ID NO.1058 |
| 3'-UGUUUUCUACGUCUUUCUCCGUUC-5' | SEQ ID NO.1059 |
| 3'-UUACAAUAACUCAUAUAUCUCUCU-5' | SEQ ID NO.1060 |
| 3'-GUAAACUACUAGACCGUAAGGUUGA-5' | SEQ ID NO.1061 |
| 3'-CUUCCCUCCGACUAGGUCUUGUCA-5' | SEQ ID NO.1062 |

TABLE 2-continued

Antisense sequence listing of the target of the RNA virus

| Antisense fragment coding sequence | ID number |
|---|---|
| 3'-CCGUGUUGACCUCACCUCAGACGA-5' | SEQ ID NO.1063 |
| 3'-GUUUUCUUUUCUUUCUUCUCGAG-5' | SEQ ID NO.1064 |
| 3'-AGGUUUAACGAAGUUUACUUUU-5' | SEQ ID NO.1065 |
| 3'-UUAACAUGUUUUUGGGACUAUG-5' | SEQ ID NO.1066 |
| 3'-UACUCCUUACCUCCCUUAUCGA-5' | SEQ ID NO.1067 |
| 3'-UAACGAGGAAACGACCUACCUA-5' | SEQ ID NO.1068 |
| 3'-AAGGUUAGACUUACUACGUUGU-5' | SEQ ID NO.1069 |
| 3'-AUUUUCGACGUAGUUAUCCACA-5' | SEQ ID NO.1070 |
| 3'-CCCUCUAACUAGGUUUUGUCGU-5' | SEQ ID NO.1071 |
| 3'-UCCCCCUUCGGGUCUAGGACCU-5' | SEQ ID NO.1072 |
| 3'-ACGGUGUCUCCUCUGUGUGUUU-5' | SEQ ID NO.1073 |
| 3'-CUCUUUCCUUUCACCUGUUGU-5' | SEQ ID NO.1074 |
| 3'-GUAUUGUUGUUGUUAUUAUUGACUU-5' | SEQ ID NO.1075 |
| 3'-UCCUUCCCUUUUAUGUUUUUUA-5' | SEQ ID NO.1076 |
| 3'-CUCCUUUACUCUUCUUCCGAU-5' | SEQ ID NO.1077 |
| 3'-GACCUCGACGACCUCGUCGUC-5' | SEQ ID NO.1078 |
| 3'-AGAGUUUGAACGUCAACCAG-5' | SEQ ID NO.1079 |
| 3'-AACUGAUACCCUCACUACAAA-5' | SEQ ID NO.1080 |
| 3'-UCAAACUUAAGUAACGACUUC-5' | SEQ ID NO.1081 |
| 3'-CUUUUUGUUCUAAAGAGGGUCAC-5' | SEQ ID NO.1082 |
| 3'-UGUCCCACUACCACAGGGGG-5' | SEQ ID NO.1083 |
| 3'-UUUACCUGGUGUUUGUGUCUUUG-5' | SEQ ID NO.1084 |
| 3'-UACAGAAGAAGUUAGUGAAGUUG-5' | SEQ ID NO.1085 |
| 3'-AUGACGAUUCCUUCGUGUUCUAC-5' | SEQ ID NO.1086 |
| 3'-UUUUUAACUUUGCUUGUUUAAG-5' | SEQ ID NO.1087 |
| 3'-UUAUUUAUGUUGUAAUGGGAAA-5' | SEQ ID NO.1088 |
| 3'-UUCGUUCUAAUUUUUCUCUCCU-5' | SEQ ID NO.1089 |
| 3'-AAUCUCGUAGACAACCUUCUUA-5' | SEQ ID NO.1090 |
| 3'-UUGUCUCCGACUUGUUCUCCU-5' | SEQ ID NO.1091 |
| 3'-ACGUCUUCCUUGUCCUUGCCG-5' | SEQ ID NO.1092 |
| 3'-UAACAUACCUGUGUUAAUCUUUG-5' | SEQ ID NO.1093 |
| 3'-UACUCUUUGCACGGACUCUUUGU-5' | SEQ ID NO.1094 |
| 3'-ACAAAAGAAGACAGACUUCU-5' | SEQ ID NO.1095 |
| 3'-GUAUAUUAAUCGUAGUGUUA-5' | SEQ ID NO.1096 |
| 3'-UGUUUAGUCGUCAAACUUGACUAU-5' | SEQ ID NO.1097 |
| 3'-CUUUCUCCAUUUAAUUUUUC-5' | SEQ ID NO.1098 |
| 3'-UUCAUCGUCCGAGUGAGACG-5' | SEQ ID NO.1099 |
| 3'-UCUUCCUCUCUUCCUUUUACC-5' | SEQ ID NO.1100 |

TABLE 2-continued

Antisense sequence listing of the target of the RNA virus

| Antisense fragment coding sequence | ID number |
|---|---|
| 3'-UGUUUAUGGACGUCUUUACG-5' | SEQ ID NO.1101 |
| 3'-UUACUUAGUUGUUCUUUCUUUU-5' | SEQ ID NO.1102 |
| 3'-UUACUUAGUUGUUCUUUCUU-5' | SEQ ID NO.1103 |
| 3'-CUCUUACUUCUCUUUUGAGG-5' | SEQ ID NO.1104 |
| 3'-UAAGUCACUUUAACCUUUUA-5' | SEQ ID NO.1105 |
| 3'-UCUUUAUGUGGUUCUGGUGUAU-5' | SEQ ID NO.1106 |
| 3'-GAACUUGAAUCUUCGUCUAUA-5' | SEQ ID NO.1107 |
| 3'-UGUUACGAUAGUUAACAUUAG-5' | SEQ ID NO.1108 |
| 3'-UGUUACGAUAGUUAACAUUA-5' | SEQ ID NO.1109 |
| 3'-CUUGAAGUCCUGUAUCUUUUA-5' | SEQ ID NO.1110 |
| 3'-CGGAAGGAAAGGUCUUACAC-5' | SEQ ID NO.1111 |
| 3'-CUAUACUGAAACUUUCCCUC-5' | SEQ ID NO.1112 |
| 3'-UCCCCAACCUUACCGACGUC-5' | SEQ ID NO.1113 |
| 3'-GUCUCAUCUUACGUUAAGAGGAGU-5' | SEQ ID NO.1114 |
| 3'-AAGGACGAAAUGGUAUUACUGACU-5' | SEQ ID NO.1115 |
| 3'-AAAGUAUUACAGUCGUUUAUACGU-5' | SEQ ID NO.1116 |
| 3'-CCAGAUGUUUUGUAUGAAACUCUU-5' | SEQ ID NO.1117 |
| 3'-GUUUUAAUCUCUCUGUCUUUUAUCU-5' | SEQ ID NO.1118 |
| 3'-CUUCGUUUUGACAAACACGA-5' | SEQ ID NO.1119 |
| 3'-AACAAAAAUACACCUCGAUUAGU-5' | SEQ ID NO.1120 |
| 3'-GUGUUUCCUGUUAUCCUUUCUUU-5' | SEQ ID NO.1121 |
| 3'-AUUUCUUUAACUUAGUCAUUUAUU-5' | SEQ ID NO.1122 |
| 3'-UCACUCUGUGUCCCUUGUCUCUUU-5' | SEQ ID NO.1123 |
| 3'-GUAUACUUUCUUACACGUUGUAG-5' | SEQ ID NO.1124 |
| 3'-AAGUUACUUAGUUGUUUUUUCUUU-5' | SEQ ID NO.1125 |
| 3'-GUCGUCUAUUUUCUUAUUACCUUUAC-5' | SEQ ID NO.1126 |
| 3'-UCAACUAUUAUUGUUGACCAGACCA-5' | SEQ ID NO.1127 |
| 3'-UCUUCUUCUUUUUUCUCCUGAUAAA-5' | SEQ ID NO.1128 |
| 3'-GAAGGGUCAAAACCUCACAGACCCUA-5' | SEQ ID NO.1129 |
| 3'-UUUAAAUUUAUUCUUUUACCUUCUA-5' | SEQ ID NO.1130 |
| 3'-UUAGAUUACCCUUAAAUUAUCGAG-5' | SEQ ID NO.1131 |
| 3'-UACGUCUUGAAAGAAAAACUGAG-5' | SEQ ID NO.1132 |
| 3'-UGUAAGAAAAGUACACCCCGUAUU-5' | SEQ ID NO.1133 |
| 3'-GAUCAGUCCGAUCCGUCUACCA-5' | SEQ ID NO.1134 |
| 3'-GUUUCGUCUUACGUCAAGAGAA-5' | SEQ ID NO.1135 |
| 3'-ACGUGGUUAAUUUUAUGUCUAUA-5' | SEQ ID NO.1136 |
| 3'-UCUCAUUCUCUGUUGUACUGGU-5' | SEQ ID NO.1137 |
| 3'-CCCUUAACCCUGUUACCACUAC-5' | SEQ ID NO.1138 |

TABLE 2-continued

Antisense sequence listing of the target of the RNA virus

| Antisense fragment coding sequence | ID number |
| --- | --- |
| 3'-UUACGGAACAAAGAUGAUUAUG-5' | SEQ ID NO.1139 |
| 3'-AUUCUCCUAGUCCUUACUCUUA-5' | SEQ ID NO.1140 |
| 3'-UAGAGUAAAUUCCUUACUGUGU-5' | SEQ ID NO.1141 |
| 3'-UCUGUUACGAUUCCUUUAUCCC-5' | SEQ ID NO.1142 |
| 3'-UUUCGUUACUUUCUCAUACCCCUC-5' | SEQ ID NO.1143 |
| 3'-AACCAGACUCCUUACACGGACGA-5' | SEQ ID NO.1144 |
| 3'-UAGUUACUUGUUUCUCCUUUAU-5' | SEQ ID NO.1145 |
| 3'-GUCUCUCUCCGUUUAAUUUUUC-5' | SEQ ID NO.1146 |
| 3'-GUGUUUAACUUCUACUGUCUCU-5' | SEQ ID NO.1147 |
| 3'-UUUGUUCUUCACGAAUACUCUC-5' | SEQ ID NO.1148 |
| 3'-AAAAAAAGUUUACGUAGAUAGUU-5' | SEQ ID NO.1149 |
| 3'-GUCUUUAAGCUUCUUUAUUUUAC-5' | SEQ ID NO.1150 |
| 3'-GUCGGAUUAGUCUGGUUUACUU-5' | SEQ ID NO.1151 |
| 3'-CCUGCCUAAUUCUUUCUUCUCA-5' | SEQ ID NO.1152 |
| 3'-ACCUCAACUAUUCCCCUUCCCU-5' | SEQ ID NO.1153 |
| 3'-UGUCUAAACUUUAUUAACUUCC-5' | SEQ ID NO.1154 |
| 3'-ACGUACACAUUUACCGAGAAC-5' | SEQ ID NO.1155 |
| 3'-GAAAAGGACUUUCACGGUCGU-5' | SEQ ID NO.1156 |
| 3'-UUCUGUUCUUUACCGGUCAUCC-5' | SEQ ID NO.1157 |
| 3'-GACGUAAACUUCUAAAUUCUAAC-5' | SEQ ID NO.1158 |
| 3'-GGUAAUAGGUUUCCAGAUGUUU-5' | SEQ ID NO.1159 |
| 3'-ACUCUGAAGGUUCUAGUUCUAC-5' | SEQ ID NO.1160 |
| 3'-CGUCCUCACCUAUCUAAGAUGU-5' | SEQ ID NO.1161 |
| 3'-UUUCGUUUAACAUCUUUUCUAA-5' | SEQ ID NO.1162 |
| 3'-ACGUCCCUUCUUGUGUCUAGAG-5' | SEQ ID NO.1163 |
| 3'-AGUUUACGUACUUCUGUAAGAA-5' | SEQ ID NO.1164 |
| 3'-UCUUCAAUAUUCCUACUACCU-5' | SEQ ID NO.1165 |
| 3'-GACGGGUAGCCACUUCGAGG-5' | SEQ ID NO.1166 |
| 3'-UUAUGGUCGGAAGGUAAAGUCUUA-5' | SEQ ID NO.1167 |
| 3'-UUACUUAGGUUUAGUUUCCU-5' | SEQ ID NO.1168 |
| 3'-UACGGAACAAAGAUGAUUAUG-5' | SEQ ID NO.1169 |
| 3'-ACUCAACGGUAAGUGGUAACU-5' | SEQ ID NO.1170 |
| 3'-UAUGUAACUUCAAAAUGUAAA-5' | SEQ ID NO.1171 |
| 3'-CACACUACCCUUACCAACCUCAUA-5' | SEQ ID NO.1172 |
| 3'-UAUACGUGUUUGUCUUACACA-5' | SEQ ID NO.1173 |
| 3'-ACCUAAACAACGGUUAAAGU-5' | SEQ ID NO.1174 |
| 3'-UAAUAUUUUCCUUCCAGAGU-5' | SEQ ID NO.1175 |
| 3'-GGUUUCUCCCUUCUGCUUUC-5' | SEQ ID NO.1176 |

TABLE 2-continued

Antisense sequence listing of the target of the RNA virus

| Antisense fragment coding sequence | ID number |
|---|---|
| 3'-AUAUAUUUAUCUUGUCCUUGUA-5' | SEQ ID NO.1177 |
| 3'-UGUUAUUUUUCAACCUCUUUGU-5' | SEQ ID NO.1178 |
| 3'-UUUCGGUACCUUGUUUACCGAC-5' | SEQ ID NO.1179 |
| 3'-CCAGAUGUUUUGUAUGAAACUCUUU-5' | SEQ ID NO.1180 |
| 3'-UUAUCAAAUGAACUUAUUAUGU-5' | SEQ ID NO.1181 |
| 3'-AAGUUCUACCUCUUUCCCUUCU-5' | SEQ ID NO.1182 |
| 3'-UUUUCUUUAUGUGGUUUUGUCA-5' | SEQ ID NO.1183 |
| 3'-UUGGAUUUAAAGAGGGUCUAAA-5' | SEQ ID NO.1184 |
| 3'-UGUUGGAUGAAAGAGUCAUGUCU-5' | SEQ ID NO.1185 |
| 3'-UUUAAGUUUGUUCCUCUAGUAA-5' | SEQ ID NO.1186 |
| 3'-ACCAGUCCAAUAAGACCGUAAA-5' | SEQ ID NO.1187 |
| 3'-GUUGGACCUUGGACCUUGGA-5' | SEQ ID NO.1188 |
| 3'-GGUCGUGACUCUCCCACUGACA-5' | SEQ ID NO.1189 |
| 3'-CUUUAGUUGGACUUACCAAA-5' | SEQ ID NO.1190 |
| 3'-AAUAGUUUAUGAACGAUAUAUG-5' | SEQ ID NO.1191 |
| 3'-GAAAAGAAUUUUUAAGGUCGCG-5' | SEQ ID NO.1192 |
| 3'-UCUCUUCCUAUAAGAGACCAG-5' | SEQ ID NO.1193 |
| 3'-CCCCUCUGUGUGUUUAAGUCUG-5' | SEQ ID NO.1194 |
| 3'-ACUAAUAACGACGAUCUUUGUAU-5' | SEQ ID NO.1195 |
| 3'-ACUAAUAACGACGAUCUUUGUA-5' | SEQ ID NO.1196 |
| 3'-ACCUCUUUCGGUUGUUCUAUUUU-5' | SEQ ID NO.1197 |
| 3'-UGUUUCUUGUACUUUUUUUGUUC-5' | SEQ ID NO.1198 |
| 3'-UCCCGUUCGAAAGGGUUUACAGA-5' | SEQ ID NO.1199 |
| 3'-UCCCGUUCGAAAGGGUUUACAG-5' | SEQ ID NO.1200 |
| 3'-GGUUUUGAUGUAUGACCACCCU-5' | SEQ ID NO.1201 |
| 3'-UCCGUUUCACCACACACACACG-5' | SEQ ID NO.1202 |
| 3'-AGUUUCUCUUUCUGUACUGGU-5' | SEQ ID NO.1203 |
| 3'-UGAAACAUUAGGGUACUUAGG-5' | SEQ ID NO.1204 |
| 3'-AAAGUCCGUCUUACUUACGUC-5' | SEQ ID NO.1205 |
| 3'-CUUUGUGUCCCUUGUCUCUUU-5' | SEQ ID NO.1206 |
| 3'-UUCCUUCUAGAGUAAACUCCU-5' | SEQ ID NO.1207 |
| 3'-CUAUCAUUCACCUUCUCUACUU-5' | SEQ ID NO.1208 |
| 3'-GUAUACUUUCUUACACGUUGUA-5' | SEQ ID NO.1209 |
| 3'-UAUUAUGAUCAUCAUUGUCAUU-5' | SEQ ID NO.1210 |
| 3'-AACUGACUUCUAGGUCUACUU-5' | SEQ ID NO.1211 |
| 3'-UUUUUACUACUGGUUAAGAGU-5' | SEQ ID NO.1212 |
| 3'-AUACCUUAAGAGAGAAUGACU-5' | SEQ ID NO.1213 |
| 3'-UUUUUUGUUUCUAACUCAUUCU-5' | SEQ ID NO.1214 |

TABLE 2-continued

Antisense sequence listing of the target of the RNA virus

| Antisense fragment coding sequence | ID number |
|---|---|
| 3'-UUCGUUGGUCCUCUAACCAAGU-5' | SEQ ID NO.1215 |
| 3'-GGUCUCCUGUUCUCGAGAACAA-5' | SEQ ID NO.1216 |
| 3'-CUUUCUUGUAAGAAAAGUACAC-5' | SEQ ID NO.1217 |
| 3'-GACAUUACUCUUACCCUCUGGA-5' | SEQ ID NO.1218 |
| 3'-CCUUUAACACUUUUAAGUUACC-5' | SEQ ID NO.1219 |
| 3'-AAAACGAAACACAACAAAACGAC-5' | SEQ ID NO.1220 |
| 3'-UCCUGAAGCUCUUUAUACAACU-5' | SEQ ID NO.1221 |
| 3'-UUUGUUGUAUUGUUGUUGUUAUU-5' | SEQ ID NO.1222 |
| 3'-UUUUACGACUCCUAUACCCGUU-5' | SEQ ID NO.1223 |
| 3'-AAAGUGGUAAUGGAAGAGAAGG-5' | SEQ ID NO.1224 |
| 3'-AGAAUAAAGAAGUCUCUGUUAC-5' | SEQ ID NO.1225 |
| 3'-UCUCUUUUAUGAACUUUUAACAC-5' | SEQ ID NO.1226 |
| 3'-UGUCUUUACAGUGACUCUCCUC-5' | SEQ ID NO.1227 |
| 3'-UUUCCCCCAUCCCUGUUACCAC-5' | SEQ ID NO.1228 |
| 3'-CUGAUGUCUAUAUGUAUAUCUA-5' | SEQ ID NO.1229 |
| 3'-CUUUUUCCUCUCACUCUCUGUU-5' | SEQ ID NO.1230 |
| 3'-AUCUAUAUUUACACUUUCUAAU-5' | SEQ ID NO.1231 |
| 3'-AGUCUGUCGACGGGUCUCCCGU-5' | SEQ ID NO.1232 |
| 3'-UGAAUGGUCAGAGUAGAAGAU-5' | SEQ ID NO.1233 |
| 3'-AAAAGAUAGGGAGUCUUUUAGG-5' | SEQ ID NO.1234 |
| 3'-GAAACUAGAGCCCGAACUCU-5' | SEQ ID NO.1235 |
| 3'-AGAGAGACGGAACAUCAACC-5' | SEQ ID NO.1236 |
| 3'-AUAUUGAAUAAUGAAGUCUU-5' | SEQ ID NO.1237 |
| 3'-UCUUUAGUAUAGUUUAGGAA-5' | SEQ ID NO.1238 |
| 3'-AAGUCUGUCUAGUCUGGAGU-5' | SEQ ID NO.1239 |
| 3'-UUAUAGGUCUUACCAAAGAC-5' | SEQ ID NO.1240 |
| 3'-UUCAGUUGUACUUUUUUGUC-5' | SEQ ID NO.1241 |
| 3'-ACUUUUUUGUUCUAGAAUU-5' | SEQ ID NO.1242 |
| 3'-CCCCCCAAGAAAAACUUUUU-5' | SEQ ID NO.1243 |
| 3'-CUCUACCGGUUCCACCCUCU-5' | SEQ ID NO.1244 |
| 3'-AAAAAUGGUUAUCAUCUCCC-5' | SEQ ID NO.1245 |
| 3'-CACGAGGAGUACUUUACAGACA-5' | SEQ ID NO.1246 |
| 3'-AUGGUGGAAUUUAUAGUCUC-5' | SEQ ID NO.1247 |
| 3'-GAGUCGGUAUUUUUACUUGC-5' | SEQ ID NO.1248 |
| 3'-UAACGUCUUUCAAAGAGGUUUU-5' | SEQ ID NO.1249 |
| 3'-UCUGACCUGGUCGAUACCUUAG-5' | SEQ ID NO.1250 |
| 3'-UACAUUAGUGGAAUAUGUACUUG-5' | SEQ ID NO.1251 |
| 3'-CCUUCCUGAACCAUUUCAAG-5' | SEQ ID NO.1252 |

TABLE 2-continued

Antisense sequence listing of the target of the RNA virus

| Antisense fragment coding sequence | ID number |
|---|---|
| 3'-UUUAGGACUCCGUGAAGUUGUA-5' | SEQ ID NO.1253 |
| 3'-CAGACAGUAGAGUGACCUAG-5' | SEQ ID NO.1254 |
| 3'-ACCCGUGUCAACAGUGACGA-5' | SEQ ID NO.1255 |
| 3'-UUUGUAACGUCUGUCCUAUC-5' | SEQ ID NO.1256 |
| 3'-ACAUUAAGAUCGGACUCAGA-5' | SEQ ID NO.1257 |
| 3'-GGUCCUUUCAGAAGUCUCCUA-5' | SEQ ID NO.1258 |
| 3'-AUUUUCUAGAAAAGAACAGA-5' | SEQ ID NO.1259 |
| 3'-UCUGUUUAUUCCAGUCCUCU-5' | SEQ ID NO.1260 |
| 3'-UCUGUUGUGGGUGAGGAAGA-5' | SEQ ID NO.1261 |
| 3'-AUCCAAGUUCAGACGGUCUAUGU-5' | SEQ ID NO.1262 |
| 3'-GAAUGGUCAGAGUAGAAGAUG-5' | SEQ ID NO.1263 |
| 3'-CCGGAACGAGAAGUCUCUCC-5' | SEQ ID NO.1264 |
| 3'-GUACGUCGAUCUUGGUACUG-5' | SEQ ID NO.1265 |
| 3'-CCCCUUCUUUUCACCAUCCGU-5' | SEQ ID NO.1266 |
| 3'-UGUCCUAUCUCGUCUAAAAA-5' | SEQ ID NO.1267 |
| 3'-AACUUUUACUUGGAACUACU-5' | SEQ ID NO.1268 |
| 3'-GUACUCGUUCUAGAAACAGUU-5' | SEQ ID NO.1269 |
| 3'-AGAACACUGUAAAAAUGGUUA-5' | SEQ ID NO.1270 |
| 3'-GUCCUUGUGUUCUUGGUUUC-5' | SEQ ID NO.1271 |
| 3'-AAGUGUAAUUUUUUCACUAU-5' | SEQ ID NO.1272 |
| 3'-GACAACCUUACCGGUCCUAC-5' | SEQ ID NO.1273 |
| 3'-UUCCACCUCUUGAGUCUCAAA-5' | SEQ ID NO.1274 |
| 3'-CGUAAACCUUCCAUAGAACG-5' | SEQ ID NO.1275 |
| 3'-GAGAUAAAGAACGUGAACAC-5' | SEQ ID NO.1276 |
| 3'-UUCUUCUCUGGUACACAUCAAUA-5' | SEQ ID NO.1277 |
| 3'-UAUUACGUAAACCUUCCAUA-5' | SEQ ID NO.1278 |
| 3'-GAUACUUCAGUAGUUUUAUA-5' | SEQ ID NO.1279 |
| 3'-AAGAGUAAAAACAACAAAUAAA-5' | SEQ ID NO.1280 |
| 3'-UAUUGUCUGGAUAUUGAAUA-5' | SEQ ID NO.1281 |
| 3'-UCUCUCUGUGUUCCGAUUCU-5' | SEQ ID NO.1282 |
| 3'-AAUCAGGUCUCUCGUCUUUU-5' | SEQ ID NO.1283 |
| 3'-GUGACGGAGGAAGUCGUUAGU-5' | SEQ ID NO.1284 |
| 3'-AUACUUCAGUAGUUUUAUAA-5' | SEQ ID NO.1285 |
| 3'-GUAAUUUUUUCACUAUCUAU-5' | SEQ ID NO.1286 |
| 3'-UCUCUCGUAGGUUUCCCUCAC-5' | SEQ ID NO.1287 |
| 3'-UUUUUUACAUGGUCCACACU-5' | SEQ ID NO.1288 |
| 3'-UUGUACUCGUUCUAGAAACA-5' | SEQ ID NO.1289 |
| 3'-UUAGUGUAAGAAAGUGGUCUU-5' | SEQ ID NO.1290 |

TABLE 2-continued

Antisense sequence listing of the target of the RNA virus

| Antisense fragment coding sequence | ID number |
| --- | --- |
| 3'-GGAGUGAGAAUAAAGUAGGU-5' | SEQ ID NO.1291 |
| 3'-GUAAGUGAAACAUCCUACGA-5' | SEQ ID NO.1292 |
| 3'-UAGUCUUUCCGAAAUAUACUG-5' | SEQ ID NO.1293 |
| 3'-ACAUAAAUAUUUUCUGUUCCA-5' | SEQ ID NO.1294 |
| 3'-GAGUAAAAACAACAAAUAAA-5' | SEQ ID NO.1295 |
| 3'-ACGGUUCGAACACAAGUUGU-5' | SEQ ID NO.1296 |
| 3'-ACCCGAGACUGUCCUCCGUAC-5' | SEQ ID NO.1297 |
| 3'-UUCAAUUAAUGGAAAUGUAA-5' | SEQ ID NO.1298 |
| 3'-AUGAUACUACAUAGAUAGAU-5' | SEQ ID NO.1299 |
| 3'-UCCUCCCAUAAGAAGACAUA-5' | SEQ ID NO.1300 |
| 3'-CUUGGGUCUCCUUGGGGGUG-5' | SEQ ID NO.1301 |
| 3'-GUGACGGAGGAAGUCGUUAGU-5' | SEQ ID NO.1302 |
| 3'-UCUCGAGUUCUUCCUCUGUU-5' | SEQ ID NO.1303 |
| 3'-UUCUCCCCGAGGAGAUACUU-5' | SEQ ID NO.1304 |
| 3'-AGAUGACGAAAUCCACUGCA-5' | SEQ ID NO.1305 |
| 3'-UCUACCCACCUAGUUCUCCA-5' | SEQ ID NO.1306 |
| 3'-UUGCCACUGCUCCGACUCCU-5' | SEQ ID NO.1307 |
| 3'-GUCUCCUACAUAAAAGACAG-5' | SEQ ID NO.1308 |
| 3'-GUGUAGGUGACGGAGGAAGU-5' | SEQ ID NO.1309 |
| 3'-UCCCUACAGAACACUGUAAAAA-5' | SEQ ID NO.1310 |
| 3'-GAAGUCUUUCGUUCAGUAAGAU-5' | SEQ ID NO.1311 |
| 3'-AUGUAGAGUCGGUAUUUUUAC-5' | SEQ ID NO.1312 |
| 3'-AAUGACUCACGUCCCCGGGACU-5' | SEQ ID NO.1313 |
| 3'-AGUUGAAAGGGUUGGGAGGU-5' | SEQ ID NO.1314 |
| 3'-GUCUCCCUGUCCCUCCCUCCA-5' | SEQ ID NO.1315 |
| 3'-UCAGUCUUGAACCUUACUCUA-5' | SEQ ID NO.1316 |
| 3'-AGUUUCUAAUCUCAGUUGUCU-5' | SEQ ID NO.1317 |
| 3'-GUACUUGACCCAUAUGUUCAA-5' | SEQ ID NO.1318 |
| 3'-GACUACUGUACGACCUCUUCU-5' | SEQ ID NO.1319 |
| 3'-ACCAGUGCACAAGUUAGAGUA-5' | SEQ ID NO.1320 |
| 3'-AAUACUUCUGACAAGUCCUGA-5' | SEQ ID NO.1321 |
| 3'-GACCACCUCUAUUUUGCAUGACU-5' | SEQ ID NO.1322 |
| 3'-AACUAACAAAAAGAGUAAAA-5' | SEQ ID NO.1323 |
| 3'-ACCAAAGACCCCGACACGGAG-5' | SEQ ID NO.1324 |
| 3'-CUCGGUCCCGUCCUCUGUCG-5' | SEQ ID NO.1325 |
| 3'-CCCAAGAAAAACUUUUUUUU-5' | SEQ ID NO.1326 |

The second object of the present invention is to provide a primer composition for constructing any of the above-mentioned target sequences of the RNA virus.

Further, The primer composition of a part of the target sequence of the RNA virus comprises any one or more of the following groups: the primers of the target sequence SEQ ID NO. 1 are SEQ ID NO. 616-SEQ ID NO. 619; and/or, the primers of the target sequence SEQ ID NO. 2 are SEQ ID NO. 620-SEQ ID NO. 623; and/or, the primers of the target sequence SEQ ID NO. 3 are SEQ ID NO. 624-SEQ ID NO. 627; and/or, the primers of the target sequence SEQ ID NO. 4 are SEQ ID NO. 628-SEQ ID NO. 631; and/or, the primers of the target sequence SEQ ID NO. 5 are SEQ ID NO. 632-SEQ ID NO. 635; and/or, the primers of the target sequence SEQ ID NO. 7 are SEQ ID NO. 636-SEQ ID NO. 639; and/or, the primers of the target sequence SEQ ID NO. 8 are SEQ ID NO. 640-SEQ ID NO. 643; and/or, the primers of the target sequence SEQ ID NO. 10 are SEQ ID NO. 644-SEQ ID NO. 647; and/or, the primers of the target sequence SEQ ID NO. 11 are SEQ ID NO. 648-SEQ ID NO. 651; and/or, the primers of the target sequence SEQ ID NO. 12 are SEQ ID NO. 652-SEQ ID NO. 655; and/or, the primers of the target sequence SEQ ID NO. 13 are SEQ ID NO. 656-SEQ ID NO. 659; and/or, the primers of the target sequence SEQ ID NO. 14 are SEQ ID NO. 660-SEQ ID NO. 663; and/or, the primers of the target sequence SEQ ID NO. 15 are SEQ ID NO. 664-SEQ ID NO. 667; and/or, the primers of the target sequence SEQ ID NO. 16 are SEQ ID NO. 668-SEQ ID NO. 671; and/or, the primers of the target sequence SEQ ID NO. 17 are SEQ ID NO. 672-SEQ ID NO. 675; and/or, the primers of the target sequence SEQ ID NO. 18 are SEQ ID NO. 676-SEQ ID NO. 679; and/or, the primers of the target sequence SEQ ID NO. 19 are SEQ ID NO. 680-SEQ ID NO. 683; and/or, the primers of the target sequence SEQ ID NO. 20 are SEQ ID NO. 684-SEQ ID NO. 687; and/or, the primers of the target sequence SEQ ID NO. 21 are SEQ ID NO. 688-SEQ ID NO. 691; and/or, the primers of the target sequence SEQ ID NO. 22 are SEQ ID NO. 692-SEQ ID NO. 695; and/or, the primers of the target sequence SEQ ID NO. 23 are SEQ ID NO. 696-SEQ ID NO. 699; and/or, the primers of the target sequence SEQ ID NO. 24 are SEQ ID NO. 700-SEQ ID NO. 703; and/or, the primers of the target sequence SEQ ID NO. 25 are SEQ ID NO. 704-SEQ ID NO. 707; and/or, the primers of the target sequence SEQ ID NO. 26 are SEQ ID-NO. 708-SEQ ID NO. 711.

Further, The protective base and EcoRI restriction site sequence CGGAATTC are added to 5' end of the upstream primer, and the protective base and BamHI restriction site sequence CGGGATCC are added to 5' end of the downstream primer.

Further, the specific sequences of the above-mentioned primers are shown in the following table:

TABLE 3

Amplification primer sequence listing of the target sequence of the RNA virus

| Virus type | Fragment number | Primer number | Amplification primer sequence | ID number |
|---|---|---|---|---|
| Severe acute respiratory syndrome-related coronavirus 2 (SARS-CoV-2 | SARS-CoV-2-HIS-1 | F123 | 5'-attctagagctagcgaattctcatca acttgtatgatgtgttacaaacgtaataga gca-3' | SEQ ID NO. 616 |
| | | R1 | 5'-gaccttctaacaccattaacaatagt tgtacattcgactcttgttgctctattacg ttt-3' | SEQ ID NO. 617 |
| | | R2 | 5'-gtagtttgcaaaagcctttacctcca ttagcatagacataaaggaccttctaaca cca-3' | SEQ ID NO. 618 |
| | | R3 | 5'-tccttcgcggccgoggatcacaatta acacaattccaattgtgtagtttgcaaaag c-3' | SEQ ID NO. 619 |
| | SARS-CoV-2-HIS-2 | F123 | 5'-attctagagctagcgaattcaacaac attatcaacaatgcaagagatggttgtgtt c-3' | SEQ ID NO. 620 |
| | | R1 | 5'-aaccattagtttggctgctgttgtaa gaggtattatgttcaagggaacacaaccat ctc-3' | SEQ ID NO. 621 |
| | | R2 | 5'-gtaccatcacacgtatttttatatgt gttatagtctggtatgacaaccattagttt ggc-3' | SEQ ID NO. 622 |
| | | R3 | 5'-tccttcgcggccgcggatcCaatgct gatgcataagtaaatgttgtaccatcacac gta-3' | SEQ ID NO. 623 |
| | SARS-CoV-2-HIS-3 | F123 | 5'-attctagagctagcgaattccttaac aaagttgttagtacaactactaacatagtt aca-3' | SEQ ID NO. 624 |
| | | R1 | 5'-aagaaataaggcatataattagtaca aacacggtttaaacaccgtgtaactatgtt agt-3' | SEQ ID NO. 625 |
| | | R2 | 5'-aatttgtacttctagtaaaagtacac aattgtagcaataaagtaaagaaataaggc ata-3' | SEQ ID NO. 626 |
| | | R3 | 5'-tccttcgcggccgcggatcctcggca tagatgctttaattctagaatttgtacttc tag-3' | SEQ ID NO. 627 |
| | SARS-CoV-2-HIS-4 | F123 | 5'-attctagagctagcgaattcggagta cgatcgagtgtacagtgaacaatgctaggg aga-3' | SEQ ID NO. 628 |
| | | R1 | 5'-actaaaattaattttacacattaggg ctcttccatataggcagctctccctagcat tgt-3' | SEQ ID NO. 629 |
| | | R2 | 5'-gtcattctcctaagaagctattaaaa tcacatggggatagcactactaaaattaat ttt-3' | SEQ ID NO. 630 |
| | | R3 | 5'-tccttcgcggccgcggatcCtttttt ttttttttttttttttgtcattctccta aga-3' | SEQ ID NO. 631 |
| | SARS-CoV-2-HIS-5 | F123 | 5'-attctagagctagcgaattcgttaat aattggttgaagcagttaattaaagttaca ctt-3' | SEQ ID NO. 632 |
| | | R1 | 5'-acaggtgttattaaatagaaaatagc agcaacaaaaaggaacacaagtgtaacttt aat-3' | SEQ ID NO. 633 |
| | | R2 | 5'-ctatgatttcacttgaaaagtcagta tgtttagacatgacatgaacaggtgttatt aaa-3' | SEQ ID NO. 634 |
| | | R3 | 5'-tccttegcggccgeggatcccaccac catcaatagccttgtatcctatgatttcac ttg-3' | SEQ ID NO. 635 |

TABLE 3-continued

Amplification primer sequence listing of the target sequence of the RNA virus

| Virus type | Fragment number | Primer number | Amplification primer sequence | ID number |
|---|---|---|---|---|
| severe acute respiratory syndrome-related coronavirus SARS-CoV | SARS-CoV-HIS-1 | F1 | 5'-ctccctctggaatttggtgcctcagc tgaaacagttcgagttgaggaagaagaaga gga-3' | SEQ ID NO. 636 |
| | | R1 | 5'-tggctcaatctctgattgctcagtag tatcatccagccagtcttcctcttcttctt cct-3' | SEQ ID NO. 637 |
| | | F2 | 5'-attctagagctagcgaattcctccct ctggaatttggtgc-3' | SEQ ID NO. 638 |
| | | R2 | 5'-tccttcgcggccgcggatcatggctc aatctctgattgct-3' | SEQ ID NO. 639 |
| | SARS-CoV-HIS-2 | F1 | 5'-tatggggttgggattatccaaaatgtg acagagccatgcctaacatgcttaggataa tgg-3' | SEQ ID NO. 640 |
| | | R1 | 5'-aagttacagcaagtgttatgtttgcg agcaagaacaagagaggccattatcctaag ca-3' | SEQ ID NO. 641 |
| | | F2 | 5'-attctagagctagcgaattctatggg ttgggattatccaa-3' | SEQ ID NO. 642 |
| | | R2 | 5'-tccttcgcggccgcggatcaaagtta cagcaagtgttatg-3' | SEQ ID NO. 643 |
| Middle East respiratory syndrome coronavirus (MERS-CoV) | MERS-CoV-HIS-1 | F1 | 5'-gtgttggctggactgctggcttatcc tcctttgctgctattccatttgcacagagt atc-3' | SEQ ID NO. 644 |
| | | R1 | 5'-gaaagaacctgttgagtaatgccaac accgtttaacctataaaagatactctgtcg aaa-3' | SEQ ID NO. 645 |
| | | F2 | 5'-attctagagctagcgaattcgtgttg gctggactgctggc-3' | SEQ ID NO. 646 |
| | | R2 | 5'-tccttcgcggccgcggatcagaaaga acctgttgagtaat-3' | SEQ ID NO. 647 |
| | MERS-CoV-HIS-2 | F1 | 5'-aataaagtaaaacgtgcttttgcaga ttacacccagtgtgctgtaattgctgttgt tgc-3' | SEQ ID NO. 648 |
| | | R1 | 5'-gtatagaggtaacaaagcagatgcac aagctattaagaacagcagcaacaacagcaatt-3' | SEQ ID NO. 649 |
| | | F2 | 5'-attctagagctagcgaattcaataaa gtaaaacgtgctttt-3' | SEQ ID NO. 650 |
| | | R2 | 5'-tccttcgcggccgcggatcagtatag aggtaacaaagcag-3' | SEQ ID NO. 651 |
| Zika virus | Zika-HIS-1 | F1 | 5'-tgagaggagagtgccagagttgtgtg tacaacatgatgggaaaaagagaaaagaaa caa-3' | SEQ ID NO. 652 |
| | | R1 | 5'-tataccagatggcgcggctgcccttg gccttttccaaattccccttgtttctttct ctt-3' | SEQ ID NO. 653 |
| | | F2 | 5'-gaagattctagagctagcgaattctg agaggagagtgccagagtt-3' | SEQ ID NO. 654 |
| | | R2 | 5'-cagatccttcgcggccgcggatccta taccagatggcgcggctgc-3' | SEQ ID NO. 655 |
| | Zika-HIS-2 | F1 | 5'-gtgatcaaaaatgggagttatgttag tgccatcacccaaggaggagggaggaaga gac-3' | SEQ ID NO. 656 |
| | | R1 | 5'-ctgcttcttcttcagcatcgaaggct cgaagcactcaacaggagtctcttcctccc tcc-3' | SEQ ID NO. 657 |
| | | F2 | 5'-gaagattctagagctagcgaattcgt gatcaaaaatgggagttat-3' | SEQ ID NO. 658 |
| | | R2 | 5'-cagatccttcgcggccgcggatccct gcttcttcttcagcatcga-3' | SEQ ID NO. 659 |
| | Zika-HIS-3 | F1 | 5'-ctagtggtgcaactcattcggaatat ggaggctgaggaagttctagagatgcaaga ctt-3' | SEQ ID NO. 660 |
| | | R1 | 5'-ctgcaaccagttggtcactttctctg acctccgcagcagccacaagtcttgcatct cta-3' | SEQ ID NO. 661 |
| | | F2 | 5'-gaagattctagagctagcgaattcct agtggtgcaactcattcgg-3' | SEQ ID NO. 662 |
| | | R2 | 5'-cagatccttcgcggccgcggatccct gcaaccagttggtcacttt-3' | SEQ ID NO. 663 |
| Ebola virus | Ebola-HIS-1 | F1 | 5'-aatactccaccaacagatgatgtatc aagtcctcaccgactcattctaccatttttaa-3' | SEQ ID NO. 664 |
| | | R1 | 5'-ttcttgggcatcttgatcatgtgcat ggttgtgatttcccaatttaaaaaatggta gaa-3' | SEQ ID NO. 665 |
| | | F2 | 5'-gaagattctagagctagcgaattcaa tactccaccaacagatgat-3' | SEQ ID NO. 666 |
| | | R2 | 5'-cagatccttcgcggccgcggatcctt cttgggcatcttgatcatg-3' | SEQ ID NO. 667 |
| | Ebola-HIS-2 | F1 | 5'-ttttctaaatccagaaaagtgttttt atcgaacttcggagatcctgtgacttctg gac-3' | SEQ ID NO. 668 |
| | | R1 | 5'-tctttcatgttaaccatttctaggta cacccgtagctggaaaagtccagaagtcac agg-3' | SEQ ID NO. 669 |
| | | F2 | 5'-gaagattctagagctagcgaattctt ttctaaatccagaaaagtg-3' | SEQ ID NO. 670 |
| | | R2 | 5'-cagatccttcgcggccgcggatcctc tttcatgttaaccatttct-3' | SEQ ID NO. 671 |

TABLE 3-continued

Amplification primer sequence listing of the target sequence of the RNA virus

| Virus type | Fragment number | Primer number | Amplification primer sequence | ID number |
|---|---|---|---|---|
| | Ebola-HIS-3 | F1 | 5'-gaagattctagagctagcgaattcag atctgagagagaaaaatctc TABLE 3-continued Amplification primer sequence listing of the target sequence of the RNA virus

| Virus type | Fragment number | Primer number | Amplification primer sequence | ID number |
|---|---|---|---|---|
| | | R1 | 5'-atcatcatgtctgcttgtttgtctg ggtgtactaagcagttggcctcatcttcct ctg-3' | SEQ ID NO. 709 |
| | | F2 | 5'-gaagattctagagctagcgaattcgg gtggctgtggaagctagt-3' | SEQ ID NO. 710 |
| | | R2 | 5'-cagatccttegcggccgcggatccat catcatgtctgcttgttt-3' | SEQ ID NO. 711 |

In the third aspect, the present invention provides an RNA drug against viruses, characterized in that, the RNA drug comprises the reverse complementary sequence of any of the above-mentioned target sequences of the RNA virus, and cholesterol modification and four phosphorothioate backbone modifications are made at the 3' end of the reverse complementary sequence of any of the above-mentioned target sequences of the RNA virus, two phosphorothioate backbone modifications are made at the 5' end, and methoxy modification is made on the whole chain, or, cholesterol modification and four phosphorothioate backbone modifications are made at the 3' end of any of the above-mentioned target sequences of the RNA virus, two phosphorothioate backbone modifications are made at the 5' end, and methoxy modification is made on the whole chain.

Further, the reverse complementary sequence of the target sequence of the RNA virus comprises reverse complementary RNA sequence or reverse complementary DNA.

Further, the RNA drug further comprises a pharmaceutically acceptable carrier or excipient.

Further, the dosage form of the RNA drug comprises powder, tablet, granule, capsule, solution, aerosol, injection, emulsion or suspension.

In the fourth aspect, the present invention provides a biomaterial related to any of the above-mentioned target sequences of the RNA virus. The biomaterial is selected from one of the following A)-B):

A) a DNA and/or RNA molecule that is complementary to any of the above-mentioned target sequences of the RNA virus;
B) an expression cassette, a recombinant vector, a recombinant microorganism, a recombinant cell line containing any of the above-mentioned target sequences of the RNA virus or the DNA molecule described in A).

It is understandable that the above-mentioned DNA molecule, expression cassette, recombinant vector, recombinant microorganism, and recombinant cell line can all be biomaterials conventionally used in the art, and can all be prepared by conventional methods in the art.

Further, the biomaterial is a recombinant vector, and the construction steps of the recombinant vector comprise: 1) designing a primer, and amplifying the target sequence of the RNA virus by PCR; 2) digesting the amplified sequence fragment and an expression vector, and ligating a sequence fragment of interest and the expression vector; 3) transferring the ligated product into *Escherichia coli* and cultivating the *Escherichia coli*; 4) after identification, extracting recombinant plasmid and packaging the recombinant plasmid. Specifically, the target sequences of the RNA viruses are shown in Table 1 above, and a part of primer sequences is shown in Table 2 above.

Further, the expression vector comprises but is not limited to pCDH vector, other vectors such as pCMVp-NEO-BAN vector, pEGFP vector, pEGFT-Actin, pSV2 vector, pCDNA vector, pLVX vector, pAAV vector, pET vector, pDsRed vector, and virus-related recombinant vector backbones for these vectors can be any suitable vectors used in the art.

Further, the recombinant vector has the function of expressing a virus-related target fragment; wherein, the related target fragment has the function of interacting (binding) with human genome.

Further, the recombinant vector has target sequences expressing severe acute respiratory syndrome-related coronavirus 2 (SARS-CoV-2), severe acute respiratory syndrome-related coronavirus (SARS-CoV), and middle east respiratory syndrome coronavirus (MERS-CoV). The above-mentioned target sequence fragments can interact (bind) with human genome; specifically, the target sequences comprise but are not limited to: SARS-CoV-2-HIS-1, SARS-CoV-2-HIS-2, SARS-CoV-2-HIS-3, SARS-CoV-2-HIS-4, SARS-CoV-2-HIS-5, SARS-CoV-HIS-1, SARS-CoV-HIS-2, MERS-CoV-HIS-1 and MERS-CoV-HIS-2.

In the fifth aspect, the present invention provides use of any of the above-mentioned target sequences of the RNA virus. The use is a use in the preparation of an RNA virus detection or diagnostic reagent, a use in the preparation of a drug for preventing or treating a condition caused by an RNA virus, or a use in the preparation of a vaccine against an RNA virus.

Further, the condition comprises a human disease, an animal disease and zoonosis.

Further, when the use is a use in the preparation of a drug for preventing or treating a condition caused by the RNA virus, an effective substance that regulates the target sequence is directly screened; alternatively, according to the effect of the gene regulated by the target sequence, an effective substance against the gene and gene product regulated by the target sequence is screened.

Further, when the use is a use in the preparation of a vaccine against the RNA virus, the target sequence is knocked out during the design process of the vaccine.

Further, the method for knocking out the target sequence comprises: CRASPER system and/or ribozyme technology.

CRISPR comes from the immune system of microorganisms. In such engineering editing system, an enzyme is used to cut a small RNA as a guiding tool into DNA, where cut or other changes can be made. Previous studies have shown that CRISPR can make changes or mutations in the genome more efficiently through these interventions, and the efficiency is higher than other gene editing technologies such as TALEN (transcription activator-like effector nuclease). Although CRISPR has many advantages, in the human cancer cell line, it may also produce a large number of "accidentally injured targets", especially the modification of genes that are not desired to be changed.

Ribozyme technology is a technology by means of a ribozyme, and is mainly used for the design of ribozymes for use. Ribozymes are RNA molecules that can cleave RNA sequence-specifically and can be designed. The designed ribozyme can be used to select specific mRNA fragments, or can bind to specific mRNA to block the expression of mRNA. Therefore, this technology can be used to study the structure of RNA, and can also be used to treat diseases caused by abnormal gene expression.

Further, the vaccine is a live attenuated vaccine.

In the sixth aspect, the present invention provides a live attenuated vaccine. The whole genome of the live attenuated vaccine does not contain the above-mentioned target sequences of the RNA virus.

In the seventh aspect, the present invention provides use of any of the above-mentioned target sequences of the RNA virus in activating related genes at the cellular level and screening therapeutic drugs against the related genes.

Further, the RNA virus is a coronavirus, specifically severe acute respiratory syndrome-related coronavirus 2 (SARS-CoV-2), severe acute respiratory syndrome-related coronavirus (SARS-CoV), and middle east respiratory syndrome coronavirus (MERS-CoV).

Further, in the above-mentioned use, the related genes comprise the ACE2 gene, the coding genes of the hyaluronic acid synthase family HAS1, HAS2, and HAS3, and/or genes within 200 k around the fragment. Further, the genes within 200 k around the fragment comprise but are not limited to FBXO15, MYL9, KALRN, ATP8B1, ZHX2, IGF2R, C5AR1, EPAS1 and TIMM21. It is understandable that, depending on the type of RNA virus, the related genes activated thereby are also different.

Further, the drug comprises a miRNA inhibitor.

Further, the miRNA inhibitor comprises antagomir inhibitor.

It is understandable that the above-mentioned drug may also comprise other drugs that can inhibit activated target genes and other drugs that can regulate the level of hyaluronic acid (inhibit the synthesis of hyaluronic acid, reduce the concentration of hyaluronic acid, etc.).

In the eighth aspect, the present invention provides use of the target sequences of the RNA virus in the study of drug targets against diseases caused by the RNA virus.

Further, the target sequences of the RNA virus in the cells of the diseases caused by the RNA virus are found, and the drug targets are found within 200 k around the target sequence of the RNA virus or the drug targets are found beyond 200 k using the prediction software blast 2.2.30 or bedtools 2.29.2.

In the ninth aspect, the present invention provides a method for virus detection, which detects the above-mentioned target sequences of the RNA virus.

Further, the detection of the target sequences comprises RCR amplification and nucleotide sequencing.

Furthermore, the detection of the target sequences of the RNA virus can be used to determine the diagnosis of viral diseases, determine the pathogenicity and test the susceptibility of the population.

BRIEF DESCRIPTION OF THE DRAWINGS

Figures 1, 2, 3:
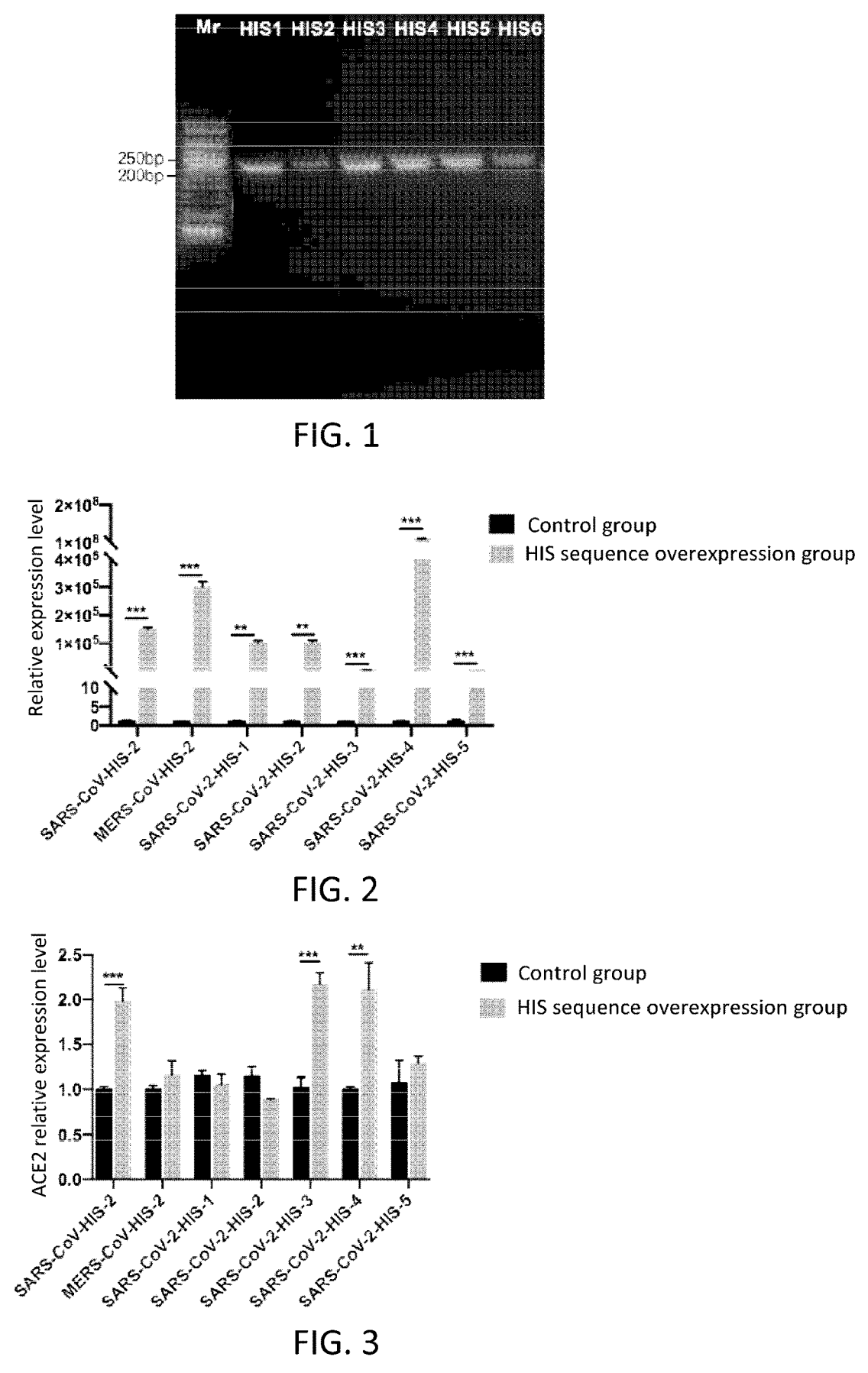

FIG. 1 is a running gel electropherogram of 6 target viral vectors related to the coronavirus SARS-CoV-2 amplified by PCR in an embodiment of the present invention.

FIG. 2 is a schematic diagram of the result of the mRNA level after overexpression of the target fragments of coronavirus in 293T cells by qPCR detection in an embodiment of the present invention; wherein, ***, p<0.001.

FIG. 3 is a schematic diagram of the result of the mRNA level of the gene ACE2 after overexpression of the target fragments of coronavirus in 293T cells by qPCR detection in an embodiment of the present invention; wherein, , p<0.01, *, p<0.001.

Figures 4, 5:
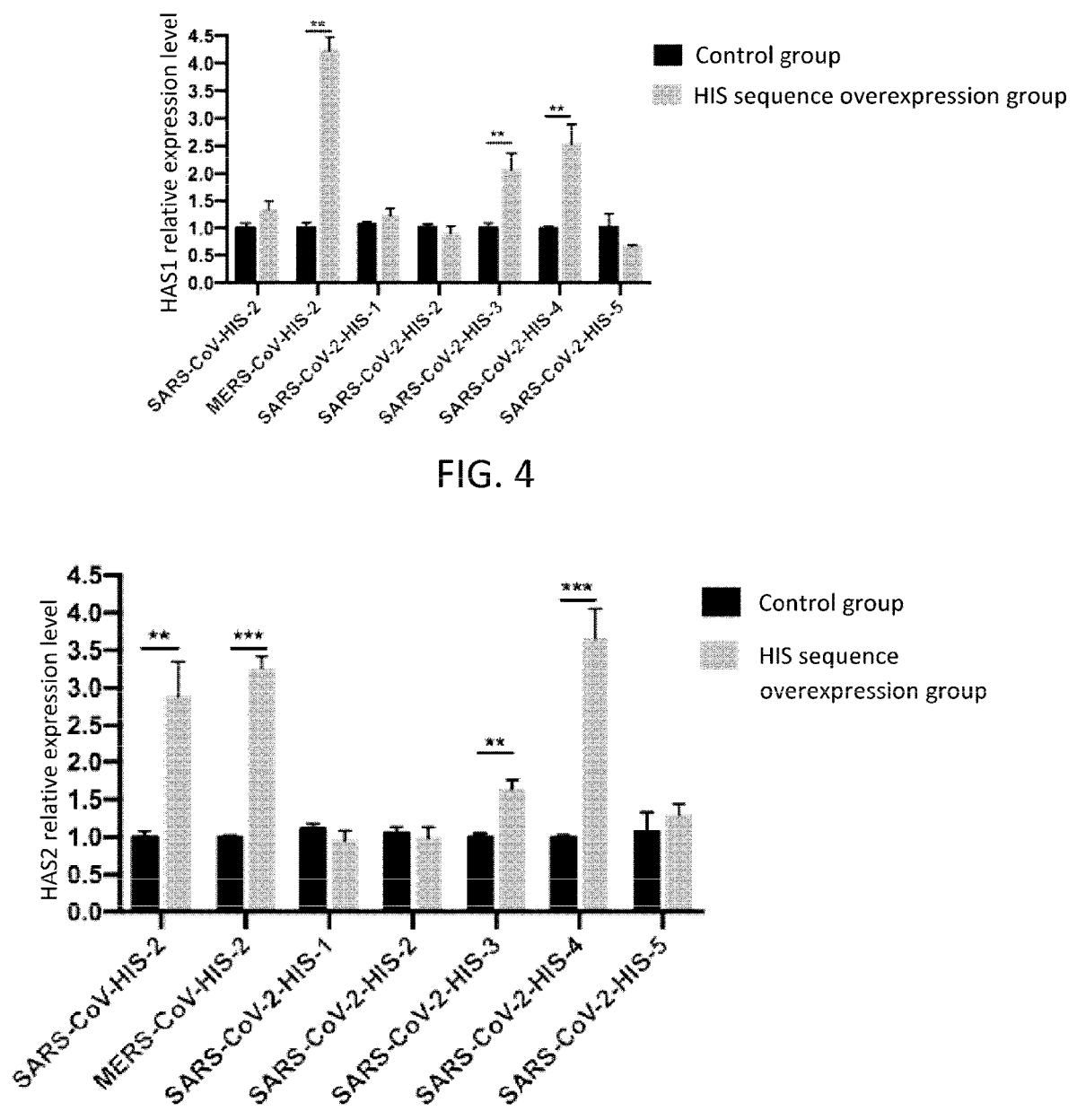

FIG. 4 is a schematic diagram of the result of the mRNA level of the gene HAS1 after overexpression of the target fragments of coronavirus in 293T cells by qPCR detection in an embodiment of the present invention; wherein, , p<0.01, *, p<0.001.

FIG. 5 is a schematic diagram of the result of the mRNA level of the gene HAS2 after overexpression of the target fragments of coronavirus in 293T cells by qPCR detection in an embodiment of the present invention; wherein, **, p<0.01.

Figures 12, 13, 14:
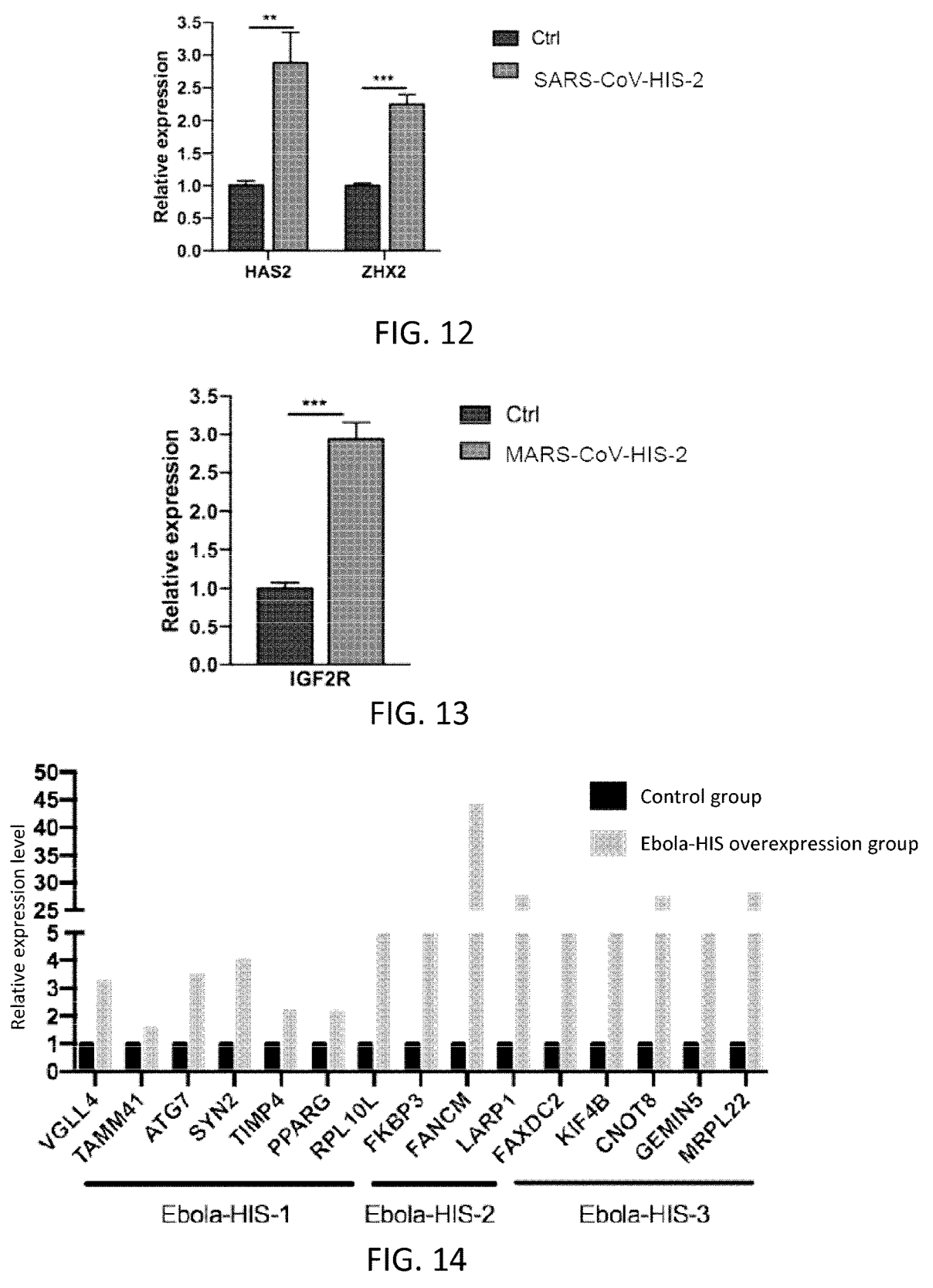

FIG. 12 is a schematic diagram of the result of the mRNA level of the surrounding genes after overexpression of the target fragment SARS-CoV-HIS-2 of coronavirus in 293T cells by qPCR detection in an embodiment of the present invention; wherein, , p<0.01.*, p<0.001.

FIG. 13 is a schematic diagram of the result of the mRNA level of the surrounding gene after overexpression of the target fragment MERS-CoV-HIS-2 of coronavirus in 293T cells by qPCR detection in an embodiment of the present invention; wherein, **, p<0.01.

FIG. 14 is a schematic diagram of the result of the mRNA level of the surrounding genes after overexpression of target fragments of zika virus in 293T cells by qPCR detection in an embodiment of the present invention.

DETAILED DESCRIPTION OF THE INVENTION

Figure 6:
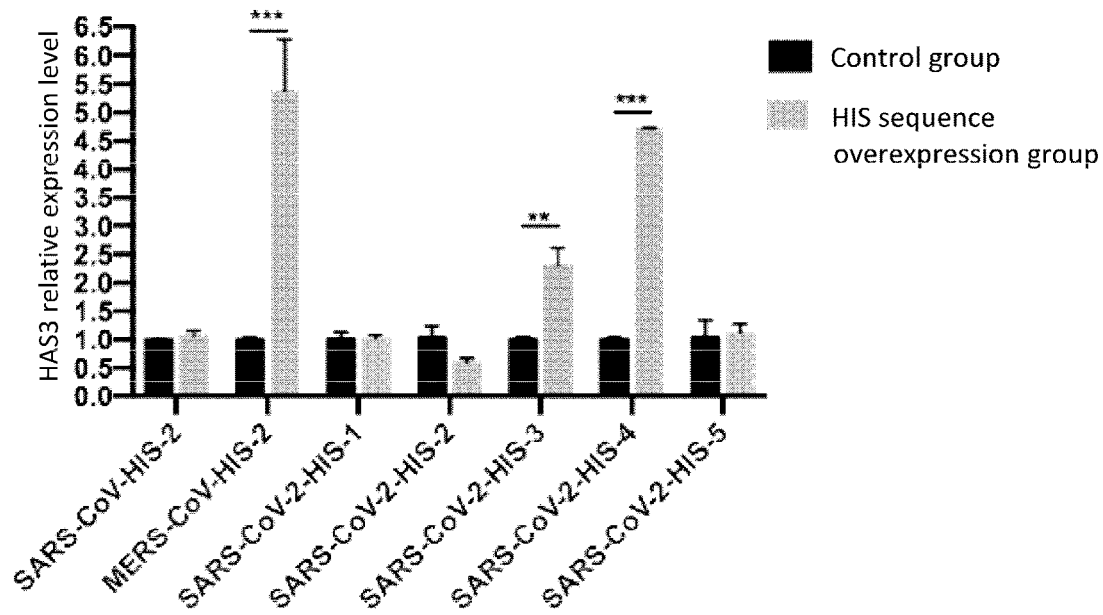
FIG. 6 is a schematic diagram of the result of the mRNA level of the gene HAS3 after overexpression of the target fragments of coronavirus in 293T cells by qPCR detection in an embodiment of the present invention; wherein, , p<0.01, *, p<0.001.
Figure 7:
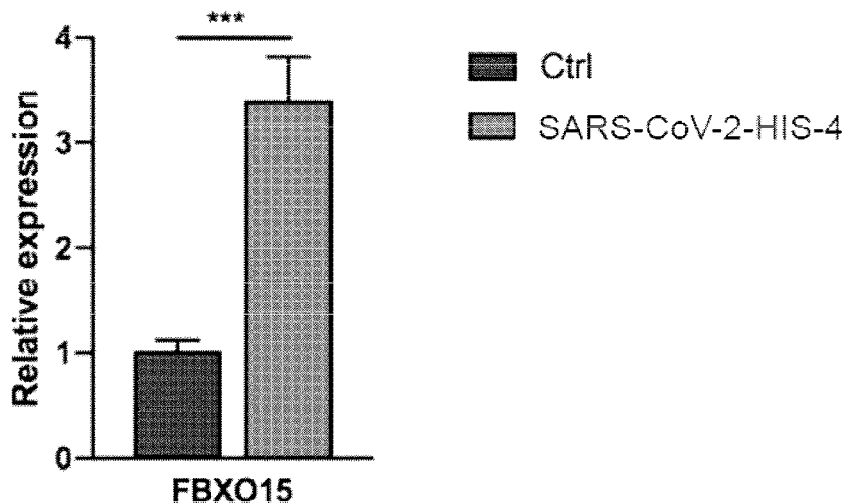
FIG. 7 is a schematic diagram of the result of the mRNA level of the surrounding gene FBXO15 after overexpression of the target fragment SARS-CoV-2-HIS-4 of coronavirus in 293T cells by qPCR detection in an embodiment of the present invention; wherein, ***, p<0.001.
Figure 8:
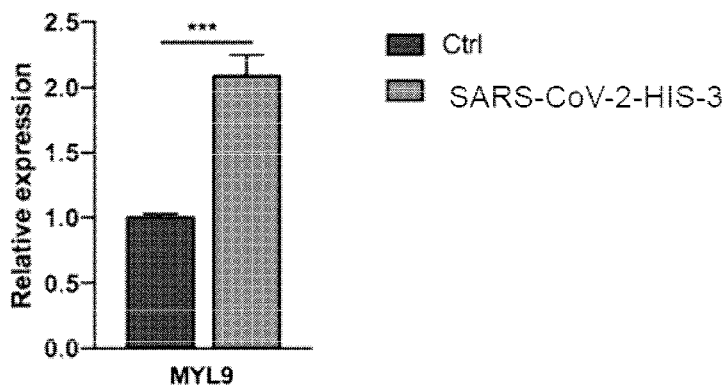
FIG. 8 is a schematic diagram of the result of the mRNA level of the surrounding gene MYL9 after overexpression of the target fragment SARS-CoV-2-HIS-3 of coronavirus in 293T cells by qPCR detection in an embodiment of the present invention; wherein, ***, p<0.001.
Figure 9:
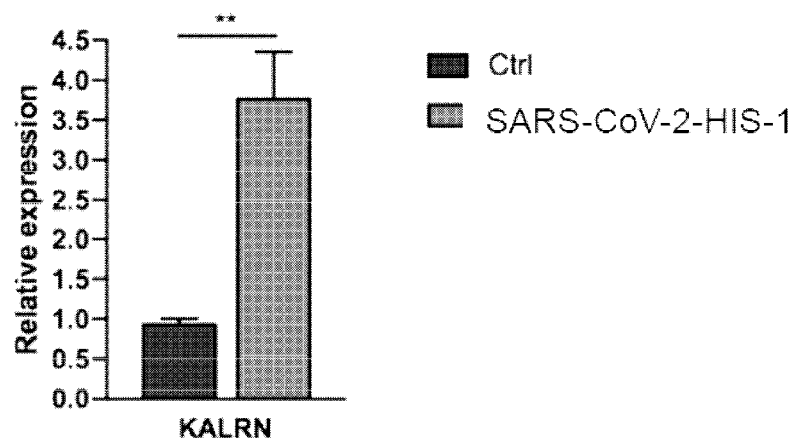
FIG. 9 is a schematic diagram of the result of the mRNA level of the surrounding gene ATP8B1 after overexpression of the target fragment SARS-CoV-2-HIS-1 of coronavirus in 293T cells by qPCR detection in an embodiment of the present invention; wherein, **, p<0.01.
Figure 10:
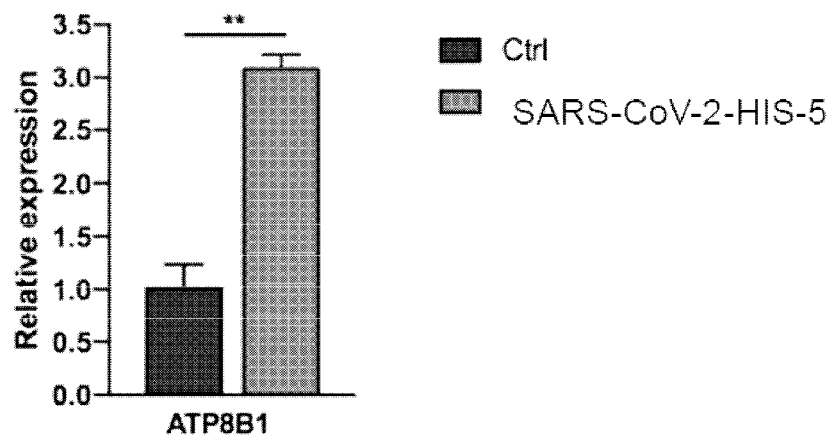
FIG. 10 is a schematic diagram of the result of the mRNA level of the surrounding gene KALRN after overexpression of the target fragment SARS-CoV-2-HIS-5 of coronavirus in 293T cells by qPCR detection in an embodiment of the present invention; wherein, **, p<0.01.
Figure 11:
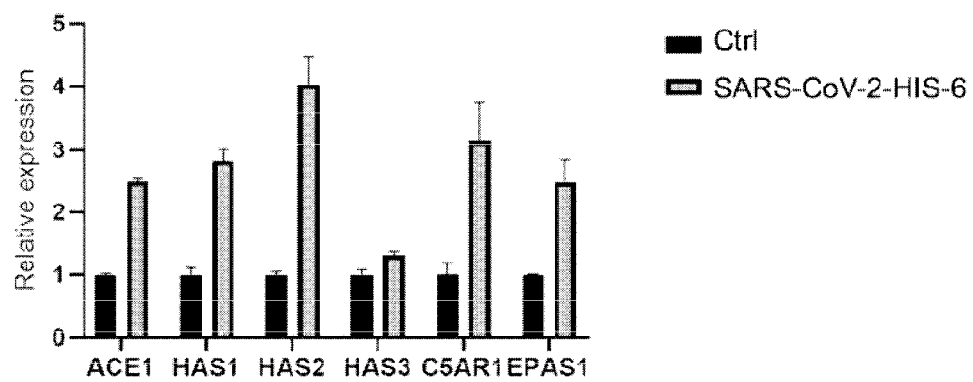
FIG. 11 is a schematic diagram of the result of the mRNA level of the surrounding genes after overexpression of the target fragment SARS-CoV-2-HIS-6 of coronavirus in 293T cells by qPCR detection in an embodiment of the present invention.
Figure 15:
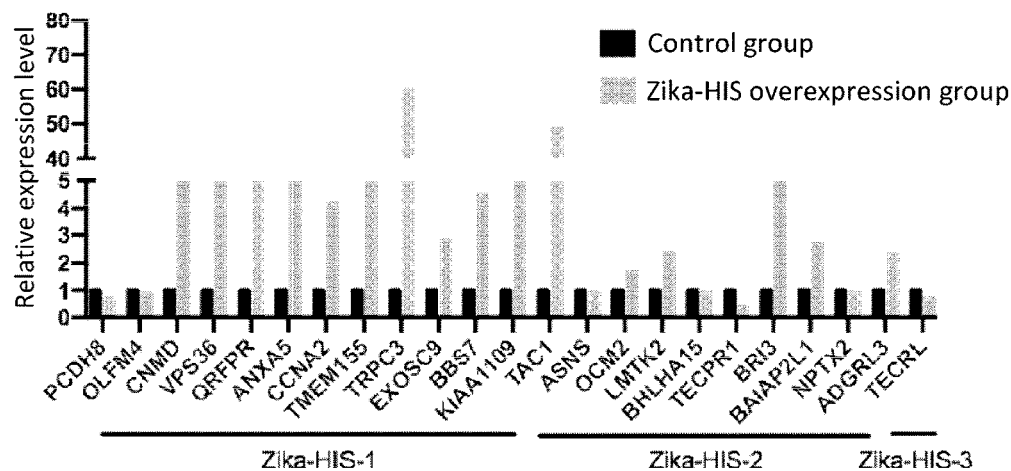
FIG. 15 is a schematic diagram of the result of the mRNA level of the surrounding genes after overexpression of target fragments of ebola virus in 293T cells by qPCR detection in an embodiment of the present invention.
Figure 16:
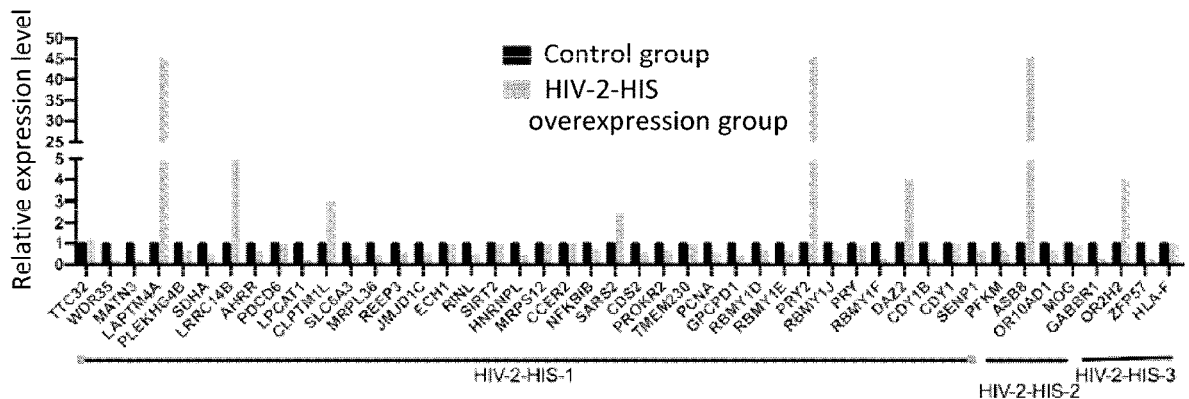
FIG. 16 is a schematic diagram of the result of the mRNA level of the surrounding genes after overexpression of HIV-2 target fragments in 293T cells by qPCR detection in an embodiment of the present invention.

The specific implementations of the present invention will be further described below in conjunction with the drawings and examples. The following examples are only used to illustrate the technical solutions of the present invention more clearly, and cannot be used to limit the scope of protection of the present invention. In experimental methods in the following examples where no specific conditions are indicated, choices can be made according to conventional methods and conditions in the art or commodity instructions; the relevant reagents and biomaterials in the following examples are all commercially available products; The molecular cloning technology in the following examples provides a method for purifying and amplifying specific DNA fragments at the molecular level in the prior art. The coronavirus, zika virus, ebola virus and HIV are mainly used as examples for discussion in the following examples.

Example 1—Construction of an Overexpression Vector of the Target of the RNA Virus This example is the construction of an overexpression vector of the target of the RNA virus, and the steps comprise:
1. Sequence Acquisition and Primer Design SARS-CoV-2 gene sequences were found from Nucleotide database Genbank of NCBI, and then the whole genome nucleotide sequences of the virus were Blast-aligned with the whole genome sequence in human, and finally, the virus nucleotide sequence fragments with a similarity of not less than 95% were screened as viral RNA target sequences (hereinafter referred to as targets). 5 sequences that were completely complementary and paired to the human genome and 1 sequence that was not completely complementary to human genes were screened from SARS-CoV-2. For zika virus, ebola virus, HIV, SARS-CoV, MERS-CoV, and other RNA viruses, the same method was used to obtain target sequences. The screened target sequences are shown in Table 1 above.

The upstream and downstream primers were determined using primer 5 software, respectively, and the protective base and EcoRI restriction site sequence (CGGAATTC) were added to 5' end of the upstream primer, and the protective base and BamHI restriction site sequence (CGGGATCC) were added to 5' end of the downstream primer.

The primers were synthesized by Shanghai Sunny Biotechnology Co., Ltd. The primer sequences of some targets are shown in Table 3 above.

2. Obtainment of the Target Fragment Sequence of Interest of the RNA Virus

Taking severe acute respiratory syndrome-related coronavirus 2 target sequence as an example, the viral target fragment was artificially synthesized by means of homologous recombination. After the primers of F123 and R1 designed according to the sequence were annealed, two rounds of nested PCR were performed using F123 and R2 and F123 and R3, and the gene fragments of interest were amplified with Q5 enzyme. The amplification system and program were as follows:

| PCR system | Total volume 50 μl |
| --- | --- |
| 5 × Reaction buffer | 10 μl |
| dNTPs (10 mM) | 1 μl |
| Upstream primer (10 μM) | 2.5 μl |
| Downstream primer (10 μM) | 2.5 μl |
| cDNA template | 1 μl |
| Q5 polymerase | 0.5 μl |
| ddH2O | 32.5 μl |

PCR program: 98° C. for 30 s;
98° C. for 10 s, 55-72° C. for 30 s, 72° C. for 30 s/kb, 35 cycles;
and 72° C. for 2 min.

For severe acute respiratory syndrome-related coronavirus and middle east respiratory syndrome coronavirus, F1 and R1 primers were used to anneal, and then F2 and R2 and the annealed product were subjected to nested PCR to obtain the fragments of interest.

3. Recovery, Restriction Digestion and Purification of PCR Products

The PCR products were detected by electrophoresis in 1% agarose gel, the gel was cut and recovered, and the fragments of interest were recovered using a ordinary agarose gel DNA recovery kit (Tiangen Biotech Co., Ltd.); the enzyme digestion process referred to the enzyme digestion system on NEB website, and the enzyme digestion was carried out at 37° coVernight, and a PCR product recovery kit (Tiangen Biotech Co., Ltd.) was used for purification and recovery.

4. Ligation

The digested PCR product and the digested pCDH vector were ligated with T4 ligase according to the following ligation system at 16° coVernight.

| Ligation system | |
| --- | --- |
| Reagents | Volume |
| PCR product | 1 μl |
| Digested pCDH vector | 1 μl |
| T4DNA ligase buffer | 1 μl |
| T4DNA ligase | 1 μl |
| $H_2O$ | 6 μl |
| Total | 10 μl |

5. Transforming and Picking Monoclonal Ligation (1) 10 μl of ligation product was added to 50 μl of DH5a competent cells, and incubated on ice for 30 min.

(2) The competent cells were heat shocked at 42° C. for 90 s, and then immediately placed on ice for 5 min.

(3) 300 μl of LB liquid medium without antibiotics was added on a clean bench, and the bacteria was shaken on a constant temperature shaker at 37° C. for 30 min.

(4) 1000 g of bacterial solution was centrifuged for 5 min and the supernatant was discarded. The remaining 50 μl of bacterial solution was spread evenly on the LB solid plate supplemented with ampicillin, and the plate was incubated in a constant temperature incubator at 37° coVernight.

(5) An appropriate amount of monoclonal colonies was picked from the overnight-cultured plate, and put into EP tubes containing 200 μl of LB liquid medium supplemented with ampicillin. The bacteria were shaken in a constant temperature shaker at 37° C. for 2 hours, and then subjected to sequencing and identification. Finally, the target band can be obtained by vector PCR (FIG. 1).

The results showed that: The length of each target-vector is 200-250 bp. FIG. 1 shows the electrophoresis results of the target-vectors containing 6 targets from severe acute respiratory syndrome-related coronavirus 2, respectively. Specifically, HIS1 is the target-vector containing SARS-CoV-2-HIS-1, and HIS2 is the target-vector containing SARS-CoV-2-HIS-2, HIS3 is the target-vector containing SARS-CoV-2-HIS-3, HIS4 is the target-vector containing SARS-CoV-2-HIS-4, HIS5 is the target-vector containing SARS-CoV-2-HIS-5, and HIS6 is the target-vector containing SARS-CoV-2-HIS-6.

The same operation as above applied to SARS-CoV, MERS-CoV, zika virus, ebola virus and HIV.

Example 2—The Effect of Overexpression of the Target Sequences of the RNA Virus in Cells on the Expression Level of Surrounding Genes In this example, the effect of the overexpression of the target sequences of the RNA virus in 293T cells on the expression level of surrounding genes was detected. The steps are briefly described as follows:

1. Preparation of lentivirus by liposome method: According to molecular cloning, SARS-CoV-2, SARS-CoV, MERS-CoV overexpression plasmid, virus packaging plasmid psPAX2 and capsid plasmid pMD2.G-VSVG were transferred into 293T cells, and the supernatant was collected after 48 hr and 72 hr, respectively. The cell debris was filtered through a 0.45 μm filter to obtain the lentivirus stock solution.

2. Cell infection: 200,000 cells to be infected (lentiviral stock solution) was spread in a 6 cm culture dish in advance, after the cells adhered on the second day, the first infection was carried out, and the infection was repeated again on the third day; on the fourth day, the cells were allowed to recover for one day without adding any stimulation; on the fifth day, drug screening was started to perform based on corresponding markers carried by the plasmid that reduce the potency of the drug.

3. Real-time fluorescence quantitative PCR (1) Total RNA Extraction $10^6$-$10^7$ cells were prepared, resuspended in PBS, and then centrifuged to remove the supernatant, 1 ml of Trizol was added for lysis at room temperature for 5 min, then 0.2 ml of chloroform was added. The mixture was shaken in a vortex shaker for 15 s, and left to stand at room temperature for 2 min. The mixture was centrifuged in a centrifuge at 4° C. for 15 min at 13,300 rpm. The upper colorless water phase was transferred into another EP tube. An equal volume of isopropanol was added, mixed thoroughly in a vortex shaker, and the mixture was centrifuged in a centrifuge at 4° C. at 13,300 rpm for 10 min. The supernatant was discarded, and 1 ml of 75% ethanol prepared with DEPC water was added, turned upside down until the precipitate was suspended, and centrifuged in a centrifuge at 4° C. at 13,300 rpm for 5 min. The supernatant was aspirated with a pipette, during the period of drying at room temperature for 5-20 min, the morphology of the precipitation was observed. When just being transparent, 40-100 μl of DEPC water was used for dissolution according to the amount of precipitation. 1 μl was taken and the concentration and OD260/OD280 was measured on Nanodrop. The extracted RNA was stored in a refrigerator at −80° C.

(2) Reverse Transcription Synthesis of cDNA

Takara (D2680A) reverse transcription PCR kit was used, the PCR reaction system and program were as follows:

| Reverse transcription PCR system | Total volume 20 μl |
|---|---|
| 5 × PrimeScript Buffer | 4 μl |
| dNTP Mixture (2.5 mM each) | 4 μl |
| Random 6 mers (100 μM) | 1 μl |
| OligodT Primer (50 μM) | 1 μl |
| PrimeScript Reverse Transcriptase (200 U/μl) | 0.5 μl |
| RNase Inhibitor (40 U/μl) | 0.5 μl |
| Total RNA | 1 μg |
| RNase Freed H2O up to 20 μl | |

Reverse transcription PCR program: 42° C. for 10 min, 95° C. for 2 min.

(3) RT-qPCR

The expression of the gene of interest at the transcription level was detected using Takara real-time fluorescent quantitative PCRkit.

| Real-time fluorescence quantitative PCR system | Total volume 10 μl |
|---|---|
| Sybr Green Mix | 5 μl |
| Forward (10 μm) | 1 μl |
| Reverse (10 μm) | 1 μl |
| cDNA | 3 μl |

Experimental results: After overexpression of the target sequence fragment, the expression level of the fragment was up-regulated tens of thousands of times (FIG. 2). Specifically, the ACE2 gene, which is very related to the coronavirus, was activated after overexpression of the SARS-CoV-HIS, SARS-COV-2-HIS-3 and SARS-COV-2-HIS-4 fragments (FIG. 3). The HAS1 (FIG. 4), HAS2 (FIG. 5) and HAS3 (FIG. 6) genes of the hyaluronic acid synthase family related to severe acute respiratory syndrome-related coronavirus 2 were also significantly activated by SARS-CoV-HIS, MERS-CoV-HIS, SARS-COV-2-HIS-3 and SARS-COV-2-HIS-4 fragments. Finally, it can be seen from the detection that the genes within 200 k around the SARS-COV-2-HIS-4 (FIG. 7), SARS-COV-2-HIS-3 (FIG. 8), SARS-COV-2-HIS-1 (FIG. 9) and SARS-COV-2-HIS-5 (FIG. 10) fragments were all significantly activated. The same results were obtained for the fragment SARS-CoV-2-HIS-6, which was not completely complementary (FIG. 11). The specific genes comprised: FBXO15, MYL9, KALRN, ATP8B1, C5AR1, EPAS1, etc. The same results were also obtained for SARS-COV-HIS-2 (FIG. 12) and MERS-COV-HIS-2 (FIG. 13). Specifically, the expression of the gene IGF2R around the target fragment of SARS virus was increased, and the expression of the gene IGF2R around the target fragment of MERS virus was increased. In addition, zika virus (FIG. 14), ebola virus (FIG. 15), and HIV-2 (FIG. 16) were also detected in this example, and the results were also the same, specifically: after overexpression of the target fragment of zika virus in 293T cells, the expression of surrounding 16 genes such as CNMD and VPS36 was increased; after overexpression of the target fragment of ebola virus in 293T cells, the expression of surrounding 15 genes such as VGLL4 and TAMM41 was all increased; after overexpression of HIV target fragment in 293T cells, the expression of surrounding genes BMP5, MMP1 and ADCYAP1 was increased; after overexpression of HIV2 target fragment in 293T cells, the expression of surrounding 8 genes such as LAPTM4A and LRRC14B was increased.

The above results prove that the constructed vector plays a certain function in the expression of miRNA related to SARS-CoV-2, and provides a research basis for subsequent research.

Example 3—Inhibitory Effect of miRNA Inhibitor (antagomiR) or Antisense Sequence for the Target of the RNA Virus on Activated Target Genes This example verifies the inhibitory effect of the inhibitor antagomir for the target of the RNA virus on activated target genes, and comprises the following steps:
- step one: preparation of the inhibitor antagomir for the viral target: cholesterol modification and four phosphorothioate backbone modifications were made at the 3' end of the reverse complementary sequence of the target sequence of the RNA virus, two phosphorothioate backbone modifications were made at the 5' end, and methoxy modification was made on the whole chain to obtain the corresponding inhibitor antagomir for the target of the virus.
- step two: the virus stock solution was prepared by the method of example 2, and the cells were infected with the virus stock solution. The infected cells were divided into two groups: an experimental group and a control group, wherein the experimental group was: 10 μM of virus-infected cell solution added with corresponding inhibitor for the viral target; the control group was: M of virus-infected cell solution. After 48 hours, the cell solution of the experimental group and the control group were tested according to the method of real-time fluorescent quantitative PCR in example 4.

Figure 17:
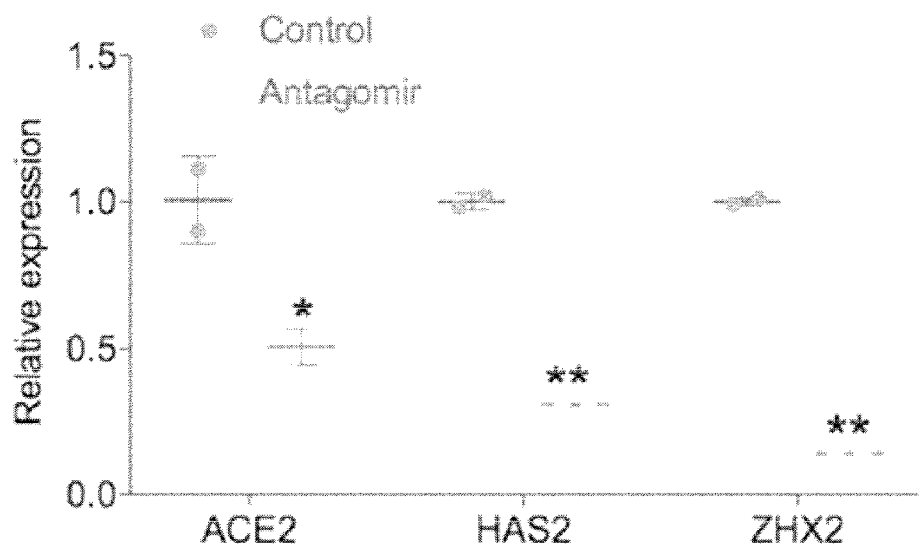
FIG. 17 is a schematic diagram of the result of antagomir on the mRNA level of the surrounding genes after overexpression of the target fragment SARS-CoV-HIS-2 of coronavirus in 293T cells by qPCR detection in an embodiment of the present invention.
Figure 18:
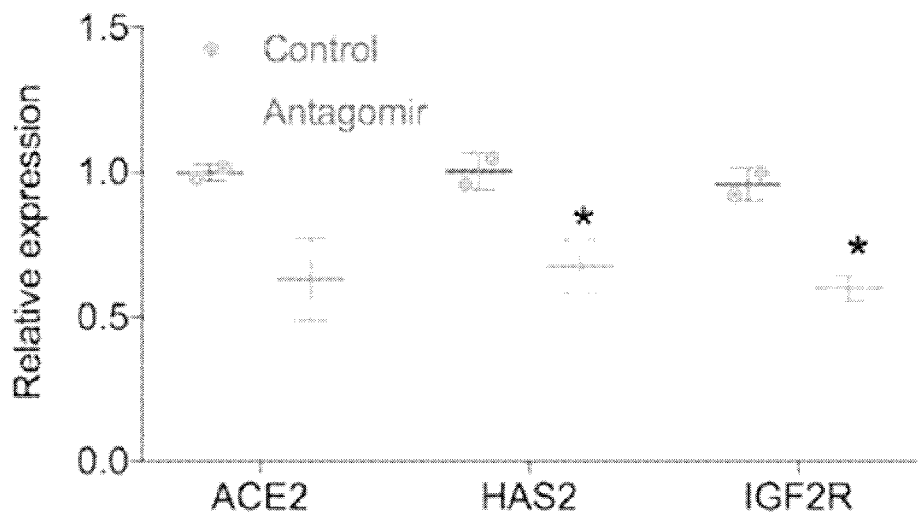
FIG. 18 is a schematic diagram of the result of the inhibitory effect of antagomir on the mRNA level of genes activated by the target fragment MERS-CoV-HIS-2 of coronavirus by qPCR detection in an embodiment of the present invention; wherein, *<0.05.
Figure 19:
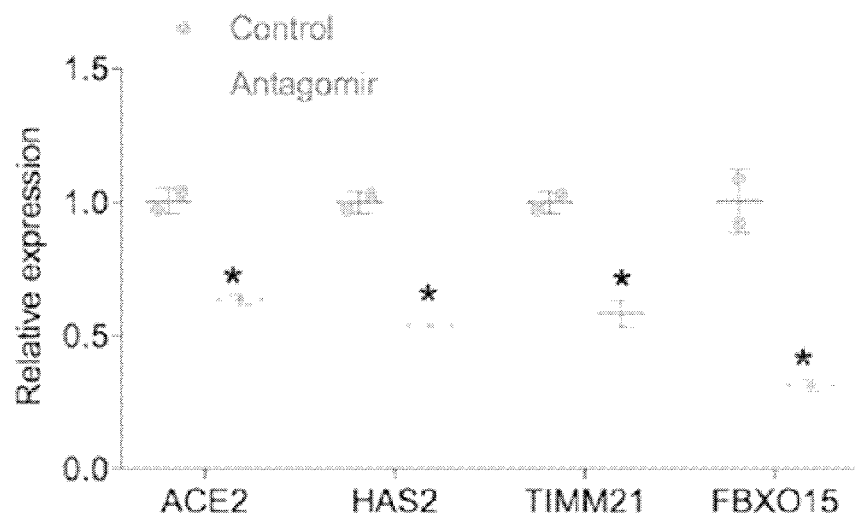
FIG. 19 is a schematic diagram of the result of the inhibitory effect of antagomir on the mRNA level of genes activated by the target fragment SARS-CoV-2-HIS-4 of coronavirus by qPCR detection in an embodiment of the present invention; wherein, *<0.05.
Figure 20:
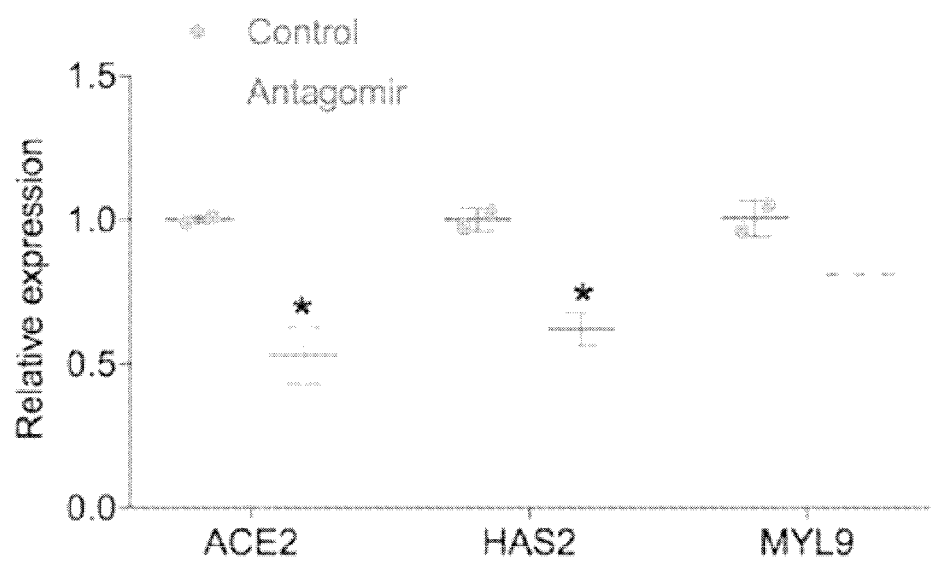
FIG. 20 is a schematic diagram of the result of the inhibitory effect of antagomir on the mRNA level of genes activated by the target fragment SARS-CoV-2-HIS-3 of coronavirus by qPCR detection in an embodiment of the present invention; wherein, *<0.05.

The results of the test were shown in FIGS. 18-21. The inhibitor for the viral target can specifically inhibit the replication of the target sequence, and the antagomir can target the target sequence well, so that the surrounding genes activated by SARS-CoV-HIS-2 (FIG. 17), MERS-CoV-HIS-2 (FIG. 18), SARS-CoV-2-HIS-4 (FIG. 19) and SARS-CoV-2-HIS-3 (FIG. 20) shown a significant tendency to decrease, further verifying the therapeutic value of targets in RNA virus.

This experiment further verified the inhibitory effect of the reverse complementary sequence of the target sequence of the RNA virus (comprising antisense DNA sequence and antisense RNA sequence), as well as cholesterol modification and four phosphorothioate backbone modifications made at the 3' end of the target sequence of the RNA virus, two phosphorothioate backbone modifications made at the 5' end, and methoxy modification made on the whole chain as an inhibitor on the activated target genes was verified. The test results were similar to that of the inhibitor antagomiR. It can be seen that the above-mentioned three inhibitors all had an inhibitory effect on activated target genes. Antisense RNA or antisense DNA of the target sequence of the RNA virus can be used to inhibit RNA virus nucleic acid and block important pathogenic pathways of RNA virus. The different modified or unmodified products of the antisense RNA or antisense DNA provided an important material basis for the treatment of RNA virus diseases. The detailed sequences of the antisense RNA or antisense DNA are shown in Table 2.

Example 4—The Increase in Hyaluronic Acid Affected by the Target can be Reduced by the Hyaluronic Acid Inhibitor 4-MU This example verifies that the increase in hyaluronic acid affected by the target can be reduced by the hyaluronic acid inhibitor 4-MU and comprises the following steps: the lentivirus and infected cells were prepared by the method of example 2; Replacement with the fresh medium was performed, 100 μM of hyaluronic acid inhibitor 4-MU was added in the experimental group, and DMSO (the solvent for 4-MU) was added in the control group. After 24 hours, the cell supernatant was collected and detected with hyaluronic acid ELISA kit (R&D, DY3614-05). The steps are briefly described as follows:

1) Coating ELISA plate: The plate was coated with 100 μl/well of Capture Reagent overnight.
2) Sealing: The Capture Reagent was removed by patting the plate. The plate was washed 3 times with 400 μl/well of Wash buffer and patted to dryness. The plate was sealed with 100 μl/well of Dilute Reagent for 1 h.
3) Washing the plate and incubating the sample: The plate was washed with 400 μl/well of Wash buffer 3 times, 100 μl/well of standard and serum to be tested were added (100 μl of the serum from patients with mild and severe COVID-19 was diluted with 200 μl of Dilute Reagent in the kit to a total volume of 300 μl, 3 replicate wells were made), and incubated at room temperature for 2 h. 4) Washing the plate and incubation with the Detect Reagent. The plate was washed with 400 μl/well of Wash buffer 3 times, 100 μl/well of Detect Reagent was added and incubated at room temperature for 2 h.
5) Washing the plate and incubation with HRP. The plate was washed with 400 μl/well of Wash buffer 3 times, 100 μl/well of HRP was added and incubated at room temperature for 20 min.
6) Washing the plate and incubation with the substrate. The plate was washed with 400 μl/well of Wash buffer 3 times, 100 μl/well of mixed solution of substrates A and B was added and incubated at room temperature for 20 min.
7) Stopping color development. 50 μl/well of stop solution was added.

Absorbance was read at 450 nm within 15 min. The test results are shown in Table 4 and Table 5: After overexpression of the target sequence of the virus in cell lines 293T and MRC5, the hyaluronic acid content was significantly increased (Table 4). The hyaluronic acid produced due to overexpression of the target sequence can be reduced using hyaluronic acid inhibitor 4-MU (Table 5). This example proves that the target of the virus has scientific research value and 4-MU has the potential to become a therapeutic drug targeting the target and has a therapeutic value for complications related to the target of the RNA virus.

TABLE 4

Determination of hyaluronic acid content in 293T and MRC5 cells in which the target of the virus is overexpressed

| | Hyaluronic acid (ng/ml) | | | |
|---|---|---|---|---|
| | 293T | p value | MRC5 | p value |
| CTRL | 7.39 ± 0.26 | * | 59.55 ± 4.73 | * |
| HIS-MERS-CoV-2 | 76.91 ± 2.29 | ** | 106.97 ± 4.69 | ** |
| HIS-SARS-CoV-1-2 | 115.60 ± 18.10 | ** | 116.84 ± 1.52 | ** |
| HIS-SARS-CoV-2-3 | 62.68 ± 7.14 | ** | 72.40 ± 8.75 | ns |
| HIS-SARS-CoV-2-4 | 113.95 ± 13.14 | ** | 117.44 ± 2.03 | ** |

TABLE 5

Determination of the inhibitory ability of hyaluronic acid inhibitor on hyaluronic acid in the case of overexpression of the target of the virus

| | Hyaluronic acid (ng/ml) | | |
|---|---|---|---|
| | DMSO | 4-MU (100 µM) | p value |
| CTRL | 7.39 ± 0.26 | 3.20 ± 0.39 | ** |
| HIS-MERS-CoV-2 | 76.91 ± 2.29 | 39.72 ± 5.75 | ** |
| HIS-SARS-CoV-1-2 | 115.60 ± 18.10 | 23.50 ± 3.44 | ** |
| HIS-SARS-CoV-2-3 | 62.68 ± 7.14 | 30.02 ± 2.00 | ** |
| HIS-SARS-CoV-2-4 | 113.95 ± 13.14 | 19.76 ± 11.3 | * |

Example 5—Detection of Blood Routine Index

The blood routine index was provided by the hospital, and the hyaluronic acid in the blood was detected using the hyaluronic acid ELISA kit (R&D, DY3614-05). Specifically, the HA content in the serum of a patient with severe COVID-19 was significantly increased compared with that in a patient with mild COVID-19 (Table 6). In addition, the number of lymphocytes in a patient with severe COVID-19 was significantly lower than that in a patient with mild COVID-19, suggesting that the number of the immune cells in a patient was decreased with the disease progressing to severe; furthermore, D-dimer is a fibrin degradation product, and the increase of D-dimer level indicates the existence of hypercoagulable state and secondary hyper fibrinolysis in the body. Therefore, the mass concentration of D-dimer has diagnostic significance for thrombotic diseases. The content of D-dimer in the serum of a patient with severe COVID-19 was significantly higher than that in a patient with mild COVID-19, indicating that the risk of coagulation in a patient was increased with the condition of COVID-19 progressing to severe, and also indicating that there was a certain feasibility of subsequent anticoagulation therapy.

TABLE 6

Hematological indicators of a patient with mild or severe COVID-19

| | HA (ng/ml) | LYMPH# (10^9/L) | CRP (mg/L) | D-D (ug/ml) |
|---|---|---|---|---|
| Mild (n = 37) | 3.77 ± 2.86 | 1.79 ± 0.50 | 0.77 ± 0.68 | 0.28 ± 0.12 |
| Severe (n = 22) | 35.41 ± 28.88*** | 1.40 ± 0.43** | 8.49 ± 9.66*** | 0.49 ± 0.36* |

The above results provide a basis for the changes in hematological indicators caused by the target sequences of the RNA virus to become clinical diagnosis, and reflects the clinical diagnostic value of the targets of the RNA virus. Moreover, the targets have the potential to become a vaccine. In addition, in the process of preparing vaccines, common attenuated live vaccines still have certain risks that need to be further optimized. The pathogenic risk of a vaccine will be greatly reduced by knockout of the targets.

The specific examples of the present invention are described in detail above and are only for illustration, and the present invention is not limited to the specific examples described above. For a person skilled in the art, any equivalent modifications and alternatives made to the present invention are also within the scope of the present invention. Therefore, all equivalent changes and modifications made without departing from the spirit and scope of the present invention should fall within the scope of the present invention.

The invention claimed is:

1. A biomaterial related to a target sequence of a RNA virus, wherein the target sequence is a nucleic acid sequence fragment in the gene sequence in the RNA virus containing 20-40 bases and having not less than 95% similarity to human genome sequence, and the biomaterial is:
A) a DNA and/or RNA molecule that is complementary and paired to the target sequence of the RNA virus; or
B) an expression cassette, a recombinant vector, a recombinant microorganism, a recombinant cell line containing the target sequence of the RNA virus or the DNA molecule in A).

2. The biomaterial according to claim 1, wherein the biomaterial is a recombinant vector, and whose construction steps comprise: 1) designing a primer, and amplifying the target sequence of the RNA virus by PCR; 2) digesting the amplified sequence fragment and an expression vector, and ligating a sequence fragment of interest and the expression vector; 3) transferring the ligated product into *Escherichia coli* and cultivating the *Escherichia coli;* and 4) after identification, extracting recombinant plasmid and packaging the recombinant plasmid.

3. The biomaterial according to claim 1, wherein the recombinant vector has target sequences expressing severe acute respiratory syndrome-related coronavirus 2 (SARS-CoV-2), severe acute respiratory syndrome-related coronavirus (SARS-CoV), or middle east respiratory syndrome coronavirus (MERS-CoV).

4. The biomaterial according to claim 1, wherein the target sequence is a nucleic acid sequence fragment in the gene sequence in the RNA virus containing 20-28 bases and having 100% similarity to human genome sequence.

5. The biomaterial according to claim 1, wherein the RNA virus comprises severe acute respiratory syndrome-related coronavirus 2, severe acute respiratory syndrome-related coronavirus, middle east respiratory syndrome coronavirus, zika virus, ebola virus, HIV, norwalk virus, alkhurma virus, enterovirus, kemerovo virus, coxsackievirus, hepatitis A virus, dengue virus 2, rubella virus, marburg marburgvirus, poliovirus, respiratory syncytial virus, mumps virus, australian bat lyssavirus, andes virus, powassan virus, langat virus, eyach virus, colorado tick fever virus, lassa virus, omsk hemorrhagic fever virus, machupo virus, junin virus, guanarito virus, sin nombre virus, hantaan virus, puumala virus, dobrava virus, seoul virus, crimean-congo hemorrhagic fever virus, sabia virus, thogoto virus, black creek canal virus, european bat lyssavirus 1, european bat lyssavirus 2, chapare virus, rotavirus, tai forest ebolavirus, bundibugyo ebolavirus, rift valley fever virus, irkut virus, influenza A virus, bayou virus, kyasanur forest disease virus, black creek canal virus, japanese encephalitis virus, duvenhage lyssavirus, Lujo mammarenavirus, measles morbillivirus, tick-borne encephalitis virus, avian influenza virus, swine influenza virus and rabies virus.

6. The biomaterial according to claim 1, wherein the target sequence of the RNA virus is selected from any one or more of SEQ ID NO. 1-615.

7. The biomaterial according to claim 6, wherein the target sequence of severe acute respiratory syndrome-related coronavirus 2 comprises SEQ ID NO. 1-SEQ ID NO. 6; and/or, the target sequence of severe acute respiratory syndrome-related coronavirus comprises SEQ ID NO. 7-SEQ ID NO. 9; and/or, the target sequence of middle east respiratory syndrome coronavirus comprises SEQ ID NO. 10, SEQ ID NO. 11; and/or, the target sequence of zika virus comprises SEQ ID NO. 12-SEQ ID NO. 14; and/or, the target sequence of ebola virus comprises SEQ ID NO. 15-SEQ ID NO. 17; and/or, the target sequence of HIV comprises SEQ ID NO. 18-SEQ ID NO. 26; and/or, the target sequence of norwalk virus comprises SEQ ID NO. 27; and/or, the target sequence of alkhurma virus comprises SEQ ID NO. 28-SEQ ID NO. 30; and/or, the target sequence of enterovirus comprises SEQ ID NO. 31, SEQ ID NO. 32; and/or, the target sequence of kemerovo virus comprises SEQ ID NO. 33, SEQ ID NO. 34; and/or, the target sequence of coxsackievirus comprises SEQ ID NO. 35; and/or, the target sequence of hepatitis A virus comprises SEQ ID NO. 36-SEQ ID NO. 46; and/or, the target sequence of dengue virus 2 comprises SEQ ID NO. 47-SEQ ID NO. 50; and/or, the target sequence of rubella virus comprises SEQ ID NO. 51; and/or, the target sequence of marburg marburgvirus comprises SEQ ID NO. 52-SEQ ID NO. 56; and/or, the target sequence of poliovirus comprises SEQ ID NO. 57; and/or, the target sequence of respiratory syncytial virus comprises SEQ ID NO. 58-SEQ ID NO. 85; and/or, the target sequence of mumps virus comprises SEQ ID NO. 86; and/or, the target sequence of australian bat lyssavirus comprises SEQ ID NO. 87; and/or, the target sequence of andes virus comprises SEQ ID NO. 88-SEQ ID NO. 95; and/or, the target sequence of powassan virus comprises SEQ ID NO. 96, SEQ ID NO. 97; and/or, the target sequence of langat virus comprises SEQ ID NO. 98-SEQ ID NO. 102; and/or, the target sequence of eyach virus comprises SEQ ID NO. 103-SEQ ID NO. 113; and/or, the target sequence of colorado tick fever virus comprises SEQ ID NO. 114-SEQ ID NO. 134; and/or, the target sequence of lassa virus comprises SEQ ID NO. 135, SEQ ID NO. 136; and/or, the target sequence of omsk hemorrhagic fever virus comprises SEQ ID NO. 137, SEQ ID NO. 138; and/or, the target sequence of machupo virus comprises SEQ ID NO. 139-SEQ ID NO. 140; and/or, the target sequence of junin virus comprises SEQ ID NO. 141; and/or, the target sequence of guanarito virus comprises SEQ ID NO. 142-SEQ ID NO. 147; and/or, the target sequence of sin nombre virus comprises SEQ ID NO. 148-SEQ ID NO. 152; and/or, the target sequence of hantaan virus comprises SEQ ID NO. 153-SEQ ID NO. 161; and/or, the target sequence of puumala virus comprises SEQ ID NO. 162-SEQ ID NO. 173; and/or, the target sequence of dobrava virus comprises SEQ ID NO. 174-SEQ ID NO. 185; and/or, the target sequence of seoul virus comprises SEQ ID NO. 186-SEQ ID NO. 199; and/or, the target sequence of crimean-congo hemorrhagic fever virus comprises SEQ ID NO. 200-SEQ ID NO. 204; and/or, the target sequence of sabia virus comprises SEQ ID NO. 205-SEQ ID NO. 212; and/or, the target sequence of thogoto virus comprises SEQ ID NO. 213-SEQ ID NO. 227; and/or, the target sequence of european bat lyssavirus 1 comprises SEQ ID NO. 228-SEQ ID NO. 232; and/or, the target sequence of european bat lyssavirus 2 comprises SEQ ID NO. 233; and/or, the target sequence of chapare virus comprises SEQ ID NO. 234; and/or, the target sequence of rotavirus comprises SEQ ID NO. 235-SEQ ID NO. 277; and/or, the target sequence of tai forest ebolavirus comprises SEQ ID NO. 278, SEQ ID NO. 279; and/or, the target sequence of bundibugyo ebolavirus comprises SEQ ID NO. 280; and/or, the target sequence of rift valley fever virus comprises SEQ ID NO. 281; and/or, the target sequence of irkut virus comprises SEQ ID NO. 282-SEQ ID NO. 285; and/or, the target sequence of influenza A virus comprises SEQ ID NO. 286-SEQ ID NO. 313; and/or, the target sequence of bayou virus comprises SEQ ID NO. 314-SEQ ID NO. 327; and/or, the target sequence of kyasanur forest disease virus comprises SEQ ID NO. 328; and/or, the target sequence of black creek canal virus comprises SEQ ID NO. 329-SEQ ID NO. 334; and/or, the target sequence of japanese encephalitis virus comprises SEQ ID NO. 335-SEQ ID NO. 337; and/or, the target sequence of duvenhage lyssavirus comprises SEQ ID NO. 338-SEQ ID NO. 344; and/or, the target sequence of Lujo mammarenavirus comprises SEQ ID NO. 345; and/or, the target sequence of measles morbillivirus comprises SEQ ID NO. 346; and/or, the target sequence of tick-borne encephalitis virus comprises SEQ ID NO. 347; and/or, the target sequence of avian influenza virus comprises SEQ ID NO. 348-SEQ ID NO. 420; and/or, the target sequence of swine influenza virus comprises SEQ ID NO. 421-SEQ ID NO. 521; and/or, the target sequence of rabies virus comprises SEQ ID NO. 522-SEQ ID NO. 615.

* * * * *